US008580542B2

(12) United States Patent
Ridley

(10) Patent No.: US 8,580,542 B2
(45) Date of Patent: Nov. 12, 2013

(54) METHODS AND COMPOSITIONS FOR PRODUCING ALKENES OF VARIOUS CHAIN LENGTH

(75) Inventor: Christian P. Ridley, Acton, MA (US)

(73) Assignee: Joule Unlimited Technologies, Inc., Bedford, MA (US)

( * ) Notice: Subject to any disclaimer, the term of this patent is extended or adjusted under 35 U.S.C. 154(b) by 0 days.

(21) Appl. No.: 13/370,654

(22) Filed: Feb. 10, 2012

(65) Prior Publication Data

US 2012/0208253 A1 Aug. 16, 2012

Related U.S. Application Data

(60) Provisional application No. 61/441,619, filed on Feb. 10, 2011.

(51) Int. Cl.

| | |
|---|---|
| ***C12P 5/00*** | (2006.01) |
| ***C12P 5/02*** | (2006.01) |
| ***C12N 9/00*** | (2006.01) |
| ***C07H 21/04*** | (2006.01) |

(52) U.S. Cl.
USPC ........... 435/166; 435/167; 435/183; 536/23.2

(58) Field of Classification Search
None
See application file for complete search history.

(56) References Cited

U.S. PATENT DOCUMENTS

| | | | |
|---|---|---|---|
| 6,960,453 | B1 | 11/2005 | Leadlay et al. |
| 2010/0330642 | A1 | 12/2010 | Ridley et al. |
| 2011/0009674 | A1 | 1/2011 | Reppas et al. |

FOREIGN PATENT DOCUMENTS

| | | | |
|---|---|---|---|
| WO | WO 2011/005548 A1 | 1/2011 | |
| WO | WO 2011/011689 A2 | 1/2011 | |

OTHER PUBLICATIONS

Arora, P. et al., "Mechanistic and Functional Insights Into Fatty Acid Activation in *Mycobacterium tuberculosis*," Nature Chemical Biology, Mar. 2009, pp. 166-173, vol. 5, No. 3.

Chang, Z. et al., "Biosynthetic Pathway and Gene Cluster Analysis of a Curacin A , an Antitubulin Natural Product from the Tropical Marine Cyanobacterium *Lyngbya Majuscula*," J. Nat. Prod., 2004, pp. 1356-1367, vol. 67.

Gu, L. et al., "Polyketide Decarboxylative Chain Termination Preceded by *O*-Sulfonation in Curacin A Biosynthesis," Journal of the American Chemical Society, 2009, pp. 16033-16035, vol. 131.

Hansen, D.B. et al., "The Loading Module of Mycosubtilin: An Adenylation Domain with Fatty Acid Selectivity," Journal of the American Chemical Society, 2007, pp. 6366-6367, vol. 129.

Khosla, C. et al., "Genetic Construction and Functional Analysis of Hybrid Polyketide Synthases Containing Heterologous Acyl Carrier Proteins," Journal of Bacteriology, Apr. 1, 1993, pp. 2197-2204, vol. 175, No. 8.

Koketsu, K. et al., "Reconstruction of the Saframycin Core Scaffold Defines Dual Pictet-Spengler Mechanisms," Nature Chemical Biology, Jun. 2010, pp. 408-410, vol. 6.

Kopp, F. et al., "Harnessing the Chemical Activation Inherent to Carrier Protein-Bound Thioesters for the Characterization of Lipopeptide Fatty Acid Tailoring Enzymes," Journal of the American Chemical Society, 2008, pp. 2656-2666, vol. 130.

Li, L. et al., "Characterization of the Saframycin a Gene Cluster from *Streptomyces lavendulae* NRRL 11002 Revealing a Nonribosomal Peptide Synthetase System for Assembling the Unusual Tetrapeptidyl Skeleton in an Iterative Manner," Journal of Bacteriology, Jan. 2008, pp. 251-263, vol. 190, No. 1.

Lin, J.-W. et al., "Nucleotide Sequence and Functional Analysis of the *luxE* Gene Encoding acyl-protein synthetase of the *lux* Operon from *Photobacterium leiognathi*,"Biochemical and Biophysical Research Communications, 1996, pp. 764-773, vol. 228.

Murata, N. et al., "Modes of Fatty-Acid Desaturation in Cyanobacteria," Plant Cell Physiology, 1992, pp. 933-941, vol. 33.

Oliynyk, M. et al., "A Hybrid Modular Polyketide Synthase Obtained by Domain Swapping," Chemistry and Biology Journal, Oct. 1, 1996, pp. 833-839, vol. 3, No. 10.

PCT Invitation to Pay Additional Fees, PCT Application No. PCT/US2012/024742, Jun. 4, 2012, 2 pages.

PCT International Search Report and Written Opinion, PCT Application No. PCT/US2012/024742, Aug. 16, 2012, 16 pages.

Wittmann, M. et al., "Role of DptE and DptF in the Lipidation Reaction of Daptomycin," FEBS Journal, 2008, pp. 5343-5354, vol. 275.

Wong, F.T. et al., "Protein-Protein Recognition Between Acyltransferases and Acyl Carrier Proteins in Multimodular Polyketide Synthases," Biochemistry, Jan. 12, 2010, pp. 95-102, vol. 49, No. 1.

Wyckoff, T.J.O. et al., "Hydrocarbon Rulers in UDP-*N*-acetylglucosamine acyltransferases," The Journal of Biological Chemistry, Dec. 4, 1998, pp. 32369-32372, vol. 273, No. 49.

Yuan, L. et al., "Modification in the Substrate Specificity of an acyl-acyl Carrier Protein thioesterase by Protein Engineering," Proceedings of the National Academy of Sciences of the United States of America, Nov. 1995, pp. 10639-10643, vol. 92.

*Primary Examiner* — Anand Desai
*Assistant Examiner* — Iqbal H Chowdhury
(74) *Attorney, Agent, or Firm* — Fenwick & West LLP; Chang B. Hong, Esq.

(57) ABSTRACT

The NonA alkene synthase in *Synechococcus* sp. displays selective synthesis of 1-nonadecene. Heterologous recombination of a domain, i.e. the acyl binding domain, with other acyl binding proteins, affects acyl substrate chain-length binding selectivity and therefore the chain-length of the synthesized 1-alkenes. Compositions and methods are provided to selectively synthesize 1-alkenes of various chain lengths.

6 Claims, 10 Drawing Sheets

| 1-Alkene | Melting Point (°C)[a] | Boiling Point (°C)[a] |
|---|---|---|
| 1-dodecene | - 35 | 214 to 216 |
| 1-tridecene | -23 | 232 to 233 |
| 1-tetradecene | -13 to -15 | 251 |
| 1-pentadecene | -4 | 268 to 269 |
| 1-hexadecene | 3 to 5 | 274 |
| 1-heptadecene | 10 to 11 | 157 to 159 (11 mm Hg) |
| 1-octadecene | 14 to 16 | 179 (15 mm Hg) |
| 1-nonadecene | 23 | Not available |

[a] Data obtained from the Sigma-Aldrich website.

*FIG. 1*

SEQUENCE LISTING

```
<160> NUMBER OF SEQ ID NOS: 40

<210> SEQ ID NO 1
<211> LENGTH: 8163
<212> TYPE: DNA
<213> ORGANISM: Synechococcus sp.

<400> SEQUENCE: 1

atggttggtc aatttgcaaa tttcgtcgat ctgctccagt acagagctaa acttcaggcg     60

cggaaaaccg tgtttagttt tctggctgat ggcgaagcgg aatctgcggc cctgacctac    120

ggagaattag accaaaaagc ccaggcgatc gccgcttttt tgcaagctaa ccaggctcaa    180

gggcaacggg cattattact ttatccaccg ggtttagagt ttatcggtgc ctttttggga    240

tgtttgtatg ctggtgttgt tgcggtgcca gcttacccac cacggccgaa taaatccttt    300

gaccgcctcc atagcattat ccaagatgcc caggcaaaat ttgccctcac cacaacagaa    360

cttaaagata aaattgccga tcgcctcgaa gctttagaag gtacggattt tcattgtttg    420

gctacagatc aagttgaatt aatttcagga aaaaattggc aaaaaccgaa catttccggc    480

acagatctcg ctttttttgca atacaccagt ggctccacgg gcgatcctaa aggagtgatg    540

gtttcccacc acaatttgat ccacaactcc ggcttgatta accaaggatt ccaggataca    600

gaggcgagta tgggcgtttc ctggttgccg ccctaccatg atatgggctt gatcggtggg    660

attttacagc ccatctatgt gggagcaacg caaattttaa tgcctcccgt ggccttttttg    720

cagcgacctt ttcggtggct aaaggcgatc aacgattatc gggtttccac cagcggtgcg    780

ccgaattttg cctatgatct ctgtgccagc caaattaccc cggaacaaat cagagaactc    840

gatttgagct gttggcgact ggctttttcc ggggccgaac cgatccgcgc tgtgaccctc    900

gaaaattttg cgaaaacctt cgctacagca ggctttcaaa aatcagcatt ttatccctgt    960
```

-continued

```
tatggtatgg ctgaaaccac cctgatcgtt tccggtggta atggtcgtgc ccagcttccc   1020
caggaaatta tcgtcagcaa acagggcatc gaagcaaacc aagttcgccc tgcccaaggg   1080
acagaaacaa cggtgacctt ggtcggcagt ggtgaagtga ttggcgacca aattgtcaaa   1140
attgttgacc cccaggcttt aacagaatgt accgtcggtg aaattggcga agtatgggtt   1200
aagggcgaaa gtgttgccca gggctattgg caaaagccag acctcaccca gcaacaattc   1260
cagggaaacg tcggtgcaga aacgggcttt ttacgcacgg gcgatctggg tttttgcaa    1320
ggtggcgaac tgtatattac gggtcgttta aaggatctcc tgattatccg gggcgcaac    1380
cactatcccc aggacattga attaaccgtc gaagtggccc atcccgcttt acgacagggg   1440
gccggagccg ctgtatcagt agacgttaac ggggaagaac agttagtcat tgtccaggaa   1500
gttgagcgta aatatgcccg caaattaaat gtcgcggcag tagcccaagc tattcgtggg   1560
gcgatcgccg ccgaacatca actgcaaccc caggccattt gttttattaa acccggtagc   1620
attcccaaaa catccagcgg gaagattcgt cgccatgcct gcaaagctgg ttttctagac   1680
ggaagcttgg ctgtggttgg ggagtggcaa cccagccacc aaaaagaagg aaaaggaatt   1740
gggacacaag ccgttacccc ttctacgaca acatcaacga attttcccct gcctgaccag   1800
caccaacagc aaattgaagc ctggcttaag gataatattg cccatcgcct cggcattacg   1860
ccccaacaat tagacgaaac ggaacccttt gcaagttatg ggctggattc agtgcaagca   1920
gtacaggtca cagccgactt agaggattgg ctaggtcgaa aattagaccc cactctggcc   1980
tacgattatc cgaccattcg caccctggct cagtttttgg tccagggtaa tcaagcgcta   2040
gagaaaatac cacaggtgcc gaaaattcag ggcaaagaaa ttgccgtggt gggtctcagt   2100
tgtcgttttc cccaagctga caaccccgaa gctttttggg aattattacg taatggtaaa   2160
gatggagttc gccccccttaa aactcgctgg gccacgggag aatggggtgg tttttagaa    2220
gatattgacc agtttgagcc gcaatttttt ggcatttccc cccgggaagc ggaacaaatg   2280
gatccccagc aacgcttact gttagaagta acctgggaag ccttggaacg ggcaaatatt   2340
ccggcagaaa gtttacgcca ttcccaaacg ggggtttttg tcggcattag taatagtgat   2400
tatgcccagt tgcaggtgcg ggaaaacaat ccgatcaatc cctacatggg gacgggcaac   2460
gcccacagta ttgctgcgaa tcgtctgtct tatttcctcg atctccgggg cgtttctctg   2520
agcatcgata cggcctgttc ctcttctctg gtggcggtac atctggcctg tcaaagttta   2580
atcaacggcg aatcggagtt ggcgatcgcc gccggggtga atttgatttt gacccccgat   2640
gtgacccaga cttttaccca ggcgggcatg atgagtaaga cgggccgttg ccagaccttt   2700
gatgccgagg ctgatggcta tgtgcggggc gaaggttgtg ggtcgttct cctcaaaccc    2760
ctggcccagg cagaacggga cggggataat attctcgcgg tgatccacgg ttcggcggtg   2820
aatcaagatg gacgcagtaa cggtttgacg gctcccaacg ggcgatcgca acaggccgtt   2880
attcgccaag ccctggccca agccggcatt accgccgccg atttagctta cctagaggcc   2940
cacggcaccg gcacgcccct gggtgatccc attgaaatta attccctgaa ggcggtttta   3000
caaacggcgc agcgggaaca gccctgtgtg gtgggttctg tgaaaacaaa cattggtcac   3060
ctcgaggcag cggcgggcat cgcgggctta atcaaggtga ttttgtccct agagcatgga   3120
atgattcccc aacatttgca ttttaagcag ctcaatcccc gcattgatct agacggttta   3180
gtgaccattg cgagcaaaga tcagccttgg tcaggcgggt cacaaaaacg gtttgctggg   3240
gtaagttcct ttgggtttgg tggcaccaat gcccacgtga ttgtcgggga ctatgctcaa   3300
caaaaatctc cccttgctcc tccggctacc caagaccgcc cttggcattt gctgaccctt   3360
```

-continued

```
tctgctaaaa atgcccaggc cttaaatgcc ctgcaaaaaa gctatggaga ctatctggcc   3420
caacatccca gcgttgaccc acgcgatctc tgtttgtctg ccaataccgg gcgatcgccc   3480
ctcaaagaac gtcgtttttt tgtctttaaa caagtcgccg atttacaaca aactctcaat   3540
caagattttc tggcccaacc acgcctcagt tcccccgcaa aaattgcctt tttgtttacg   3600
gggcaaggtt cccaatacta cggcatgggg caacaactgt accaaaccag cccagtattt   3660
cggcaagtgc tggatgagtg cgatcgcctc tggcagacct attcccccga agcccctgcc   3720
ctcaccgacc tgctgtacgg taaccataac cctgacctcg tccacgaaac tgtctatacc   3780
cagcccctcc tctttgctgt tgaatatgcg atcgcccaac tatggttaag ctggggcgtg   3840
acgccagact tttgcatggg ccatagcgtc ggcgaatatg tcgcggcttg tctggcgggg   3900
gtattttccc tggcagacgg catgaaatta attacggccc ggggcaaact gatgcacgcc   3960
ctacccagca atggcagtat ggcggcggtc tttgccgata aaacggtcat caaaccctac   4020
ctatcggagc atttgaccgt cggagccgaa aacggttccc atttggtgct atcaggaaag   4080
acccccctgcc tcgaagccag tattcacaaa ctccaaagcc aagggatcaa aaccaaaccc  4140
ctcaaggttt cccatgcttt ccactcccct ttgatggctc ccatgctggc agagtttcgg   4200
gaaattgctg aacaaattac tttccacccg ccgcgtatcc cgctcatttc caatgtcacg   4260
ggcggccaga ttgaagcgga aattgcccag gccgactatt gggttaagca cgtttcgcaa   4320
cccgtcaaat ttgtccagag catccaaacc ctggcccaag cgggtgtcaa tgtttatctc   4380
gaaatcggcg taaaaccagt gctcctgagt atgggacgcc attgcttagc tgaacaagaa   4440
gcggtttggt tgcccagttt acgtccccat agtgagcctt ggccggaaat tttgaccagt   4500
ctcggcaaac tgtatgagca agggctaaac attgactggc agaccgtgga agctggcgat   4560
cgccgccgga aactgattct gcccacctat cccttccaac ggcaacgata ttggtttaat   4620
caaggctctt ggcaaactgt tgagaccgaa tctgtgaacc caggccctga cgatctcaat   4680
gattggttgt atcaggtggc gtggacgccc ctggacactt tgcccccggc cccttgaaccg  4740
tcggctaagc tgtggttaat cttgggcgat cgccatgatc accagcccat tgaagcccaa   4800
tttaaaaacg cccagcgggt gtatctcggc caaagcaatc attttccgac gaatgccccc   4860
tgggaagtat ctgccgatgc gttggataat ttatttactc acgtcggctc ccaaaattta   4920
gcaggcatcc tttacctgtg tcccccaggg gaagacccag aagacctaga tgaaattcaa   4980
aagcaaacca gtggcttcgc cctccaactg atccaaaccc tgtatcaaca aaagatcgcg   5040
gttccctgct ggtttgtgac ccaccagagc caacgggtgc ttgaaaccga tgctgtcacc   5100
ggatttgccc aagggggatt atggggactc gcccaggcga tcgccctcga acatccagag   5160
ttgtgggggg gaattattga tgtcgatgac agcctgccaa attttgccca gatttgccaa   5220
caaagacagg tgcagcagtt ggccgtgcgg caccaaaaac tctacggggc acagctcaaa   5280
aagcaaccgt cactgcccca gaaaaatctc cagattcaac cccaacagac ctatctagtg   5340
acagggggac tgggggccat tggccgtaaa attgcccaat ggctagccgc agcaggagca   5400
gaaaaagtaa ttctcgtcag ccggcgcgct ccggcagcgg atcagcagac gttaccgacc   5460
aatgcggtgg tttatccttg cgatttagcc gacgcagccc aggtggcaaa gctgtttcaa   5520
acctatcccc acatcaaagg aattttccat gcggcgggta ccttagctga tggtttgctg   5580
caacaacaaa cttggcaaaa gttccagacc gtcgccgccg ccaaaatgaa agggacatgg   5640
catctgcacc gccatagtca aaagctcgat ctggattttt ttgtgttgtt ttcctctgtg   5700
gcaggggtgc tcggttcacc gggacagggg aattatgccg ccgcaaaccg ggcatggcg    5760
```

gcgatcgccc aatatcgaca agcccaaggt ttacccgccc tggcgatcca ttgggggcct 5820
tgggccgaag ggggaatggc caactccctc agcaaccaaa atttagcgtg gctgccgccc 5880
ccccagggac taacaatcct cgaaaaagtc ttgggcgccc agggggaaat gggggtcttt 5940
aaaccggact ggcaaaacct ggccaaacag ttccccgaat ttgccaaaac ccattacttt 6000
gcagccgtta ttccctctgc tgaggctgtg cccccaacgg cttcaatttt tgacaaatta 6060
atcaacctag aagcttctca gcgggctgac tatctactgg attatctgcg gcggtctgtg 6120
gcgcaaatcc tcaagttaga aattgagcaa attcaaagcc acgatagcct gttggatctg 6180
ggcatggatt cgttgatgat catggaggcg atcgccagcc tcaagcagga tttacaactg 6240
atgttgtacc ccagggaaat ctacgaacgg cccagacttg atgtgttgac ggcctatcta 6300
gcggcggaat tcaccaaggc ccatgattct gaagcagcaa cggcggcagc agcgattccc 6360
tcccaaagcc tttcggtcaa aacaaaaaaa cagtggcaaa aacctgacca caaaaacccg 6420
aatcccattg cctttatcct ctctagcccc cggtcgggtt cgacgttgct gcgggtgatg 6480
ttagccggac atccggggtt atattcgccg ccagagctgc atttgctccc ctttgagact 6540
atgggcgatc gccaccagga attgggtcta tcccacctcg gcgaagggtt acaacgggcc 6600
ttaatggatc tagaaaacct caccccagag gcaagccagg cgaaggtcaa ccaatgggtc 6660
aaagcgaata cacccattgc agacatctat gcctatctcc aacggcaggc ggaacaacgt 6720
ttactcatcg acaaatctcc cagctacggc agcgatcgcc atattctaga ccacagcgaa 6780
atcctctttg accaggccaa atatatccat ctggtacgcc atccctacgc ggtgattgaa 6840
tcctttaccc gactgcggat ggataaactg ctgggggccg agcagcagaa cccctacgcc 6900
ctcgcggagt ccatttggcg caccagcaac cgcaatattt tagacctggg tcgcacggtt 6960
ggtgcggatc gatatctcca ggtgatttac gaagatctcg tccgtgaccc ccgcaaagtt 7020
ttgacaaata tttgtgattt cctgggggtg gactttgacg aagcgctcct caatccctac 7080
agcggcgatc gccttaccga tggcctccac caacagtcca tgggcgtcgg ggatcccaat 7140
ttcctccagc acaaaaccat tgatccggcc ctcgccgaca aatggcgctc aattaccctg 7200
cccgctgctc tccagctgga tacgatccag ttggccgaaa cgtttgctta cgatctcccc 7260
caggaacccc agctaacacc ccagacccaa tccttgccct cgatggtgga gcggttcgtg 7320
acagtgcgcg gtttagaaac ctgtctctgt gagtggggcg atcgccacca accattggtg 7380
ctacttctcc acggcatcct cgaacagggg gcctcctggc aactcatcgc gccccagttg 7440
gcggcccagg gctattgggt tgtggcccca gacctgcgtg gtcacggcaa atccgcccat 7500
gcccagtcct acagcatgct tgattttttg gctgacgtag atgcccttgc caaacaatta 7560
ggcgatcgcc cctttacctt ggtgggccac tccatgggtt ccatcatcgg tgccatgtat 7620
gcaggaattc gccaaaccca ggtagaaaag ttgatcctcg ttgaaaccat tgtccccaac 7680
gacatcgacg acgctgaaac cggtaatcac ctgacgaccc atctcgatta cctcgccgcg 7740
cccccccaac acccgatctt ccccagccta gaagtggccg cccgtcgcct ccgccaagcc 7800
acgccccaac tacccaaaga cctctcggcg ttcctcaccc agcgcagcac caaatccgtc 7860
gaaaaagggg tgcagtggcg ttgggatgct ttcctccgta cccgggcggg cattgaattc 7920
aatggcatta gcagacgacg ttacctggcc ctgctcaaag atatccaagc gccgatcacc 7980
ctcatctatg gcgatcagag tgaatttaac cgccctgctg atctccaggc gatccaagcg 8040
gctctccccc aggcccaacg tttaacggtt gctggcggcc ataacctcca ttttgagaat 8100
ccccaggcga tcgcccaaat tgtttatcaa caactccaga cccctgtacc caaaacacaa 8160
taa 8163

<210> SEQ ID NO 2
<211> LENGTH: 2720
<212> TYPE: PRT
<213> ORGANISM: Synechococcus sp.

<400> SEQUENCE: 2

Met Val Gly Gln Phe Ala Asn Phe Val Asp Leu Leu Gln Tyr Arg Ala
1 5 10 15

Lys Leu Gln Ala Arg Lys Thr Val Phe Ser Phe Leu Ala Asp Gly Glu
20 25 30

Ala Glu Ser Ala Ala Leu Thr Tyr Gly Glu Leu Asp Gln Lys Ala Gln
35 40 45

Ala Ile Ala Ala Phe Leu Gln Ala Asn Gln Ala Gln Gly Gln Arg Ala
50 55 60

Leu Leu Leu Tyr Pro Pro Gly Leu Glu Phe Ile Gly Ala Phe Leu Gly
65 70 75 80

Cys Leu Tyr Ala Gly Val Val Ala Val Pro Ala Tyr Pro Pro Arg Pro
85 90 95

Asn Lys Ser Phe Asp Arg Leu His Ser Ile Ile Gln Asp Ala Gln Ala
100 105 110

Lys Phe Ala Leu Thr Thr Thr Glu Leu Lys Asp Lys Ile Ala Asp Arg
115 120 125

Leu Glu Ala Leu Glu Gly Thr Asp Phe His Cys Leu Ala Thr Asp Gln
130 135 140

Val Glu Leu Ile Ser Gly Lys Asn Trp Gln Lys Pro Asn Ile Ser Gly
145 150 155 160

Thr Asp Leu Ala Phe Leu Gln Tyr Thr Ser Gly Ser Thr Gly Asp Pro
165 170 175

Lys Gly Val Met Val Ser His His Asn Leu Ile His Asn Ser Gly Leu
180 185 190

Ile Asn Gln Gly Phe Gln Asp Thr Glu Ala Ser Met Gly Val Ser Trp
195 200 205

Leu Pro Pro Tyr His Asp Met Gly Leu Ile Gly Gly Ile Leu Gln Pro
210 215 220

Ile Tyr Val Gly Ala Thr Gln Ile Leu Met Pro Pro Val Ala Phe Leu
225 230 235 240

Gln Arg Pro Phe Arg Trp Leu Lys Ala Ile Asn Asp Tyr Arg Val Ser
245 250 255

Thr Ser Gly Ala Pro Asn Phe Ala Tyr Asp Leu Cys Ala Ser Gln Ile
260 265 270

Thr Pro Glu Gln Ile Arg Glu Leu Asp Leu Ser Cys Trp Arg Leu Ala
275 280 285

Phe Ser Gly Ala Glu Pro Ile Arg Ala Val Thr Leu Glu Asn Phe Ala
290 295 300

Lys Thr Phe Ala Thr Ala Gly Phe Gln Lys Ser Ala Phe Tyr Pro Cys
305 310 315 320

Tyr Gly Met Ala Glu Thr Thr Leu Ile Val Ser Gly Gly Asn Gly Arg
325 330 335

Ala Gln Leu Pro Gln Glu Ile Ile Val Ser Lys Gln Gly Ile Glu Ala
340 345 350

Asn Gln Val Arg Pro Ala Gln Gly Thr Glu Thr Thr Val Thr Leu Val
355 360 365

-continued

```
Gly Ser Gly Glu Val Ile Gly Asp Gln Ile Val Lys Ile Val Asp Pro
    370                 375                 380

Gln Ala Leu Thr Glu Cys Thr Val Gly Glu Ile Gly Glu Val Trp Val
385                 390                 395                 400

Lys Gly Glu Ser Val Ala Gln Gly Tyr Trp Gln Lys Pro Asp Leu Thr
                405                 410                 415

Gln Gln Gln Phe Gln Gly Asn Val Gly Ala Glu Thr Gly Phe Leu Arg
            420                 425                 430

Thr Gly Asp Leu Gly Phe Leu Gln Gly Gly Glu Leu Tyr Ile Thr Gly
        435                 440                 445

Arg Leu Lys Asp Leu Leu Ile Ile Arg Gly Arg Asn His Tyr Pro Gln
    450                 455                 460

Asp Ile Glu Leu Thr Val Glu Val Ala His Pro Ala Leu Arg Gln Gly
465                 470                 475                 480

Ala Gly Ala Ala Val Ser Val Asp Val Asn Gly Glu Glu Gln Leu Val
                485                 490                 495

Ile Val Gln Glu Val Glu Arg Lys Tyr Ala Arg Lys Leu Asn Val Ala
            500                 505                 510

Ala Val Ala Gln Ala Ile Arg Gly Ala Ile Ala Ala Glu His Gln Leu
        515                 520                 525

Gln Pro Gln Ala Ile Cys Phe Ile Lys Pro Gly Ser Ile Pro Lys Thr
    530                 535                 540

Ser Ser Gly Lys Ile Arg Arg His Ala Cys Lys Ala Gly Phe Leu Asp
545                 550                 555                 560

Gly Ser Leu Ala Val Val Gly Glu Trp Gln Pro Ser His Gln Lys Glu
                565                 570                 575

Gly Lys Gly Ile Gly Thr Gln Ala Val Thr Pro Ser Thr Thr Thr Ser
            580                 585                 590

Thr Asn Phe Pro Leu Pro Asp Gln His Gln Gln Gln Ile Glu Ala Trp
        595                 600                 605

Leu Lys Asp Asn Ile Ala His Arg Leu Gly Ile Thr Pro Gln Gln Leu
    610                 615                 620

Asp Glu Thr Glu Pro Phe Ala Ser Tyr Gly Leu Asp Ser Val Gln Ala
625                 630                 635                 640

Val Gln Val Thr Ala Asp Leu Glu Asp Trp Leu Gly Arg Lys Leu Asp
                645                 650                 655

Pro Thr Leu Ala Tyr Asp Tyr Pro Thr Ile Arg Thr Leu Ala Gln Phe
            660                 665                 670

Leu Val Gln Gly Asn Gln Ala Leu Glu Lys Ile Pro Gln Val Pro Lys
        675                 680                 685

Ile Gln Gly Lys Glu Ile Ala Val Val Gly Leu Ser Cys Arg Phe Pro
    690                 695                 700

Gln Ala Asp Asn Pro Glu Ala Phe Trp Glu Leu Leu Arg Asn Gly Lys
705                 710                 715                 720

Asp Gly Val Arg Pro Leu Lys Thr Arg Trp Ala Thr Gly Glu Trp Gly
                725                 730                 735

Gly Phe Leu Glu Asp Ile Asp Gln Phe Glu Pro Gln Phe Phe Gly Ile
            740                 745                 750

Ser Pro Arg Glu Ala Glu Gln Met Asp Pro Gln Gln Arg Leu Leu Leu
        755                 760                 765

Glu Val Thr Trp Glu Ala Leu Glu Arg Ala Asn Ile Pro Ala Glu Ser
    770                 775                 780

Leu Arg His Ser Gln Thr Gly Val Phe Val Gly Ile Ser Asn Ser Asp
785                 790                 795                 800
```

-continued

```
Tyr Ala Gln Leu Gln Val Arg Glu Asn Asn Pro Ile Asn Pro Tyr Met
                805                 810                 815

Gly Thr Gly Asn Ala His Ser Ile Ala Ala Asn Arg Leu Ser Tyr Phe
            820                 825                 830

Leu Asp Leu Arg Gly Val Ser Leu Ser Ile Asp Thr Ala Cys Ser Ser
        835                 840                 845

Ser Leu Val Ala Val His Leu Ala Cys Gln Ser Leu Ile Asn Gly Glu
    850                 855                 860

Ser Glu Leu Ala Ile Ala Ala Gly Val Asn Leu Ile Leu Thr Pro Asp
865                 870                 875                 880

Val Thr Gln Thr Phe Thr Gln Ala Gly Met Met Ser Lys Thr Gly Arg
                885                 890                 895

Cys Gln Thr Phe Asp Ala Glu Ala Asp Gly Tyr Val Arg Gly Glu Gly
            900                 905                 910

Cys Gly Val Val Leu Leu Lys Pro Leu Ala Gln Ala Glu Arg Asp Gly
        915                 920                 925

Asp Asn Ile Leu Ala Val Ile His Gly Ser Ala Val Asn Gln Asp Gly
    930                 935                 940

Arg Ser Asn Gly Leu Thr Ala Pro Asn Gly Arg Ser Gln Gln Ala Val
945                 950                 955                 960

Ile Arg Gln Ala Leu Ala Gln Ala Gly Ile Thr Ala Ala Asp Leu Ala
                965                 970                 975

Tyr Leu Glu Ala His Gly Thr Gly Thr Pro Leu Gly Asp Pro Ile Glu
            980                 985                 990

Ile Asn Ser Leu Lys Ala Val Leu  Gln Thr Ala Gln Arg  Glu Gln Pro
        995                 1000                1005

Cys Val  Val Gly Ser Val Lys  Thr Asn Ile Gly His  Leu Glu Ala
    1010                 1015                 1020

Ala Ala  Gly Ile Ala Gly Leu  Ile Lys Val Ile Leu  Ser Leu Glu
    1025                 1030                 1035

His Gly  Met Ile Pro Gln His  Leu His Phe Lys Gln  Leu Asn Pro
    1040                 1045                 1050

Arg Ile  Asp Leu Asp Gly Leu  Val Thr Ile Ala Ser  Lys Asp Gln
    1055                 1060                 1065

Pro Trp  Ser Gly Gly Ser Gln  Lys Arg Phe Ala Gly  Val Ser Ser
    1070                 1075                 1080

Phe Gly  Phe Gly Gly Thr Asn  Ala His Val Ile Val  Gly Asp Tyr
    1085                 1090                 1095

Ala Gln  Gln Lys Ser Pro Leu  Ala Pro Pro Ala Thr  Gln Asp Arg
    1100                 1105                 1110

Pro Trp  His Leu Leu Thr Leu  Ser Ala Lys Asn Ala  Gln Ala Leu
    1115                 1120                 1125

Asn Ala  Leu Gln Lys Ser Tyr  Gly Asp Tyr Leu Ala  Gln His Pro
    1130                 1135                 1140

Ser Val  Asp Pro Arg Asp Leu  Cys Leu Ser Ala Asn  Thr Gly Arg
    1145                 1150                 1155

Ser Pro  Leu Lys Glu Arg Arg  Phe Phe Val Phe Lys  Gln Val Ala
    1160                 1165                 1170

Asp Leu  Gln Gln Thr Leu Asn  Gln Asp Phe Leu Ala  Gln Pro Arg
    1175                 1180                 1185

Leu Ser  Ser Pro Ala Lys Ile  Ala Phe Leu Phe Thr  Gly Gln Gly
    1190                 1195                 1200

Ser Gln  Tyr Tyr Gly Met Gly  Gln Gln Leu Tyr Gln  Thr Ser Pro
```

1205 1210 1215

Val Phe Arg Gln Val Leu Asp Glu Cys Asp Arg Leu Trp Gln Thr
1220 1225 1230

Tyr Ser Pro Glu Ala Pro Ala Leu Thr Asp Leu Leu Tyr Gly Asn
1235 1240 1245

His Asn Pro Asp Leu Val His Glu Thr Val Tyr Thr Gln Pro Leu
1250 1255 1260

Leu Phe Ala Val Glu Tyr Ala Ile Ala Gln Leu Trp Leu Ser Trp
1265 1270 1275

Gly Val Thr Pro Asp Phe Cys Met Gly His Ser Val Gly Glu Tyr
1280 1285 1290

Val Ala Ala Cys Leu Ala Gly Val Phe Ser Leu Ala Asp Gly Met
1295 1300 1305

Lys Leu Ile Thr Ala Arg Gly Lys Leu Met His Ala Leu Pro Ser
1310 1315 1320

Asn Gly Ser Met Ala Ala Val Phe Ala Asp Lys Thr Val Ile Lys
1325 1330 1335

Pro Tyr Leu Ser Glu His Leu Thr Val Gly Ala Glu Asn Gly Ser
1340 1345 1350

His Leu Val Leu Ser Gly Lys Thr Pro Cys Leu Glu Ala Ser Ile
1355 1360 1365

His Lys Leu Gln Ser Gln Gly Ile Lys Thr Lys Pro Leu Lys Val
1370 1375 1380

Ser His Ala Phe His Ser Pro Leu Met Ala Pro Met Leu Ala Glu
1385 1390 1395

Phe Arg Glu Ile Ala Glu Gln Ile Thr Phe His Pro Pro Arg Ile
1400 1405 1410

Pro Leu Ile Ser Asn Val Thr Gly Gly Gln Ile Glu Ala Glu Ile
1415 1420 1425

Ala Gln Ala Asp Tyr Trp Val Lys His Val Ser Gln Pro Val Lys
1430 1435 1440

Phe Val Gln Ser Ile Gln Thr Leu Ala Gln Ala Gly Val Asn Val
1445 1450 1455

Tyr Leu Glu Ile Gly Val Lys Pro Val Leu Leu Ser Met Gly Arg
1460 1465 1470

His Cys Leu Ala Glu Gln Glu Ala Val Trp Leu Pro Ser Leu Arg
1475 1480 1485

Pro His Ser Glu Pro Trp Pro Glu Ile Leu Thr Ser Leu Gly Lys
1490 1495 1500

Leu Tyr Glu Gln Gly Leu Asn Ile Asp Trp Gln Thr Val Glu Ala
1505 1510 1515

Gly Asp Arg Arg Arg Lys Leu Ile Leu Pro Thr Tyr Pro Phe Gln
1520 1525 1530

Arg Gln Arg Tyr Trp Phe Asn Gln Gly Ser Trp Gln Thr Val Glu
1535 1540 1545

Thr Glu Ser Val Asn Pro Gly Pro Asp Asp Leu Asn Asp Trp Leu
1550 1555 1560

Tyr Gln Val Ala Trp Thr Pro Leu Asp Thr Leu Pro Pro Ala Pro
1565 1570 1575

Glu Pro Ser Ala Lys Leu Trp Leu Ile Leu Gly Asp Arg His Asp
1580 1585 1590

His Gln Pro Ile Glu Ala Gln Phe Lys Asn Ala Gln Arg Val Tyr
1595 1600 1605

```
Leu Gly Gln Ser Asn His Phe Pro Thr Asn Ala Pro Trp Glu Val
    1610                1615                1620

Ser Ala Asp Ala Leu Asp Asn Leu Phe Thr His Val Gly Ser Gln
    1625                1630                1635

Asn Leu Ala Gly Ile Leu Tyr Leu Cys Pro Pro Gly Glu Asp Pro
    1640                1645                1650

Glu Asp Leu Asp Glu Ile Gln Lys Gln Thr Ser Gly Phe Ala Leu
    1655                1660                1665

Gln Leu Ile Gln Thr Leu Tyr Gln Gln Lys Ile Ala Val Pro Cys
    1670                1675                1680

Trp Phe Val Thr His Gln Ser Gln Arg Val Leu Glu Thr Asp Ala
    1685                1690                1695

Val Thr Gly Phe Ala Gln Gly Gly Leu Trp Gly Leu Ala Gln Ala
    1700                1705                1710

Ile Ala Leu Glu His Pro Glu Leu Trp Gly Gly Ile Ile Asp Val
    1715                1720                1725

Asp Asp Ser Leu Pro Asn Phe Ala Gln Ile Cys Gln Gln Arg Gln
    1730                1735                1740

Val Gln Gln Leu Ala Val Arg His Gln Lys Leu Tyr Gly Ala Gln
    1745                1750                1755

Leu Lys Lys Gln Pro Ser Leu Pro Gln Lys Asn Leu Gln Ile Gln
    1760                1765                1770

Pro Gln Gln Thr Tyr Leu Val Thr Gly Gly Leu Gly Ala Ile Gly
    1775                1780                1785

Arg Lys Ile Ala Gln Trp Leu Ala Ala Ala Gly Ala Glu Lys Val
    1790                1795                1800

Ile Leu Val Ser Arg Arg Ala Pro Ala Ala Asp Gln Gln Thr Leu
    1805                1810                1815

Pro Thr Asn Ala Val Val Tyr Pro Cys Asp Leu Ala Asp Ala Ala
    1820                1825                1830

Gln Val Ala Lys Leu Phe Gln Thr Tyr Pro His Ile Lys Gly Ile
    1835                1840                1845

Phe His Ala Ala Gly Thr Leu Ala Asp Gly Leu Leu Gln Gln Gln
    1850                1855                1860

Thr Trp Gln Lys Phe Gln Thr Val Ala Ala Ala Lys Met Lys Gly
    1865                1870                1875

Thr Trp His Leu His Arg His Ser Gln Lys Leu Asp Leu Asp Phe
    1880                1885                1890

Phe Val Leu Phe Ser Ser Val Ala Gly Val Leu Gly Ser Pro Gly
    1895                1900                1905

Gln Gly Asn Tyr Ala Ala Ala Asn Arg Gly Met Ala Ala Ile Ala
    1910                1915                1920

Gln Tyr Arg Gln Ala Gln Gly Leu Pro Ala Leu Ala Ile His Trp
    1925                1930                1935

Gly Pro Trp Ala Glu Gly Gly Met Ala Asn Ser Leu Ser Asn Gln
    1940                1945                1950

Asn Leu Ala Trp Leu Pro Pro Pro Gln Gly Leu Thr Ile Leu Glu
    1955                1960                1965

Lys Val Leu Gly Ala Gln Gly Glu Met Gly Val Phe Lys Pro Asp
    1970                1975                1980

Trp Gln Asn Leu Ala Lys Gln Phe Pro Glu Phe Ala Lys Thr His
    1985                1990                1995

Tyr Phe Ala Ala Val Ile Pro Ser Ala Glu Ala Val Pro Pro Thr
    2000                2005                2010
```

Ala Ser Ile Phe Asp Lys Leu Ile Asn Leu Glu Ala Ser Gln Arg
2015 2020 2025

Ala Asp Tyr Leu Leu Asp Tyr Leu Arg Arg Ser Val Ala Gln Ile
2030 2035 2040

Leu Lys Leu Glu Ile Glu Gln Ile Gln Ser His Asp Ser Leu Leu
2045 2050 2055

Asp Leu Gly Met Asp Ser Leu Met Ile Met Glu Ala Ile Ala Ser
2060 2065 2070

Leu Lys Gln Asp Leu Gln Leu Met Leu Tyr Pro Arg Glu Ile Tyr
2075 2080 2085

Glu Arg Pro Arg Leu Asp Val Leu Thr Ala Tyr Leu Ala Ala Glu
2090 2095 2100

Phe Thr Lys Ala His Asp Ser Glu Ala Ala Thr Ala Ala Ala Ala
2105 2110 2115

Ile Pro Ser Gln Ser Leu Ser Val Lys Thr Lys Lys Gln Trp Gln
2120 2125 2130

Lys Pro Asp His Lys Asn Pro Asn Pro Ile Ala Phe Ile Leu Ser
2135 2140 2145

Ser Pro Arg Ser Gly Ser Thr Leu Leu Arg Val Met Leu Ala Gly
2150 2155 2160

His Pro Gly Leu Tyr Ser Pro Pro Glu Leu His Leu Leu Pro Phe
2165 2170 2175

Glu Thr Met Gly Asp Arg His Gln Glu Leu Gly Leu Ser His Leu
2180 2185 2190

Gly Glu Gly Leu Gln Arg Ala Leu Met Asp Leu Glu Asn Leu Thr
2195 2200 2205

Pro Glu Ala Ser Gln Ala Lys Val Asn Gln Trp Val Lys Ala Asn
2210 2215 2220

Thr Pro Ile Ala Asp Ile Tyr Ala Tyr Leu Gln Arg Gln Ala Glu
2225 2230 2235

Gln Arg Leu Leu Ile Asp Lys Ser Pro Ser Tyr Gly Ser Asp Arg
2240 2245 2250

His Ile Leu Asp His Ser Glu Ile Leu Phe Asp Gln Ala Lys Tyr
2255 2260 2265

Ile His Leu Val Arg His Pro Tyr Ala Val Ile Glu Ser Phe Thr
2270 2275 2280

Arg Leu Arg Met Asp Lys Leu Leu Gly Ala Glu Gln Gln Asn Pro
2285 2290 2295

Tyr Ala Leu Ala Glu Ser Ile Trp Arg Thr Ser Asn Arg Asn Ile
2300 2305 2310

Leu Asp Leu Gly Arg Thr Val Gly Ala Asp Arg Tyr Leu Gln Val
2315 2320 2325

Ile Tyr Glu Asp Leu Val Arg Asp Pro Arg Lys Val Leu Thr Asn
2330 2335 2340

Ile Cys Asp Phe Leu Gly Val Asp Phe Asp Glu Ala Leu Leu Asn
2345 2350 2355

Pro Tyr Ser Gly Asp Arg Leu Thr Asp Gly Leu His Gln Gln Ser
2360 2365 2370

Met Gly Val Gly Asp Pro Asn Phe Leu Gln His Lys Thr Ile Asp
2375 2380 2385

Pro Ala Leu Ala Asp Lys Trp Arg Ser Ile Thr Leu Pro Ala Ala
2390 2395 2400

Leu Gln Leu Asp Thr Ile Gln Leu Ala Glu Thr Phe Ala Tyr Asp

-continued 2405 2410 2415

Leu Pro Gln Glu Pro Gln Leu Thr Pro Gln Thr Gln Ser Leu Pro
2420 2425 2430

Ser Met Val Glu Arg Phe Val Thr Val Arg Gly Leu Glu Thr Cys
2435 2440 2445

Leu Cys Glu Trp Gly Asp Arg His Gln Pro Leu Val Leu Leu Leu
2450 2455 2460

His Gly Ile Leu Glu Gln Gly Ala Ser Trp Gln Leu Ile Ala Pro
2465 2470 2475

Gln Leu Ala Ala Gln Gly Tyr Trp Val Val Ala Pro Asp Leu Arg
2480 2485 2490

Gly His Gly Lys Ser Ala His Ala Gln Ser Tyr Ser Met Leu Asp
2495 2500 2505

Phe Leu Ala Asp Val Asp Ala Leu Ala Lys Gln Leu Gly Asp Arg
2510 2515 2520

Pro Phe Thr Leu Val Gly His Ser Met Gly Ser Ile Ile Gly Ala
2525 2530 2535

Met Tyr Ala Gly Ile Arg Gln Thr Gln Val Glu Lys Leu Ile Leu
2540 2545 2550

Val Glu Thr Ile Val Pro Asn Asp Ile Asp Asp Ala Glu Thr Gly
2555 2560 2565

Asn His Leu Thr Thr His Leu Asp Tyr Leu Ala Ala Pro Pro Gln
2570 2575 2580

His Pro Ile Phe Pro Ser Leu Glu Val Ala Ala Arg Arg Leu Arg
2585 2590 2595

Gln Ala Thr Pro Gln Leu Pro Lys Asp Leu Ser Ala Phe Leu Thr
2600 2605 2610

Gln Arg Ser Thr Lys Ser Val Glu Lys Gly Val Gln Trp Arg Trp
2615 2620 2625

Asp Ala Phe Leu Arg Thr Arg Ala Gly Ile Glu Phe Asn Gly Ile
2630 2635 2640

Ser Arg Arg Arg Tyr Leu Ala Leu Leu Lys Asp Ile Gln Ala Pro
2645 2650 2655

Ile Thr Leu Ile Tyr Gly Asp Gln Ser Glu Phe Asn Arg Pro Ala
2660 2665 2670

Asp Leu Gln Ala Ile Gln Ala Ala Leu Pro Gln Ala Gln Arg Leu
2675 2680 2685

Thr Val Ala Gly Gly His Asn Leu His Phe Glu Asn Pro Gln Ala
2690 2695 2700

Ile Ala Gln Ile Val Tyr Gln Gln Leu Gln Thr Pro Val Pro Lys
2705 2710 2715

Thr Gln
2720

<210> SEQ ID NO 3
<211> LENGTH: 294
<212> TYPE: DNA
<213> ORGANISM: Synechococcus sp.

<400> SEQUENCE: 3
attaaccaag gattccagga tacagaggcg agtatgggcg tttcctggtt gccgccctac 60
catgatatgg gcttgatcgg tgggatttta cagcccatct atgtgggagc aacgcaaatt 120
ttaatgcctc ccgtggcctt tttgcagcga ccttttcggt ggctaaaggc gatcaacgat 180
tatcgggttt ccaccagcgg tgcgccgaat tttgcctatg atctctgtgc cagccaaatt 240
accccggaac aaatcagaga actcgatttg agctgttggc gactggcttt ttcc 294

<210> SEQ ID NO 4
<211> LENGTH: 97
<212> TYPE: PRT
<213> ORGANISM: Synechococcus sp.

<400> SEQUENCE: 4

```
Ile Asn Gln Gly Phe Gln Asp Thr Glu Ala Ser Met Gly Val Ser Trp
1               5                   10                  15

Leu Pro Pro Tyr His Asp Met Gly Leu Ile Gly Gly Ile Leu Gln Pro
            20                  25                  30

Ile Tyr Val Gly Ala Thr Gln Ile Leu Met Pro Pro Val Ala Phe Leu
        35                  40                  45

Gln Arg Pro Phe Arg Trp Leu Lys Ala Ile Asn Asp Tyr Arg Val Ser
    50                  55                  60

Thr Ser Gly Ala Pro Asn Phe Ala Tyr Asp Leu Cys Ser Gln Ile Thr
65                  70                  75                  80

Pro Glu Gln Ile Arg Glu Leu Asp Leu Ser Cys Trp Arg Leu Ala Phe
                85                  90                  95

Ser
```

<210> SEQ ID NO 5
<211> LENGTH: 1746
<212> TYPE: DNA
<213> ORGANISM: Legionella pneumophila

<400> SEQUENCE: 5

```
gtgaaaaaag aatatttgca gtgccagtct ctggttgacg tcgtcaggtt acgtgcttta      60
cacagcccta acaagaaaag ctgtactttt ctgaacaaag agttggaaga gacgatgact     120
tatgagcaac tggatcaaca cgccaaagca attgcggcaa ctttgcaagc agaaggagca     180
aaacctgggg atagggtctt gttattgttt gcacctggat taccccttat ccaggcattt     240
ttgggctgcc tttatgcagg ctgcattgct gtacccattt acccaccagc ccaagaaaaa     300
ttattggaca aggcacaacg catagttacc aactcaaaac cggtcatagt actgatgatt     360
gcggatcaca tcaaaaaatt caccgcagac gaattaaata caaatcccaa attcctgaaa     420
attcctgcta ttgcgcttga gagcattgag ttaaacagaa gtagtagttg gcaaccaacc     480
tccattaaga gcaatgacat tgcgtttctg caatacactt ccggctcaac catgcaccct     540
aaaggagtga tggtaagcca ccataattta ctggataatc tgaataaaat ttttacctct     600
tttcatatga atgatgaaac cattattttc agctggctgc ccccacatca tgatatgggt     660
ttgattggct gcattctgac ccccatctat ggtggaattc aggcaatcat gatgtcccct     720
ttctcatttt tacaaaaccc gctttcctgg ttaaaacata ttaccaaata caaagcaact     780
atcagtggaa gccctaactt cgcttacgat tattgtgtca aacgaatcag ggaagaaaaa     840
aaagaagggc tggatttaag ttcatgggtg actgctttca acggtgctga gccagtacga     900
gaagaaacca tggaacattt ttatcaggca tttaaagagt ttggatttcg taaagaagcc     960
ttctatccat gctatggcct ggctgaggcc actttgttag tgacgggagg aacaccagga    1020
agttcataca aaacattaac tctggccaaa gaacaatttc aagatcatcg cgtgcatttt    1080
gcagacgata acagtccagg cagttacaag ttagtcagca gtggtaatcc cattcaagaa    1140
gttaaaatta tagatcctga taccttgatc ccatgtgatt ttgaccaggt tggtgaaatt    1200
tgggtacaaa gtaacagtgt cgccaaagga tattggaatc aacccgaaga aacaaggcat    1260
```

```
gcgttcgcag gaaaaattaa agacgatgag cgtagcgcaa tctatttaag aaccggggac   1320

ttgggctttc tccatgaaaa tgagttatac gttactggac gcattaaaga cttaattatt   1380

atttatggta aaaatcatta tcctcaggac atagagttca gcctgatgca ttctccgctc   1440

catcacgtat tgggcaaatg cgctgctttt gtgattcagg aggagcatga atataaactg   1500

actgtgatgt gtgaagtaaa aaatcgattc atggatgacg tagctcaaga caatttattc   1560

aatgagattt ttgagcttgt ttacgaaaac caccaattgg aggtacatac tatagtcctg   1620

attcctctta aagcaatgcc acatactacc agcggaaaaa ttcgcaggaa tttttgtcga   1680

aaacatcttt tggataaaac tctgccaata gtggctacct ggcaactcaa taaaattgag   1740

gaataa                                                              1746
```

<210> SEQ ID NO 6
<211> LENGTH: 581
<212> TYPE: PRT
<213> ORGANISM: Legionella pneumophila

<400> SEQUENCE: 6

```
Met Lys Lys Glu Tyr Leu Gln Cys Gln Ser Leu Val Asp Val Val Arg
1               5                   10                  15

Leu Arg Ala Leu His Ser Pro Asn Lys Lys Ser Cys Thr Phe Leu Asn
            20                  25                  30

Lys Glu Leu Glu Glu Thr Met Thr Tyr Glu Gln Leu Asp Gln His Ala
        35                  40                  45

Lys Ala Ile Ala Ala Thr Leu Gln Ala Glu Gly Ala Lys Pro Gly Asp
    50                  55                  60

Arg Val Leu Leu Leu Phe Ala Pro Gly Leu Pro Leu Ile Gln Ala Phe
65                  70                  75                  80

Leu Gly Cys Leu Tyr Ala Gly Cys Ile Ala Val Pro Ile Tyr Pro Pro
                85                  90                  95

Ala Gln Glu Lys Leu Leu Asp Lys Ala Gln Arg Ile Val Thr Asn Ser
            100                 105                 110

Lys Pro Val Ile Val Leu Met Ile Ala Asp His Ile Lys Lys Phe Thr
        115                 120                 125

Ala Asp Glu Leu Asn Thr Asn Pro Lys Phe Leu Lys Ile Pro Ala Ile
    130                 135                 140

Ala Leu Glu Ser Ile Glu Leu Asn Arg Ser Ser Ser Trp Gln Pro Thr
145                 150                 155                 160

Ser Ile Lys Ser Asn Asp Ile Ala Phe Leu Gln Tyr Thr Ser Gly Ser
                165                 170                 175

Thr Met His Pro Lys Gly Val Met Val Ser His His Asn Leu Leu Asp
            180                 185                 190

Asn Leu Asn Lys Ile Phe Thr Ser Phe His Met Asn Asp Glu Thr Ile
        195                 200                 205

Ile Phe Ser Trp Leu Pro Pro His His Asp Met Gly Leu Ile Gly Cys
    210                 215                 220

Ile Leu Thr Pro Ile Tyr Gly Gly Ile Gln Ala Ile Met Met Ser Pro
225                 230                 235                 240

Phe Ser Phe Leu Gln Asn Pro Leu Ser Trp Leu Lys His Ile Thr Lys
                245                 250                 255

Tyr Lys Ala Thr Ile Ser Gly Ser Pro Asn Phe Ala Tyr Asp Tyr Cys
            260                 265                 270

Val Lys Arg Ile Arg Glu Glu Lys Lys Glu Gly Leu Asp Leu Ser Ser
        275                 280                 285
```

-continued

```
Trp Val Thr Ala Phe Asn Gly Ala Glu Pro Val Arg Glu Glu Thr Met
    290                 295                 300

Glu His Phe Tyr Gln Ala Phe Lys Glu Phe Gly Phe Arg Lys Glu Ala
305                 310                 315                 320

Phe Tyr Pro Cys Tyr Gly Leu Ala Glu Ala Thr Leu Leu Val Thr Gly
                325                 330                 335

Gly Thr Pro Gly Ser Ser Tyr Lys Thr Leu Thr Leu Ala Lys Glu Gln
            340                 345                 350

Phe Gln Asp His Arg Val His Phe Ala Asp Asp Asn Ser Pro Gly Ser
        355                 360                 365

Tyr Lys Leu Val Ser Ser Gly Asn Pro Ile Gln Glu Val Lys Ile Ile
    370                 375                 380

Asp Pro Asp Thr Leu Ile Pro Cys Asp Phe Asp Gln Val Gly Glu Ile
385                 390                 395                 400

Trp Val Gln Ser Asn Ser Val Ala Lys Gly Tyr Trp Asn Gln Pro Glu
                405                 410                 415

Glu Thr Arg His Ala Phe Ala Gly Lys Ile Lys Asp Asp Glu Arg Ser
            420                 425                 430

Ala Ile Tyr Leu Arg Thr Gly Asp Leu Gly Phe Leu His Glu Asn Glu
        435                 440                 445

Leu Tyr Val Thr Gly Arg Ile Lys Asp Leu Ile Ile Ile Tyr Gly Lys
    450                 455                 460

Asn His Tyr Pro Gln Asp Ile Glu Phe Ser Leu Met His Ser Pro Leu
465                 470                 475                 480

His His Val Leu Gly Lys Cys Ala Ala Phe Val Ile Gln Glu Glu His
                485                 490                 495

Glu Tyr Lys Leu Thr Val Met Cys Glu Val Lys Asn Arg Phe Met Asp
            500                 505                 510

Asp Val Ala Gln Asp Asn Leu Phe Asn Glu Ile Phe Glu Leu Val Tyr
        515                 520                 525

Glu Asn His Gln Leu Glu Val His Thr Ile Val Leu Ile Pro Leu Lys
    530                 535                 540

Ala Met Pro His Thr Thr Ser Gly Lys Ile Arg Arg Asn Phe Cys Arg
545                 550                 555                 560

Lys His Leu Leu Asp Lys Thr Leu Pro Ile Val Ala Thr Trp Gln Leu
                565                 570                 575

Asn Lys Ile Glu Glu
            580


<210> SEQ ID NO 7
<211> LENGTH: 294
<212> TYPE: DNA
<213> ORGANISM: Legionella pneumophila

<400> SEQUENCE: 7

atttttacct cttttcatat gaatgatgaa accattattt tcagctggct gcccccacat     60

catgatatgg gtttgattgg ctgcattctg acccccatct atggtggaat tcaggcaatc    120

atgatgtccc ctttctcatt tttacaaaac ccgctttcct ggttaaaaca tattaccaaa    180

tacaaagcaa ctatcagtgg aagccctaac ttcgcttacg attattgtgt caaacgaatc    240

agggaagaaa aaaaagaagg gctggattta agttcatggg tgactgcttt caac          294


<210> SEQ ID NO 8
<211> LENGTH: 98
<212> TYPE: PRT
```

-continued

<213> ORGANISM: Legionella pneumophila

<400> SEQUENCE: 8

```
Ile Phe Thr Ser Phe His Met Asn Asp Glu Thr Ile Ile Phe Ser Trp
1               5                   10                  15

Leu Pro Pro His His Asp Met Gly Leu Ile Gly Cys Ile Leu Thr Pro
            20                  25                  30

Ile Tyr Gly Gly Ile Gln Ala Ile Met Met Ser Pro Phe Ser Phe Leu
        35                  40                  45

Gln Asn Pro Leu Ser Trp Leu Lys His Ile Thr Lys Tyr Lys Ala Thr
    50                  55                  60

Ile Ser Gly Ser Pro Asn Phe Ala Tyr Asp Tyr Cys Val Lys Arg Ile
65                  70                  75                  80

Arg Glu Glu Lys Lys Glu Gly Leu Asp Leu Ser Ser Trp Val Thr Ala
                85                  90                  95

Phe Asn
```

<210> SEQ ID NO 9
<211> LENGTH: 11916
<212> TYPE: DNA
<213> ORGANISM: Bacillus subtilis

<400> SEQUENCE: 9

```
atgtatacca gtcaatttca aaccttagtc gatgttattc ggaatagaag caatatatca     60
gatcgcggga tccgttttat cgaatccgat aaaatcgaga catttgtctc ttatcgccaa    120
ttgtttgacg aggcgcaagg ttttcttggc tacttacaac atatcggcat tcagccaaag    180
caagaaattg tgtttcaaat tcaagaaaac aaatcatttg tcgtcgcttt ttgggcgtgt    240
ttattaggag gaatgattcc ggtacccgtc agtatcggag aagataatga ccacaagcta    300
aaggtatggc gcatttggaa tattttaaac aatccattct tgctagcctc tgaaacagta    360
ttagataaaa tgaaaaaatt tgctgctgat cacgatttac aagatttcca tcatcaatta    420
atcgagaaat ccgacatcat tcaggatcga atctacgatc acccggcttc gcaatatgaa    480
cctgaagccg atgaattggc ctttattcaa ttttcttcgg gatcaacagg agacccgaaa    540
ggagtcatgc taacccatca taacttaata cataatacat gtgcaatccg gaatgcgctg    600
gctatcgact taaaagatac tcttttatct tggatgccct taacccatga catggggctc    660
atagcttgcc accttgttcc tgccttagcc ggaatcaatc aaaatttaat gccgacagaa    720
ttatttattc gaagacctat tctctggatg aaaaaagctc atgaacataa agccagcatt    780
ctatcctcac ctaattttgg atacaattac tttcttaaat ttctgaaaga caataaaagt    840
tacgactggg atttatccca tatcagggtc attgcaaacg gagcagaacc tatattgcca    900
gagctatgtg atgaattttt gactagatgc gcagcattca atatgaaacg atctgccatc    960
ttaaatgttt acggtttagc tgaggcttcg gttggcgcaa cattctctaa catcggagaa   1020
agatttgtcc ctgtttattt gcatcgcgat catctaaatc taggtgaaag agccgttgaa   1080
gtaagcaaag aggatcaaaa ttgcgcttca ttcgtcgaag taggaaagcc tattgattac   1140
tgccaaattc gaatctgtaa tgaagcaaac gaaggattgg aagacggatt tatcggtcat   1200
atccagatca agggggagaa tgtgacccaa gggtattata acaaccccga aagtacgaac   1260
agagcgctga ctcccgatgg atgggtgaaa acgggagatc ttggcttcat tagaaaaggg   1320
aatttagtcg taaccggaag ggaaaaagac attatttttg tgaacggaaa aaatgtgtat   1380
cctcacgata ttgaacgagt cgccattgaa ttagaggaca ttgatttagg aagagttgca   1440
```

-continued

```
gcctgtggtg tatatgatca agagacacga agcagagaaa ttgtactttt tgctgtttac   1500
aaaaaatcag cggagcagtt tgcaccactt gttaaagaca ttaaaaagca tttgtaccag   1560
cgaggcggat ggagcatcaa agaaatcctg ccgatccgaa agctgccaaa aacgacaagc   1620
gggaaagtta aacgctatga gctggctgag cagtatgagt cggggaaatt tgcgctagag   1680
tcaaccaaaa tcaaggaatt tttggagggt cattcgacgg aaccggtaca gactcctatt   1740
catgaaatcg aaacagcatt gctgtctatc ttttcagaag tgatggatgg aaaaaagatt   1800
cacctaaatg atcattattt tgacatgggt gcaacctcat tacagttatc tcaaattgcc   1860
gaacgcattg aacaaaagtt tggttgtgag cttacggttg ctgatctctt tacatatcct   1920
tcaatcgctg atttagcggc attccttgtc gaaaaccatt ccgaaatcaa gcaaactgat   1980
acagcgaagc caagccgctc ttcgtcaaaa gacatcgcta ttatcgggat gtccctcaat   2040
gttccagggg catcgaataa gagtgatttt tggcacctgc tcgaaaacgg tgagcatggc   2100
attcgggaat atcctgcacc aagagttaaa gatgcgatag attatttacg atccattaaa   2160
agcgaacgta acgaaaaaca atttgtgaag ggcggctatt tagatgagat agaccgtttt   2220
gattattcgt tctttggttt agctcccaaa accgcaaaat tcatggatcc caatcaaagg   2280
ctatttttgc aatccgcatg gcatgcgatt gaagatgcag gctatgccgg cgacaccatt   2340
agcgggagtc agctcggggt atatgtaggg tactcgaagg tgggatacga ttacgaacgt   2400
ctcctttctg cgaattatcc ggaggagctt catcattata ttgtgggcaa tcttccctcg   2460
gtgttggcga gtcgaattgc ttactttcta aatttgaaag gaccagcggt taccgtggat   2520
acagcttgct cttcgtcact tgttgctgtt catatggcat gtaaagcttt gcttacaggc   2580
gattgtgaaa tggctcttgc cgggggtatt cgaacttcgc tattaccgat gcgtatcggt   2640
ctcgatatgg aatcttctga cgggctcacg aaaacgttca gcaaggattc ggacggaaca   2700
ggctctggcg aaggcgtggc agcagtcctg ttgaaacctt tgcaggctgc gattcgcgat   2760
ggagatcata tttatggtgt gatcaaggga agcgcgataa accaagacgg gacaaccgtt   2820
ggaatcaccg caccgagccc ggcagctcag accgaggtga ttgagatggc ctggaaagac   2880
gctggcattg ctcctgaaac attgtctttc attgaagcac acggcaccgg aaccaagctc   2940
ggggatcctg ttgaatttaa cggtctttgt aaagcgtttg agaaggttac ggaaaagaaa   3000
cagttttgtg cgatcggctc tgttaaagca aacatcggtc atttgtttga agcggcaggc   3060
atcgttggac tgataaaatc tgcccttatg ttgaatcaca aaaaaatccc gccgctggct   3120
cactttaata aaccgaatcc attaattcca tttcactctt ctcctttttta tgtgaaccaa   3180
gaagtgatgg atttcacacc tgaagaccga ccgctgcggg gtggtatcag ttcattcggt   3240
tttagcggaa cgaatgccca tgtagtattg gaagaatata ctcctgaaag tgagtatgca   3300
ccggaggacg ggaatgatcc gcatttattt gtgttatccg cccatactga agcttcacta   3360
tatgaactga ctcatcagta tcggcaatat atttcagatg acagccaatc atcattgagg   3420
tcaatttgct atacggccag tacaggaagg gctcatttag attattgttt agccatgatt   3480
gtatccagca accaagaatt aatagataag ctgaccagtt tgattcaagg cgaaagaaat   3540
cttccccaag tacactttgg ctataaaaac atcaaggaaa tgcagcctgc cgaaaaagac   3600
aatctgagta aacaaatctc tgatctcatg cagcatcggc cctgcacaaa ggatgaacga   3660
atcacatggt tgaatcgtat tgcagaatta tatgtgcaaa gagccgtgat tgactggcga   3720
gcggtttatt ccaatgaagt tgtacaaaaa acgccattgc ctttgtatcc atttgaacgg   3780
aatcgctgtt gggttgaggc tgtctatgaa agcgccaagg aaagaaaaga gaaaggggaa   3840
```

-continued

```
gtagcattgg atataaatca tacgaagaca catattgagt cctttctgaa gactgtcatc   3900

agcaatgcat cgggaatcag agcggatgag atcgattcga atgcccattt tatcggattc   3960

ggattggatt ccattatgct gacacaggtc aaaaaagcga tcgcagacga atttaatgtg   4020

gatatcccga tggaacgttt ttttgatacg atgaacaaca ttgaaagtgt tgtcgattat   4080

ttggcagaaa atgttccatc agctgcatcc actccgcctc aagaaagtgt tacggcacag   4140

gaagagcttg tgatatcagg agcacagccc gagttggaac atcaagagca tatgttggac   4200

aaaattattg cttctcagaa tcaattaatc cagcaaactt tacaagctca attggatagc   4260

tttaatttgt tgagaaacaa cagccatttt gtatcgaaag aatccgagat ttcgcaagat   4320

aaaacgagcc tttctcctaa atctgtcact gcaaaaaaga attcggctca agaagcaaaa   4380

ccttatattc cttttcagcg tcagaccttg aatgaacagg tcaactatac tccgcagcaa   4440

agacaatatt tagaatcatt tatagagaaa tacgtagaca aaacgaaagg ttccaagcaa   4500

tatacggacg aaacccgatt tgctcatgcc aataaccgca acttgtccag cttccggtct   4560

tattggaaag aaatggttta cccgatcatc gctgaacgct cggacggttc tagaatgtgg   4620

gatattgatg gaaatgaata tatcgatatc accatgggat ttggggttaa tctttttggg   4680

catcacccgt cctttattac tcaaaccgtc gttgattcaa cacattctgc attgccgcct   4740

cttggtccga tgtcaaatgt cgccggagaa gttgcagatc gaattcgtgc atgcacagga   4800

gtagaaaggg tcgcttttta taattcaggc acggaggcag tcatggttgc cctgcgtttg   4860

gcgagggcgg caacaggaag aacgaaagtg gtagtgtttg cgggctctta tcacggcacc   4920

tttgacggcg tattaggtgt tgccaacaca aaaggcgggg ctgagcctgc gaatccgctg   4980

gctccgggca taccgcaaag ctttatgaat gatttgatta ttttgcatta caaccatccg   5040

gattcattgg acgtgattcg caatttggga aatgaattgg cagccgttct ggtggaaccg   5100

gtacaaagcc gcaggccgga tttgcagcca gaatcatttt tgaaagaact gcgggcaatc   5160

acacagcaat ccggaacagc tctgattatg gatgaaatta ttacaggatt tcggatcggt   5220

ctcggcggcg cgcaggaatg gttcgacatc caagcagatt tagtcactta cgggaaaatc   5280

atcggcggcg gccagcctct aggtattgtt gccggaaaag cagagttcat gaatacgatc   5340

gatggcggca catggcagta tggagacgac tcctatccaa cggatgaggc aaaacgcacg   5400

tttgtagcgg gcacctttaa tactcacccg cttacgatga gaatgtcatt agccgtgctt   5460

cgatatcttc aagccgaggg agaaactctg tatgaacggt taaatcaaaa gacaacctac   5520

ttggttgatc aattgaattc ctattttgaa caatcgcaag tgcccattcg tatggtccaa   5580

tttggttcct tattccggtt tgtctcttcg gttgataatg atttgttctt ttaccatctc   5640

aattataaag gagtctatgt ttgggaagga cgcaactgct tcttgtctac ggcccatact   5700

tccgatgata ttgcttatat cattcaagcc gttcaagaaa cggtgaaaga tcttcgccgc   5760

ggcggattta ttccagaagg gccggattct cctaatgacg gaggccataa agaacccgaa   5820

acatacgagc tttctcctga acaaaaacaa ttggctgtag tatcccagta tgggaatgat   5880

gcttctgcgg cattgaatca atctattatg ctaaaagtga aaggggcggt gcagcatacg   5940

ctgttaaaac aagcggtgcg aaatattgta aaacgccatg acgctttacg cacagtcatt   6000

catgtcgatg acgaagtaca gcaagtgcag gctcgaataa atgttgaaat tcctatcatc   6060

gattttaccg gttacccgaa tgaacagcga gagtcggagg ttcaaaaatg gctgacggaa   6120

gatgccaagc gcccgtttca tttccatgaa cagaagccct tgtttagagt tcatgtactt   6180

acgtcgaaac aagacgaaca tctgatcgtt ctgacatttc atcatatcat cgccgatggc   6240
```

-continued

```
tggtcgatcg ctgtttttgt acaagagcta gagagcacgt acgccgccat tgtacaagga   6300
agcccgcttc catctcatga ggttgtttcg tttcgccaat atttagattg gcagcaagct   6360
cagatagaga atggtcatta tgaagaagga attcgttatt ggcggcagta tctctctgaa   6420
ccaatcccgc aggcaatctt gaccagtatg agttcttccc gttatccgca tggttacgag   6480
ggagatcgct atacagttac actggaccgt ccattgagca aggcgataaa gtcattaagc   6540
attcggatga aaaatagcgt ttttgcaact attctgggag catttcatct tttctgcag    6600
cagcttacca agcaggctgg ccttgtaatt gggattccaa ccgcaggcca gttgcatatg   6660
aaacaaccta tgctggttgg aaattgtgtc aacatggttc ccgtgaagaa cactgcttct   6720
tcagaaagca cattagccga ttatctgggt catatgaagg aaaacatgga tcaagtcatg   6780
cggcatcaag atgttccgat gacattagtg gccagccagc ttccacacga tcaaatgccg   6840
gatatgcgta ttatttttaa tttggataga ccttttcgaa agctgcattt cggacagatg   6900
gaagctgagc tcattgcgta ccctataaaa tgcatttcat acgatttatt tcttaacgta   6960
acggaatttg atcaagagta tgttcttgat ttcgatttta atacaagcgt catcagttcg   7020
gaaatcatga acaagtgggg aacgggcttt gtaaacttgc tgaaaaaaat ggttgagggg   7080
gactccgcct ctcttgattc cttaaaaatg ttttcgaagg aagatcaaca cgacttgctt   7140
gagctgtatg ctgatcatca gctgcgaatc tcttcaacat tagaccataa gggtgttcgt   7200
gccgtttacg aagagccgga aaatgaaaca gagctgcaaa ttgcgcagat ttgggcggag   7260
cttctcggcc tggagaaagt gggcagatct gaccactttc tgtctctggg tggaaactcg   7320
ctaaaagcga cgcttatgct ttctaagatt cagcaaacat ttaatcaaaa ggtatctata   7380
gggcaattct tcagccatca gactgttaag gagttggcga atttcatccg gggtgaaaag   7440
aatgtcaagt atcccccgat gaagcctgtt gagcagaaag ccttttaccg gacatctcca   7500
gctcagcaaa gagtatattt cctgcatcaa atggaaccga atcaagtttc gcaaaatatg   7560
tttggccaaa tatcgattat agggaagtac gatgaaaaag ccttgattgc atcccttcaa   7620
caggtcatgc agcggcatga agcgtttcgc acttcttttc acatcataga tggtgaaatt   7680
gtgcagcaga ttgctggcga gcttgatttt aacgttcgtg tccattcgat ggaccgtgaa   7740
gaatttgaag cctacgcaga tgggtatgta aaacctttcc gtctggaaca agctcctttg   7800
gttcgtgcgg agctgatcaa ggtcgataac gaacaggctg aattgctcat cgatatgcat   7860
catatcattt ccgacggcta ttccatgagc atacttacaa atgaattgtt cgctttgtat   7920
catggtaacc cattaccgga aattccattt gaatataaag acttcgcaga gtggcaaaac   7980
cagctgttaa tcggagaggt catggagcag caggaagaat actggctcga gcaattcaag   8040
caagaagttc ctatccttca attgccggca gacggttcaa gagcgatgga atggtcttcc   8100
gaagggcagc gtgtgacctg ttccttgcag tcgagtttaa tccgttcgct tcaagaaatg   8160
gcgcaacaga agggaacgac tctgtatatg gtgcttctgg ctgcttacaa cgtgctgctt   8220
cacaaatata cgggccaaga agatatcgtc gtaggcacgc cagtttccgg aagaaatcaa   8280
ccgaatattg aaagcatgat tggtatattc attcaaacca tggggattcg cacgaaacca   8340
caggctaata aaaggtttac ggattatttg gacgaagtta aacggcaaac gcttgatgcg   8400
ttcgaaaacc aggattatcc gtttgactgg ctagtagaaa aagtaaacgt acaacgggaa   8460
acaacaggta agtcactatt taacacaatg tttgtgtatc aaaatattga atttcaagag   8520
atccatcaag atgggtgtac gtttagggta aaagaacgta atcccggagt ctctttatat   8580
gatttgatgt taacgatcga ggatgcagaa aaacagttag atattcattt cgattttaat   8640
```

-continued

```
ccaaaccagt ttgaacaaga aacgattgaa caaatcataa ggcactacac cagcctttta   8700
gacagtcttg ttaaggagcc ggagaaatcc ttgtcttccg ttcctatgct gtctgacatc   8760
gagaggcacc agcttctgat ggggtgtaat gacacggaga cgccgtttcc gcacaatgac   8820
acagtatgtc aatggtttga aacgcaagca gaacagcggc ctgatgatga agccgttata   8880
tttggcaatg aacggtgcac gtacgggcag ctaaatgagc gggtaaatca attggcgcgc   8940
acgttaagaa cgaagggcgt tcaagcggat cagtttgttg ccatcatctg cccgcatcgc   9000
atcgagctga ttgttggaat tttggctgtt ctaaaagccg gcggcgcata cgtgccaatt   9060
gatccggagt atccagagga ccggatacaa tatatgctga aggattcaga ggctaagatc   9120
gttttggcac agctcgattt gcataaacac ttaacgtttg atgctgacgt tgtgcttttg   9180
gatgaggaaa gctcatatca tgaggatcgt tcgaatcttg aaccgacctg cggtgcaaat   9240
gatttggcat acatgatcta tacgtcgggc tccacaggga acccgaaagg tgtactcatt   9300
gagcaccggg gattagctaa ttatattgag tgggcgaaag aggtttatgt gaatgatgag   9360
aaaaccaact tccctttata ctcgtccatc tcttttgatc taacggtgac gtcgattttt   9420
acaccgctgg ttacaggaaa taccatcatt gtctttgatg gtgaagacaa aagtgcggtg   9480
ctttcaacaa ttatgcagga tccgagaata gatatcatca aattgacgcc ggcgcatttg   9540
catgtgctca aagaaatgaa gatagcagat ggaacgacaa ttcgaaaaat gattgtcggc   9600
ggggaaaatt taagcacccg gcttgcccaa agtgtcagtg agcagtttaa aggccaactg   9660
gacatattca atgaatacgg accgacagaa gcggtcgtcg gatgtatgat ttatcggtac   9720
gacactaaac gtgacaggcg agaatttgtg ccaataggct cccctgccgc caatacgagc   9780
atttatgtgt tggatgccag catgaacttg gttccggtcg gcgtaccggg tgaaatgtat   9840
atcggtggag ccggtgtagc cagaggatac tggaatcgcc cggatttaac agcagagaag   9900
ttcgttcaca acccgtttgc tccgggaacg ataatgtaca aaacgggtga cttggcaaaa   9960
cgattacgtg atggaaatct catatattta ggccgaatcg atgaacaagt caaaatccga  10020
ggacatcgaa ttgaacttgg tgaagttgaa gctgcaatgc ataaagtgga agcggtccaa  10080
aaggccgtag ttttagccag agaagaagag gatggcttac aacaactgtg tgcgtattat  10140
gtgagcaata aacctataac aattgcggag attagagaac aattatcact ggagctgccg  10200
gactacatgg ttccgtccca ttatatccaa cttgagcaat taccgttaac gtccaacggg  10260
aaaataaatc gtaaagcact gcctgcacca gaggtaagtt tagagcaaat agctgaatat  10320
gtaccgccag gcaatgaggt tgaatctaag cttgcagtct tatggcaaga gatgctcgga  10380
atacatcgtg tggggatcaa gcacaatttc ttcgatcttg gaggaaattc catacgcgcg  10440
acggccttag ccgccagaat ccacaaagaa ctggatgtca atctgtctgt aaaagacata  10500
tttaagtttc ctactattga acagttggct aacatggcgt tacgcatgga gaaaattcga  10560
tatgtatcaa ttccgtctgc acagaaaatc tcctattatc cagtttcttc ggcacagaaa  10620
cggatgtatt tgttaagtca tacagaagga ggcgagctga cgtacaatat gacgggcgcc  10680
atgagtgtag aaggggctat tgatctagaa cgattgaccg ctgcttttca aaaattaatt  10740
gaacgtcatg aagttttgcg gaccagcttt gaactatacg aaggcgagcc ggcacagcga  10800
attcatccaa gcattgaatt tacaatagaa cagattcaag cgagagaaga ggaagtggaa  10860
gaccatgtac ttgattttat caaatcgttt gatttagcca agccgccgtt aatgcgagtg  10920
ggactgattg aacttacacc cgaaaagcat gtactgctag tcgatatgca tcatatcatt  10980
tccgatggcg tgtctatgaa cattctaatg aaagatttaa atcaatttta taaagggatc  11040
```

```
gaaccggatc cgcttcccat tcaatataag gactatgcgg tttggcagca aacggaagct  11100

cagaggcaaa acatcaaaaa acaggaagcg tattggctta atcgttttca tgatgagatt  11160

cctgtattgg atatgccaac ggattacgag agacctgcta tacgcgatta cgaaggcgaa  11220

tcatttgaat ttcttatacc gatagaatta aaacagcgct taagtcaaat ggaagaagct  11280

acaggaacaa cattgtatat gattttaatg gcagcttata caattctttt atccaaatac  11340

agcggacagg aagatatcgt cgtagggacc ccggtctccg gccgaagtca tatggatgta  11400

gagtctgttg tgggaatgtt tgtaaacacc ttagtcattc gcaatcaccc ggcaggccgt  11460

aaaatattcg aggattactt aaacgaagtg aaggaaaaca tgctaaatgc ctatcaaaat  11520

caagactatc cattggaaga attgatccaa catgtacatc ttctaaaaga ttcaagccgc  11580

aaccctttat tcgatacgat gtttgtgctg caaaatctcg atcaggttga attgaacctt  11640

gattcccttc gattcacgcc ttataagctt catcatacag ttgccaaatt cgatttgacc  11700

ttgtcgattc agacagatca agacaaacat cacggtctgt tcgaatattc gaagaaacta  11760

tttaagaaaa gcagaatcga agctttgtca aaagactatt tacacatctt atccgttatc  11820

agtcaacagc caagtataca aatcgaacat atcgaattaa gcggcagcac cgcggaagat  11880

gataacttga tccattctat tgaactgaac ttttaa                             11916


<210> SEQ ID NO 10
<211> LENGTH: 3971
<212> TYPE: PRT
<213> ORGANISM: Bacillus subtilis

<400> SEQUENCE: 10

Met Tyr Thr Ser Gln Phe Gln Thr Leu Val Asp Val Ile Arg Asn Arg
1               5                   10                  15

Ser Asn Ile Ser Asp Arg Gly Ile Arg Phe Ile Glu Ser Asp Lys Ile
            20                  25                  30

Glu Thr Phe Val Ser Tyr Arg Gln Leu Phe Asp Glu Ala Gln Gly Phe
        35                  40                  45

Leu Gly Tyr Leu Gln His Ile Gly Ile Gln Pro Lys Gln Glu Ile Val
    50                  55                  60

Phe Gln Ile Gln Glu Asn Lys Ser Phe Val Val Ala Phe Trp Ala Cys
65                  70                  75                  80

Leu Leu Gly Gly Met Ile Pro Val Pro Val Ser Ile Gly Glu Asp Asn
                85                  90                  95

Asp His Lys Leu Lys Val Trp Arg Ile Trp Asn Ile Leu Asn Asn Pro
            100                 105                 110

Phe Leu Leu Ala Ser Glu Thr Val Leu Asp Lys Met Lys Lys Phe Ala
        115                 120                 125

Ala Asp His Asp Leu Gln Asp Phe His His Gln Leu Ile Glu Lys Ser
    130                 135                 140

Asp Ile Ile Gln Asp Arg Ile Tyr Asp His Pro Ala Ser Gln Tyr Glu
145                 150                 155                 160

Pro Glu Ala Asp Glu Leu Ala Phe Ile Gln Phe Ser Ser Gly Ser Thr
                165                 170                 175

Gly Asp Pro Lys Gly Val Met Leu Thr His His Asn Leu Ile His Asn
            180                 185                 190

Thr Cys Ala Ile Arg Asn Ala Leu Ala Ile Asp Leu Lys Asp Thr Leu
        195                 200                 205

Leu Ser Trp Met Pro Leu Thr His Asp Met Gly Leu Ile Ala Cys His
    210                 215                 220
```

-continued

```
Leu Val Pro Ala Leu Ala Gly Ile Asn Gln Asn Leu Met Pro Thr Glu
225                 230                 235                 240

Leu Phe Ile Arg Arg Pro Ile Leu Trp Met Lys Lys Ala His Glu His
                245                 250                 255

Lys Ala Ser Ile Leu Ser Ser Pro Asn Phe Gly Tyr Asn Tyr Phe Leu
            260                 265                 270

Lys Phe Leu Lys Asp Asn Lys Ser Tyr Asp Trp Asp Leu Ser His Ile
        275                 280                 285

Arg Val Ile Ala Asn Gly Ala Glu Pro Ile Leu Pro Glu Leu Cys Asp
    290                 295                 300

Glu Phe Leu Thr Arg Cys Ala Ala Phe Asn Met Lys Arg Ser Ala Ile
305                 310                 315                 320

Leu Asn Val Tyr Gly Leu Ala Glu Ala Ser Val Gly Ala Thr Phe Ser
                325                 330                 335

Asn Ile Gly Glu Arg Phe Val Pro Val Tyr Leu His Arg Asp His Leu
            340                 345                 350

Asn Leu Gly Glu Arg Ala Val Glu Val Ser Lys Glu Asp Gln Asn Cys
        355                 360                 365

Ala Ser Phe Val Glu Val Gly Lys Pro Ile Asp Tyr Cys Gln Ile Arg
    370                 375                 380

Ile Cys Asn Glu Ala Asn Glu Gly Leu Glu Asp Gly Phe Ile Gly His
385                 390                 395                 400

Ile Gln Ile Lys Gly Glu Asn Val Thr Gln Gly Tyr Tyr Asn Asn Pro
                405                 410                 415

Glu Ser Thr Asn Arg Ala Leu Thr Pro Asp Gly Trp Val Lys Thr Gly
            420                 425                 430

Asp Leu Gly Phe Ile Arg Lys Gly Asn Leu Val Val Thr Gly Arg Glu
        435                 440                 445

Lys Asp Ile Ile Phe Val Asn Gly Lys Asn Val Tyr Pro His Asp Ile
    450                 455                 460

Glu Arg Val Ala Ile Glu Leu Glu Asp Ile Asp Leu Gly Arg Val Ala
465                 470                 475                 480

Ala Cys Gly Val Tyr Asp Gln Glu Thr Arg Ser Arg Glu Ile Val Leu
                485                 490                 495

Phe Ala Val Tyr Lys Lys Ser Ala Glu Gln Phe Ala Pro Leu Val Lys
            500                 505                 510

Asp Ile Lys Lys His Leu Tyr Gln Arg Gly Gly Trp Ser Ile Lys Glu
        515                 520                 525

Ile Leu Pro Ile Arg Lys Leu Pro Lys Thr Thr Ser Gly Lys Val Lys
    530                 535                 540

Arg Tyr Glu Leu Ala Glu Gln Tyr Glu Ser Gly Lys Phe Ala Leu Glu
545                 550                 555                 560

Ser Thr Lys Ile Lys Glu Phe Leu Glu Gly His Ser Thr Glu Pro Val
                565                 570                 575

Gln Thr Pro Ile His Glu Ile Glu Thr Ala Leu Leu Ser Ile Phe Ser
            580                 585                 590

Glu Val Met Asp Gly Lys Lys Ile His Leu Asn Asp His Tyr Phe Asp
        595                 600                 605

Met Gly Ala Thr Ser Leu Gln Leu Ser Gln Ile Ala Glu Arg Ile Glu
    610                 615                 620

Gln Lys Phe Gly Cys Glu Leu Thr Val Ala Asp Leu Phe Thr Tyr Pro
625                 630                 635                 640

Ser Ile Ala Asp Leu Ala Ala Phe Leu Val Glu Asn His Ser Glu Ile
                645                 650                 655
```

-continued

```
Lys Gln Thr Asp Thr Ala Lys Pro Ser Arg Ser Ser Ser Lys Asp Ile
            660                 665                 670

Ala Ile Ile Gly Met Ser Leu Asn Val Pro Gly Ala Ser Asn Lys Ser
        675                 680                 685

Asp Phe Trp His Leu Leu Glu Asn Gly Glu His Gly Ile Arg Glu Tyr
    690                 695                 700

Pro Ala Pro Arg Val Lys Asp Ala Ile Asp Tyr Leu Arg Ser Ile Lys
705                 710                 715                 720

Ser Glu Arg Asn Glu Lys Gln Phe Val Lys Gly Gly Tyr Leu Asp Glu
                725                 730                 735

Ile Asp Arg Phe Asp Tyr Ser Phe Phe Gly Leu Ala Pro Lys Thr Ala
            740                 745                 750

Lys Phe Met Asp Pro Asn Gln Arg Leu Phe Leu Gln Ser Ala Trp His
        755                 760                 765

Ala Ile Glu Asp Ala Gly Tyr Ala Gly Asp Thr Ile Ser Gly Ser Gln
    770                 775                 780

Leu Gly Val Tyr Val Gly Tyr Ser Lys Val Gly Tyr Asp Tyr Glu Arg
785                 790                 795                 800

Leu Leu Ser Ala Asn Tyr Pro Glu Glu Leu His His Tyr Ile Val Gly
                805                 810                 815

Asn Leu Pro Ser Val Leu Ala Ser Arg Ile Ala Tyr Phe Leu Asn Leu
            820                 825                 830

Lys Gly Pro Ala Val Thr Val Asp Thr Ala Cys Ser Ser Ser Leu Val
        835                 840                 845

Ala Val His Met Ala Cys Lys Ala Leu Leu Thr Gly Asp Cys Glu Met
    850                 855                 860

Ala Leu Ala Gly Gly Ile Arg Thr Ser Leu Leu Pro Met Arg Ile Gly
865                 870                 875                 880

Leu Asp Met Glu Ser Ser Asp Gly Leu Thr Lys Thr Phe Ser Lys Asp
                885                 890                 895

Ser Asp Gly Thr Gly Ser Gly Glu Gly Val Ala Ala Val Leu Leu Lys
            900                 905                 910

Pro Leu Gln Ala Ala Ile Arg Asp Gly Asp His Ile Tyr Gly Val Ile
        915                 920                 925

Lys Gly Ser Ala Ile Asn Gln Asp Gly Thr Thr Val Gly Ile Thr Ala
    930                 935                 940

Pro Ser Pro Ala Ala Gln Thr Glu Val Ile Glu Met Ala Trp Lys Asp
945                 950                 955                 960

Ala Gly Ile Ala Pro Glu Thr Leu Ser Phe Ile Glu Ala His Gly Thr
                965                 970                 975

Gly Thr Lys Leu Gly Asp Pro Val Glu Phe Asn Gly Leu Cys Lys Ala
            980                 985                 990

Phe Glu Lys Val Thr Glu Lys Lys  Gln Phe Cys Ala Ile  Gly Ser Val
        995                 1000                1005

Lys Ala  Asn Ile Gly His Leu  Phe Glu Ala Ala Gly  Ile Val Gly
    1010                1015                1020

Leu Ile  Lys Ser Ala Leu Met  Leu Asn His Lys Lys  Ile Pro Pro
    1025                1030                1035

Leu Ala  His Phe Asn Lys Pro  Asn Pro Leu Ile Pro  Phe His Ser
    1040                1045                1050

Ser Pro  Phe Tyr Val Asn Gln  Glu Val Met Asp Phe  Thr Pro Glu
    1055                1060                1065

Asp Arg  Pro Leu Arg Gly Gly  Ile Ser Ser Phe Gly  Phe Ser Gly
```

-continued

```
    1070                1075                1080

Thr Asn  Ala His Val Val Leu  Glu Glu Tyr Thr Pro  Glu Ser Glu
    1085                1090                1095

Tyr Ala  Pro Glu Asp Gly Asn  Asp Pro His Leu Phe  Val Leu Ser
    1100                1105                1110

Ala His  Thr Glu Ala Ser Leu  Tyr Glu Leu Thr His  Gln Tyr Arg
    1115                1120                1125

Gln Tyr  Ile Ser Asp Asp Ser  Gln Ser Ser Leu Arg  Ser Ile Cys
    1130                1135                1140

Tyr Thr  Ala Ser Thr Gly Arg  Ala His Leu Asp Tyr  Cys Leu Ala
    1145                1150                1155

Met Ile  Val Ser Ser Asn Gln  Glu Leu Ile Asp Lys  Leu Thr Ser
    1160                1165                1170

Leu Ile  Gln Gly Glu Arg Asn  Leu Pro Gln Val His  Phe Gly Tyr
    1175                1180                1185

Lys Asn  Ile Lys Glu Met Gln  Pro Ala Glu Lys Asp  Asn Leu Ser
    1190                1195                1200

Lys Gln  Ile Ser Asp Leu Met  Gln His Arg Pro Cys  Thr Lys Asp
    1205                1210                1215

Glu Arg  Ile Thr Trp Leu Asn  Arg Ile Ala Glu Leu  Tyr Val Gln
    1220                1225                1230

Arg Ala  Val Ile Asp Trp Arg  Ala Val Tyr Ser Asn  Glu Val Val
    1235                1240                1245

Gln Lys  Thr Pro Leu Pro Leu  Tyr Pro Phe Glu Arg  Asn Arg Cys
    1250                1255                1260

Trp Val  Glu Ala Val Tyr Glu  Ser Ala Lys Glu Arg  Lys Glu Lys
    1265                1270                1275

Gly Glu  Val Ala Leu Asp Ile  Asn His Thr Lys Thr  His Ile Glu
    1280                1285                1290

Ser Phe  Leu Lys Thr Val Ile  Ser Asn Ala Ser Gly  Ile Arg Ala
    1295                1300                1305

Asp Glu  Ile Asp Ser Asn Ala  His Phe Ile Gly Phe  Gly Leu Asp
    1310                1315                1320

Ser Ile  Met Leu Thr Gln Val  Lys Lys Ala Ile Ala  Asp Glu Phe
    1325                1330                1335

Asn Val  Asp Ile Pro Met Glu  Arg Phe Phe Asp Thr  Met Asn Asn
    1340                1345                1350

Ile Glu  Ser Val Val Asp Tyr  Leu Ala Glu Asn Val  Pro Ser Ala
    1355                1360                1365

Ala Ser  Thr Pro Pro Gln Glu  Ser Val Thr Ala Gln  Glu Glu Leu
    1370                1375                1380

Val Ile  Ser Gly Ala Gln Pro  Glu Leu Glu His Gln  Glu His Met
    1385                1390                1395

Leu Asp  Lys Ile Ile Ala Ser  Gln Asn Gln Leu Ile  Gln Gln Thr
    1400                1405                1410

Leu Gln  Ala Gln Leu Asp Ser  Phe Asn Leu Leu Arg  Asn Asn Ser
    1415                1420                1425

His Phe  Val Ser Lys Glu Ser  Glu Ile Ser Gln Asp  Lys Thr Ser
    1430                1435                1440

Leu Ser  Pro Lys Ser Val Thr  Ala Lys Lys Asn Ser  Ala Gln Glu
    1445                1450                1455

Ala Lys  Pro Tyr Ile Pro Phe  Gln Arg Gln Thr Leu  Asn Glu Gln
    1460                1465                1470
```

-continued

```
Val Asn  Tyr Thr Pro Gln Gln  Arg Gln Tyr Leu Glu  Ser Phe Ile
    1475                 1480                 1485

Glu Lys  Tyr Val Asp Lys Thr  Lys Gly Ser Lys Gln  Tyr Thr Asp
    1490                 1495                 1500

Glu Thr  Arg Phe Ala His Ala  Asn Asn Arg Asn Leu  Ser Ser Phe
    1505                 1510                 1515

Arg Ser  Tyr Trp Lys Glu Met  Val Tyr Pro Ile Ile  Ala Glu Arg
    1520                 1525                 1530

Ser Asp  Gly Ser Arg Met Trp  Asp Ile Asp Gly Asn  Glu Tyr Ile
    1535                 1540                 1545

Asp Ile  Thr Met Gly Phe Gly  Val Asn Leu Phe Gly  His His Pro
    1550                 1555                 1560

Ser Phe  Ile Thr Gln Thr Val  Val Asp Ser Thr His  Ser Ala Leu
    1565                 1570                 1575

Pro Pro  Leu Gly Pro Met Ser  Asn Val Ala Gly Glu  Val Ala Asp
    1580                 1585                 1590

Arg Ile  Arg Ala Cys Thr Gly  Val Glu Arg Val Ala  Phe Tyr Asn
    1595                 1600                 1605

Ser Gly  Thr Glu Ala Val Met  Val Ala Leu Arg Leu  Ala Arg Ala
    1610                 1615                 1620

Ala Thr  Gly Arg Thr Lys Val  Val Val Phe Ala Gly  Ser Tyr His
    1625                 1630                 1635

Gly Thr  Phe Asp Gly Val Leu  Gly Val Ala Asn Thr  Lys Gly Gly
    1640                 1645                 1650

Ala Glu  Pro Ala Asn Pro Leu  Ala Pro Gly Ile Pro  Gln Ser Phe
    1655                 1660                 1665

Met Asn  Asp Leu Ile Ile Leu  His Tyr Asn His Pro  Asp Ser Leu
    1670                 1675                 1680

Asp Val  Ile Arg Asn Leu Gly  Asn Glu Leu Ala Ala  Val Leu Val
    1685                 1690                 1695

Glu Pro  Val Gln Ser Arg Arg  Pro Asp Leu Gln Pro  Glu Ser Phe
    1700                 1705                 1710

Leu Lys  Glu Leu Arg Ala Ile  Thr Gln Gln Ser Gly  Thr Ala Leu
    1715                 1720                 1725

Ile Met  Asp Glu Ile Ile Thr  Gly Phe Arg Ile Gly  Leu Gly Gly
    1730                 1735                 1740

Ala Gln  Glu Trp Phe Asp Ile  Gln Ala Asp Leu Val  Thr Tyr Gly
    1745                 1750                 1755

Lys Ile  Ile Gly Gly Gly Gln  Pro Leu Gly Ile Val  Ala Gly Lys
    1760                 1765                 1770

Ala Glu  Phe Met Asn Thr Ile  Asp Gly Gly Thr Trp  Gln Tyr Gly
    1775                 1780                 1785

Asp Asp  Ser Tyr Pro Thr Asp  Glu Ala Lys Arg Thr  Phe Val Ala
    1790                 1795                 1800

Gly Thr  Phe Asn Thr His Pro  Leu Thr Met Arg Met  Ser Leu Ala
    1805                 1810                 1815

Val Leu  Arg Tyr Leu Gln Ala  Glu Gly Glu Thr Leu  Tyr Glu Arg
    1820                 1825                 1830

Leu Asn  Gln Lys Thr Thr Tyr  Leu Val Asp Gln Leu  Asn Ser Tyr
    1835                 1840                 1845

Phe Glu  Gln Ser Gln Val Pro  Ile Arg Met Val Gln  Phe Gly Ser
    1850                 1855                 1860

Leu Phe  Arg Phe Val Ser Ser  Val Asp Asn Asp Leu  Phe Phe Tyr
    1865                 1870                 1875
```

-continued

```
His Leu Asn Tyr Lys Gly Val Tyr Val Trp Glu Gly Arg Asn Cys
    1880                1885                1890

Phe Leu Ser Thr Ala His Thr Ser Asp Asp Ile Ala Tyr Ile Ile
    1895                1900                1905

Gln Ala Val Gln Glu Thr Val Lys Asp Leu Arg Arg Gly Gly Phe
    1910                1915                1920

Ile Pro Glu Gly Pro Asp Ser Pro Asn Asp Gly Gly His Lys Glu
    1925                1930                1935

Pro Glu Thr Tyr Glu Leu Ser Pro Glu Gln Lys Gln Leu Ala Val
    1940                1945                1950

Val Ser Gln Tyr Gly Asn Asp Ala Ser Ala Ala Leu Asn Gln Ser
    1955                1960                1965

Ile Met Leu Lys Val Lys Gly Ala Val Gln His Thr Leu Leu Lys
    1970                1975                1980

Gln Ala Val Arg Asn Ile Val Lys Arg His Asp Ala Leu Arg Thr
    1985                1990                1995

Val Ile His Val Asp Asp Glu Val Gln Gln Val Gln Ala Arg Ile
    2000                2005                2010

Asn Val Glu Ile Pro Ile Ile Asp Phe Thr Gly Tyr Pro Asn Glu
    2015                2020                2025

Gln Arg Glu Ser Glu Val Gln Lys Trp Leu Thr Glu Asp Ala Lys
    2030                2035                2040

Arg Pro Phe His Phe His Glu Gln Lys Pro Leu Phe Arg Val His
    2045                2050                2055

Val Leu Thr Ser Lys Gln Asp Glu His Leu Ile Val Leu Thr Phe
    2060                2065                2070

His His Ile Ile Ala Asp Gly Trp Ser Ile Ala Val Phe Val Gln
    2075                2080                2085

Glu Leu Glu Ser Thr Tyr Ala Ala Ile Val Gln Gly Ser Pro Leu
    2090                2095                2100

Pro Ser His Glu Val Val Ser Phe Arg Gln Tyr Leu Asp Trp Gln
    2105                2110                2115

Gln Ala Gln Ile Glu Asn Gly His Tyr Glu Glu Gly Ile Arg Tyr
    2120                2125                2130

Trp Arg Gln Tyr Leu Ser Glu Pro Ile Pro Gln Ala Ile Leu Thr
    2135                2140                2145

Ser Met Ser Ser Ser Arg Tyr Pro His Gly Tyr Glu Gly Asp Arg
    2150                2155                2160

Tyr Thr Val Thr Leu Asp Arg Pro Leu Ser Lys Ala Ile Lys Ser
    2165                2170                2175

Leu Ser Ile Arg Met Lys Asn Ser Val Phe Ala Thr Ile Leu Gly
    2180                2185                2190

Ala Phe His Leu Phe Leu Gln Gln Leu Thr Lys Gln Ala Gly Leu
    2195                2200                2205

Val Ile Gly Ile Pro Thr Ala Gly Gln Leu His Met Lys Gln Pro
    2210                2215                2220

Met Leu Val Gly Asn Cys Val Asn Met Val Pro Val Lys Asn Thr
    2225                2230                2235

Ala Ser Ser Glu Ser Thr Leu Ala Asp Tyr Leu Gly His Met Lys
    2240                2245                2250

Glu Asn Met Asp Gln Val Met Arg His Gln Asp Val Pro Met Thr
    2255                2260                2265

Leu Val Ala Ser Gln Leu Pro His Asp Gln Met Pro Asp Met Arg
```

-continued

```
    2270                2275                2280

Ile Ile  Phe Asn Leu Asp Arg  Pro Phe Arg Lys Leu  His Phe Gly
    2285                2290                2295

Gln Met  Glu Ala Glu Leu Ile  Ala Tyr Pro Ile Lys  Cys Ile Ser
    2300                2305                2310

Tyr Asp  Leu Phe Leu Asn Val  Thr Glu Phe Asp Gln  Glu Tyr Val
    2315                2320                2325

Leu Asp  Phe Asp Phe Asn Thr  Ser Val Ile Ser Ser  Glu Ile Met
    2330                2335                2340

Asn Lys  Trp Gly Thr Gly Phe  Val Asn Leu Leu Lys  Lys Met Val
    2345                2350                2355

Glu Gly  Asp Ser Ala Ser Leu  Asp Ser Leu Lys Met  Phe Ser Lys
    2360                2365                2370

Glu Asp  Gln His Asp Leu Leu  Glu Leu Tyr Ala Asp  His Gln Leu
    2375                2380                2385

Arg Ile  Ser Ser Thr Leu Asp  His Lys Gly Val Arg  Ala Val Tyr
    2390                2395                2400

Glu Glu  Pro Glu Asn Glu Thr  Glu Leu Gln Ile Ala  Gln Ile Trp
    2405                2410                2415

Ala Glu  Leu Leu Gly Leu Glu  Lys Val Gly Arg Ser  Asp His Phe
    2420                2425                2430

Leu Ser  Leu Gly Gly Asn Ser  Leu Lys Ala Thr Leu  Met Leu Ser
    2435                2440                2445

Lys Ile  Gln Gln Thr Phe Asn  Gln Lys Val Ser Ile  Gly Gln Phe
    2450                2455                2460

Phe Ser  His Gln Thr Val Lys  Glu Leu Ala Asn Phe  Ile Arg Gly
    2465                2470                2475

Glu Lys  Asn Val Lys Tyr Pro  Pro Met Lys Pro Val  Glu Gln Lys
    2480                2485                2490

Ala Phe  Tyr Arg Thr Ser Pro  Ala Gln Gln Arg Val  Tyr Phe Leu
    2495                2500                2505

His Gln  Met Glu Pro Asn Gln  Val Ser Gln Asn Met  Phe Gly Gln
    2510                2515                2520

Ile Ser  Ile Ile Gly Lys Tyr  Asp Glu Lys Ala Leu  Ile Ala Ser
    2525                2530                2535

Leu Gln  Gln Val Met Gln Arg  His Glu Ala Phe Arg  Thr Ser Phe
    2540                2545                2550

His Ile  Ile Asp Gly Glu Ile  Val Gln Gln Ile Ala  Gly Glu Leu
    2555                2560                2565

Asp Phe  Asn Val Arg Val His  Ser Met Asp Arg Glu  Glu Phe Glu
    2570                2575                2580

Ala Tyr  Ala Asp Gly Tyr Val  Lys Pro Phe Arg Leu  Glu Gln Ala
    2585                2590                2595

Pro Leu  Val Arg Ala Glu Leu  Ile Lys Val Asp Asn  Glu Gln Ala
    2600                2605                2610

Glu Leu  Leu Ile Asp Met His  His Ile Ile Ser Asp  Gly Tyr Ser
    2615                2620                2625

Met Ser  Ile Leu Thr Asn Glu  Leu Phe Ala Leu Tyr  His Gly Asn
    2630                2635                2640

Pro Leu  Pro Glu Ile Pro Phe  Glu Tyr Lys Asp Phe  Ala Glu Trp
    2645                2650                2655

Gln Asn  Gln Leu Leu Ile Gly  Glu Val Met Glu Gln  Gln Glu Glu
    2660                2665                2670
```

-continued

```
Tyr Trp  Leu Glu Gln Phe Lys  Gln Glu Val Pro Ile  Leu Gln Leu
    2675                 2680                 2685

Pro Ala  Asp Gly Ser Arg Ala  Met Glu Trp Ser Ser  Glu Gly Gln
    2690                 2695                 2700

Arg Val  Thr Cys Ser Leu Gln  Ser Ser Leu Ile Arg  Ser Leu Gln
    2705                 2710                 2715

Glu Met  Ala Gln Gln Lys Gly  Thr Thr Leu Tyr Met  Val Leu Leu
    2720                 2725                 2730

Ala Ala  Tyr Asn Val Leu Leu  His Lys Tyr Thr Gly  Gln Glu Asp
    2735                 2740                 2745

Ile Val  Val Gly Thr Pro Val  Ser Gly Arg Asn Gln  Pro Asn Ile
    2750                 2755                 2760

Glu Ser  Met Ile Gly Ile Phe  Ile Gln Thr Met Gly  Ile Arg Thr
    2765                 2770                 2775

Lys Pro  Gln Ala Asn Lys Arg  Phe Thr Asp Tyr Leu  Asp Glu Val
    2780                 2785                 2790

Lys Arg  Gln Thr Leu Asp Ala  Phe Glu Asn Gln Asp  Tyr Pro Phe
    2795                 2800                 2805

Asp Trp  Leu Val Glu Lys Val  Asn Val Gln Arg Glu  Thr Thr Gly
    2810                 2815                 2820

Lys Ser  Leu Phe Asn Thr Met  Phe Val Tyr Gln Asn  Ile Glu Phe
    2825                 2830                 2835

Gln Glu  Ile His Gln Asp Gly  Cys Thr Phe Arg Val  Lys Glu Arg
    2840                 2845                 2850

Asn Pro  Gly Val Ser Leu Tyr  Asp Leu Met Leu Thr  Ile Glu Asp
    2855                 2860                 2865

Ala Glu  Lys Gln Leu Asp Ile  His Phe Asp Phe Asn  Pro Asn Gln
    2870                 2875                 2880

Phe Glu  Gln Glu Thr Ile Glu  Gln Ile Ile Arg His  Tyr Thr Ser
    2885                 2890                 2895

Leu Leu  Asp Ser Leu Val Lys  Glu Pro Glu Lys Ser  Leu Ser Ser
    2900                 2905                 2910

Val Pro  Met Leu Ser Asp Ile  Glu Arg His Gln Leu  Leu Met Gly
    2915                 2920                 2925

Cys Asn  Asp Thr Glu Thr Pro  Phe Pro His Asn Asp  Thr Val Cys
    2930                 2935                 2940

Gln Trp  Phe Glu Thr Gln Ala  Glu Gln Arg Pro Asp  Asp Glu Ala
    2945                 2950                 2955

Val Ile  Phe Gly Asn Glu Arg  Cys Thr Tyr Gly Gln  Leu Asn Glu
    2960                 2965                 2970

Arg Val  Asn Gln Leu Ala Arg  Thr Leu Arg Thr Lys  Gly Val Gln
    2975                 2980                 2985

Ala Asp  Gln Phe Val Ala Ile  Ile Cys Pro His Arg  Ile Glu Leu
    2990                 2995                 3000

Ile Val  Gly Ile Leu Ala Val  Leu Lys Ala Gly Gly  Ala Tyr Val
    3005                 3010                 3015

Pro Ile  Asp Pro Glu Tyr Pro  Glu Asp Arg Ile Gln  Tyr Met Leu
    3020                 3025                 3030

Lys Asp  Ser Glu Ala Lys Ile  Val Leu Ala Gln Leu  Asp Leu His
    3035                 3040                 3045

Lys His  Leu Thr Phe Asp Ala  Asp Val Val Leu Leu  Asp Glu Glu
    3050                 3055                 3060

Ser Ser  Tyr His Glu Asp Arg  Ser Asn Leu Glu Pro  Thr Cys Gly
    3065                 3070                 3075
```

-continued

```
Ala Asn  Asp Leu Ala Tyr Met  Ile Tyr Thr Ser Gly  Ser Thr Gly
    3080                 3085                 3090

Asn Pro  Lys Gly Val Leu Ile  Glu His Arg Gly Leu  Ala Asn Tyr
    3095                 3100                 3105

Ile Glu  Trp Ala Lys Glu Val  Tyr Val Asn Asp Glu  Lys Thr Asn
    3110                 3115                 3120

Phe Pro  Leu Tyr Ser Ser Ile  Ser Phe Asp Leu Thr  Val Thr Ser
    3125                 3130                 3135

Ile Phe  Thr Pro Leu Val Thr  Gly Asn Thr Ile Ile  Val Phe Asp
    3140                 3145                 3150

Gly Glu  Asp Lys Ser Ala Val  Leu Ser Thr Ile Met  Gln Asp Pro
    3155                 3160                 3165

Arg Ile  Asp Ile Ile Lys Leu  Thr Pro Ala His Leu  His Val Leu
    3170                 3175                 3180

Lys Glu  Met Lys Ile Ala Asp  Gly Thr Thr Ile Arg  Lys Met Ile
    3185                 3190                 3195

Val Gly  Gly Glu Asn Leu Ser  Thr Arg Leu Ala Gln  Ser Val Ser
    3200                 3205                 3210

Glu Gln  Phe Lys Gly Gln Leu  Asp Ile Phe Asn Glu  Tyr Gly Pro
    3215                 3220                 3225

Thr Glu  Ala Val Val Gly Cys  Met Ile Tyr Arg Tyr  Asp Thr Lys
    3230                 3235                 3240

Arg Asp  Arg Arg Glu Phe Val  Pro Ile Gly Ser Pro  Ala Ala Asn
    3245                 3250                 3255

Thr Ser  Ile Tyr Val Leu Asp  Ala Ser Met Asn Leu  Val Pro Val
    3260                 3265                 3270

Gly Val  Pro Gly Glu Met Tyr  Ile Gly Gly Ala Gly  Val Ala Arg
    3275                 3280                 3285

Gly Tyr  Trp Asn Arg Pro Asp  Leu Thr Ala Glu Lys  Phe Val His
    3290                 3295                 3300

Asn Pro  Phe Ala Pro Gly Thr  Ile Met Tyr Lys Thr  Gly Asp Leu
    3305                 3310                 3315

Ala Lys  Arg Leu Arg Asp Gly  Asn Leu Ile Tyr Leu  Gly Arg Ile
    3320                 3325                 3330

Asp Glu  Gln Val Lys Ile Arg  Gly His Arg Ile Glu  Leu Gly Glu
    3335                 3340                 3345

Val Glu  Ala Ala Met His Lys  Val Glu Ala Val Gln  Lys Ala Val
    3350                 3355                 3360

Val Leu  Ala Arg Glu Glu Glu  Asp Gly Leu Gln Gln  Leu Cys Ala
    3365                 3370                 3375

Tyr Tyr  Val Ser Asn Lys Pro  Ile Thr Ile Ala Glu  Ile Arg Glu
    3380                 3385                 3390

Gln Leu  Ser Leu Glu Leu Pro  Asp Tyr Met Val Pro  Ser His Tyr
    3395                 3400                 3405

Ile Gln  Leu Glu Gln Leu Pro  Leu Thr Ser Asn Gly  Lys Ile Asn
    3410                 3415                 3420

Arg Lys  Ala Leu Pro Ala Pro  Glu Val Ser Leu Glu  Gln Ile Ala
    3425                 3430                 3435

Glu Tyr  Val Pro Pro Gly Asn  Glu Val Glu Ser Lys  Leu Ala Val
    3440                 3445                 3450

Leu Trp  Gln Glu Met Leu Gly  Ile His Arg Val Gly  Ile Lys His
    3455                 3460                 3465

Asn Phe  Phe Asp Leu Gly Gly  Asn Ser Ile Arg Ala  Thr Ala Leu
```

-continued 3470 3475 3480

Ala Ala Arg Ile His Lys Glu Leu Asp Val Asn Leu Ser Val Lys
3485 3490 3495

Asp Ile Phe Lys Phe Pro Thr Ile Glu Gln Leu Ala Asn Met Ala
3500 3505 3510

Leu Arg Met Glu Lys Ile Arg Tyr Val Ser Ile Pro Ser Ala Gln
3515 3520 3525

Lys Ile Ser Tyr Tyr Pro Val Ser Ser Ala Gln Lys Arg Met Tyr
3530 3535 3540

Leu Leu Ser His Thr Glu Gly Gly Glu Leu Thr Tyr Asn Met Thr
3545 3550 3555

Gly Ala Met Ser Val Glu Gly Ala Ile Asp Leu Glu Arg Leu Thr
3560 3565 3570

Ala Ala Phe Gln Lys Leu Ile Glu Arg His Glu Val Leu Arg Thr
3575 3580 3585

Ser Phe Glu Leu Tyr Glu Gly Glu Pro Ala Gln Arg Ile His Pro
3590 3595 3600

Ser Ile Glu Phe Thr Ile Glu Gln Ile Gln Ala Arg Glu Glu Glu
3605 3610 3615

Val Glu Asp His Val Leu Asp Phe Ile Lys Ser Phe Asp Leu Ala
3620 3625 3630

Lys Pro Pro Leu Met Arg Val Gly Leu Ile Glu Leu Thr Pro Glu
3635 3640 3645

Lys His Val Leu Leu Val Asp Met His His Ile Ile Ser Asp Gly
3650 3655 3660

Val Ser Met Asn Ile Leu Met Lys Asp Leu Asn Gln Phe Tyr Lys
3665 3670 3675

Gly Ile Glu Pro Asp Pro Leu Pro Ile Gln Tyr Lys Asp Tyr Ala
3680 3685 3690

Val Trp Gln Gln Thr Glu Ala Gln Arg Gln Asn Ile Lys Lys Gln
3695 3700 3705

Glu Ala Tyr Trp Leu Asn Arg Phe His Asp Glu Ile Pro Val Leu
3710 3715 3720

Asp Met Pro Thr Asp Tyr Glu Arg Pro Ala Ile Arg Asp Tyr Glu
3725 3730 3735

Gly Glu Ser Phe Glu Phe Leu Ile Pro Ile Glu Leu Lys Gln Arg
3740 3745 3750

Leu Ser Gln Met Glu Glu Ala Thr Gly Thr Thr Leu Tyr Met Ile
3755 3760 3765

Leu Met Ala Ala Tyr Thr Ile Leu Leu Ser Lys Tyr Ser Gly Gln
3770 3775 3780

Glu Asp Ile Val Val Gly Thr Pro Val Ser Gly Arg Ser His Met
3785 3790 3795

Asp Val Glu Ser Val Val Gly Met Phe Val Asn Thr Leu Val Ile
3800 3805 3810

Arg Asn His Pro Ala Gly Arg Lys Ile Phe Glu Asp Tyr Leu Asn
3815 3820 3825

Glu Val Lys Glu Asn Met Leu Asn Ala Tyr Gln Asn Gln Asp Tyr
3830 3835 3840

Pro Leu Glu Glu Leu Ile Gln His Val His Leu Leu Lys Asp Ser
3845 3850 3855

Ser Arg Asn Pro Leu Phe Asp Thr Met Phe Val Leu Gln Asn Leu
3860 3865 3870

Asp Gln Val Glu Leu Asn Leu Asp Ser Leu Arg Phe Thr Pro Tyr
    3875                3880                3885

Lys Leu His His Thr Val Ala Lys Phe Asp Leu Thr Leu Ser Ile
    3890                3895                3900

Gln Thr Asp Gln Asp Lys His His Gly Leu Phe Glu Tyr Ser Lys
    3905                3910                3915

Lys Leu Phe Lys Lys Ser Arg Ile Glu Ala Leu Ser Lys Asp Tyr
    3920                3925                3930

Leu His Ile Leu Ser Val Ile Ser Gln Gln Pro Ser Ile Gln Ile
    3935                3940                3945

Glu His Ile Glu Leu Ser Gly Ser Thr Ala Glu Asp Asp Asn Leu
    3950                3955                3960

Ile His Ser Ile Glu Leu Asn Phe
    3965                3970

<210> SEQ ID NO 11
<211> LENGTH: 294
<212> TYPE: DNA
<213> ORGANISM: Bacillus subtilis

<400> SEQUENCE: 11
atccggaatg cgctggctat cgacttaaaa gatactcttt tatcttggat gcccttaacc 60
catgacatgg ggctcatagc ttgccacctt gttcctgcct tagccggaat caatcaaaat 120
ttaatgccga cagaattatt tattcgaaga cctattctct ggatgaaaaa agctcatgaa 180
cataaagcca gcattctatc ctcacctaat tttggataca attactttct taaatttctg 240
aaagacaata aaagttacga ctgggattta tcccatatca gggtcattgc aaac 294

<210> SEQ ID NO 12
<211> LENGTH: 98
<212> TYPE: PRT
<213> ORGANISM: Bacillus subtilis

<400> SEQUENCE: 12

Ile Arg Asn Ala Leu Ala Ile Asp Leu Lys Asp Thr Leu Leu Ser Trp
1               5                   10                  15

Met Pro Leu Thr His Asp Met Gly Leu Ile Ala Cys His Leu Val Pro
            20                  25                  30

Ala Leu Ala Gly Ile Asn Gln Asn Leu Met Pro Thr Glu Leu Phe Ile
        35                  40                  45

Arg Arg Pro Ile Leu Trp Met Lys Lys Ala His Glu His Lys Ala Ser
    50                  55                  60

Ile Leu Ser Ser Pro Asn Phe Gly Tyr Asn Tyr Phe Leu Lys Phe Leu
65                  70                  75                  80

Lys Asp Asn Lys Ser Tyr Asp Trp Asp Leu Ser His Ile Arg Val Ile
                85                  90                  95

Ala Asn

<210> SEQ ID NO 13
<211> LENGTH: 1794
<212> TYPE: DNA
<213> ORGANISM: Streptomyces roseosporus

<400> SEQUENCE: 13
gtgagtgaga gccgctgtgc cgggcagggc ctggtggggg cactgcggac ctgggcacgg 60
acacgtgccc gggagactgc cgtggttctc gtacgggaca ccggaaccac cgacgacacg 120
gcgtcggtgg actacggaca gctggacgag tgggccagaa gcatcgcggt gaccctccga 180

```
cagcaactcg cgccgggggg acgggcactt ctgctgctgc cgtccggccc ggagttcacg    240

gccgcgtacc tcggctgcct gtacgcgggt ctggccgccg taccggcgcc gctgcccggg    300

gggcgccact tcgaacgccg ccgtgtcgcg gccatcgccg ccgacagcgg agccggcgtg    360

gtgctgaccg tcgcgggtga gaccgcctcc gtccacgact ggctgaccga gaccacggcc    420

ccggctactc gcgtcgtggc cgtggacgac cgggcggcgc tcggcgaccc ggcgcagtgg    480

gacgacccgg gcgtcgcgcc cgacgacgtg gctctcatcc agtacacctc gggctcgacc    540

ggcaacccca agggcgtggt cgtgacccac gccaacctgc tggcgaacgc gcggaatctc    600

gccgaggcct gcgagctgac cgccgccact cccatgggcg gctggctgcc catgtaccac    660

gacatggggc tcctgggcac gctgacaccg gccctgtacc tcggcaccac gtgcgtgctg    720

atgagctcca cggcattcat caaacggccg cacctgtggc tacggaccat cgaccggttc    780

ggcctggtct ggtcgtcggc tcccgacttc gcgtacgaca tgtgtctgaa gcgcgtcacc    840

gacgagcaga tcgccgggct ggacctgtcc cgctggcggt gggccggcaa cggcgcggag    900

cccatccggg cagccaccgt acgggccttc ggcgaacggt tcgcccggta cggcctgcgc    960

cccgaggcgc tcaccgccgg ctacgggctg gccgaggcca ccctgttcgt gtcgaggtcg   1020

caggggctgc acacggcacg agtcgccacc gccgccctcg aacgccacga attccgcctc   1080

gccgtacccg gcgaggcagc ccgggagatc gtcagctgcg gtcccgtcgg ccacttccgc   1140

gcccgcatcg tcgaacccgg cgggcaccgt gttctgccgc ccggccaggt cggcgagctg   1200

gtcctccagg gagccgccgt ctgcgccggc tactggcagg ccaaggagga gaccgagcag   1260

accttcggcc tcaccctcga cggcgaggac ggtcactggc tgcgcaccgg cgatctcgcc   1320

gccctgcacg aagggaatct ccacatcacc ggccgctgca aagaggccct ggtgatacga   1380

ggacgcaatc tgtacccgca ggacatcgag cacgaactcc gcctgcaaca cccggaactt   1440

gagagcgtcg gcgccgcgtt caccgtcccg gcggcacctg gcacgccggg cttgatggtg   1500

gtccacgaag tccgcacccc ggtccccgcc gacgaccacc cggccctggt cagcgccctg   1560

cgggggacga tcaaccgcga attcggactc gacgcccagg gcatcgccct ggtgagccgc   1620

ggcaccgtac tgcgtaccac cagcggcaag gtccgccggg gcgccatgcg tgacctctgc   1680

ctccgcgggg agctgaacat cgtccacgcg gacaagggct ggcacgccat cgccggcacg   1740

gccggagagg acatcgcccc cactgaccac gctccacatc cgcaccccgc gtaa         1794
```

<210> SEQ ID NO 14
<211> LENGTH: 597
<212> TYPE: PRT
<213> ORGANISM: Streptomyces roseosporus

<400> SEQUENCE: 14

```
Met Ser Glu Ser Arg Cys Ala Gly Gln Gly Leu Val Gly Ala Leu Arg
1               5                   10                  15

Thr Trp Ala Arg Thr Arg Ala Arg Glu Thr Ala Val Val Leu Val Arg
            20                  25                  30

Asp Thr Gly Thr Thr Asp Asp Thr Ala Ser Val Asp Tyr Gly Gln Leu
        35                  40                  45

Asp Glu Trp Ala Arg Ser Ile Ala Val Thr Leu Arg Gln Gln Leu Ala
    50                  55                  60

Pro Gly Gly Arg Ala Leu Leu Leu Leu Pro Ser Gly Pro Glu Phe Thr
65                  70                  75                  80

Ala Ala Tyr Leu Gly Cys Leu Tyr Ala Gly Leu Ala Ala Val Pro Ala
                85                  90                  95
```

-continued

```
Pro Leu Pro Gly Gly Arg His Phe Glu Arg Arg Arg Val Ala Ala Ile
            100                 105                 110

Ala Ala Asp Ser Gly Ala Gly Val Val Leu Thr Val Ala Gly Glu Thr
        115                 120                 125

Ala Ser Val His Asp Trp Leu Thr Glu Thr Thr Ala Pro Ala Thr Arg
    130                 135                 140

Val Val Ala Val Asp Asp Arg Ala Ala Leu Gly Asp Pro Ala Gln Trp
145                 150                 155                 160

Asp Asp Pro Gly Val Ala Pro Asp Asp Val Ala Leu Ile Gln Tyr Thr
                165                 170                 175

Ser Gly Ser Thr Gly Asn Pro Lys Gly Val Val Val Thr His Ala Asn
            180                 185                 190

Leu Leu Ala Asn Ala Arg Asn Leu Ala Glu Ala Cys Glu Leu Thr Ala
        195                 200                 205

Ala Thr Pro Met Gly Gly Trp Leu Pro Met Tyr His Asp Met Gly Leu
    210                 215                 220

Leu Gly Thr Leu Thr Pro Ala Leu Tyr Leu Gly Thr Thr Cys Val Leu
225                 230                 235                 240

Met Ser Ser Thr Ala Phe Ile Lys Arg Pro His Leu Trp Leu Arg Thr
                245                 250                 255

Ile Asp Arg Phe Gly Leu Val Trp Ser Ser Ala Pro Asp Phe Ala Tyr
            260                 265                 270

Asp Met Cys Leu Lys Arg Val Thr Asp Glu Gln Ile Ala Gly Leu Asp
        275                 280                 285

Leu Ser Arg Trp Arg Trp Ala Gly Asn Gly Ala Glu Pro Ile Arg Ala
    290                 295                 300

Ala Thr Val Arg Ala Phe Gly Glu Arg Phe Ala Arg Tyr Gly Leu Arg
305                 310                 315                 320

Pro Glu Ala Leu Thr Ala Gly Tyr Gly Leu Ala Glu Ala Thr Leu Phe
                325                 330                 335

Val Ser Arg Ser Gln Gly Leu His Thr Ala Arg Val Ala Thr Ala Ala
            340                 345                 350

Leu Glu Arg His Glu Phe Arg Leu Ala Val Pro Gly Glu Ala Ala Arg
        355                 360                 365

Glu Ile Val Ser Cys Gly Pro Val Gly His Phe Arg Ala Arg Ile Val
    370                 375                 380

Glu Pro Gly Gly His Arg Val Leu Pro Pro Gly Gln Val Gly Glu Leu
385                 390                 395                 400

Val Leu Gln Gly Ala Ala Val Cys Ala Gly Tyr Trp Gln Ala Lys Glu
                405                 410                 415

Glu Thr Glu Gln Thr Phe Gly Leu Thr Leu Asp Gly Glu Asp Gly His
            420                 425                 430

Trp Leu Arg Thr Gly Asp Leu Ala Ala Leu His Glu Gly Asn Leu His
        435                 440                 445

Ile Thr Gly Arg Cys Lys Glu Ala Leu Val Ile Arg Gly Arg Asn Leu
    450                 455                 460

Tyr Pro Gln Asp Ile Glu His Glu Leu Arg Leu Gln His Pro Glu Leu
465                 470                 475                 480

Glu Ser Val Gly Ala Ala Phe Thr Val Pro Ala Ala Pro Gly Thr Pro
                485                 490                 495

Gly Leu Met Val Val His Glu Val Arg Thr Pro Val Pro Ala Asp Asp
            500                 505                 510

His Pro Ala Leu Val Ser Ala Leu Arg Gly Thr Ile Asn Arg Glu Phe
```

```
        515                 520                 525

Gly Leu Asp Ala Gln Gly Ile Ala Leu Val Ser Arg Gly Thr Val Leu
    530                 535                 540

Arg Thr Thr Ser Gly Lys Val Arg Arg Gly Ala Met Arg Asp Leu Cys
545                 550                 555                 560

Leu Arg Gly Glu Leu Asn Ile Val His Ala Asp Lys Gly Trp His Ala
                565                 570                 575

Ile Ala Gly Thr Ala Gly Glu Asp Ile Ala Pro Thr Asp His Ala Pro
            580                 585                 590

His Pro His Pro Ala
        595


<210> SEQ ID NO 15
<211> LENGTH: 294
<212> TYPE: DNA
<213> ORGANISM: Streptomyces roseosporus

<400> SEQUENCE: 15

ctcgccgagg cctgcgagct gaccgccgcc actcccatgg gcggctggct gcccatgtac      60

cacgacatgg ggctcctggg cacgctgaca ccggccctgt acctcggcac cacgtgcgtg     120

ctgatgagct ccacggcatt catcaaacgg ccgcacctgt ggctacggac catcgaccgg     180

ttcggcctgg tctggtcgtc ggctcccgac ttcgcgtacg acatgtgtct gaagcgcgtc     240

accgacgagc agatcgccgg gctggacctg tcccgctggc ggtgggccgg caac           294


<210> SEQ ID NO 16
<211> LENGTH: 98
<212> TYPE: PRT
<213> ORGANISM: Streptomyces roseosporus

<400> SEQUENCE: 16

Leu Ala Glu Ala Cys Glu Leu Thr Ala Ala Thr Pro Met Gly Gly Trp
1               5                   10                  15

Leu Pro Met Tyr His Asp Met Gly Leu Leu Gly Thr Leu Thr Pro Ala
            20                  25                  30

Leu Tyr Leu Gly Thr Thr Cys Val Leu Met Ser Ser Thr Ala Phe Ile
        35                  40                  45

Lys Arg Pro His Leu Trp Leu Arg Thr Ile Asp Arg Phe Gly Leu Val
    50                  55                  60

Trp Ser Ser Ala Pro Asp Phe Ala Tyr Asp Met Cys Leu Lys Arg Val
65                  70                  75                  80

Thr Asp Glu Gln Ile Ala Gly Leu Asp Leu Ser Arg Trp Arg Trp Ala
                85                  90                  95

Gly Asn


<210> SEQ ID NO 17
<211> LENGTH: 8163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

atggttggtc aatttgcaaa tttcgtcgat ctgctccagt acagagctaa acttcaggcg      60

cggaaaaccg tgtttagttt tctggctgat ggcgaagcgg aatctgcggc cctgacctac     120

ggagaattag accaaaaagc ccaggcgatc gccgcttttt tgcaagctaa ccaggctcaa     180
```

-continued

```
gggcaacggg cattattact ttatccaccg ggtttagagt ttatcggtgc ctttttggga    240
tgtttgtatg ctggtgttgt tgcggtgcca gcttacccac cacggccgaa taaatccttt    300
gaccgcctcc atagcattat ccaagatgcc caggcaaaat ttgccctcac cacaacagaa    360
cttaaagata aaattgccga tcgcctcgaa gctttagaag gtacggattt tcattgtttg    420
gctacagatc aagttgaatt aatttcagga aaaaattggc aaaaaccgaa catttccggc    480
acagatctcg ctttttttgca atacaccagt ggctccacgg gcgatcctaa aggagtgatg    540
gtttcccacc acaatttgat ccacaactcc ggcttgattt ttacctcttt tcatatgaat    600
gatgaaacca ttattttcag ctggctgccc ccacatcatg atatgggttt gattggctgc    660
attctgaccc ccatctatgg tggaattcag gcaatcatga tgtccccttt ctcattttta    720
caaaacccgc tttcctggtt aaaacatatt accaaataca aagcaactat cagtggaagc    780
cctaacttcg cttacgatta ttgtgtcaaa cgaatcaggg aagaaaaaaa agaagggctg    840
gatttaagtt catgggtgac tgctttcaac ggggccgaac cgatccgcgc tgtgaccctc    900
gaaaattttg cgaaaacctt cgctacagca ggctttcaaa aatcagcatt ttatccctgt    960
tatggtatgg ctgaaaccac cctgatcgtt tccggtggta atggtcgtgc ccagcttccc   1020
caggaaatta tcgtcagcaa acagggcatc gaagcaaacc aagttcgccc tgcccaaggg   1080
acagaaacaa cggtgacctt ggtcggcagt ggtgaagtga ttggcgacca aattgtcaaa   1140
attgttgacc cccaggcttt aacagaatgt accgtcggtg aaattggcga agtatgggtt   1200
aagggcgaaa gtgttgccca gggctattgg caaaagccag acctcaccca gcaacaattc   1260
cagggaaacg tcggtgcaga aacgggcttt ttacgcacgg gcgatctggg tttttttgcaa   1320
ggtggcgaac tgtatattac gggtcgttta aaggatctcc tgattatccg ggggcgcaac   1380
cactatcccc aggacattga attaaccgtc gaagtggccc atcccgcttt acgacagggg   1440
gccggagccg ctgtatcagt agacgttaac ggggaagaac agttagtcat tgtccaggaa   1500
gttgagcgta aatatgcccg caaattaaat gtcgcggcag tagcccaagc tattcgtggg   1560
gcgatcgccg ccgaacatca actgcaaccc caggccattt gttttattaa acccggtagc   1620
attcccaaaa catccagcgg gaagattcgt cgccatgcct gcaaagctgg ttttctagac   1680
ggaagcttgg ctgtggttgg ggagtggcaa cccagccacc aaaaagaagg aaaaggaatt   1740
gggacacaag ccgttacccc ttctacgaca acatcaacga attttcccct gcctgaccag   1800
caccaacagc aaattgaagc ctggcttaag gataatattg cccatcgcct cggcattacg   1860
ccccaacaat tagacgaaac ggaacccttt gcaagttatg ggctggattc agtgcaagca   1920
gtacaggtca cagccgactt agaggattgg ctaggtcgaa aattagaccc cactctggcc   1980
tacgattatc cgaccattcg caccctggct cagtttttgg tccagggtaa tcaagcgcta   2040
gagaaaatac cacaggtgcc gaaaattcag ggcaaagaaa ttgccgtggt gggtctcagt   2100
tgtcgttttc cccaagctga caaccccgaa gctttttggg aattattacg taatggtaaa   2160
gatggagttc gccccccttaa aactcgctgg gccacgggag aatggggtgg tttttttagaa   2220
gatattgacc agtttgagcc gcaatttttt ggcatttccc cccgggaagc ggaacaaatg   2280
gatccccagc aacgcttact gttagaagta acctgggaag ccttggaacg ggcaaatatt   2340
ccggcagaaa gtttacgcca ttcccaaacg gggtttttttg tcggcattag taatagtgat   2400
tatgcccagt tgcaggtgcg ggaaaacaat ccgatcaatc cctacatggg gacgggcaac   2460
gcccacagta ttgctgcgaa tcgtctgtct tatttcctcg atctccgggg cgtttctctg   2520
agcatcgata cggcctgttc ctcttctctg gtggcggtac atctggcctg tcaaagttta   2580
```

-continued

```
atcaacggcg aatcggagtt ggcgatcgcc gccggggtga atttgatttt gaccccccgat   2640
gtgacccaga cttttaccca ggcgggcatg atgagtaaga cgggccgttg ccagaccttt   2700
gatgccgagg ctgatggcta tgtgcggggc gaaggttgtg gggtcgttct cctcaaaccc   2760
ctggcccagg cagaacggga cggggataat attctcgcgg tgatccacgg ttcggcggtg   2820
aatcaagatg gacgcagtaa cggtttgacg gctcccaacg ggcgatcgca acaggccgtt   2880
attcgccaag ccctggccca agccggcatt accgccgccg atttagctta cctagaggcc   2940
cacggcaccg gcacgcccct gggtgatccc attgaaatta attccctgaa ggcggtttta   3000
caaacggcgc agcgggaaca gccctgtgtg gtgggttctg tgaaaacaaa cattggtcac   3060
ctcgaggcag cggcgggcat cgcgggctta atcaaggtga ttttgtccct agagcatgga   3120
atgattcccc aacatttgca ttttaagcag ctcaatcccc gcattgatct agacggttta   3180
gtgaccattg cgagcaaaga tcagccttgg tcaggcgggt cacaaaaacg gtttgctggg   3240
gtaagttcct ttgggtttgg tggcaccaat gcccacgtga ttgtcgggga ctatgctcaa   3300
caaaaatctc cccttgctcc tccggctacc caagaccgcc cttggcattt gctgaccctt   3360
tctgctaaaa atgcccaggc cttaaatgcc ctgcaaaaaa gctatggaga ctatctggcc   3420
caacatccca gcgttgaccc acgcgatctc tgtttgtctg ccaataccgg gcgatcgccc   3480
ctcaaagaac gtcgtttttt tgtctttaaa caagtcgccg atttacaaca aactctcaat   3540
caagattttc tggcccaacc acgcctcagt tcccccgcaa aaattgcctt tttgtttacg   3600
gggcaaggtt cccaatacta cggcatgggg caacaactgt accaaaccag cccagtattt   3660
cggcaagtgc tggatgagtg cgatcgcctc tggcagacct attcccccga agcccctgcc   3720
ctcaccgacc tgctgtacgg taaccataac cctgacctcg tccacgaaac tgtctatacc   3780
cagcccctcc tctttgctgt tgaatatgcg atcgcccaac tatggttaag ctggggcgtg   3840
acgccagact tttgcatggg ccatagcgtc ggcgaatatg tcgcggcttg tctggcgggg   3900
gtattttccc tggcagacgg catgaaatta attacggccc ggggcaaact gatgcacgcc   3960
ctacccagca atggcagtat ggcggcggtc tttgccgata aaacggtcat caaaccctac   4020
ctatcggagc atttgaccgt cggagccgaa aacggttccc atttggtgct atcaggaaag   4080
accccctgcc tcgaagccag tattcacaaa ctccaaagcc aagggatcaa aaccaaaccc   4140
ctcaaggttt cccatgcttt ccactcccct ttgatggctc ccatgctggc agagtttcgg   4200
gaaattgctg aacaaattac tttccacccg ccgcgtatcc cgctcatttc caatgtcacg   4260
ggcggccaga ttgaagcgga aattgcccag gccgactatt gggttaagca cgtttcgcaa   4320
cccgtcaaat ttgtccagag catccaaacc ctggcccaag cgggtgtcaa tgtttatctc   4380
gaaatcggcg taaaaccagt gctcctgagt atgggacgcc attgcttagc tgaacaagaa   4440
gcggtttggt tgcccagttt acgtccccat agtgagcctt ggccggaaat tttgaccagt   4500
ctcggcaaac tgtatgagca agggctaaac attgactggc agaccgtgga agctggcgat   4560
cgccgccgga aactgattct gcccacctat cccttccaac ggcaacgata ttggtttaat   4620
caaggctctt ggcaaactgt tgagaccgaa tctgtgaacc caggccctga cgatctcaat   4680
gattggttgt atcaggtggc gtggacgccc ctggacactt tgcccccggc ccctgaaccg   4740
tcggctaagc tgtggttaat cttgggcgat cgccatgatc accagcccat tgaagcccaa   4800
tttaaaaacg cccagcgggt gtatctcggc caaagcaatc attttccgac gaatgccccc   4860
tgggaagtat ctgccgatgc gttggataat ttatttactc acgtcggctc ccaaaattta   4920
gcaggcatcc tttacctgtg tcccccaggg gaagacccag aagacctaga tgaaattcaa   4980
```

-continued

```
aagcaaacca gtggcttcgc cctccaactg atccaaaccc tgtatcaaca aaagatcgcg   5040
gttccctgct ggtttgtgac ccaccagagc caacgggtgc ttgaaaccga tgctgtcacc   5100
ggatttgccc aaggggggatt atggggactc gcccaggcga tcgccctcga acatccagag  5160
ttgtgggggg gaattattga tgtcgatgac agcctgccaa attttgccca gatttgccaa   5220
caaagacagg tgcagcagtt ggccgtgcgg caccaaaaac tctacggggc acagctcaaa   5280
aagcaaccgt cactgcccca gaaaaatctc cagattcaac cccaacagac ctatctagtg   5340
acagggggac tgggggccat tggccgtaaa attgcccaat ggctagccgc agcaggagca   5400
gaaaaagtaa ttctcgtcag ccggcgcgct ccggcagcgg atcagcagac gttaccgacc   5460
aatgcggtgg tttatccttg cgatttagcc gacgcagccc aggtggcaaa gctgtttcaa   5520
acctatcccc acatcaaagg aattttccat gcggcgggta ccttagctga tggtttgctg   5580
caacaacaaa cttggcaaaa gttccagacc gtcgccgccg ccaaaatgaa agggacatgg   5640
catctgcacc gccatagtca aaagctcgat ctggattttt ttgtgttgtt ttcctctgtg   5700
gcaggggtgc tcggttcacc gggacagggg aattatgccg ccgcaaaccg gggcatggcg   5760
gcgatcgccc aatatcgaca agcccaaggt ttacccgccc tggcgatcca ttgggggcct   5820
tgggccgaag gggaatggc caactccctc agcaaccaaa atttagcgtg gctgccgccc   5880
ccccagggac taacaatcct cgaaaaagtc ttgggcgccc aggggggaaat gggggtcttt  5940
aaaccggact ggcaaaacct ggccaaacag ttccccgaat ttgccaaaac ccattacttt   6000
gcagccgtta ttccctctgc tgaggctgtg cccccaacgg cttcaatttt tgacaaatta   6060
atcaacctag aagcttctca gcgggctgac tatctactgg attatctgcg gcggtctgtg   6120
gcgcaaatcc tcaagttaga aattgagcaa attcaaagcc acgatagcct gttggatctg   6180
ggcatggatt cgttgatgat catggaggcg atcgccagcc tcaagcagga tttacaactg   6240
atgttgtacc ccagggaaat ctacgaacgg cccagacttg atgtgttgac ggcctatcta   6300
gcggcggaat tcaccaaggc ccatgattct gaagcagcaa cggcggcagc agcgattccc   6360
tcccaaagcc tttcggtcaa aacaaaaaaa cagtggcaaa aacctgacca caaaaacccg   6420
aatcccattg cctttatcct ctctagcccc cggtcgggtt cgacgttgct gcgggtgatg   6480
ttagccggac atccggggtt atattcgccg ccagagctgc atttgctccc ctttgagact   6540
atgggcgatc gccaccagga attgggtcta tcccacctcg gcgaagggtt acaacgggcc   6600
ttaatggatc tagaaaacct caccccagag gcaagccagg cgaaggtcaa ccaatgggtc   6660
aaagcgaata cacccattgc agacatctat gcctatctcc aacggcaggc ggaacaacgt   6720
ttactcatcg acaaatctcc cagctacggc agcgatcgcc atattctaga ccacagcgaa   6780
atcctctttg accaggccaa atatatccat ctggtacgcc atccctacgc ggtgattgaa   6840
tcctttaccc gactgcggat ggataaactg ctgggggccg agcagcagaa cccctacgcc   6900
ctcgcggagt ccatttggcg caccagcaac cgcaatattt tagacctggg tcgcacggtt   6960
ggtgcggatc gatatctcca ggtgatttac gaagatctcg tccgtgaccc ccgcaaagtt   7020
ttgacaaata tttgtgattt cctgggggtg gactttgacg aagcgctcct caatccctac   7080
agcggcgatc gccttaccga tggcctccac caacagtcca tgggcgtcgg ggatcccaat   7140
ttcctccagc acaaaaccat tgatccggcc ctcgccgaca aatggcgctc aattaccctg   7200
cccgctgctc tccagctgga tacgatccag ttggccgaaa cgtttgctta cgatctcccc   7260
caggaacccc agctaacacc ccagacccaa tccttgccct cgatggtgga gcggttcgtg   7320
acagtgcgcg gtttagaaac ctgtctctgt gagtggggcg atcgccacca accattggtg   7380
```

-continued

```
ctacttctcc acggcatcct cgaacagggg gcctcctggc aactcatcgc gccccagttg   7440

gcggcccagg gctattgggt tgtggcccca gacctgcgtg gtcacggcaa atccgcccat   7500

gcccagtcct acagcatgct tgattttttg gctgacgtag atgcccttgc caaacaatta   7560

ggcgatcgcc cctttacctt ggtgggccac tccatgggtt ccatcatcgg tgccatgtat   7620

gcaggaattc gccaaaccca ggtagaaaag ttgatcctcg ttgaaaccat tgtccccaac   7680

gacatcgacg acgctgaaac cggtaatcac ctgacgaccc atctcgatta cctcgccgcg   7740

cccccccaac acccgatctt ccccagccta gaagtggccg cccgtcgcct ccgccaagcc   7800

acgccccaac tacccaaaga cctctcggcg ttcctcaccc agcgcagcac caaatccgtc   7860

gaaaaagggg tgcagtggcg ttgggatgct ttcctccgta cccgggcggg cattgaattc   7920

aatggcatta gcagacgacg ttacctggcc ctgctcaaag atatccaagc gccgatcacc   7980

ctcatctatg gcgatcagag tgaatttaac cgccctgctg atctccaggc gatccaagcg   8040

gctctccccc aggcccaacg tttaacggtt gctggcggcc ataacctcca ttttgagaat   8100

ccccaggcga tcgcccaaat tgtttatcaa caactccaga cccctgtacc caaaacacaa   8160

taa                                                                 8163
```

```
<210> SEQ ID NO 18
<211> LENGTH: 2720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Val Gly Gln Phe Ala Asn Phe Val Asp Leu Leu Gln Tyr Arg Ala
1               5                   10                  15

Lys Leu Gln Ala Arg Lys Thr Val Phe Ser Phe Leu Ala Asp Gly Glu
            20                  25                  30

Ala Glu Ser Ala Ala Leu Thr Tyr Gly Glu Leu Asp Gln Lys Ala Gln
        35                  40                  45

Ala Ile Ala Ala Phe Leu Gln Ala Asn Gln Ala Gln Gly Gln Arg Ala
    50                  55                  60

Leu Leu Leu Tyr Pro Pro Gly Leu Glu Phe Ile Gly Ala Phe Leu Gly
65                  70                  75                  80

Cys Leu Tyr Ala Gly Val Val Ala Val Pro Ala Tyr Pro Pro Arg Pro
                85                  90                  95

Asn Lys Ser Phe Asp Arg Leu His Ser Ile Ile Gln Asp Ala Gln Ala
            100                 105                 110

Lys Phe Ala Leu Thr Thr Thr Glu Leu Lys Asp Lys Ile Ala Asp Arg
        115                 120                 125

Leu Glu Ala Leu Glu Gly Thr Asp Phe His Cys Leu Ala Thr Asp Gln
    130                 135                 140

Val Glu Leu Ile Ser Gly Lys Asn Trp Gln Lys Pro Asn Ile Ser Gly
145                 150                 155                 160

Thr Asp Leu Ala Phe Leu Gln Tyr Thr Ser Gly Ser Thr Gly Asp Pro
                165                 170                 175

Lys Gly Val Met Val Ser His His Asn Leu Ile His Asn Ser Gly Leu
            180                 185                 190

Ile Phe Thr Ser Phe His Met Asn Asp Glu Thr Ile Ile Phe Ser Trp
        195                 200                 205

Leu Pro Pro His His Asp Met Gly Leu Ile Gly Cys Ile Leu Thr Pro
    210                 215                 220
```

-continued

```
Ile Tyr Gly Gly Ile Gln Ala Ile Met Met Ser Pro Phe Ser Phe Leu
225                 230                 235                 240

Gln Asn Pro Leu Ser Trp Leu Lys His Ile Thr Lys Tyr Lys Ala Thr
                245                 250                 255

Ile Ser Gly Ser Pro Asn Phe Ala Tyr Asp Tyr Cys Val Lys Arg Ile
            260                 265                 270

Arg Glu Glu Lys Lys Glu Gly Leu Asp Leu Ser Ser Trp Val Thr Ala
        275                 280                 285

Phe Asn Gly Ala Glu Pro Ile Arg Ala Val Thr Leu Glu Asn Phe Ala
    290                 295                 300

Lys Thr Phe Ala Thr Ala Gly Phe Gln Lys Ser Ala Phe Tyr Pro Cys
305                 310                 315                 320

Tyr Gly Met Ala Glu Thr Thr Leu Ile Val Ser Gly Gly Asn Gly Arg
                325                 330                 335

Ala Gln Leu Pro Gln Glu Ile Ile Val Ser Lys Gln Gly Ile Glu Ala
            340                 345                 350

Asn Gln Val Arg Pro Ala Gln Gly Thr Glu Thr Thr Val Thr Leu Val
        355                 360                 365

Gly Ser Gly Glu Val Ile Gly Asp Gln Ile Val Lys Ile Val Asp Pro
    370                 375                 380

Gln Ala Leu Thr Glu Cys Thr Val Gly Glu Ile Gly Glu Val Trp Val
385                 390                 395                 400

Lys Gly Glu Ser Val Ala Gln Gly Tyr Trp Gln Lys Pro Asp Leu Thr
                405                 410                 415

Gln Gln Gln Phe Gln Gly Asn Val Gly Ala Glu Thr Gly Phe Leu Arg
            420                 425                 430

Thr Gly Asp Leu Gly Phe Leu Gln Gly Gly Glu Leu Tyr Ile Thr Gly
        435                 440                 445

Arg Leu Lys Asp Leu Leu Ile Ile Arg Gly Arg Asn His Tyr Pro Gln
    450                 455                 460

Asp Ile Glu Leu Thr Val Glu Val Ala His Pro Ala Leu Arg Gln Gly
465                 470                 475                 480

Ala Gly Ala Ala Val Ser Val Asp Val Asn Gly Glu Glu Gln Leu Val
                485                 490                 495

Ile Val Gln Glu Val Glu Arg Lys Tyr Ala Arg Lys Leu Asn Val Ala
            500                 505                 510

Ala Val Ala Gln Ala Ile Arg Gly Ala Ile Ala Ala Glu His Gln Leu
        515                 520                 525

Gln Pro Gln Ala Ile Cys Phe Ile Lys Pro Gly Ser Ile Pro Lys Thr
    530                 535                 540

Ser Ser Gly Lys Ile Arg Arg His Ala Cys Lys Ala Gly Phe Leu Asp
545                 550                 555                 560

Gly Ser Leu Ala Val Val Gly Glu Trp Gln Pro Ser His Gln Lys Glu
                565                 570                 575

Gly Lys Gly Ile Gly Thr Gln Ala Val Thr Pro Ser Thr Thr Thr Ser
            580                 585                 590

Thr Asn Phe Pro Leu Pro Asp Gln His Gln Gln Gln Ile Glu Ala Trp
        595                 600                 605

Leu Lys Asp Asn Ile Ala His Arg Leu Gly Ile Thr Pro Gln Gln Leu
    610                 615                 620

Asp Glu Thr Glu Pro Phe Ala Ser Tyr Gly Leu Asp Ser Val Gln Ala
625                 630                 635                 640

Val Gln Val Thr Ala Asp Leu Glu Asp Trp Leu Gly Arg Lys Leu Asp
```

-continued

```
                645                 650                 655

Pro Thr Leu Ala Tyr Asp Tyr Pro Thr Ile Arg Thr Leu Ala Gln Phe
            660                 665                 670

Leu Val Gln Gly Asn Gln Ala Leu Glu Lys Ile Pro Gln Val Pro Lys
        675                 680                 685

Ile Gln Gly Lys Glu Ile Ala Val Val Gly Leu Ser Cys Arg Phe Pro
    690                 695                 700

Gln Ala Asp Asn Pro Glu Ala Phe Trp Glu Leu Leu Arg Asn Gly Lys
705                 710                 715                 720

Asp Gly Val Arg Pro Leu Lys Thr Arg Trp Ala Thr Gly Glu Trp Gly
                725                 730                 735

Gly Phe Leu Glu Asp Ile Asp Gln Phe Glu Pro Gln Phe Phe Gly Ile
            740                 745                 750

Ser Pro Arg Glu Ala Glu Gln Met Asp Pro Gln Gln Arg Leu Leu Leu
        755                 760                 765

Glu Val Thr Trp Glu Ala Leu Glu Arg Ala Asn Ile Pro Ala Glu Ser
    770                 775                 780

Leu Arg His Ser Gln Thr Gly Val Phe Val Gly Ile Ser Asn Ser Asp
785                 790                 795                 800

Tyr Ala Gln Leu Gln Val Arg Glu Asn Asn Pro Ile Asn Pro Tyr Met
                805                 810                 815

Gly Thr Gly Asn Ala His Ser Ile Ala Ala Asn Arg Leu Ser Tyr Phe
            820                 825                 830

Leu Asp Leu Arg Gly Val Ser Leu Ser Ile Asp Thr Ala Cys Ser Ser
        835                 840                 845

Ser Leu Val Ala Val His Leu Ala Cys Gln Ser Leu Ile Asn Gly Glu
    850                 855                 860

Ser Glu Leu Ala Ile Ala Ala Gly Val Asn Leu Ile Leu Thr Pro Asp
865                 870                 875                 880

Val Thr Gln Thr Phe Thr Gln Ala Gly Met Met Ser Lys Thr Gly Arg
                885                 890                 895

Cys Gln Thr Phe Asp Ala Glu Ala Asp Gly Tyr Val Arg Gly Glu Gly
            900                 905                 910

Cys Gly Val Val Leu Leu Lys Pro Leu Ala Gln Ala Glu Arg Asp Gly
        915                 920                 925

Asp Asn Ile Leu Ala Val Ile His Gly Ser Ala Val Asn Gln Asp Gly
    930                 935                 940

Arg Ser Asn Gly Leu Thr Ala Pro Asn Gly Arg Ser Gln Gln Ala Val
945                 950                 955                 960

Ile Arg Gln Ala Leu Ala Gln Ala Gly Ile Thr Ala Ala Asp Leu Ala
                965                 970                 975

Tyr Leu Glu Ala His Gly Thr Gly Thr Pro Leu Gly Asp Pro Ile Glu
            980                 985                 990

Ile Asn Ser Leu Lys Ala Val Leu  Gln Thr Ala Gln Arg  Glu Gln Pro
        995                 1000                1005

Cys Val  Val Gly Ser Val Lys  Thr Asn Ile Gly His  Leu Glu Ala
    1010                1015                1020

Ala Ala  Gly Ile Ala Gly Leu  Ile Lys Val Ile Leu  Ser Leu Glu
    1025                1030                1035

His Gly  Met Ile Pro Gln His  Leu His Phe Lys Gln  Leu Asn Pro
    1040                1045                1050

Arg Ile  Asp Leu Asp Gly Leu  Val Thr Ile Ala Ser  Lys Asp Gln
    1055                1060                1065
```

```
Pro Trp  Ser Gly Gly Ser Gln  Lys Arg Phe Ala Gly  Val Ser Ser
    1070                 1075                 1080

Phe Gly  Phe Gly Gly Thr Asn  Ala His Val Ile Val  Gly Asp Tyr
    1085                 1090                 1095

Ala Gln  Gln Lys Ser Pro Leu  Ala Pro Pro Ala Thr  Gln Asp Arg
    1100                 1105                 1110

Pro Trp  His Leu Leu Thr Leu  Ser Ala Lys Asn Ala  Gln Ala Leu
    1115                 1120                 1125

Asn Ala  Leu Gln Lys Ser Tyr  Gly Asp Tyr Leu Ala  Gln His Pro
    1130                 1135                 1140

Ser Val  Asp Pro Arg Asp Leu  Cys Leu Ser Ala Asn  Thr Gly Arg
    1145                 1150                 1155

Ser Pro  Leu Lys Glu Arg Arg  Phe Phe Val Phe Lys  Gln Val Ala
    1160                 1165                 1170

Asp Leu  Gln Gln Thr Leu Asn  Gln Asp Phe Leu Ala  Gln Pro Arg
    1175                 1180                 1185

Leu Ser  Ser Pro Ala Lys Ile  Ala Phe Leu Phe Thr  Gly Gln Gly
    1190                 1195                 1200

Ser Gln  Tyr Tyr Gly Met Gly  Gln Gln Leu Tyr Gln  Thr Ser Pro
    1205                 1210                 1215

Val Phe  Arg Gln Val Leu Asp  Glu Cys Asp Arg Leu  Trp Gln Thr
    1220                 1225                 1230

Tyr Ser  Pro Glu Ala Pro Ala  Leu Thr Asp Leu Leu  Tyr Gly Asn
    1235                 1240                 1245

His Asn  Pro Asp Leu Val His  Glu Thr Val Tyr Thr  Gln Pro Leu
    1250                 1255                 1260

Leu Phe  Ala Val Glu Tyr Ala  Ile Ala Gln Leu Trp  Leu Ser Trp
    1265                 1270                 1275

Gly Val  Thr Pro Asp Phe Cys  Met Gly His Ser Val  Gly Glu Tyr
    1280                 1285                 1290

Val Ala  Ala Cys Leu Ala Gly  Val Phe Ser Leu Ala  Asp Gly Met
    1295                 1300                 1305

Lys Leu  Ile Thr Ala Arg Gly  Lys Leu Met His Ala  Leu Pro Ser
    1310                 1315                 1320

Asn Gly  Ser Met Ala Ala Val  Phe Ala Asp Lys Thr  Val Ile Lys
    1325                 1330                 1335

Pro Tyr  Leu Ser Glu His Leu  Thr Val Gly Ala Glu  Asn Gly Ser
    1340                 1345                 1350

His Leu  Val Leu Ser Gly Lys  Thr Pro Cys Leu Glu  Ala Ser Ile
    1355                 1360                 1365

His Lys  Leu Gln Ser Gln Gly  Ile Lys Thr Lys Pro  Leu Lys Val
    1370                 1375                 1380

Ser His  Ala Phe His Ser Pro  Leu Met Ala Pro Met  Leu Ala Glu
    1385                 1390                 1395

Phe Arg  Glu Ile Ala Glu Gln  Ile Thr Phe His Pro  Pro Arg Ile
    1400                 1405                 1410

Pro Leu  Ile Ser Asn Val Thr  Gly Gly Gln Ile Glu  Ala Glu Ile
    1415                 1420                 1425

Ala Gln  Ala Asp Tyr Trp Val  Lys His Val Ser Gln  Pro Val Lys
    1430                 1435                 1440

Phe Val  Gln Ser Ile Gln Thr  Leu Ala Gln Ala Gly  Val Asn Val
    1445                 1450                 1455

Tyr Leu  Glu Ile Gly Val Lys  Pro Val Leu Leu Ser  Met Gly Arg
    1460                 1465                 1470
```

-continued

His Cys Leu Ala Glu Gln Glu Ala Val Trp Leu Pro Ser Leu Arg
1475 1480 1485

Pro His Ser Glu Pro Trp Pro Glu Ile Leu Thr Ser Leu Gly Lys
1490 1495 1500

Leu Tyr Glu Gln Gly Leu Asn Ile Asp Trp Gln Thr Val Glu Ala
1505 1510 1515

Gly Asp Arg Arg Arg Lys Leu Ile Leu Pro Thr Tyr Pro Phe Gln
1520 1525 1530

Arg Gln Arg Tyr Trp Phe Asn Gln Gly Ser Trp Gln Thr Val Glu
1535 1540 1545

Thr Glu Ser Val Asn Pro Gly Pro Asp Asp Leu Asn Asp Trp Leu
1550 1555 1560

Tyr Gln Val Ala Trp Thr Pro Leu Asp Thr Leu Pro Pro Ala Pro
1565 1570 1575

Glu Pro Ser Ala Lys Leu Trp Leu Ile Leu Gly Asp Arg His Asp
1580 1585 1590

His Gln Pro Ile Glu Ala Gln Phe Lys Asn Ala Gln Arg Val Tyr
1595 1600 1605

Leu Gly Gln Ser Asn His Phe Pro Thr Asn Ala Pro Trp Glu Val
1610 1615 1620

Ser Ala Asp Ala Leu Asp Asn Leu Phe Thr His Val Gly Ser Gln
1625 1630 1635

Asn Leu Ala Gly Ile Leu Tyr Leu Cys Pro Pro Gly Glu Asp Pro
1640 1645 1650

Glu Asp Leu Asp Glu Ile Gln Lys Gln Thr Ser Gly Phe Ala Leu
1655 1660 1665

Gln Leu Ile Gln Thr Leu Tyr Gln Gln Lys Ile Ala Val Pro Cys
1670 1675 1680

Trp Phe Val Thr His Gln Ser Gln Arg Val Leu Glu Thr Asp Ala
1685 1690 1695

Val Thr Gly Phe Ala Gln Gly Gly Leu Trp Gly Leu Ala Gln Ala
1700 1705 1710

Ile Ala Leu Glu His Pro Glu Leu Trp Gly Gly Ile Ile Asp Val
1715 1720 1725

Asp Asp Ser Leu Pro Asn Phe Ala Gln Ile Cys Gln Gln Arg Gln
1730 1735 1740

Val Gln Gln Leu Ala Val Arg His Gln Lys Leu Tyr Gly Ala Gln
1745 1750 1755

Leu Lys Lys Gln Pro Ser Leu Pro Gln Lys Asn Leu Gln Ile Gln
1760 1765 1770

Pro Gln Gln Thr Tyr Leu Val Thr Gly Gly Leu Gly Ala Ile Gly
1775 1780 1785

Arg Lys Ile Ala Gln Trp Leu Ala Ala Ala Gly Ala Glu Lys Val
1790 1795 1800

Ile Leu Val Ser Arg Arg Ala Pro Ala Ala Asp Gln Gln Thr Leu
1805 1810 1815

Pro Thr Asn Ala Val Val Tyr Pro Cys Asp Leu Ala Asp Ala Ala
1820 1825 1830

Gln Val Ala Lys Leu Phe Gln Thr Tyr Pro His Ile Lys Gly Ile
1835 1840 1845

Phe His Ala Ala Gly Thr Leu Ala Asp Gly Leu Leu Gln Gln Gln
1850 1855 1860

Thr Trp Gln Lys Phe Gln Thr Val Ala Ala Ala Lys Met Lys Gly

```
    1865                1870                1875

Thr Trp  His Leu His Arg His  Ser Gln Lys Leu Asp  Leu Asp Phe
    1880                1885                1890

Phe Val  Leu Phe Ser Ser Val  Ala Gly Val Leu Gly  Ser Pro Gly
    1895                1900                1905

Gln Gly  Asn Tyr Ala Ala Ala  Asn Arg Gly Met Ala  Ala Ile Ala
    1910                1915                1920

Gln Tyr  Arg Gln Ala Gln Gly  Leu Pro Ala Leu Ala  Ile His Trp
    1925                1930                1935

Gly Pro  Trp Ala Glu Gly Gly  Met Ala Asn Ser Leu  Ser Asn Gln
    1940                1945                1950

Asn Leu  Ala Trp Leu Pro Pro  Pro Gln Gly Leu Thr  Ile Leu Glu
    1955                1960                1965

Lys Val  Leu Gly Ala Gln Gly  Glu Met Gly Val Phe  Lys Pro Asp
    1970                1975                1980

Trp Gln  Asn Leu Ala Lys Gln  Phe Pro Glu Phe Ala  Lys Thr His
    1985                1990                1995

Tyr Phe  Ala Ala Val Ile Pro  Ser Ala Glu Ala Val  Pro Pro Thr
    2000                2005                2010

Ala Ser  Ile Phe Asp Lys Leu  Ile Asn Leu Glu Ala  Ser Gln Arg
    2015                2020                2025

Ala Asp  Tyr Leu Leu Asp Tyr  Leu Arg Arg Ser Val  Ala Gln Ile
    2030                2035                2040

Leu Lys  Leu Glu Ile Glu Gln  Ile Gln Ser His Asp  Ser Leu Leu
    2045                2050                2055

Asp Leu  Gly Met Asp Ser Leu  Met Ile Met Glu Ala  Ile Ala Ser
    2060                2065                2070

Leu Lys  Gln Asp Leu Gln Leu  Met Leu Tyr Pro Arg  Glu Ile Tyr
    2075                2080                2085

Glu Arg  Pro Arg Leu Asp Val  Leu Thr Ala Tyr Leu  Ala Ala Glu
    2090                2095                2100

Phe Thr  Lys Ala His Asp Ser  Glu Ala Ala Thr Ala  Ala Ala Ala
    2105                2110                2115

Ile Pro  Ser Gln Ser Leu Ser  Val Lys Thr Lys Lys  Gln Trp Gln
    2120                2125                2130

Lys Pro  Asp His Lys Asn Pro  Asn Pro Ile Ala Phe  Ile Leu Ser
    2135                2140                2145

Ser Pro  Arg Ser Gly Ser Thr  Leu Leu Arg Val Met  Leu Ala Gly
    2150                2155                2160

His Pro  Gly Leu Tyr Ser Pro  Pro Glu Leu His Leu  Leu Pro Phe
    2165                2170                2175

Glu Thr  Met Gly Asp Arg His  Gln Glu Leu Gly Leu  Ser His Leu
    2180                2185                2190

Gly Glu  Gly Leu Gln Arg Ala  Leu Met Asp Leu Glu  Asn Leu Thr
    2195                2200                2205

Pro Glu  Ala Ser Gln Ala Lys  Val Asn Gln Trp Val  Lys Ala Asn
    2210                2215                2220

Thr Pro  Ile Ala Asp Ile Tyr  Ala Tyr Leu Gln Arg  Gln Ala Glu
    2225                2230                2235

Gln Arg  Leu Leu Ile Asp Lys  Ser Pro Ser Tyr Gly  Ser Asp Arg
    2240                2245                2250

His Ile  Leu Asp His Ser Glu  Ile Leu Phe Asp Gln  Ala Lys Tyr
    2255                2260                2265
```

```
Ile His Leu Val Arg His Pro Tyr Ala Val Ile Glu Ser Phe Thr
    2270                2275                2280

Arg Leu Arg Met Asp Lys Leu Leu Gly Ala Glu Gln Gln Asn Pro
    2285                2290                2295

Tyr Ala Leu Ala Glu Ser Ile Trp Arg Thr Ser Asn Arg Asn Ile
    2300                2305                2310

Leu Asp Leu Gly Arg Thr Val Gly Ala Asp Arg Tyr Leu Gln Val
    2315                2320                2325

Ile Tyr Glu Asp Leu Val Arg Asp Pro Arg Lys Val Leu Thr Asn
    2330                2335                2340

Ile Cys Asp Phe Leu Gly Val Asp Phe Asp Glu Ala Leu Leu Asn
    2345                2350                2355

Pro Tyr Ser Gly Asp Arg Leu Thr Asp Gly Leu His Gln Gln Ser
    2360                2365                2370

Met Gly Val Gly Asp Pro Asn Phe Leu Gln His Lys Thr Ile Asp
    2375                2380                2385

Pro Ala Leu Ala Asp Lys Trp Arg Ser Ile Thr Leu Pro Ala Ala
    2390                2395                2400

Leu Gln Leu Asp Thr Ile Gln Leu Ala Glu Thr Phe Ala Tyr Asp
    2405                2410                2415

Leu Pro Gln Glu Pro Gln Leu Thr Pro Gln Thr Gln Ser Leu Pro
    2420                2425                2430

Ser Met Val Glu Arg Phe Val Thr Val Arg Gly Leu Glu Thr Cys
    2435                2440                2445

Leu Cys Glu Trp Gly Asp Arg His Gln Pro Leu Val Leu Leu Leu
    2450                2455                2460

His Gly Ile Leu Glu Gln Gly Ala Ser Trp Gln Leu Ile Ala Pro
    2465                2470                2475

Gln Leu Ala Ala Gln Gly Tyr Trp Val Val Ala Pro Asp Leu Arg
    2480                2485                2490

Gly His Gly Lys Ser Ala His Ala Gln Ser Tyr Ser Met Leu Asp
    2495                2500                2505

Phe Leu Ala Asp Val Asp Ala Leu Ala Lys Gln Leu Gly Asp Arg
    2510                2515                2520

Pro Phe Thr Leu Val Gly His Ser Met Gly Ser Ile Ile Gly Ala
    2525                2530                2535

Met Tyr Ala Gly Ile Arg Gln Thr Gln Val Glu Lys Leu Ile Leu
    2540                2545                2550

Val Glu Thr Ile Val Pro Asn Asp Ile Asp Asp Ala Glu Thr Gly
    2555                2560                2565

Asn His Leu Thr Thr His Leu Asp Tyr Leu Ala Ala Pro Pro Gln
    2570                2575                2580

His Pro Ile Phe Pro Ser Leu Glu Val Ala Ala Arg Arg Leu Arg
    2585                2590                2595

Gln Ala Thr Pro Gln Leu Pro Lys Asp Leu Ser Ala Phe Leu Thr
    2600                2605                2610

Gln Arg Ser Thr Lys Ser Val Glu Lys Gly Val Gln Trp Arg Trp
    2615                2620                2625

Asp Ala Phe Leu Arg Thr Arg Ala Gly Ile Glu Phe Asn Gly Ile
    2630                2635                2640

Ser Arg Arg Arg Tyr Leu Ala Leu Leu Lys Asp Ile Gln Ala Pro
    2645                2650                2655

Ile Thr Leu Ile Tyr Gly Asp Gln Ser Glu Phe Asn Arg Pro Ala
    2660                2665                2670
```

Asp Leu Gln Ala Ile Gln Ala Ala Leu Pro Gln Ala Gln Arg Leu
2675 2680 2685

Thr Val Ala Gly Gly His Asn Leu His Phe Glu Asn Pro Gln Ala
2690 2695 2700

Ile Ala Gln Ile Val Tyr Gln Gln Leu Gln Thr Pro Val Pro Lys
2705 2710 2715

Thr Gln
2720

<210> SEQ ID NO 19
<211> LENGTH: 8163
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
atggttggtc aatttgcaaa tttcgtcgat ctgctccagt acagagctaa acttcaggcg 60
cggaaaaccg tgtttagttt tctggctgat ggcgaagcgg aatctgcggc cctgacctac 120
ggagaattag accaaaaagc ccaggcgatc gccgcttttt tgcaagctaa ccaggctcaa 180
gggcaacggg cattattact ttatccaccg ggtttagagt ttatcggtgc ctttttggga 240
tgtttgtatg ctggtgttgt tgcggtgcca gcttacccac cacggccgaa taaatccttt 300
gaccgcctcc atagcattat ccaagatgcc caggcaaaat ttgccctcac cacaacagaa 360
cttaaagata aaattgccga tcgcctcgaa gctttagaag gtacggattt tcattgtttg 420
gctacagatc aagttgaatt aatttcagga aaaaattggc aaaaaccgaa catttccggc 480
acagatctcg ctttttgca atacaccagt ggctccacgg gcgatcctaa aggagtgatg 540
gtttcccacc acaatttgat ccacaactcc ggcttgatcc ggaatgcgct ggctatcgac 600
ttaaaagata ctcttttatc ttggatgccc ttaacccatg acatggggct catagcttgc 660
caccttgttc ctgccttagc cggaatcaat caaaatttaa tgccgacaga attatttatt 720
cgaagaccta ttctctggat gaaaaaagct catgaacata aagccagcat tctatcctca 780
cctaattttg gatacaatta ctttcttaaa tttctgaaag acaataaaag ttacgactgg 840
gatttatccc atatcagggt cattgcaaac ggggccgaac cgatccgcgc tgtgaccctc 900 gaaaatttg cgaaaacctt cgctacagca ggctttcaaa aatcagcatt ttatccctgt 960
tatggtatgg ctgaaaccac cctgatcgtt tccggtggta atggtcgtgc ccagcttccc 1020
caggaaatta tcgtcagcaa acagggcatc gaagcaaacc aagttcgccc tgcccaaggg 1080
acagaaacaa cggtgacctt ggtcggcagt ggtgaagtga ttggcgacca aattgtcaaa 1140
attgttgacc cccaggcttt aacagaatgt accgtcggtg aaattggcga agtatgggtt 1200
aagggcgaaa gtgttgccca gggctattgg caaaagccag acctcaccca gcaacaattc 1260
cagggaaacg tcggtgcaga aacgggcttt ttacgcacgg gcgatctggg tttttgcaa 1320 ggtggcgaac tgtatattac gggtcgttta aaggatctcc tgattatccg ggggcgcaac 1380
cactatcccc aggacattga attaaccgtc gaagtggccc atcccgcttt acgacagggg 1440
gccggagccg ctgtatcagt agacgttaac ggggaagaac agttagtcat tgtccaggaa 1500
gttgagcgta aatatgcccg caaattaaat gtcgcggcag tagcccaagc tattcgtggg 1560
gcgatcgccg ccgaacatca actgcaaccc caggccattt gttttattaa acccggtagc 1620
attcccaaaa catccagcgg gaagattcgt cgccatgcct gcaaagctgg ttttctagac 1680

-continued

```
ggaagcttgg ctgtggttgg ggagtggcaa cccagccacc aaaaagaagg aaaaggaatt   1740
gggacacaag ccgttacccc ttctacgaca acatcaacga attttcccct gcctgaccag   1800
caccaacagc aaattgaagc ctggcttaag gataatattg cccatcgcct cggcattacg   1860
ccccaacaat tagacgaaac ggaacccttt gcaagttatg ggctggattc agtgcaagca   1920
gtacaggtca cagccgactt agaggattgg ctaggtcgaa aattagaccc cactctggcc   1980
tacgattatc cgaccattcg caccctggct cagtttttgg tccagggtaa tcaagcgcta   2040
gagaaaatac cacaggtgcc gaaaattcag ggcaaagaaa ttgccgtggt gggtctcagt   2100
tgtcgttttc cccaagctga caaccccgaa gctttttggg aattattacg taatggtaaa   2160
gatggagttc gccccctaa aactcgctgg gccacgggag aatggggtgg ttttttagaa    2220
gatattgacc agtttgagcc gcaatttttt ggcatttccc cccgggaagc ggaacaaatg   2280
gatccccagc aacgcttact gttagaagta acctgggaag ccttggaacg ggcaaatatt   2340
ccggcagaaa gtttacgcca ttcccaaacg gggtttttg tcggcattag taatagtgat    2400
tatgcccagt tgcaggtgcg ggaaaacaat ccgatcaatc cctacatggg gacgggcaac   2460
gcccacagta ttgctgcgaa tcgtctgtct tatttcctcg atctccgggg cgtttctctg   2520
agcatcgata cggcctgttc ctcttctctg gtggcggtac atctggcctg tcaaagttta   2580
atcaacggcg aatcggagtt ggcgatcgcc gccggggtga atttgatttt gacccccgat   2640
gtgacccaga cttttaccca ggcgggcatg atgagtaaga cgggccgttg ccagaccttt   2700
gatgccgagg ctgatggcta tgtgcggggc gaaggttgtg ggtcgttct cctcaaaccc    2760
ctggcccagg cagaacggga cggggataat attctcgcgg tgatccacgg ttcggcggtg   2820
aatcaagatg gacgcagtaa cggtttgacg gctcccaacg ggcgatcgca acaggccgtt   2880
attcgccaag ccctggccca agccggcatt accgccgccg atttagctta cctagaggcc   2940
cacggcaccg gcacgcccct gggtgatccc attgaaatta attccctgaa ggcggtttta   3000
caaacggcgc agcgggaaca gccctgtgtg gtgggttctg tgaaaacaaa cattggtcac   3060
ctcgaggcag cggcgggcat cgcgggctta atcaaggtga ttttgtccct agagcatgga   3120
atgattcccc aacatttgca ttttaagcag ctcaatcccc gcattgatct agacggttta   3180
gtgaccattg cgagcaaaga tcagccttgg tcaggcgggt cacaaaaacg gtttgctggg   3240
gtaagttcct ttgggtttgg tggcaccaat gcccacgtga ttgtcgggga ctatgctcaa   3300
caaaaatctc cccttgctcc tccggctacc caagaccgcc cttggcattt gctgaccctt   3360
tctgctaaaa atgcccaggc cttaaatgcc ctgcaaaaaa gctatggaga ctatctggcc   3420
caacatccca gcgttgaccc acgcgatctc tgtttgtctg ccaataccgg gcgatcgccc   3480
ctcaaagaac gtcgtttttt tgtctttaaa caagtcgccg atttacaaca aactctcaat   3540
caagattttc tggcccaacc acgcctcagt tcccccgcaa aaattgcctt tttgtttacg   3600
gggcaaggtt cccaatacta cggcatgggg caacaactgt accaaaccag cccagtattt   3660
cggcaagtgc tggatgagtg cgatcgcctc tggcagacct attcccccga agcccctgcc   3720
ctcaccgacc tgctgtacgg taaccataac cctgacctcg tccacgaaac tgtctatacc   3780
cagcccctcc tctttgctgt tgaatatgcg atcgcccaac tatggttaag ctggggcgtg   3840
acgccagact tttgcatggg ccatagcgtc ggcgaatatg tcgcggcttg tctggcgggg   3900
gtattttccc tggcagacgg catgaaatta attacggccc ggggcaaact gatgcacgcc   3960
ctacccagca atggcagtat ggcggcggtc tttgccgata aaacggtcat caaaccctac   4020
ctatcggagc atttgaccgt cggagccgaa aacggttccc atttggtgct atcaggaaag   4080
```

-continued accccctgcc tcgaagccag tattcacaaa ctccaaagcc aagggatcaa aaccaaaccc 4140
ctcaaggttt cccatgcttt ccactcccct ttgatggctc ccatgctggc agagtttcgg 4200
gaaattgctg aacaaattac tttccacccg ccgcgtatcc cgctcatttc caatgtcacg 4260
ggcggccaga ttgaagcgga aattgcccag gccgactatt gggttaagca cgtttcgcaa 4320
cccgtcaaat ttgtccagag catccaaacc ctggcccaag cgggtgtcaa tgtttatctc 4380
gaaatcggcg taaaaccagt gctcctgagt atgggacgcc attgcttagc tgaacaagaa 4440
gcggtttggt tgcccagttt acgtccccat agtgagcctt ggccggaaat tttgaccagt 4500
ctcggcaaac tgtatgagca agggctaaac attgactggc agaccgtgga agctggcgat 4560
cgccgccgga aactgattct gcccacctat cccttccaac ggcaacgata ttggtttaat 4620
caaggctctt ggcaaactgt tgagaccgaa tctgtgaacc caggccctga cgatctcaat 4680
gattggttgt atcaggtggc gtggacgccc ctggacactt tgcccccggc ccctgaaccg 4740
tcggctaagc tgtggttaat cttgggcgat cgccatgatc accagcccat tgaagcccaa 4800
tttaaaaacg cccagcgggt gtatctcggc caaagcaatc attttccgac gaatgccccc 4860
tgggaagtat ctgccgatgc gttggataat ttatttactc acgtcggctc ccaaaattta 4920
gcaggcatcc tttacctgtg tcccccaggg gaagacccag aagacctaga tgaaattcaa 4980
aagcaaacca gtggcttcgc cctccaactg atccaaaccc tgtatcaaca aaagatcgcg 5040
gttccctgct ggtttgtgac ccaccagagc caacgggtgc ttgaaaccga tgctgtcacc 5100
ggatttgccc aaggggatt atggggactc gcccaggcga tcgccctcga acatccagag 5160
ttgtgggggg gaattattga tgtcgatgac agcctgccaa attttgccca gatttgccaa 5220
caaagacagg tgcagcagtt ggccgtgcgg caccaaaaac tctacggggc acagctcaaa 5280
aagcaaccgt cactgcccca gaaaaatctc cagattcaac cccaacagac ctatctagtg 5340
acagggggac tgggggccat tggccgtaaa attgcccaat ggctagccgc agcaggagca 5400
gaaaaagtaa ttctcgtcag ccggcgcgct ccggcagcgg atcagcagac gttaccgacc 5460
aatgcggtgg tttatccttg cgatttagcc gacgcagccc aggtggcaaa gctgtttcaa 5520
acctatcccc acatcaaagg aattttccat gcggcgggta ccttagctga tggtttgctg 5580
caacaacaaa cttggcaaaa gttccagacc gtcgccgccg ccaaaatgaa agggacatgg 5640
catctgcacc gccatagtca aaagctcgat ctggattttt ttgtgttgtt ttcctctgtg 5700
gcaggggtgc tcggttcacc gggacagggg aattatgccg ccgcaaaccg gggcatggcg 5760
gcgatcgccc aatatcgaca agcccaaggt ttacccgccc tggcgatcca ttgggggcct 5820
tgggccgaag gggaatggc caactccctc agcaaccaaa atttagcgtg gctgccgccc 5880
ccccagggac taacaatcct cgaaaaagtc ttgggcgccc agggggaaat gggggtcttt 5940
aaaccggact ggcaaaacct ggccaaacag ttccccgaat ttgccaaaac ccattacttt 6000
gcagccgtta ttccctctgc tgaggctgtg cccccaacgg cttcaatttt tgacaaatta 6060
atcaacctag aagcttctca gcgggctgac tatctactgg attatctgcg gcggtctgtg 6120
gcgcaaatcc tcaagttaga aattgagcaa attcaaagcc acgatagcct gttggatctg 6180
ggcatggatt cgttgatgat catggaggcg atcgccagcc tcaagcagga tttacaactg 6240
atgttgtacc ccagggaaat ctacgaacgg cccagacttg atgtgttgac ggcctatcta 6300
gcggcggaat tcaccaaggc ccatgattct gaagcagcaa cggcggcagc agcgattccc 6360
tcccaaagcc tttcggtcaa aacaaaaaaa cagtggcaaa aacctgacca caaaaacccg 6420
aatcccattg cctttatcct ctctagcccc cggtcgggtt cgacgttgct gcgggtgatg 6480

-continued

```
ttagccggac atccggggtt atattcgccg ccagagctgc atttgctccc ctttgagact   6540

atgggcgatc gccaccagga attgggtcta tcccacctcg gcgaagggtt acaacgggcc   6600

ttaatggatc tagaaaacct caccccagag gcaagccagg cgaaggtcaa ccaatgggtc   6660

aaagcgaata cacccattgc agacatctat gcctatctcc aacggcaggc ggaacaacgt   6720

ttactcatcg acaaatctcc cagctacggc agcgatcgcc atattctaga ccacagcgaa   6780

atcctctttg accaggccaa atatatccat ctggtacgcc atccctacgc ggtgattgaa   6840

tcctttaccc gactgcggat ggataaactg ctgggggccg agcagcagaa cccctacgcc   6900

ctcgcggagt ccatttggcg caccagcaac cgcaatattt tagacctggg tcgcacggtt   6960

ggtgcggatc gatatctcca ggtgatttac gaagatctcg tccgtgaccc ccgcaaagtt   7020

ttgacaaata tttgtgattt cctgggggtg gactttgacg aagcgctcct caatccctac   7080

agcggcgatc gccttaccga tggcctccac caacagtcca tgggcgtcgg ggatcccaat   7140

ttcctccagc acaaaaccat tgatccggcc ctcgccgaca aatggcgctc aattaccctg   7200

cccgctgctc tccagctgga tacgatccag ttggccgaaa cgtttgctta cgatctcccc   7260

caggaacccc agctaacacc ccagacccaa tccttgccct cgatggtgga gcggttcgtg   7320

acagtgcgcg gtttagaaac ctgtctctgt gagtggggcg atcgccacca accattggtg   7380

ctacttctcc acggcatcct cgaacagggg gcctcctggc aactcatcgc gccccagttg   7440

gcggcccagg gctattgggt tgtggcccca gacctgcgtg gtcacggcaa atccgcccat   7500

gcccagtcct acagcatgct tgattttttg gctgacgtag atgcccttgc caaacaatta   7560

ggcgatcgcc cctttacctt ggtgggccac tccatgggtt ccatcatcgg tgccatgtat   7620

gcaggaattc gccaaaccca ggtagaaaag ttgatcctcg ttgaaaccat tgtccccaac   7680

gacatcgacg acgctgaaac cggtaatcac ctgacgaccc atctcgatta cctcgccgcg   7740

cccccccaac acccgatctt ccccagccta gaagtggccg cccgtcgcct ccgccaagcc   7800

acgccccaac tacccaaaga cctctcggcg ttcctcaccc agcgcagcac caaatccgtc   7860

gaaaaagggg tgcagtggcg ttgggatgct ttcctccgta cccgggcggg cattgaattc   7920

aatggcatta gcagacgacg ttacctggcc ctgctcaaag atatccaagc gccgatcacc   7980

ctcatctatg gcgatcagag tgaatttaac cgccctgctg atctccaggc gatccaagcg   8040

gctctccccc aggcccaacg tttaacggtt gctggcggcc ataacctcca ttttgagaat   8100

ccccaggcga tcgcccaaat tgtttatcaa caactccaga cccctgtacc caaaacacaa   8160

taa                                                                 8163
```

<210> SEQ ID NO 20
<211> LENGTH: 2720
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Met Val Gly Gln Phe Ala Asn Phe Val Asp Leu Leu Gln Tyr Arg Ala
1               5                   10                  15

Lys Leu Gln Ala Arg Lys Thr Val Phe Ser Phe Leu Ala Asp Gly Glu
            20                  25                  30

Ala Glu Ser Ala Ala Leu Thr Tyr Gly Glu Leu Asp Gln Lys Ala Gln
        35                  40                  45

Ala Ile Ala Ala Phe Leu Gln Ala Asn Gln Ala Gln Gly Gln Arg Ala
    50                  55                  60
```

-continued

```
Leu Leu Leu Tyr Pro Pro Gly Leu Glu Phe Ile Gly Ala Phe Leu Gly
65                  70                  75                  80

Cys Leu Tyr Ala Gly Val Val Ala Val Pro Ala Tyr Pro Pro Arg Pro
                85                  90                  95

Asn Lys Ser Phe Asp Arg Leu His Ser Ile Ile Gln Asp Ala Gln Ala
            100                 105                 110

Lys Phe Ala Leu Thr Thr Thr Glu Leu Lys Asp Lys Ile Ala Asp Arg
        115                 120                 125

Leu Glu Ala Leu Glu Gly Thr Asp Phe His Cys Leu Ala Thr Asp Gln
    130                 135                 140

Val Glu Leu Ile Ser Gly Lys Asn Trp Gln Lys Pro Asn Ile Ser Gly
145                 150                 155                 160

Thr Asp Leu Ala Phe Leu Gln Tyr Thr Ser Gly Ser Thr Gly Asp Pro
                165                 170                 175

Lys Gly Val Met Val Ser His His Asn Leu Ile His Asn Ser Gly Leu
            180                 185                 190

Ile Arg Asn Ala Leu Ala Ile Asp Leu Lys Asp Thr Leu Leu Ser Trp
        195                 200                 205

Met Pro Leu Thr His Asp Met Gly Leu Ile Ala Cys His Leu Val Pro
    210                 215                 220

Ala Leu Ala Gly Ile Asn Gln Asn Leu Met Pro Thr Glu Leu Phe Ile
225                 230                 235                 240

Arg Arg Pro Ile Leu Trp Met Lys Lys Ala His Glu His Lys Ala Ser
                245                 250                 255

Ile Leu Ser Ser Pro Asn Phe Gly Tyr Asn Tyr Phe Leu Lys Phe Leu
            260                 265                 270

Lys Asp Asn Lys Ser Tyr Asp Trp Asp Leu Ser His Ile Arg Val Ile
        275                 280                 285

Ala Asn Gly Ala Glu Pro Ile Arg Ala Val Thr Leu Glu Asn Phe Ala
    290                 295                 300

Lys Thr Phe Ala Thr Ala Gly Phe Gln Lys Ser Ala Phe Tyr Pro Cys
305                 310                 315                 320

Tyr Gly Met Ala Glu Thr Thr Leu Ile Val Ser Gly Gly Asn Gly Arg
                325                 330                 335

Ala Gln Leu Pro Gln Glu Ile Ile Val Ser Lys Gln Gly Ile Glu Ala
            340                 345                 350

Asn Gln Val Arg Pro Ala Gln Gly Thr Glu Thr Thr Val Thr Leu Val
        355                 360                 365

Gly Ser Gly Glu Val Ile Gly Asp Gln Ile Val Lys Ile Val Asp Pro
    370                 375                 380

Gln Ala Leu Thr Glu Cys Thr Val Gly Glu Ile Gly Glu Val Trp Val
385                 390                 395                 400

Lys Gly Glu Ser Val Ala Gln Gly Tyr Trp Gln Lys Pro Asp Leu Thr
                405                 410                 415

Gln Gln Gln Phe Gln Gly Asn Val Gly Ala Glu Thr Gly Phe Leu Arg
            420                 425                 430

Thr Gly Asp Leu Gly Phe Leu Gln Gly Gly Glu Leu Tyr Ile Thr Gly
        435                 440                 445

Arg Leu Lys Asp Leu Leu Ile Ile Arg Gly Arg Asn His Tyr Pro Gln
    450                 455                 460

Asp Ile Glu Leu Thr Val Glu Val Ala His Pro Ala Leu Arg Gln Gly
465                 470                 475                 480

Ala Gly Ala Ala Val Ser Val Asp Val Asn Gly Glu Glu Gln Leu Val
```

-continued

```
                485                 490                 495

Ile Val Gln Glu Val Glu Arg Lys Tyr Ala Arg Lys Leu Asn Val Ala
            500                 505                 510

Ala Val Ala Gln Ala Ile Arg Gly Ala Ile Ala Ala Glu His Gln Leu
        515                 520                 525

Gln Pro Gln Ala Ile Cys Phe Ile Lys Pro Gly Ser Ile Pro Lys Thr
    530                 535                 540

Ser Ser Gly Lys Ile Arg Arg His Ala Cys Lys Ala Gly Phe Leu Asp
545                 550                 555                 560

Gly Ser Leu Ala Val Val Gly Glu Trp Gln Pro Ser His Gln Lys Glu
                565                 570                 575

Gly Lys Gly Ile Gly Thr Gln Ala Val Thr Pro Ser Thr Thr Thr Ser
            580                 585                 590

Thr Asn Phe Pro Leu Pro Asp Gln His Gln Gln Gln Ile Glu Ala Trp
        595                 600                 605

Leu Lys Asp Asn Ile Ala His Arg Leu Gly Ile Thr Pro Gln Gln Leu
    610                 615                 620

Asp Glu Thr Glu Pro Phe Ala Ser Tyr Gly Leu Asp Ser Val Gln Ala
625                 630                 635                 640

Val Gln Val Thr Ala Asp Leu Glu Asp Trp Leu Gly Arg Lys Leu Asp
                645                 650                 655

Pro Thr Leu Ala Tyr Asp Tyr Pro Thr Ile Arg Thr Leu Ala Gln Phe
            660                 665                 670

Leu Val Gln Gly Asn Gln Ala Leu Glu Lys Ile Pro Gln Val Pro Lys
        675                 680                 685

Ile Gln Gly Lys Glu Ile Ala Val Val Gly Leu Ser Cys Arg Phe Pro
    690                 695                 700

Gln Ala Asp Asn Pro Glu Ala Phe Trp Glu Leu Leu Arg Asn Gly Lys
705                 710                 715                 720

Asp Gly Val Arg Pro Leu Lys Thr Arg Trp Ala Thr Gly Glu Trp Gly
                725                 730                 735

Gly Phe Leu Glu Asp Ile Asp Gln Phe Glu Pro Gln Phe Phe Gly Ile
            740                 745                 750

Ser Pro Arg Glu Ala Glu Gln Met Asp Pro Gln Gln Arg Leu Leu Leu
        755                 760                 765

Glu Val Thr Trp Glu Ala Leu Glu Arg Ala Asn Ile Pro Ala Glu Ser
    770                 775                 780

Leu Arg His Ser Gln Thr Gly Val Phe Val Gly Ile Ser Asn Ser Asp
785                 790                 795                 800

Tyr Ala Gln Leu Gln Val Arg Glu Asn Asn Pro Ile Asn Pro Tyr Met
                805                 810                 815

Gly Thr Gly Asn Ala His Ser Ile Ala Ala Asn Arg Leu Ser Tyr Phe
            820                 825                 830

Leu Asp Leu Arg Gly Val Ser Leu Ser Ile Asp Thr Ala Cys Ser Ser
        835                 840                 845

Ser Leu Val Ala Val His Leu Ala Cys Gln Ser Leu Ile Asn Gly Glu
    850                 855                 860

Ser Glu Leu Ala Ile Ala Ala Gly Val Asn Leu Ile Leu Thr Pro Asp
865                 870                 875                 880

Val Thr Gln Thr Phe Thr Gln Ala Gly Met Met Ser Lys Thr Gly Arg
                885                 890                 895

Cys Gln Thr Phe Asp Ala Glu Ala Asp Gly Tyr Val Arg Gly Glu Gly
            900                 905                 910
```

```
Cys Gly Val Val Leu Leu Lys Pro Leu Ala Gln Ala Glu Arg Asp Gly
        915                 920                 925

Asp Asn Ile Leu Ala Val Ile His Gly Ser Ala Val Asn Gln Asp Gly
    930                 935                 940

Arg Ser Asn Gly Leu Thr Ala Pro Asn Gly Arg Ser Gln Gln Ala Val
945                 950                 955                 960

Ile Arg Gln Ala Leu Ala Gln Ala Gly Ile Thr Ala Ala Asp Leu Ala
                965                 970                 975

Tyr Leu Glu Ala His Gly Thr Gly Thr Pro Leu Gly Asp Pro Ile Glu
            980                 985                 990

Ile Asn Ser Leu Lys Ala Val Leu  Gln Thr Ala Gln Arg  Glu Gln Pro
        995                 1000                 1005

Cys Val  Val Gly Ser Val Lys  Thr Asn Ile Gly His  Leu Glu Ala
    1010                 1015                 1020

Ala Ala  Gly Ile Ala Gly Leu  Ile Lys Val Ile Leu  Ser Leu Glu
    1025                 1030                 1035

His Gly  Met Ile Pro Gln His  Leu His Phe Lys Gln  Leu Asn Pro
    1040                 1045                 1050

Arg Ile  Asp Leu Asp Gly Leu  Val Thr Ile Ala Ser  Lys Asp Gln
    1055                 1060                 1065

Pro Trp  Ser Gly Gly Ser Gln  Lys Arg Phe Ala Gly  Val Ser Ser
    1070                 1075                 1080

Phe Gly  Phe Gly Gly Thr Asn  Ala His Val Ile Val  Gly Asp Tyr
    1085                 1090                 1095

Ala Gln  Gln Lys Ser Pro Leu  Ala Pro Pro Ala Thr  Gln Asp Arg
    1100                 1105                 1110

Pro Trp  His Leu Leu Thr Leu  Ser Ala Lys Asn Ala  Gln Ala Leu
    1115                 1120                 1125

Asn Ala  Leu Gln Lys Ser Tyr  Gly Asp Tyr Leu Ala  Gln His Pro
    1130                 1135                 1140

Ser Val  Asp Pro Arg Asp Leu  Cys Leu Ser Ala Asn  Thr Gly Arg
    1145                 1150                 1155

Ser Pro  Leu Lys Glu Arg Arg  Phe Phe Val Phe Lys  Gln Val Ala
    1160                 1165                 1170

Asp Leu  Gln Gln Thr Leu Asn  Gln Asp Phe Leu Ala  Gln Pro Arg
    1175                 1180                 1185

Leu Ser  Ser Pro Ala Lys Ile  Ala Phe Leu Phe Thr  Gly Gln Gly
    1190                 1195                 1200

Ser Gln  Tyr Tyr Gly Met Gly  Gln Gln Leu Tyr Gln  Thr Ser Pro
    1205                 1210                 1215

Val Phe  Arg Gln Val Leu Asp  Glu Cys Asp Arg Leu  Trp Gln Thr
    1220                 1225                 1230

Tyr Ser  Pro Glu Ala Pro Ala  Leu Thr Asp Leu Leu  Tyr Gly Asn
    1235                 1240                 1245

His Asn  Pro Asp Leu Val His  Glu Thr Val Tyr Thr  Gln Pro Leu
    1250                 1255                 1260

Leu Phe  Ala Val Glu Tyr Ala  Ile Ala Gln Leu Trp  Leu Ser Trp
    1265                 1270                 1275

Gly Val  Thr Pro Asp Phe Cys  Met Gly His Ser Val  Gly Glu Tyr
    1280                 1285                 1290

Val Ala  Ala Cys Leu Ala Gly  Val Phe Ser Leu Ala  Asp Gly Met
    1295                 1300                 1305

Lys Leu  Ile Thr Ala Arg Gly  Lys Leu Met His Ala  Leu Pro Ser
    1310                 1315                 1320
```

Asn Gly Ser Met Ala Ala Val Phe Ala Asp Lys Thr Val Ile Lys
1325 1330 1335

Pro Tyr Leu Ser Glu His Leu Thr Val Gly Ala Glu Asn Gly Ser
1340 1345 1350

His Leu Val Leu Ser Gly Lys Thr Pro Cys Leu Glu Ala Ser Ile
1355 1360 1365

His Lys Leu Gln Ser Gln Gly Ile Lys Thr Lys Pro Leu Lys Val
1370 1375 1380

Ser His Ala Phe His Ser Pro Leu Met Ala Pro Met Leu Ala Glu
1385 1390 1395

Phe Arg Glu Ile Ala Glu Gln Ile Thr Phe His Pro Pro Arg Ile
1400 1405 1410

Pro Leu Ile Ser Asn Val Thr Gly Gly Gln Ile Glu Ala Glu Ile
1415 1420 1425

Ala Gln Ala Asp Tyr Trp Val Lys His Val Ser Gln Pro Val Lys
1430 1435 1440

Phe Val Gln Ser Ile Gln Thr Leu Ala Gln Ala Gly Val Asn Val
1445 1450 1455

Tyr Leu Glu Ile Gly Val Lys Pro Val Leu Leu Ser Met Gly Arg
1460 1465 1470

His Cys Leu Ala Glu Gln Glu Ala Val Trp Leu Pro Ser Leu Arg
1475 1480 1485

Pro His Ser Glu Pro Trp Pro Glu Ile Leu Thr Ser Leu Gly Lys
1490 1495 1500

Leu Tyr Glu Gln Gly Leu Asn Ile Asp Trp Gln Thr Val Glu Ala
1505 1510 1515

Gly Asp Arg Arg Arg Lys Leu Ile Leu Pro Thr Tyr Pro Phe Gln
1520 1525 1530

Arg Gln Arg Tyr Trp Phe Asn Gln Gly Ser Trp Gln Thr Val Glu
1535 1540 1545

Thr Glu Ser Val Asn Pro Gly Pro Asp Asp Leu Asn Asp Trp Leu
1550 1555 1560

Tyr Gln Val Ala Trp Thr Pro Leu Asp Thr Leu Pro Pro Ala Pro
1565 1570 1575

Glu Pro Ser Ala Lys Leu Trp Leu Ile Leu Gly Asp Arg His Asp
1580 1585 1590

His Gln Pro Ile Glu Ala Gln Phe Lys Asn Ala Gln Arg Val Tyr
1595 1600 1605

Leu Gly Gln Ser Asn His Phe Pro Thr Asn Ala Pro Trp Glu Val
1610 1615 1620

Ser Ala Asp Ala Leu Asp Asn Leu Phe Thr His Val Gly Ser Gln
1625 1630 1635

Asn Leu Ala Gly Ile Leu Tyr Leu Cys Pro Pro Gly Glu Asp Pro
1640 1645 1650

Glu Asp Leu Asp Glu Ile Gln Lys Gln Thr Ser Gly Phe Ala Leu
1655 1660 1665

Gln Leu Ile Gln Thr Leu Tyr Gln Gln Lys Ile Ala Val Pro Cys
1670 1675 1680

Trp Phe Val Thr His Gln Ser Gln Arg Val Leu Glu Thr Asp Ala
1685 1690 1695

Val Thr Gly Phe Ala Gln Gly Gly Leu Trp Gly Leu Ala Gln Ala
1700 1705 1710

Ile Ala Leu Glu His Pro Glu Leu Trp Gly Gly Ile Ile Asp Val

-continued

```
    1715                1720                1725

Asp Asp  Ser Leu Pro Asn Phe  Ala Gln Ile Cys Gln  Gln Arg Gln
    1730                1735                1740

Val Gln  Gln Leu Ala Val Arg  His Gln Lys Leu Tyr  Gly Ala Gln
    1745                1750                1755

Leu Lys  Lys Gln Pro Ser Leu  Pro Gln Lys Asn Leu  Gln Ile Gln
    1760                1765                1770

Pro Gln  Gln Thr Tyr Leu Val  Thr Gly Gly Leu Gly  Ala Ile Gly
    1775                1780                1785

Arg Lys  Ile Ala Gln Trp Leu  Ala Ala Ala Gly Ala  Glu Lys Val
    1790                1795                1800

Ile Leu  Val Ser Arg Arg Ala  Pro Ala Ala Asp Gln  Gln Thr Leu
    1805                1810                1815

Pro Thr  Asn Ala Val Val Tyr  Pro Cys Asp Leu Ala  Asp Ala Ala
    1820                1825                1830

Gln Val  Ala Lys Leu Phe Gln  Thr Tyr Pro His Ile  Lys Gly Ile
    1835                1840                1845

Phe His  Ala Ala Gly Thr Leu  Ala Asp Gly Leu Leu  Gln Gln Gln
    1850                1855                1860

Thr Trp  Gln Lys Phe Gln Thr  Val Ala Ala Ala Lys  Met Lys Gly
    1865                1870                1875

Thr Trp  His Leu His Arg His  Ser Gln Lys Leu Asp  Leu Asp Phe
    1880                1885                1890

Phe Val  Leu Phe Ser Ser Val  Ala Gly Val Leu Gly  Ser Pro Gly
    1895                1900                1905

Gln Gly  Asn Tyr Ala Ala Ala  Asn Arg Gly Met Ala  Ala Ile Ala
    1910                1915                1920

Gln Tyr  Arg Gln Ala Gln Gly  Leu Pro Ala Leu Ala  Ile His Trp
    1925                1930                1935

Gly Pro  Trp Ala Glu Gly Gly  Met Ala Asn Ser Leu  Ser Asn Gln
    1940                1945                1950

Asn Leu  Ala Trp Leu Pro Pro  Pro Gln Gly Leu Thr  Ile Leu Glu
    1955                1960                1965

Lys Val  Leu Gly Ala Gln Gly  Glu Met Gly Val Phe  Lys Pro Asp
    1970                1975                1980

Trp Gln  Asn Leu Ala Lys Gln  Phe Pro Glu Phe Ala  Lys Thr His
    1985                1990                1995

Tyr Phe  Ala Ala Val Ile Pro  Ser Ala Glu Ala Val  Pro Pro Thr
    2000                2005                2010

Ala Ser  Ile Phe Asp Lys Leu  Ile Asn Leu Glu Ala  Ser Gln Arg
    2015                2020                2025

Ala Asp  Tyr Leu Leu Asp Tyr  Leu Arg Arg Ser Val  Ala Gln Ile
    2030                2035                2040

Leu Lys  Leu Glu Ile Glu Gln  Ile Gln Ser His Asp  Ser Leu Leu
    2045                2050                2055

Asp Leu  Gly Met Asp Ser Leu  Met Ile Met Glu Ala  Ile Ala Ser
    2060                2065                2070

Leu Lys  Gln Asp Leu Gln Leu  Met Leu Tyr Pro Arg  Glu Ile Tyr
    2075                2080                2085

Glu Arg  Pro Arg Leu Asp Val  Leu Thr Ala Tyr Leu  Ala Ala Glu
    2090                2095                2100

Phe Thr  Lys Ala His Asp Ser  Glu Ala Ala Thr Ala  Ala Ala Ala
    2105                2110                2115
```

-continued

```
Ile Pro  Ser Gln Ser Leu Ser  Val Lys Thr Lys Lys  Gln Trp Gln
    2120                 2125                 2130

Lys Pro  Asp His Lys Asn Pro  Asn Pro Ile Ala Phe  Ile Leu Ser
    2135                 2140                 2145

Ser Pro  Arg Ser Gly Ser Thr  Leu Leu Arg Val Met  Leu Ala Gly
    2150                 2155                 2160

His Pro  Gly Leu Tyr Ser Pro  Pro Glu Leu His Leu  Leu Pro Phe
    2165                 2170                 2175

Glu Thr  Met Gly Asp Arg His  Gln Glu Leu Gly Leu  Ser His Leu
    2180                 2185                 2190

Gly Glu  Gly Leu Gln Arg Ala  Leu Met Asp Leu Glu  Asn Leu Thr
    2195                 2200                 2205

Pro Glu  Ala Ser Gln Ala Lys  Val Asn Gln Trp Val  Lys Ala Asn
    2210                 2215                 2220

Thr Pro  Ile Ala Asp Ile Tyr  Ala Tyr Leu Gln Arg  Gln Ala Glu
    2225                 2230                 2235

Gln Arg  Leu Leu Ile Asp Lys  Ser Pro Ser Tyr Gly  Ser Asp Arg
    2240                 2245                 2250

His Ile  Leu Asp His Ser Glu  Ile Leu Phe Asp Gln  Ala Lys Tyr
    2255                 2260                 2265

Ile His  Leu Val Arg His Pro  Tyr Ala Val Ile Glu  Ser Phe Thr
    2270                 2275                 2280

Arg Leu  Arg Met Asp Lys Leu  Leu Gly Ala Glu Gln  Gln Asn Pro
    2285                 2290                 2295

Tyr Ala  Leu Ala Glu Ser Ile  Trp Arg Thr Ser Asn  Arg Asn Ile
    2300                 2305                 2310

Leu Asp  Leu Gly Arg Thr Val  Gly Ala Asp Arg Tyr  Leu Gln Val
    2315                 2320                 2325

Ile Tyr  Glu Asp Leu Val Arg  Asp Pro Arg Lys Val  Leu Thr Asn
    2330                 2335                 2340

Ile Cys  Asp Phe Leu Gly Val  Asp Phe Asp Glu Ala  Leu Leu Asn
    2345                 2350                 2355

Pro Tyr  Ser Gly Asp Arg Leu  Thr Asp Gly Leu His  Gln Gln Ser
    2360                 2365                 2370

Met Gly  Val Gly Asp Pro Asn  Phe Leu Gln His Lys  Thr Ile Asp
    2375                 2380                 2385

Pro Ala  Leu Ala Asp Lys Trp  Arg Ser Ile Thr Leu  Pro Ala Ala
    2390                 2395                 2400

Leu Gln  Leu Asp Thr Ile Gln  Leu Ala Glu Thr Phe  Ala Tyr Asp
    2405                 2410                 2415

Leu Pro  Gln Glu Pro Gln Leu  Thr Pro Gln Thr Gln  Ser Leu Pro
    2420                 2425                 2430

Ser Met  Val Glu Arg Phe Val  Thr Val Arg Gly Leu  Glu Thr Cys
    2435                 2440                 2445

Leu Cys  Glu Trp Gly Asp Arg  His Gln Pro Leu Val  Leu Leu Leu
    2450                 2455                 2460

His Gly  Ile Leu Glu Gln Gly  Ala Ser Trp Gln Leu  Ile Ala Pro
    2465                 2470                 2475

Gln Leu  Ala Ala Gln Gly Tyr  Trp Val Val Ala Pro  Asp Leu Arg
    2480                 2485                 2490

Gly His  Gly Lys Ser Ala His  Ala Gln Ser Tyr Ser  Met Leu Asp
    2495                 2500                 2505

Phe Leu  Ala Asp Val Asp Ala  Leu Ala Lys Gln Leu  Gly Asp Arg
    2510                 2515                 2520
```

```
Pro Phe  Thr Leu Val Gly His  Ser Met Gly Ser Ile  Ile Gly Ala
    2525                 2530                 2535

Met Tyr  Ala Gly Ile Arg Gln  Thr Gln Val Glu Lys  Leu Ile Leu
    2540                 2545                 2550

Val Glu  Thr Ile Val Pro Asn  Asp Ile Asp Asp Ala  Glu Thr Gly
    2555                 2560                 2565

Asn His  Leu Thr Thr His Leu  Asp Tyr Leu Ala Ala  Pro Pro Gln
    2570                 2575                 2580

His Pro  Ile Phe Pro Ser Leu  Glu Val Ala Ala Arg  Arg Leu Arg
    2585                 2590                 2595

Gln Ala  Thr Pro Gln Leu Pro  Lys Asp Leu Ser Ala  Phe Leu Thr
    2600                 2605                 2610

Gln Arg  Ser Thr Lys Ser Val  Glu Lys Gly Val Gln  Trp Arg Trp
    2615                 2620                 2625

Asp Ala  Phe Leu Arg Thr Arg  Ala Gly Ile Glu Phe  Asn Gly Ile
    2630                 2635                 2640

Ser Arg  Arg Arg Tyr Leu Ala  Leu Leu Lys Asp Ile  Gln Ala Pro
    2645                 2650                 2655

Ile Thr  Leu Ile Tyr Gly Asp  Gln Ser Glu Phe Asn  Arg Pro Ala
    2660                 2665                 2670

Asp Leu  Gln Ala Ile Gln Ala  Ala Leu Pro Gln Ala  Gln Arg Leu
    2675                 2680                 2685

Thr Val  Ala Gly Gly His Asn  Leu His Phe Glu Asn  Pro Gln Ala
    2690                 2695                 2700

Ile Ala  Gln Ile Val Tyr Gln  Gln Leu Gln Thr Pro  Val Pro Lys
    2705                 2710                 2715

Thr Gln
    2720
```

<210> SEQ ID NO 21
<211> LENGTH: 8163
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

```
atggttggtc aatttgcaaa tttcgtcgat ctgctccagt acagagctaa acttcaggcg     60

cggaaaaccg tgtttagttt tctggctgat ggcgaagcgg aatctgcggc cctgacctac    120

ggagaattag accaaaaagc ccaggcgatc gccgcttttt tgcaagctaa ccaggctcaa    180

gggcaacggg cattattact ttatccaccg ggtttagagt ttatcggtgc ctttttggga    240

tgtttgtatg ctggtgttgt tgcggtgcca gcttacccac cacggccgaa taaatccttt    300

gaccgcctcc atagcattat ccaagatgcc caggcaaaat ttgccctcac cacaacagaa    360

cttaaagata aaattgccga tcgcctcgaa gctttagaag gtacggattt tcattgtttg    420

gctacagatc aagttgaatt aatttcagga aaaaattggc aaaaaccgaa catttccggc    480

acagatctcg ctttttttgca atacaccagt ggctccacgg gcgatcctaa aggagtgatg    540

gtttcccacc acaatttgat ccacaactcc ggcttgctcg ccgaggcctg cgagctgacc    600

gccgccactc ccatgggcgg ctggctgccc atgtaccacg acatggggct cctgggcacg    660

ctgacaccgg ccctgtacct cggcaccacg tgcgtgctga tgagctccac ggcattcatc    720

aaacggccgc acctgtggct acggaccatc gaccggttcg gcctggtctg gtcgtcggct    780
```

-continued

```
cccgacttcg cgtacgacat gtgtctgaag cgcgtcaccg acgagcagat cgccgggctg     840
gacctgtccc gctggcggtg ggccggcaac ggggccgaac cgatccgcgc tgtgaccctc     900
gaaaattttg cgaaaacctt cgctacagca ggctttcaaa aatcagcatt ttatccctgt     960
tatggtatgg ctgaaaccac cctgatcgtt tccggtggta atggtcgtgc ccagcttccc    1020
caggaaatta tcgtcagcaa acagggcatc gaagcaaacc aagttcgccc tgcccaaggg    1080
acagaaacaa cggtgacctt ggtcggcagt ggtgaagtga ttggcgacca aattgtcaaa    1140
attgttgacc cccaggcttt aacagaatgt accgtcggtg aaattggcga agtatgggtt    1200
aagggcgaaa gtgttgccca gggctattgg caaaagccag acctcaccca gcaacaattc    1260
cagggaaacg tcggtgcaga aacgggcttt ttacgcacgg gcgatctggg tttttgcaa     1320
ggtggcgaac tgtatattac gggtcgttta aaggatctcc tgattatccg gggcgcaac     1380
cactatcccc aggacattga attaaccgtc gaagtggccc atcccgcttt acgacagggg    1440
gccggagccg ctgtatcagt agacgttaac ggggaagaac agttagtcat tgtccaggaa    1500
gttgagcgta aatatgcccg caaattaaat gtcgcggcag tagcccaagc tattcgtggg    1560
gcgatcgccg ccgaacatca actgcaaccc caggccattt gttttattaa acccggtagc    1620
attcccaaaa catccagcgg gaagattcgt cgccatgcct gcaaagctgg ttttctagac    1680
ggaagcttgg ctgtggttgg ggagtggcaa cccagccacc aaaaagaagg aaaaggaatt    1740
gggacacaag ccgttacccc ttctacgaca acatcaacga attttcccct gcctgaccag    1800
caccaacagc aaattgaagc ctggcttaag gataatattg cccatcgcct cggcattacg    1860
ccccaacaat tagacgaaac ggaacccttt gcaagttatg ggctggattc agtgcaagca    1920
gtacaggtca cagccgactt agaggattgg ctaggtcgaa aattagaccc cactctggcc    1980
tacgattatc cgaccattcg caccctggct cagtttttgg tccagggtaa tcaagcgcta    2040
gagaaaatac cacaggtgcc gaaaattcag ggcaaagaaa ttgccgtggt gggtctcagt    2100
tgtcgttttc cccaagctga caaccccgaa gctttttggg aattattacg taatggtaaa    2160
gatggagttc gcccccttaa aactcgctgg gccacgggag aatggggtgg ttttttagaa    2220
gatattgacc agtttgagcc gcaatttttt ggcatttccc cccgggaagc ggaacaaatg    2280
gatccccagc aacgcttact gttagaagta acctgggaag ccttggaacg ggcaaatatt    2340
ccggcagaaa gtttacgcca ttcccaaacg gggttttttg tcggcattag taatagtgat    2400
tatgcccagt tgcaggtgcg ggaaaacaat ccgatcaatc cctacatggg gacgggcaac    2460
gcccacagta ttgctgcgaa tcgtctgtct tatttcctcg atctccgggg cgtttctctg    2520
agcatcgata cggcctgttc ctcttctctg gtggcggtac atctggcctg tcaaagttta    2580
atcaacggcg aatcggagtt ggcgatcgcc gccggggtga atttgatttt gacccccgat    2640
gtgacccaga cttttaccca ggcgggcatg atgagtaaga cgggccgttg ccagaccttt    2700
gatgccgagg ctgatggcta tgtgcggggc gaaggttgtg ggtcgttct cctcaaaccc     2760
ctggcccagg cagaacggga cggggataat attctcgcgg tgatccacgg ttcggcggtg    2820
aatcaagatg gacgcagtaa cggtttgacg gctcccaacg ggcgatcgca acaggccgtt    2880
attcgccaag ccctggccca agccggcatt accgccgccg atttagctta cctagaggcc    2940
cacggcaccg gcacgcccct gggtgatccc attgaaatta attccctgaa ggcggtttta    3000
caaacggcgc agcgggaaca gccctgtgtg gtgggttctg tgaaaacaaa cattggtcac    3060
ctcgaggcag cggcgggcat cgcgggctta atcaaggtga ttttgtccct agagcatgga    3120
atgattcccc aacatttgca ttttaagcag ctcaatcccc gcattgatct agacggttta    3180
```

-continued

```
gtgaccattg cgagcaaaga tcagccttgg tcaggcgggt cacaaaaacg gtttgctggg   3240
gtaagttcct ttgggtttgg tggcaccaat gcccacgtga ttgtcgggga ctatgctcaa   3300
caaaaatctc cccttgctcc tccggctacc caagaccgcc cttggcattt gctgaccctt   3360
tctgctaaaa atgcccaggc cttaaatgcc ctgcaaaaaa gctatggaga ctatctggcc   3420
caacatccca gcgttgaccc acgcgatctc tgtttgtctg ccaataccgg gcgatcgccc   3480
ctcaaagaac gtcgtttttt tgtctttaaa caagtcgccg atttacaaca aactctcaat   3540
caagatttc tggcccaacc acgcctcagt tcccccgcaa aaattgcctt tttgtttacg   3600
gggcaaggtt cccaatacta cggcatgggg caacaactgt accaaaccag cccagtattt   3660
cggcaagtgc tggatgagtg cgatcgcctc tggcagacct attcccccga agcccctgcc   3720
ctcaccgacc tgctgtacgg taaccataac cctgacctcg tccacgaaac tgtctatacc   3780
cagcccctcc tctttgctgt tgaatatgcg atcgcccaac tatggttaag ctggggcgtg   3840
acgccagact tttgcatggg ccatagcgtc ggcgaatatg tcgcggcttg tctggcgggg   3900
gtattttccc tggcagacgg catgaaatta attacggccc ggggcaaact gatgcacgcc   3960
ctacccagca atggcagtat ggcggcggtc tttgccgata aaacggtcat caaaccctac   4020
ctatcggagc atttgaccgt cggagccgaa aacggttccc atttggtgct atcaggaaag   4080
accccctgcc tcgaagccag tattcacaaa ctccaaagcc aagggatcaa aaccaaaccc   4140
ctcaaggttt cccatgcttt ccactcccct ttgatggctc ccatgctggc agagtttcgg   4200
gaaattgctg aacaaattac tttccacccg ccgcgtatcc cgctcatttc caatgtcacg   4260
ggcggccaga ttgaagcgga aattgcccag gccgactatt gggttaagca cgtttcgcaa   4320
cccgtcaaat ttgtccagag catccaaacc ctggcccaag cgggtgtcaa tgtttatctc   4380
gaaatcggcg taaaaccagt gctcctgagt atgggacgcc attgcttagc tgaacaagaa   4440
gcggtttggt tgcccagttt acgtccccat agtgagcctt ggccggaaat tttgaccagt   4500
ctcggcaaac tgtatgagca agggctaaac attgactggc agaccgtgga agctggcgat   4560
cgccgccgga aactgattct gcccacctat cccttccaac ggcaacgata ttggtttaat   4620
caaggctctt ggcaaactgt tgagaccgaa tctgtgaacc caggccctga cgatctcaat   4680
gattggttgt atcaggtggc gtggacgccc ctggacactt tgcccccggc ccctgaaccg   4740
tcggctaagc tgtggttaat cttgggcgat cgccatgatc accagcccat tgaagcccaa   4800
tttaaaaacg cccagcgggt gtatctcggc caaagcaatc attttccgac gaatgccccc   4860
tgggaagtat ctgccgatgc gttggataat ttatttactc acgtcggctc ccaaaattta   4920
gcaggcatcc tttacctgtg tcccccaggg gaagacccag aagacctaga tgaaattcaa   4980
aagcaaacca gtggcttcgc cctccaactg atccaaaccc tgtatcaaca aaagatcgcg   5040
gttccctgct ggtttgtgac ccaccagagc caacgggtgc ttgaaaccga tgctgtcacc   5100
ggatttgccc aagggggatt atggggactc gcccaggcga tcgccctcga acatccagag   5160
ttgtgggggg gaattattga tgtcgatgac agcctgccaa attttgccca gatttgccaa   5220
caaagacagg tgcagcagtt ggccgtgcgg caccaaaaac tctacggggc acagctcaaa   5280
aagcaaccgt cactgcccca gaaaaatctc cagattcaac cccaacagac ctatctagtg   5340
acagggggac tgggggccat tggccgtaaa attgcccaat ggctagccgc agcaggagca   5400
gaaaaagtaa ttctcgtcag ccggcgcgct ccggcagcgg atcagcagac gttaccgacc   5460
aatgcggtgg tttatccttg cgatttagcc gacgcagccc aggtggcaaa gctgtttcaa   5520
acctatcccc acatcaaagg aattttccat gcggcgggta ccttagctga tggtttgctg   5580
```

-continued

```
caacaacaaa cttggcaaaa gttccagacc gtcgccgccg ccaaaatgaa agggacatgg   5640
catctgcacc gccatagtca aaagctcgat ctggattttt ttgtgttgtt ttcctctgtg   5700
gcaggggtgc tcggttcacc gggacagggg aattatgccg ccgcaaaccg gggcatggcg   5760
gcgatcgccc aatatcgaca agcccaaggt ttacccgccc tggcgatcca ttgggggcct   5820
tgggccgaag gggaatggc caactccctc agcaaccaaa atttagcgtg gctgccgccc   5880
ccccagggac taacaatcct cgaaaaagtc ttgggcgccc agggggaaat gggggtcttt   5940
aaaccggact ggcaaaacct ggccaaacag ttccccgaat ttgccaaaac ccattacttt   6000
gcagccgtta ttccctctgc tgaggctgtg cccccaacgg cttcaatttt tgacaaatta   6060
atcaacctag aagcttctca gcgggctgac tatctactgg attatctgcg gcggtctgtg   6120
gcgcaaatcc tcaagttaga aattgagcaa attcaaagcc acgatagcct gttggatctg   6180
ggcatggatt cgttgatgat catggaggcg atcgccagcc tcaagcagga tttacaactg   6240
atgttgtacc ccagggaaat ctacgaacgg cccagacttg atgtgttgac ggcctatcta   6300
gcggcggaat tcaccaaggc ccatgattct gaagcagcaa cggcggcagc agcgattccc   6360
tcccaaagcc tttcggtcaa aacaaaaaaa cagtggcaaa aacctgacca caaaaacccg   6420
aatcccattg cctttatcct ctctagcccc cggtcgggtt cgacgttgct gcgggtgatg   6480
ttagccggac atccggggtt atattcgccg ccagagctgc atttgctccc ctttgagact   6540
atgggcgatc gccaccagga attgggtcta tcccacctcg gcgaagggtt acaacgggcc   6600
ttaatggatc tagaaaacct caccccagag gcaagccagg cgaaggtcaa ccaatgggtc   6660
aaagcgaata cacccattgc agacatctat gcctatctcc aacggcaggc ggaacaacgt   6720
ttactcatcg acaaatctcc cagctacggc agcgatcgcc atattctaga ccacagcgaa   6780
atcctctttg accaggccaa atatatccat ctggtacgcc atccctacgc ggtgattgaa   6840
tcctttaccc gactgcggat ggataaactg ctgggggccg agcagcagaa cccctacgcc   6900
ctcgcggagt ccatttggcg caccagcaac cgcaatattt tagacctggg tcgcacggtt   6960
ggtgcggatc gatatctcca ggtgatttac gaagatctcg tccgtgaccc ccgcaaagtt   7020
ttgacaaata tttgtgattt cctgggggtg gactttgacg aagcgctcct caatccctac   7080
agcggcgatc gccttaccga tggcctccac caacagtcca tgggcgtcgg ggatcccaat   7140
ttcctccagc acaaaaccat tgatccggcc ctcgccgaca aatggcgctc aattaccctg   7200
cccgctgctc tccagctgga tacgatccag ttggccgaaa cgtttgctta cgatctcccc   7260
caggaacccc agctaacacc ccagacccaa tccttgccct cgatggtgga gcggttcgtg   7320
acagtgcgcg gtttagaaac ctgtctctgt gagtggggcg atcgccacca accattggtg   7380
ctacttctcc acggcatcct cgaacagggg gcctcctggc aactcatcgc gccccagttg   7440
gcggcccagg gctattgggt tgtggcccca gacctgcgtg gtcacggcaa atccgcccat   7500
gcccagtcct acagcatgct tgattttttg gctgacgtag atgcccttgc caaacaatta   7560
ggcgatcgcc cctttacctt ggtgggccac tccatgggtt ccatcatcgg tgccatgtat   7620
gcaggaattc gccaaaccca ggtagaaaag ttgatcctcg ttgaaaccat tgtccccaac   7680
gacatcgacg acgctgaaac cggtaatcac ctgacgaccc atctcgatta cctcgccgcg   7740
ccccccccaac acccgatctt ccccagccta gaagtggccg cccgtcgcct ccgccaagcc   7800
acgccccaac tacccaaaga cctctcggcg ttcctcaccc agcgcagcac caaatccgtc   7860
gaaaaagggg tgcagtggcg ttgggatgct ttcctccgta cccgggcggg cattgaattc   7920
aatggcatta gcagacgacg ttacctggcc ctgctcaaag atatccaagc gccgatcacc   7980
```

ctcatctatg gcgatcagag tgaatttaac cgccctgctg atctccaggc gatccaagcg 8040
gctctccccc aggcccaacg tttaacggtt gctggcggcc ataacctcca ttttgagaat 8100
ccccaggcga tcgcccaaat tgtttatcaa caactccaga cccctgtacc caaaacacaa 8160
taa 8163

<210> SEQ ID NO 22
<211> LENGTH: 2720
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Met Val Gly Gln Phe Ala Asn Phe Val Asp Leu Leu Gln Tyr Arg Ala
1 5 10 15

Lys Leu Gln Ala Arg Lys Thr Val Phe Ser Phe Leu Ala Asp Gly Glu
20 25 30

Ala Glu Ser Ala Ala Leu Thr Tyr Gly Glu Leu Asp Gln Lys Ala Gln
35 40 45

Ala Ile Ala Ala Phe Leu Gln Ala Asn Gln Ala Gln Gly Gln Arg Ala
50 55 60

Leu Leu Leu Tyr Pro Pro Gly Leu Glu Phe Ile Gly Ala Phe Leu Gly
65 70 75 80

Cys Leu Tyr Ala Gly Val Val Ala Val Pro Ala Tyr Pro Pro Arg Pro
85 90 95

Asn Lys Ser Phe Asp Arg Leu His Ser Ile Ile Gln Asp Ala Gln Ala
100 105 110

Lys Phe Ala Leu Thr Thr Thr Glu Leu Lys Asp Lys Ile Ala Asp Arg
115 120 125

Leu Glu Ala Leu Glu Gly Thr Asp Phe His Cys Leu Ala Thr Asp Gln
130 135 140

Val Glu Leu Ile Ser Gly Lys Asn Trp Gln Lys Pro Asn Ile Ser Gly
145 150 155 160

Thr Asp Leu Ala Phe Leu Gln Tyr Thr Ser Gly Ser Thr Gly Asp Pro
165 170 175

Lys Gly Val Met Val Ser His His Asn Leu Ile His Asn Ser Gly Leu
180 185 190

Leu Ala Glu Ala Cys Glu Leu Thr Ala Ala Thr Pro Met Gly Gly Trp
195 200 205

Leu Pro Met Tyr His Asp Met Gly Leu Leu Gly Thr Leu Thr Pro Ala
210 215 220

Leu Tyr Leu Gly Thr Thr Cys Val Leu Met Ser Ser Thr Ala Phe Ile
225 230 235 240

Lys Arg Pro His Leu Trp Leu Arg Thr Ile Asp Arg Phe Gly Leu Val
245 250 255

Trp Ser Ser Ala Pro Asp Phe Ala Tyr Asp Met Cys Leu Lys Arg Val
260 265 270

Thr Asp Glu Gln Ile Ala Gly Leu Asp Leu Ser Arg Trp Arg Trp Ala
275 280 285

Gly Asn Gly Ala Glu Pro Ile Arg Ala Val Thr Leu Glu Asn Phe Ala
290 295 300

Lys Thr Phe Ala Thr Ala Gly Phe Gln Lys Ser Ala Phe Tyr Pro Cys
305 310 315 320

Tyr Gly Met Ala Glu Thr Thr Leu Ile Val Ser Gly Gly Asn Gly Arg

-continued

```
                325                 330                 335

Ala Gln Leu Pro Gln Glu Ile Ile Val Ser Lys Gln Gly Ile Glu Ala
            340                 345                 350

Asn Gln Val Arg Pro Ala Gln Gly Thr Glu Thr Thr Val Thr Leu Val
        355                 360                 365

Gly Ser Gly Glu Val Ile Gly Asp Gln Ile Val Lys Ile Val Asp Pro
    370                 375                 380

Gln Ala Leu Thr Glu Cys Thr Val Gly Glu Ile Gly Glu Val Trp Val
385                 390                 395                 400

Lys Gly Glu Ser Val Ala Gln Gly Tyr Trp Gln Lys Pro Asp Leu Thr
                405                 410                 415

Gln Gln Gln Phe Gln Gly Asn Val Gly Ala Glu Thr Gly Phe Leu Arg
            420                 425                 430

Thr Gly Asp Leu Gly Phe Leu Gln Gly Gly Glu Leu Tyr Ile Thr Gly
        435                 440                 445

Arg Leu Lys Asp Leu Leu Ile Ile Arg Gly Arg Asn His Tyr Pro Gln
    450                 455                 460

Asp Ile Glu Leu Thr Val Glu Val Ala His Pro Ala Leu Arg Gln Gly
465                 470                 475                 480

Ala Gly Ala Ala Val Ser Val Asp Val Asn Gly Glu Glu Gln Leu Val
                485                 490                 495

Ile Val Gln Glu Val Glu Arg Lys Tyr Ala Arg Lys Leu Asn Val Ala
            500                 505                 510

Ala Val Ala Gln Ala Ile Arg Gly Ala Ile Ala Ala Glu His Gln Leu
        515                 520                 525

Gln Pro Gln Ala Ile Cys Phe Ile Lys Pro Gly Ser Ile Pro Lys Thr
    530                 535                 540

Ser Ser Gly Lys Ile Arg Arg His Ala Cys Lys Ala Gly Phe Leu Asp
545                 550                 555                 560

Gly Ser Leu Ala Val Val Gly Glu Trp Gln Pro Ser His Gln Lys Glu
                565                 570                 575

Gly Lys Gly Ile Gly Thr Gln Ala Val Thr Pro Ser Thr Thr Thr Ser
            580                 585                 590

Thr Asn Phe Pro Leu Pro Asp Gln His Gln Gln Gln Ile Glu Ala Trp
        595                 600                 605

Leu Lys Asp Asn Ile Ala His Arg Leu Gly Ile Thr Pro Gln Gln Leu
    610                 615                 620

Asp Glu Thr Glu Pro Phe Ala Ser Tyr Gly Leu Asp Ser Val Gln Ala
625                 630                 635                 640

Val Gln Val Thr Ala Asp Leu Glu Asp Trp Leu Gly Arg Lys Leu Asp
                645                 650                 655

Pro Thr Leu Ala Tyr Asp Tyr Pro Thr Ile Arg Thr Leu Ala Gln Phe
            660                 665                 670

Leu Val Gln Gly Asn Gln Ala Leu Glu Lys Ile Pro Gln Val Pro Lys
        675                 680                 685

Ile Gln Gly Lys Glu Ile Ala Val Val Gly Leu Ser Cys Arg Phe Pro
    690                 695                 700

Gln Ala Asp Asn Pro Glu Ala Phe Trp Glu Leu Leu Arg Asn Gly Lys
705                 710                 715                 720

Asp Gly Val Arg Pro Leu Lys Thr Arg Trp Ala Thr Gly Glu Trp Gly
                725                 730                 735

Gly Phe Leu Glu Asp Ile Asp Gln Phe Glu Pro Gln Phe Phe Gly Ile
            740                 745                 750
```

```
Ser Pro Arg Glu Ala Glu Gln Met Asp Pro Gln Gln Arg Leu Leu Leu
        755                 760                 765

Glu Val Thr Trp Glu Ala Leu Glu Arg Ala Asn Ile Pro Ala Glu Ser
    770                 775                 780

Leu Arg His Ser Gln Thr Gly Val Phe Val Gly Ile Ser Asn Ser Asp
785                 790                 795                 800

Tyr Ala Gln Leu Gln Val Arg Glu Asn Asn Pro Ile Asn Pro Tyr Met
                805                 810                 815

Gly Thr Gly Asn Ala His Ser Ile Ala Ala Asn Arg Leu Ser Tyr Phe
            820                 825                 830

Leu Asp Leu Arg Gly Val Ser Leu Ser Ile Asp Thr Ala Cys Ser Ser
        835                 840                 845

Ser Leu Val Ala Val His Leu Ala Cys Gln Ser Leu Ile Asn Gly Glu
    850                 855                 860

Ser Glu Leu Ala Ile Ala Ala Gly Val Asn Leu Ile Leu Thr Pro Asp
865                 870                 875                 880

Val Thr Gln Thr Phe Thr Gln Ala Gly Met Met Ser Lys Thr Gly Arg
                885                 890                 895

Cys Gln Thr Phe Asp Ala Glu Ala Asp Gly Tyr Val Arg Gly Glu Gly
            900                 905                 910

Cys Gly Val Val Leu Leu Lys Pro Leu Ala Gln Ala Glu Arg Asp Gly
        915                 920                 925

Asp Asn Ile Leu Ala Val Ile His Gly Ser Ala Val Asn Gln Asp Gly
    930                 935                 940

Arg Ser Asn Gly Leu Thr Ala Pro Asn Gly Arg Ser Gln Gln Ala Val
945                 950                 955                 960

Ile Arg Gln Ala Leu Ala Gln Ala Gly Ile Thr Ala Ala Asp Leu Ala
                965                 970                 975

Tyr Leu Glu Ala His Gly Thr Gly Thr Pro Leu Gly Asp Pro Ile Glu
            980                 985                 990

Ile Asn Ser Leu Lys Ala Val Leu  Gln Thr Ala Gln Arg  Glu Gln Pro
        995                 1000                1005

Cys Val  Val Gly Ser Val Lys  Thr Asn Ile Gly His  Leu Glu Ala
    1010                1015                1020

Ala Ala  Gly Ile Ala Gly Leu  Ile Lys Val Ile Leu  Ser Leu Glu
    1025                1030                1035

His Gly  Met Ile Pro Gln His  Leu His Phe Lys Gln  Leu Asn Pro
    1040                1045                1050

Arg Ile  Asp Leu Asp Gly Leu  Val Thr Ile Ala Ser  Lys Asp Gln
    1055                1060                1065

Pro Trp  Ser Gly Gly Ser Gln  Lys Arg Phe Ala Gly  Val Ser Ser
    1070                1075                1080

Phe Gly  Phe Gly Gly Thr Asn  Ala His Val Ile Val  Gly Asp Tyr
    1085                1090                1095

Ala Gln  Gln Lys Ser Pro Leu  Ala Pro Pro Ala Thr  Gln Asp Arg
    1100                1105                1110

Pro Trp  His Leu Leu Thr Leu  Ser Ala Lys Asn Ala  Gln Ala Leu
    1115                1120                1125

Asn Ala  Leu Gln Lys Ser Tyr  Gly Asp Tyr Leu Ala  Gln His Pro
    1130                1135                1140

Ser Val  Asp Pro Arg Asp Leu  Cys Leu Ser Ala Asn  Thr Gly Arg
    1145                1150                1155

Ser Pro  Leu Lys Glu Arg Arg  Phe Phe Val Phe Lys  Gln Val Ala
    1160                1165                1170
```

-continued

```
Asp Leu  Gln Gln Thr Leu Asn  Gln Asp Phe Leu Ala  Gln Pro Arg
    1175                 1180                 1185

Leu Ser  Ser Pro Ala Lys Ile  Ala Phe Leu Phe Thr  Gly Gln Gly
    1190                 1195                 1200

Ser Gln  Tyr Tyr Gly Met Gly  Gln Gln Leu Tyr Gln  Thr Ser Pro
    1205                 1210                 1215

Val Phe  Arg Gln Val Leu Asp  Glu Cys Asp Arg Leu  Trp Gln Thr
    1220                 1225                 1230

Tyr Ser  Pro Glu Ala Pro Ala  Leu Thr Asp Leu Leu  Tyr Gly Asn
    1235                 1240                 1245

His Asn  Pro Asp Leu Val His  Glu Thr Val Tyr Thr  Gln Pro Leu
    1250                 1255                 1260

Leu Phe  Ala Val Glu Tyr Ala  Ile Ala Gln Leu Trp  Leu Ser Trp
    1265                 1270                 1275

Gly Val  Thr Pro Asp Phe Cys  Met Gly His Ser Val  Gly Glu Tyr
    1280                 1285                 1290

Val Ala  Ala Cys Leu Ala Gly  Val Phe Ser Leu Ala  Asp Gly Met
    1295                 1300                 1305

Lys Leu  Ile Thr Ala Arg Gly  Lys Leu Met His Ala  Leu Pro Ser
    1310                 1315                 1320

Asn Gly  Ser Met Ala Ala Val  Phe Ala Asp Lys Thr  Val Ile Lys
    1325                 1330                 1335

Pro Tyr  Leu Ser Glu His Leu  Thr Val Gly Ala Glu  Asn Gly Ser
    1340                 1345                 1350

His Leu  Val Leu Ser Gly Lys  Thr Pro Cys Leu Glu  Ala Ser Ile
    1355                 1360                 1365

His Lys  Leu Gln Ser Gln Gly  Ile Lys Thr Lys Pro  Leu Lys Val
    1370                 1375                 1380

Ser His  Ala Phe His Ser Pro  Leu Met Ala Pro Met  Leu Ala Glu
    1385                 1390                 1395

Phe Arg  Glu Ile Ala Glu Gln  Ile Thr Phe His Pro  Pro Arg Ile
    1400                 1405                 1410

Pro Leu  Ile Ser Asn Val Thr  Gly Gly Gln Ile Glu  Ala Glu Ile
    1415                 1420                 1425

Ala Gln  Ala Asp Tyr Trp Val  Lys His Val Ser Gln  Pro Val Lys
    1430                 1435                 1440

Phe Val  Gln Ser Ile Gln Thr  Leu Ala Gln Ala Gly  Val Asn Val
    1445                 1450                 1455

Tyr Leu  Glu Ile Gly Val Lys  Pro Val Leu Leu Ser  Met Gly Arg
    1460                 1465                 1470

His Cys  Leu Ala Glu Gln Glu  Ala Val Trp Leu Pro  Ser Leu Arg
    1475                 1480                 1485

Pro His  Ser Glu Pro Trp Pro  Glu Ile Leu Thr Ser  Leu Gly Lys
    1490                 1495                 1500

Leu Tyr  Glu Gln Gly Leu Asn  Ile Asp Trp Gln Thr  Val Glu Ala
    1505                 1510                 1515

Gly Asp  Arg Arg Arg Lys Leu  Ile Leu Pro Thr Tyr  Pro Phe Gln
    1520                 1525                 1530

Arg Gln  Arg Tyr Trp Phe Asn  Gln Gly Ser Trp Gln  Thr Val Glu
    1535                 1540                 1545

Thr Glu  Ser Val Asn Pro Gly  Pro Asp Asp Leu Asn  Asp Trp Leu
    1550                 1555                 1560

Tyr Gln  Val Ala Trp Thr Pro  Leu Asp Thr Leu Pro  Pro Ala Pro
```

```
    1565                1570                1575

Glu Pro  Ser Ala Lys Leu Trp  Leu Ile Leu Gly Asp  Arg His Asp
    1580                1585                1590

His Gln  Pro Ile Glu Ala Gln  Phe Lys Asn Ala Gln  Arg Val Tyr
    1595                1600                1605

Leu Gly  Gln Ser Asn His Phe  Pro Thr Asn Ala Pro  Trp Glu Val
    1610                1615                1620

Ser Ala  Asp Ala Leu Asp Asn  Leu Phe Thr His Val  Gly Ser Gln
    1625                1630                1635

Asn Leu  Ala Gly Ile Leu Tyr  Leu Cys Pro Pro Gly  Glu Asp Pro
    1640                1645                1650

Glu Asp  Leu Asp Glu Ile Gln  Lys Gln Thr Ser Gly  Phe Ala Leu
    1655                1660                1665

Gln Leu  Ile Gln Thr Leu Tyr  Gln Gln Lys Ile Ala  Val Pro Cys
    1670                1675                1680

Trp Phe  Val Thr His Gln Ser  Gln Arg Val Leu Glu  Thr Asp Ala
    1685                1690                1695

Val Thr  Gly Phe Ala Gln Gly  Gly Leu Trp Gly Leu  Ala Gln Ala
    1700                1705                1710

Ile Ala  Leu Glu His Pro Glu  Leu Trp Gly Gly Ile  Ile Asp Val
    1715                1720                1725

Asp Asp  Ser Leu Pro Asn Phe  Ala Gln Ile Cys Gln  Gln Arg Gln
    1730                1735                1740

Val Gln  Gln Leu Ala Val Arg  His Gln Lys Leu Tyr  Gly Ala Gln
    1745                1750                1755

Leu Lys  Lys Gln Pro Ser Leu  Pro Gln Lys Asn Leu  Gln Ile Gln
    1760                1765                1770

Pro Gln  Gln Thr Tyr Leu Val  Thr Gly Gly Leu Gly  Ala Ile Gly
    1775                1780                1785

Arg Lys  Ile Ala Gln Trp Leu  Ala Ala Ala Gly Ala  Glu Lys Val
    1790                1795                1800

Ile Leu  Val Ser Arg Arg Ala  Pro Ala Ala Asp Gln  Gln Thr Leu
    1805                1810                1815

Pro Thr  Asn Ala Val Val Tyr  Pro Cys Asp Leu Ala  Asp Ala Ala
    1820                1825                1830

Gln Val  Ala Lys Leu Phe Gln  Thr Tyr Pro His Ile  Lys Gly Ile
    1835                1840                1845

Phe His  Ala Ala Gly Thr Leu  Ala Asp Gly Leu Leu  Gln Gln Gln
    1850                1855                1860

Thr Trp  Gln Lys Phe Gln Thr  Val Ala Ala Ala Lys  Met Lys Gly
    1865                1870                1875

Thr Trp  His Leu His Arg His  Ser Gln Lys Leu Asp  Leu Asp Phe
    1880                1885                1890

Phe Val  Leu Phe Ser Ser Val  Ala Gly Val Leu Gly  Ser Pro Gly
    1895                1900                1905

Gln Gly  Asn Tyr Ala Ala Ala  Asn Arg Gly Met Ala  Ala Ile Ala
    1910                1915                1920

Gln Tyr  Arg Gln Ala Gln Gly  Leu Pro Ala Leu Ala  Ile His Trp
    1925                1930                1935

Gly Pro  Trp Ala Glu Gly Gly  Met Ala Asn Ser Leu  Ser Asn Gln
    1940                1945                1950

Asn Leu  Ala Trp Leu Pro Pro  Pro Gln Gly Leu Thr  Ile Leu Glu
    1955                1960                1965
```

-continued

```
Lys Val  Leu Gly Ala Gln Gly  Glu Met Gly Val Phe  Lys Pro Asp
    1970                 1975                 1980

Trp Gln  Asn Leu Ala Lys Gln  Phe Pro Glu Phe Ala  Lys Thr His
    1985                 1990                 1995

Tyr Phe  Ala Ala Val Ile Pro  Ser Ala Glu Ala Val  Pro Pro Thr
    2000                 2005                 2010

Ala Ser  Ile Phe Asp Lys Leu  Ile Asn Leu Glu Ala  Ser Gln Arg
    2015                 2020                 2025

Ala Asp  Tyr Leu Leu Asp Tyr  Leu Arg Arg Ser Val  Ala Gln Ile
    2030                 2035                 2040

Leu Lys  Leu Glu Ile Glu Gln  Ile Gln Ser His Asp  Ser Leu Leu
    2045                 2050                 2055

Asp Leu  Gly Met Asp Ser Leu  Met Ile Met Glu Ala  Ile Ala Ser
    2060                 2065                 2070

Leu Lys  Gln Asp Leu Gln Leu  Met Leu Tyr Pro Arg  Glu Ile Tyr
    2075                 2080                 2085

Glu Arg  Pro Arg Leu Asp Val  Leu Thr Ala Tyr Leu  Ala Ala Glu
    2090                 2095                 2100

Phe Thr  Lys Ala His Asp Ser  Glu Ala Ala Thr Ala  Ala Ala Ala
    2105                 2110                 2115

Ile Pro  Ser Gln Ser Leu Ser  Val Lys Thr Lys Lys  Gln Trp Gln
    2120                 2125                 2130

Lys Pro  Asp His Lys Asn Pro  Asn Pro Ile Ala Phe  Ile Leu Ser
    2135                 2140                 2145

Ser Pro  Arg Ser Gly Ser Thr  Leu Leu Arg Val Met  Leu Ala Gly
    2150                 2155                 2160

His Pro  Gly Leu Tyr Ser Pro  Pro Glu Leu His Leu  Leu Pro Phe
    2165                 2170                 2175

Glu Thr  Met Gly Asp Arg His  Gln Glu Leu Gly Leu  Ser His Leu
    2180                 2185                 2190

Gly Glu  Gly Leu Gln Arg Ala  Leu Met Asp Leu Glu  Asn Leu Thr
    2195                 2200                 2205

Pro Glu  Ala Ser Gln Ala Lys  Val Asn Gln Trp Val  Lys Ala Asn
    2210                 2215                 2220

Thr Pro  Ile Ala Asp Ile Tyr  Ala Tyr Leu Gln Arg  Gln Ala Glu
    2225                 2230                 2235

Gln Arg  Leu Leu Ile Asp Lys  Ser Pro Ser Tyr Gly  Ser Asp Arg
    2240                 2245                 2250

His Ile  Leu Asp His Ser Glu  Ile Leu Phe Asp Gln  Ala Lys Tyr
    2255                 2260                 2265

Ile His  Leu Val Arg His Pro  Tyr Ala Val Ile Glu  Ser Phe Thr
    2270                 2275                 2280

Arg Leu  Arg Met Asp Lys Leu  Leu Gly Ala Glu Gln  Gln Asn Pro
    2285                 2290                 2295

Tyr Ala  Leu Ala Glu Ser Ile  Trp Arg Thr Ser Asn  Arg Asn Ile
    2300                 2305                 2310

Leu Asp  Leu Gly Arg Thr Val  Gly Ala Asp Arg Tyr  Leu Gln Val
    2315                 2320                 2325

Ile Tyr  Glu Asp Leu Val Arg  Asp Pro Arg Lys Val  Leu Thr Asn
    2330                 2335                 2340

Ile Cys  Asp Phe Leu Gly Val  Asp Phe Asp Glu Ala  Leu Leu Asn
    2345                 2350                 2355

Pro Tyr  Ser Gly Asp Arg Leu  Thr Asp Gly Leu His  Gln Gln Ser
    2360                 2365                 2370
```

```
Met Gly Val Gly Asp Pro Asn Phe Leu Gln His Lys Thr Ile Asp
    2375                2380                2385

Pro Ala Leu Ala Asp Lys Trp Arg Ser Ile Thr Leu Pro Ala Ala
    2390                2395                2400

Leu Gln Leu Asp Thr Ile Gln Leu Ala Glu Thr Phe Ala Tyr Asp
    2405                2410                2415

Leu Pro Gln Glu Pro Gln Leu Thr Pro Gln Thr Gln Ser Leu Pro
    2420                2425                2430

Ser Met Val Glu Arg Phe Val Thr Val Arg Gly Leu Glu Thr Cys
    2435                2440                2445

Leu Cys Glu Trp Gly Asp Arg His Gln Pro Leu Val Leu Leu Leu
    2450                2455                2460

His Gly Ile Leu Glu Gln Gly Ala Ser Trp Gln Leu Ile Ala Pro
    2465                2470                2475

Gln Leu Ala Ala Gln Gly Tyr Trp Val Val Ala Pro Asp Leu Arg
    2480                2485                2490

Gly His Gly Lys Ser Ala His Ala Gln Ser Tyr Ser Met Leu Asp
    2495                2500                2505

Phe Leu Ala Asp Val Asp Ala Leu Ala Lys Gln Leu Gly Asp Arg
    2510                2515                2520

Pro Phe Thr Leu Val Gly His Ser Met Gly Ser Ile Ile Gly Ala
    2525                2530                2535

Met Tyr Ala Gly Ile Arg Gln Thr Gln Val Glu Lys Leu Ile Leu
    2540                2545                2550

Val Glu Thr Ile Val Pro Asn Asp Ile Asp Asp Ala Glu Thr Gly
    2555                2560                2565

Asn His Leu Thr Thr His Leu Asp Tyr Leu Ala Ala Pro Pro Gln
    2570                2575                2580

His Pro Ile Phe Pro Ser Leu Glu Val Ala Ala Arg Arg Leu Arg
    2585                2590                2595

Gln Ala Thr Pro Gln Leu Pro Lys Asp Leu Ser Ala Phe Leu Thr
    2600                2605                2610

Gln Arg Ser Thr Lys Ser Val Glu Lys Gly Val Gln Trp Arg Trp
    2615                2620                2625

Asp Ala Phe Leu Arg Thr Arg Ala Gly Ile Glu Phe Asn Gly Ile
    2630                2635                2640

Ser Arg Arg Arg Tyr Leu Ala Leu Leu Lys Asp Ile Gln Ala Pro
    2645                2650                2655

Ile Thr Leu Ile Tyr Gly Asp Gln Ser Glu Phe Asn Arg Pro Ala
    2660                2665                2670

Asp Leu Gln Ala Ile Gln Ala Ala Leu Pro Gln Ala Gln Arg Leu
    2675                2680                2685

Thr Val Ala Gly Gly His Asn Leu His Phe Glu Asn Pro Gln Ala
    2690                2695                2700

Ile Ala Gln Ile Val Tyr Gln Gln Leu Gln Thr Pro Val Pro Lys
    2705                2710                2715

Thr Gln
    2720
```

<210> SEQ ID NO 23
<211> LENGTH: 8286
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23

```
catatggcaa gctggtccca cccgcaattc gagaaagaag tacatcacca tcaccatcat     60
ggcgcagtgg gccagtttgc gaactttgta gacctgttgc aataccgtgc caagctgcaa    120
gcacgtaaga ccgtctttag cttcctggcg gacggcgaag cggagagcgc cgctctgacc    180
tatggtgagc tggatcaaaa ggcgcaggca atcgcggcgt tcctgcaagc aaatcaggca    240
caaggccaac gtgcattgct gctgtatccg ccaggtctgg agttcatcgg tgccttcctg    300
ggttgtctgt atgcgggtgt cgtcgcggtt ccggcatatc ctccgcgtcc gaacaagtcc    360
ttcgaccgtt tgcactccat cattcaggac gcccaagcga agtttgcact gacgacgacc    420
gagttgaagg ataagattgc agaccgtctg gaagcgctgg agggtacgga cttccattgc    480
ctggcgaccg accaagtcga gctgatcagc ggcaaaaact ggcaaaagcc gaatatctcc    540
ggtacggatc tggcgtttct gcaatacacc agcggcagca cgggtgatcc aaaaggcgtg    600
atggtcagcc accataacct gattcacaat agcggtctga ttaaccaggg tttccaagac    660
accgaagcga gcatgggtgt gtcctggctg ccgccgtatc acgacatggg tctgattggc    720
ggcatcctgc aacctatcta cgttggcgca acgcaaatcc tgatgccacc agtcgccttt    780
ctgcaacgtc cgttccgctg gctgaaggcg atcaacgatt accgtgtcag caccagcggt    840
gcgccgaact ttgcttacga cctgtgcgct tctcagatta ccccggaaca aatccgcgag    900
ctggatctga gctgttggcg tctggcattc agcggtgcag agccgattcg cgctgtcacg    960
ctggaaaact ttgcgaaaac gttcgcaacc gcgggtttcc agaaatcggc cttctaccct   1020
tgttacggta tggcggaaac caccctgatc gtgagcggtg gcaatggccg tgcccaactg   1080
ccacaggaga tcatcgttag caagcagggc attgaggcga accaagtgcg tccggctcaa   1140
ggcacggaaa cgaccgtgac cctggtgggt agcggtgagg tcattggtga ccagatcgtt   1200
aagatcgttg accctcaagc gctgaccgag tgcaccgtcg gtgaaattgg cgaggtgtgg   1260
gttaaaggtg aaagcgttgc tcagggctac tggcagaagc cggacttgac gcagcagcag   1320
ttccagggta acgtgggtgc cgaaacgggt ttcctgcgca ccggcgatct gggtttcctg   1380
caaggcggcg agctgtatat caccggccgt ctgaaggatc tgctgatcat tcgtggccgt   1440
aatcactatc ctcaggacat tgagctgacc gtggaagttg ctcacccagc cctgcgtcag   1500
ggcgcaggtg ccgcggtgag cgtggacgtt aatggtgaag aacaactggt gatcgttcaa   1560
gaggttgagc gtaagtacgc acgcaagctg aatgtggcag cagtcgctca ggccatccgt   1620
ggtgcgattg cggcagagca ccagttgcag ccgcaggcga tctgctttat caaaccgggc   1680
agcatcccga aaactagcag cggcaaaatc cgtcgtcacg catgtaaggc cggttttctg   1740
gacggaagct tggcggttgt tggtgagtgg caaccgagcc atcagaaaga gggcaaaggt   1800
attggtaccc aggcagtgac cccgagcacc acgacgtcca ccaactttcc gctgccggat   1860
caacaccagc aacagatcga ggcgtggctg aaggacaaca tcgcgcaccg cctgggtatt   1920
acgccgcagc agttggatga aacggaaccg ttcgcttctt acggtctgga cagcgttcaa   1980
gcagtccagg tcaccgcaga cctggaggac tggctgggcc gcaagctgga cccgactctg   2040
gcctatgatt acccgaccat tcgcacgctg gcgcaattcc tggttcaggg caaccaggcc   2100
ttggagaaaa tcccgcaagt tccaaagatt cagggtaaag agattgcggt ggtgggcctg   2160
agctgccgct ttccgcaggc ggacaatccg gaggcgttct gggaactgtt gcgcaatggc   2220
aaggatggcg tgcgtccgct gaaaacccgt tgggccactg gtgagtgggg tggtttcctg   2280
```

-continued gaggatatcg accagtttga gccgcagttc tttggtatta gcccgcgtga ggcggagcaa 2340
atggacccgc aacagcgtct gctgctggag gtcacctggg aggcactgga gcgtgcgaat 2400
atccctgccg aatccctgcg tcacagccag accggcgtct ttgtgggcat tagcaacagc 2460
gattacgcac aactgcaagt gcgtgagaac aacccgatca atccgtacat gggtactggt 2520
aacgcacata gcatcgcggc gaatcgtctg agctactttc tggatctgcg cggtgtctcc 2580
ctgagcattg ataccgcgtg ttctagcagc ctggtcgcag ttcatctggc gtgccaaagc 2640
ctgattaacg gcgagagcga gctggcgatt gctgcgggtg ttaatctgat tctgaccccg 2700
gatgtcacgc aaacctttac ccaagcgggt atgatgagca agacgggccg ttgccagacg 2760
tttgatgcgg aggcggacgg ctacgtgcgc ggtgaaggct gcggcgttgt tctgctgaaa 2820
ccgctggctc aggcggagcg tgatggcgac aatatcctgg cggtcatcca cggtagcgcg 2880
gttaaccagg acggtcgcag caatggtctg actgcgccga acggccgctc tcagcaagcg 2940
gttatccgtc aggccctggc gcaggcgggc atcaccgcgg cagacctggc gtatttggaa 3000
gcgcatggta cgggcacccc gctgggcgac ccgattgaaa tcaacagctt gaaagcagtg 3060
ctgcaaaccg cccagcgcga gcaaccgtgc gttgtgggca gcgtcaagac gaacattggc 3120
cacctggagg cagcagcggg tattgcaggt ctgatcaagg tgattctgtc cctggagcac 3180
ggcatgattc cgcaacacct gcactttaag caactgaatc cgcgcatcga cctggacggc 3240
ctggttacca tcgcgagcaa agaccagccg tggtcgggtg gtagccagaa gcgtttcgcc 3300
ggtgtcagca gctttggttt tggcggtacg aatgctcacg tgattgttgg tgattatgcc 3360
cagcaaaagt ccccgctggc tccgcctgcg acccaagacc gtccttggca tctgctgact 3420
ctgagcgcga agaacgcaca agcgttgaac gcgttgcaaa agagctatgg tgactacctg 3480
gcgcaacatc cgagcgttga ccctcgcgat ctgtgcctga gcgctaacac tggtcgctct 3540
ccgctgaaag aacgccgctt cttcgtgttc aagcaggttg ccgacttgca acaaaccctg 3600
aatcaggact ttctggcgca gccgaggctg agcagcccag ccaagattgc gttcctgttc 3660
acgggtcagg gcagccagta ctacggtatg ggccagcaac tgtatcagac gtccccggtt 3720
ttccgtcaag tcctggatga atgcgaccgt ctgtggcaga cgtacagccc ggaggcaccg 3780
gcgctgaccg atctgctgta cggcaatcat aatcctgacc tggttcatga aacggtttac 3840
acgcaaccgc tgctgttcgc ggtggagtat gctatcgcgc agttgtggtt gagctggggc 3900
gttactccgg atttctgcat gggtcatagc gtcggtgagt atgtggcggc ctgcctggcg 3960
ggtgtgttta gcctggcgga tggcatgaaa ctgattaccg cgcgtggtaa actgatgcat 4020
gcactgccga gcaatggcag catggcggct gtgtttgcgg acaaaaccgt tatcaagccg 4080
tatctgagcg aacacctgac cgtcggcgca gaaaatggca gccacctggt tctgagcggt 4140
aagacccctt gtctggaagc atccatccac aaactgcaaa gccagggcat caaaaccaag 4200
cctctgaaag tctcccatgc gttccactcg ccgctgatgg cgccgatgct ggcggaattt 4260
cgtgagatcg ccgaacagat tacgttccat ccgccacgta tcccgctgat tagcaacgtg 4320
acgggtggtc aaatcgaggc cgagatcgcg caagcagact attgggttaa acatgttagc 4380
cagccggtga agttcgttca gagcattcag accctggccc aagcgggtgt gaatgtgtac 4440
ctggaaatcg gtgttaaacc agtcctgctg tctatgggtc gccactgtct ggcagagcag 4500
gaagcggttt ggctgccgag cctgcgtcca catagcgagc cttggccgga aatcttgact 4560
agtctgggca aactgtacga gcaaggtctg aatatcgact ggcaaacggt tgaagccggt 4620
gatcgccgtc gtaagctgat tttgccgacc tacccgttcc agcgtcagcg ttattggttc 4680

-continued

```
aaccaaggta gctggcaaac cgtcgaaact gagagcgtga atccaggccc ggacgacctg   4740

aatgactggc tgtaccaagt ggcatggact ccgctggata cgctgccgcc tgcaccggaa   4800

ccgtcggcga aactgtggct gattctgggt gatcgtcacg atcaccaacc gattgaggcc   4860

cagttcaaaa acgcccaacg tgtgtacctg ggccaaagca accactttcc gacgaacgcc   4920

ccgtgggagg tgagcgcgga cgcactggat aacttgttta cccatgtggg tagccaaaac   4980

ctggcaggca ttctgtatct gtgcccgcct ggtgaagatc cggaggatct ggatgagatt   5040

cagaaacaaa cttccggctt tgcgttgcaa ctgattcaga ccctgtatca gcagaaaatc   5100

gcagtgccgt gttggtttgt tacccatcaa agccagcgtg tgctggaaac ggacgcggtg   5160

acgggttttg cccaaggtgg tctgtggggt ttggcgcaag cgattgcact ggaacatccg   5220

gaactgtggg gtggtatcat tgacgtggat gatagcctgc cgaacttcgc gcagatttgt   5280

cagcaacgtc aggttcagca actggctgtc cgtcaccaga aactgtatgg tgcgcaactg   5340

aagaagcagc cgagcctgcc gcagaagaat ctgcagatcc aacctcaaca gacctacctg   5400

gtcacgggcg gtttgggtgc aatcggtcgt aagattgcgc agtggctggc ggctgcgggt   5460

gctgagaaag ttatcctggt tagccgtcgt gcaccggcag cggatcaaca aaccttgccg   5520

accaacgccg tggtgtaccc gtgcgatctg gcggatgcgg cgcaggttgc gaaactgttc   5580

caaacctatc cgcacattaa gggtatcttt catgcagccg gtacgctggc tgacggtttg   5640

ctgcaacagc aaacctggca gaaattccag actgtcgctg cggcgaagat gaagggcacc   5700

tggcacctgc atcgccactc tcagaagttg gacttggatt tctttgtttt gttttcgtct   5760

gttgcgggtg tgctgggtag ccctggtcaa ggcaattacg cggcagccaa ccgtggcatg   5820

gccgccatcg ctcagtaccg ccaggctcaa ggtctgccgg cactggcgat tcactggggc   5880

ccttgggcgg aaggtggtat ggcaaacagc ttgagcaacc aaaatctggc atggttgcct   5940

ccgccgcagg gcttgaccat tctggaaaaa gttttgggtg cccaaggcga aatgggcgtg   6000

ttcaaaccgg actggcagaa cttggccaaa caattcccgg agttcgcgaa aacccattac   6060

tttgcggcgg tcattccgag cgctgaagcg gttccaccga ccgcatctat cttcgacaag   6120

ctgatcaatc tggaagcgag ccagcgcgca gattacctgc tggactatct gcgtagatct   6180

gtggcacaaa ttctgaaact ggaaattgag cagattcaga gccacgactc cctgctggat   6240

ctgggtatgg atagcctgat gatcatggag gcgattgcgt ccctgaaaca agacctgcaa   6300

ctgatgctgt atccgcgtga gatttacgag cgtccgcgtc tggatgttct gactgcttac   6360

ttggccgctg agtttaccaa agcgcatgat tctgaagcag ctaccgccgc agctgcgatc   6420

cctagccaga gcctgagcgt caaaaccaaa aagcaatggc agaaaccgga tcataagaac   6480

ccgaatccga ttgcgttcat cctgagcagc ccgcgtagcg gtagcaccct gctgcgcgtg   6540

atgctggccg gtcacccggg tctgtattcc ccaccggaac tgcacctgct gccgtttgaa   6600

acgatgggtg accgccacca ggaactgggt ctgtctcatc tgggcgaggg tctgcaacgt   6660

gccctgatgg acttggaaaa tctgacgccg gaagcatccc aggcaaaggt gaaccaatgg   6720

gtgaaggcga atacgccgat tgcagacatc tacgcatacc tgcaacgtca agccgagcaa   6780

cgtctgctga ttgacaaaag cccgagctat ggcagcgacc gccacattct ggatcacagc   6840

gagatcctgt tcgatcaggc gaaatacatc cacctggttc gccatcctta tgcggtcatt   6900

gagagcttta cccgcctgcg tatggacaag ctgctgggtg cagagcaaca gaatccgtat   6960

gcgctggcgg aaagcatttg gcgtacctcg aatcgcaaca ttctggactt gggtcgtacc   7020

gtcggcgctg accgctacct gcaagtcatc tacgaggatc tggtgcgtga cccgcgtaaa   7080
```

-continued

```
gttctgacca acatttgtga ttttctgggt gtcgatttcg acgaggcact gctgaatccg   7140

tactccggcg accgcctgac cgacggcctg caccagcaaa gcatgggtgt gggtgacccg   7200

aacttcttgc agcacaagac cattgatccg gcgctagcgg acaaatggcg tagcattacc   7260

ctgccggctg ctctgcaact ggatacgatt caactggccg aaaccttcgc atacgacctg   7320

ccgcaggagc cgcagttgac gccgcagacc caatctttgc catcgatggt cgaacgtttc   7380

gtcacggttc gcggcctgga aacctgtctg tgcgagtggg gtgatcgcca tcaacctctg   7440

gtcttgctgt tgcacggtat cctggagcaa ggcgcgtctt ggcagttgat cgcgcctcaa   7500

ctggcagcgc agggctattg ggtcgtcgct ccggatctgc gcggtcacgg taaatctgcg   7560

cacgcgcagt cttatagcat gctggatttt ctggccgatg tggacgcgct ggccaaacag   7620

ttgggcgacc gtccgttcac cttggttggt cacagcatgg gttccatcat tggcgcaatg   7680

tatgctggca ttcgtcaaac ccaggttgaa aaactgattc tggtcgaaac catcgtcccg   7740

aatgatattg atgatgccga aaccggcaat cacctgacca cccatctgga ttacctggca   7800

gcccctccgc agcacccgat ctttccgagc ctggaagttg cggctcgtcg tctgcgccaa   7860

gccaccccgc agttgccgaa agacctgtct gcatttctga cgcaacgttc cacgaagagc   7920

gtcgagaagg gtgtgcagtg gcgctgggat gccttcttgc gcacccgtgc aggtatcgag   7980

tttaacggta tcagccgtcg ccgttatctg gcgctgctga aagatatcca ggccccaatt   8040

actttgattt acggtgatca gtctgagttc aatcgcccag cagacctgca agcgatccag   8100

gcggcactgc cgcaagcgca acgcctgacg gttgctggcg gtcacaactt gcactttgag   8160

aatccgcagg ccatcgccca gattgtctat cagcagttgc agacaccggt tccgaaaacc   8220

caaggtttgc accatcacca ccatcatagc gcctggagcc acccgcagtt tgaaaagtaa   8280

gaattc                                                               8286
```

<210> SEQ ID NO 24
<211> LENGTH: 2758
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Ala Ser Trp Ser His Pro Gln Phe Glu Lys Glu Val His His His
1               5                   10                  15

His His His Gly Ala Val Gly Gln Phe Ala Asn Phe Val Asp Leu Leu
            20                  25                  30

Gln Tyr Arg Ala Lys Leu Gln Ala Arg Lys Thr Val Phe Ser Phe Leu
        35                  40                  45

Ala Asp Gly Glu Ala Glu Ser Ala Ala Leu Thr Tyr Gly Glu Leu Asp
    50                  55                  60

Gln Lys Ala Gln Ala Ile Ala Ala Phe Leu Gln Ala Asn Gln Ala Gln
65                  70                  75                  80

Gly Gln Arg Ala Leu Leu Leu Tyr Pro Pro Gly Leu Glu Phe Ile Gly
                85                  90                  95

Ala Phe Leu Gly Cys Leu Tyr Ala Gly Val Val Ala Val Pro Ala Tyr
            100                 105                 110

Pro Pro Arg Pro Asn Lys Ser Phe Asp Arg Leu His Ser Ile Ile Gln
        115                 120                 125

Asp Ala Gln Ala Lys Phe Ala Leu Thr Thr Thr Glu Leu Lys Asp Lys
    130                 135                 140
```

-continued

```
Ile Ala Asp Arg Leu Glu Ala Leu Glu Gly Thr Asp Phe His Cys Leu
145                 150                 155                 160

Ala Thr Asp Gln Val Glu Leu Ile Ser Gly Lys Asn Trp Gln Lys Pro
                165                 170                 175

Asn Ile Ser Gly Thr Asp Leu Ala Phe Leu Gln Tyr Thr Ser Gly Ser
            180                 185                 190

Thr Gly Asp Pro Lys Gly Val Met Val Ser His His Asn Leu Ile His
        195                 200                 205

Asn Ser Gly Leu Ile Asn Gln Gly Phe Gln Asp Thr Glu Ala Ser Met
    210                 215                 220

Gly Val Ser Trp Leu Pro Pro Tyr His Asp Met Gly Leu Ile Gly Gly
225                 230                 235                 240

Ile Leu Gln Pro Ile Tyr Val Gly Ala Thr Gln Ile Leu Met Pro Pro
                245                 250                 255

Val Ala Phe Leu Gln Arg Pro Phe Arg Trp Leu Lys Ala Ile Asn Asp
            260                 265                 270

Tyr Arg Val Ser Thr Ser Gly Ala Pro Asn Phe Ala Tyr Asp Leu Cys
        275                 280                 285

Ala Ser Gln Ile Thr Pro Glu Gln Ile Arg Glu Leu Asp Leu Ser Cys
    290                 295                 300

Trp Arg Leu Ala Phe Ser Gly Ala Glu Pro Ile Arg Ala Val Thr Leu
305                 310                 315                 320

Glu Asn Phe Ala Lys Thr Phe Ala Thr Ala Gly Phe Gln Lys Ser Ala
                325                 330                 335

Phe Tyr Pro Cys Tyr Gly Met Ala Glu Thr Thr Leu Ile Val Ser Gly
            340                 345                 350

Gly Asn Gly Arg Ala Gln Leu Pro Gln Glu Ile Ile Val Ser Lys Gln
        355                 360                 365

Gly Ile Glu Ala Asn Gln Val Arg Pro Ala Gln Gly Thr Glu Thr Thr
    370                 375                 380

Val Thr Leu Val Gly Ser Gly Glu Val Ile Gly Asp Gln Ile Val Lys
385                 390                 395                 400

Ile Val Asp Pro Gln Ala Leu Thr Glu Cys Thr Val Gly Glu Ile Gly
                405                 410                 415

Glu Val Trp Val Lys Gly Glu Ser Val Ala Gln Gly Tyr Trp Gln Lys
            420                 425                 430

Pro Asp Leu Thr Gln Gln Gln Phe Gln Gly Asn Val Gly Ala Glu Thr
        435                 440                 445

Gly Phe Leu Arg Thr Gly Asp Leu Gly Phe Leu Gln Gly Gly Glu Leu
    450                 455                 460

Tyr Ile Thr Gly Arg Leu Lys Asp Leu Leu Ile Ile Arg Gly Arg Asn
465                 470                 475                 480

His Tyr Pro Gln Asp Ile Glu Leu Thr Val Glu Val Ala His Pro Ala
                485                 490                 495

Leu Arg Gln Gly Ala Gly Ala Ala Val Ser Val Asp Val Asn Gly Glu
            500                 505                 510

Glu Gln Leu Val Ile Val Gln Glu Val Glu Arg Lys Tyr Ala Arg Lys
        515                 520                 525

Leu Asn Val Ala Ala Val Ala Gln Ala Ile Arg Gly Ala Ile Ala Ala
    530                 535                 540

Glu His Gln Leu Gln Pro Gln Ala Ile Cys Phe Ile Lys Pro Gly Ser
545                 550                 555                 560

Ile Pro Lys Thr Ser Ser Gly Lys Ile Arg Arg His Ala Cys Lys Ala
                565                 570                 575
```

```
Gly Phe Leu Asp Gly Ser Leu Ala Val Val Gly Glu Trp Gln Pro Ser
            580                 585                 590

His Gln Lys Glu Gly Lys Gly Ile Gly Thr Gln Ala Val Thr Pro Ser
        595                 600                 605

Thr Thr Thr Ser Thr Asn Phe Pro Leu Pro Asp Gln His Gln Gln Gln
    610                 615                 620

Ile Glu Ala Trp Leu Lys Asp Asn Ile Ala His Arg Leu Gly Ile Thr
625                 630                 635                 640

Pro Gln Gln Leu Asp Glu Thr Glu Pro Phe Ala Ser Tyr Gly Leu Asp
                645                 650                 655

Ser Val Gln Ala Val Gln Val Thr Ala Asp Leu Glu Asp Trp Leu Gly
            660                 665                 670

Arg Lys Leu Asp Pro Thr Leu Ala Tyr Asp Tyr Pro Thr Ile Arg Thr
        675                 680                 685

Leu Ala Gln Phe Leu Val Gln Gly Asn Gln Ala Leu Glu Lys Ile Pro
    690                 695                 700

Gln Val Pro Lys Ile Gln Gly Lys Glu Ile Ala Val Val Gly Leu Ser
705                 710                 715                 720

Cys Arg Phe Pro Gln Ala Asp Asn Pro Glu Ala Phe Trp Glu Leu Leu
                725                 730                 735

Arg Asn Gly Lys Asp Gly Val Arg Pro Leu Lys Thr Arg Trp Ala Thr
            740                 745                 750

Gly Glu Trp Gly Gly Phe Leu Glu Asp Ile Asp Gln Phe Glu Pro Gln
        755                 760                 765

Phe Phe Gly Ile Ser Pro Arg Glu Ala Glu Gln Met Asp Pro Gln Gln
    770                 775                 780

Arg Leu Leu Leu Glu Val Thr Trp Glu Ala Leu Glu Arg Ala Asn Ile
785                 790                 795                 800

Pro Ala Glu Ser Leu Arg His Ser Gln Thr Gly Val Phe Val Gly Ile
                805                 810                 815

Ser Asn Ser Asp Tyr Ala Gln Leu Gln Val Arg Glu Asn Asn Pro Ile
            820                 825                 830

Asn Pro Tyr Met Gly Thr Gly Asn Ala His Ser Ile Ala Ala Asn Arg
        835                 840                 845

Leu Ser Tyr Phe Leu Asp Leu Arg Gly Val Ser Leu Ser Ile Asp Thr
    850                 855                 860

Ala Cys Ser Ser Ser Leu Val Ala Val His Leu Ala Cys Gln Ser Leu
865                 870                 875                 880

Ile Asn Gly Glu Ser Glu Leu Ala Ile Ala Ala Gly Val Asn Leu Ile
                885                 890                 895

Leu Thr Pro Asp Val Thr Gln Thr Phe Thr Gln Ala Gly Met Met Ser
            900                 905                 910

Lys Thr Gly Arg Cys Gln Thr Phe Asp Ala Glu Ala Asp Gly Tyr Val
        915                 920                 925

Arg Gly Glu Gly Cys Gly Val Val Leu Leu Lys Pro Leu Ala Gln Ala
    930                 935                 940

Glu Arg Asp Gly Asp Asn Ile Leu Ala Val Ile His Gly Ser Ala Val
945                 950                 955                 960

Asn Gln Asp Gly Arg Ser Asn Gly Leu Thr Ala Pro Asn Gly Arg Ser
                965                 970                 975

Gln Gln Ala Val Ile Arg Gln Ala Leu Ala Gln Ala Gly Ile Thr Ala
            980                 985                 990

Ala Asp Leu Ala Tyr Leu Glu Ala  His Gly Thr Gly Thr  Pro Leu Gly
```

-continued 995 1000 1005

Asp Pro Ile Glu Ile Asn Ser Leu Lys Ala Val Leu Gln Thr Ala
1010 1015 1020

Gln Arg Glu Gln Pro Cys Val Val Gly Ser Val Lys Thr Asn Ile
1025 1030 1035

Gly His Leu Glu Ala Ala Ala Gly Ile Ala Gly Leu Ile Lys Val
1040 1045 1050

Ile Leu Ser Leu Glu His Gly Met Ile Pro Gln His Leu His Phe
1055 1060 1065

Lys Gln Leu Asn Pro Arg Ile Asp Leu Asp Gly Leu Val Thr Ile
1070 1075 1080

Ala Ser Lys Asp Gln Pro Trp Ser Gly Gly Ser Gln Lys Arg Phe
1085 1090 1095

Ala Gly Val Ser Ser Phe Gly Phe Gly Gly Thr Asn Ala His Val
1100 1105 1110

Ile Val Gly Asp Tyr Ala Gln Gln Lys Ser Pro Leu Ala Pro Pro
1115 1120 1125

Ala Thr Gln Asp Arg Pro Trp His Leu Leu Thr Leu Ser Ala Lys
1130 1135 1140

Asn Ala Gln Ala Leu Asn Ala Leu Gln Lys Ser Tyr Gly Asp Tyr
1145 1150 1155

Leu Ala Gln His Pro Ser Val Asp Pro Arg Asp Leu Cys Leu Ser
1160 1165 1170

Ala Asn Thr Gly Arg Ser Pro Leu Lys Glu Arg Arg Phe Phe Val
1175 1180 1185

Phe Lys Gln Val Ala Asp Leu Gln Gln Thr Leu Asn Gln Asp Phe
1190 1195 1200

Leu Ala Gln Pro Arg Leu Ser Ser Pro Ala Lys Ile Ala Phe Leu
1205 1210 1215

Phe Thr Gly Gln Gly Ser Gln Tyr Tyr Gly Met Gly Gln Gln Leu
1220 1225 1230

Tyr Gln Thr Ser Pro Val Phe Arg Gln Val Leu Asp Glu Cys Asp
1235 1240 1245

Arg Leu Trp Gln Thr Tyr Ser Pro Glu Ala Pro Ala Leu Thr Asp
1250 1255 1260

Leu Leu Tyr Gly Asn His Asn Pro Asp Leu Val His Glu Thr Val
1265 1270 1275

Tyr Thr Gln Pro Leu Leu Phe Ala Val Glu Tyr Ala Ile Ala Gln
1280 1285 1290

Leu Trp Leu Ser Trp Gly Val Thr Pro Asp Phe Cys Met Gly His
1295 1300 1305

Ser Val Gly Glu Tyr Val Ala Ala Cys Leu Ala Gly Val Phe Ser
1310 1315 1320

Leu Ala Asp Gly Met Lys Leu Ile Thr Ala Arg Gly Lys Leu Met
1325 1330 1335

His Ala Leu Pro Ser Asn Gly Ser Met Ala Ala Val Phe Ala Asp
1340 1345 1350

Lys Thr Val Ile Lys Pro Tyr Leu Ser Glu His Leu Thr Val Gly
1355 1360 1365

Ala Glu Asn Gly Ser His Leu Val Leu Ser Gly Lys Thr Pro Cys
1370 1375 1380

Leu Glu Ala Ser Ile His Lys Leu Gln Ser Gln Gly Ile Lys Thr
1385 1390 1395

-continued

```
Lys Pro  Leu Lys Val Ser His  Ala Phe His Ser Pro  Leu Met Ala
    1400                 1405                 1410

Pro Met  Leu Ala Glu Phe Arg  Glu Ile Ala Glu Gln  Ile Thr Phe
    1415                 1420                 1425

His Pro  Pro Arg Ile Pro Leu  Ile Ser Asn Val Thr  Gly Gly Gln
    1430                 1435                 1440

Ile Glu  Ala Glu Ile Ala Gln  Ala Asp Tyr Trp Val  Lys His Val
    1445                 1450                 1455

Ser Gln  Pro Val Lys Phe Val  Gln Ser Ile Gln Thr  Leu Ala Gln
    1460                 1465                 1470

Ala Gly  Val Asn Val Tyr Leu  Glu Ile Gly Val Lys  Pro Val Leu
    1475                 1480                 1485

Leu Ser  Met Gly Arg His Cys  Leu Ala Glu Gln Glu  Ala Val Trp
    1490                 1495                 1500

Leu Pro  Ser Leu Arg Pro His  Ser Glu Pro Trp Pro  Glu Ile Leu
    1505                 1510                 1515

Thr Ser  Leu Gly Lys Leu Tyr  Glu Gln Gly Leu Asn  Ile Asp Trp
    1520                 1525                 1530

Gln Thr  Val Glu Ala Gly Asp  Arg Arg Arg Lys Leu  Ile Leu Pro
    1535                 1540                 1545

Thr Tyr  Pro Phe Gln Arg Gln  Arg Tyr Trp Phe Asn  Gln Gly Ser
    1550                 1555                 1560

Trp Gln  Thr Val Glu Thr Glu  Ser Val Asn Pro Gly  Pro Asp Asp
    1565                 1570                 1575

Leu Asn  Asp Trp Leu Tyr Gln  Val Ala Trp Thr Pro  Leu Asp Thr
    1580                 1585                 1590

Leu Pro  Pro Ala Pro Glu Pro  Ser Ala Lys Leu Trp  Leu Ile Leu
    1595                 1600                 1605

Gly Asp  Arg His Asp His Gln  Pro Ile Glu Ala Gln  Phe Lys Asn
    1610                 1615                 1620

Ala Gln  Arg Val Tyr Leu Gly  Gln Ser Asn His Phe  Pro Thr Asn
    1625                 1630                 1635

Ala Pro  Trp Glu Val Ser Ala  Asp Ala Leu Asp Asn  Leu Phe Thr
    1640                 1645                 1650

His Val  Gly Ser Gln Asn Leu  Ala Gly Ile Leu Tyr  Leu Cys Pro
    1655                 1660                 1665

Pro Gly  Glu Asp Pro Glu Asp  Leu Asp Glu Ile Gln  Lys Gln Thr
    1670                 1675                 1680

Ser Gly  Phe Ala Leu Gln Leu  Ile Gln Thr Leu Tyr  Gln Gln Lys
    1685                 1690                 1695

Ile Ala  Val Pro Cys Trp Phe  Val Thr His Gln Ser  Gln Arg Val
    1700                 1705                 1710

Leu Glu  Thr Asp Ala Val Thr  Gly Phe Ala Gln Gly  Gly Leu Trp
    1715                 1720                 1725

Gly Leu  Ala Gln Ala Ile Ala  Leu Glu His Pro Glu  Leu Trp Gly
    1730                 1735                 1740

Gly Ile  Ile Asp Val Asp Asp  Ser Leu Pro Asn Phe  Ala Gln Ile
    1745                 1750                 1755

Cys Gln  Gln Arg Gln Val Gln  Gln Leu Ala Val Arg  His Gln Lys
    1760                 1765                 1770

Leu Tyr  Gly Ala Gln Leu Lys  Lys Gln Pro Ser Leu  Pro Gln Lys
    1775                 1780                 1785

Asn Leu  Gln Ile Gln Pro Gln  Gln Thr Tyr Leu Val  Thr Gly Gly
    1790                 1795                 1800
```

-continued

Leu Gly Ala Ile Gly Arg Lys Ile Ala Gln Trp Leu Ala Ala Ala
1805 1810 1815

Gly Ala Glu Lys Val Ile Leu Val Ser Arg Arg Ala Pro Ala Ala
1820 1825 1830

Asp Gln Gln Thr Leu Pro Thr Asn Ala Val Val Tyr Pro Cys Asp
1835 1840 1845

Leu Ala Asp Ala Ala Gln Val Ala Lys Leu Phe Gln Thr Tyr Pro
1850 1855 1860

His Ile Lys Gly Ile Phe His Ala Ala Gly Thr Leu Ala Asp Gly
1865 1870 1875

Leu Leu Gln Gln Gln Thr Trp Gln Lys Phe Gln Thr Val Ala Ala
1880 1885 1890

Ala Lys Met Lys Gly Thr Trp His Leu His Arg His Ser Gln Lys
1895 1900 1905

Leu Asp Leu Asp Phe Phe Val Leu Phe Ser Ser Val Ala Gly Val
1910 1915 1920

Leu Gly Ser Pro Gly Gln Gly Asn Tyr Ala Ala Ala Asn Arg Gly
1925 1930 1935

Met Ala Ala Ile Ala Gln Tyr Arg Gln Ala Gln Gly Leu Pro Ala
1940 1945 1950

Leu Ala Ile His Trp Gly Pro Trp Ala Glu Gly Gly Met Ala Asn
1955 1960 1965

Ser Leu Ser Asn Gln Asn Leu Ala Trp Leu Pro Pro Pro Gln Gly
1970 1975 1980

Leu Thr Ile Leu Glu Lys Val Leu Gly Ala Gln Gly Glu Met Gly
1985 1990 1995

Val Phe Lys Pro Asp Trp Gln Asn Leu Ala Lys Gln Phe Pro Glu
2000 2005 2010

Phe Ala Lys Thr His Tyr Phe Ala Ala Val Ile Pro Ser Ala Glu
2015 2020 2025

Ala Val Pro Pro Thr Ala Ser Ile Phe Asp Lys Leu Ile Asn Leu
2030 2035 2040

Glu Ala Ser Gln Arg Ala Asp Tyr Leu Leu Asp Tyr Leu Arg Arg
2045 2050 2055

Ser Val Ala Gln Ile Leu Lys Leu Glu Ile Glu Gln Ile Gln Ser
2060 2065 2070

His Asp Ser Leu Leu Asp Leu Gly Met Asp Ser Leu Met Ile Met
2075 2080 2085

Glu Ala Ile Ala Ser Leu Lys Gln Asp Leu Gln Leu Met Leu Tyr
2090 2095 2100

Pro Arg Glu Ile Tyr Glu Arg Pro Arg Leu Asp Val Leu Thr Ala
2105 2110 2115

Tyr Leu Ala Ala Glu Phe Thr Lys Ala His Asp Ser Glu Ala Ala
2120 2125 2130

Thr Ala Ala Ala Ala Ile Pro Ser Gln Ser Leu Ser Val Lys Thr
2135 2140 2145

Lys Lys Gln Trp Gln Lys Pro Asp His Lys Asn Pro Asn Pro Ile
2150 2155 2160

Ala Phe Ile Leu Ser Ser Pro Arg Ser Gly Ser Thr Leu Leu Arg
2165 2170 2175

Val Met Leu Ala Gly His Pro Gly Leu Tyr Ser Pro Pro Glu Leu
2180 2185 2190

His Leu Leu Pro Phe Glu Thr Met Gly Asp Arg His Gln Glu Leu 2195 2200 2205

Gly Leu Ser His Leu Gly Glu Gly Leu Gln Arg Ala Leu Met Asp
2210 2215 2220

Leu Glu Asn Leu Thr Pro Glu Ala Ser Gln Ala Lys Val Asn Gln
2225 2230 2235

Trp Val Lys Ala Asn Thr Pro Ile Ala Asp Ile Tyr Ala Tyr Leu
2240 2245 2250

Gln Arg Gln Ala Glu Gln Arg Leu Leu Ile Asp Lys Ser Pro Ser
2255 2260 2265

Tyr Gly Ser Asp Arg His Ile Leu Asp His Ser Glu Ile Leu Phe
2270 2275 2280

Asp Gln Ala Lys Tyr Ile His Leu Val Arg His Pro Tyr Ala Val
2285 2290 2295

Ile Glu Ser Phe Thr Arg Leu Arg Met Asp Lys Leu Leu Gly Ala
2300 2305 2310

Glu Gln Gln Asn Pro Tyr Ala Leu Ala Glu Ser Ile Trp Arg Thr
2315 2320 2325

Ser Asn Arg Asn Ile Leu Asp Leu Gly Arg Thr Val Gly Ala Asp
2330 2335 2340

Arg Tyr Leu Gln Val Ile Tyr Glu Asp Leu Val Arg Asp Pro Arg
2345 2350 2355

Lys Val Leu Thr Asn Ile Cys Asp Phe Leu Gly Val Asp Phe Asp
2360 2365 2370

Glu Ala Leu Leu Asn Pro Tyr Ser Gly Asp Arg Leu Thr Asp Gly
2375 2380 2385

Leu His Gln Gln Ser Met Gly Val Gly Asp Pro Asn Phe Leu Gln
2390 2395 2400

His Lys Thr Ile Asp Pro Ala Leu Ala Asp Lys Trp Arg Ser Ile
2405 2410 2415

Thr Leu Pro Ala Ala Leu Gln Leu Asp Thr Ile Gln Leu Ala Glu
2420 2425 2430

Thr Phe Ala Tyr Asp Leu Pro Gln Glu Pro Gln Leu Thr Pro Gln
2435 2440 2445

Thr Gln Ser Leu Pro Ser Met Val Glu Arg Phe Val Thr Val Arg
2450 2455 2460

Gly Leu Glu Thr Cys Leu Cys Glu Trp Gly Asp Arg His Gln Pro
2465 2470 2475

Leu Val Leu Leu Leu His Gly Ile Leu Glu Gln Gly Ala Ser Trp
2480 2485 2490

Gln Leu Ile Ala Pro Gln Leu Ala Ala Gln Gly Tyr Trp Val Val
2495 2500 2505

Ala Pro Asp Leu Arg Gly His Gly Lys Ser Ala His Ala Gln Ser
2510 2515 2520

Tyr Ser Met Leu Asp Phe Leu Ala Asp Val Asp Ala Leu Ala Lys
2525 2530 2535

Gln Leu Gly Asp Arg Pro Phe Thr Leu Val Gly His Ser Met Gly
2540 2545 2550

Ser Ile Ile Gly Ala Met Tyr Ala Gly Ile Arg Gln Thr Gln Val
2555 2560 2565

Glu Lys Leu Ile Leu Val Glu Thr Ile Val Pro Asn Asp Ile Asp
2570 2575 2580

Asp Ala Glu Thr Gly Asn His Leu Thr Thr His Leu Asp Tyr Leu
2585 2590 2595

```
Ala Ala  Pro Pro Gln His Pro  Ile Phe Pro Ser Leu  Glu Val Ala
    2600                 2605                 2610

Ala Arg  Arg Leu Arg Gln Ala  Thr Pro Gln Leu Pro  Lys Asp Leu
    2615                 2620                 2625

Ser Ala  Phe Leu Thr Gln Arg  Ser Thr Lys Ser Val  Glu Lys Gly
    2630                 2635                 2640

Val Gln  Trp Arg Trp Asp Ala  Phe Leu Arg Thr Arg  Ala Gly Ile
    2645                 2650                 2655

Glu Phe  Asn Gly Ile Ser Arg  Arg Arg Tyr Leu Ala  Leu Leu Lys
    2660                 2665                 2670

Asp Ile  Gln Ala Pro Ile Thr  Leu Ile Tyr Gly Asp  Gln Ser Glu
    2675                 2680                 2685

Phe Asn  Arg Pro Ala Asp Leu  Gln Ala Ile Gln Ala  Ala Leu Pro
    2690                 2695                 2700

Gln Ala  Gln Arg Leu Thr Val  Ala Gly Gly His Asn  Leu His Phe
    2705                 2710                 2715

Glu Asn  Pro Gln Ala Ile Ala  Gln Ile Val Tyr Gln  Gln Leu Gln
    2720                 2725                 2730

Thr Pro  Val Pro Lys Thr Gln  Gly Leu His His His  His His His
    2735                 2740                 2745

Ser Ala  Trp Ser His Pro Gln  Phe Glu Lys
    2750                 2755
```

<210> SEQ ID NO 25
<211> LENGTH: 683
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
tcatgaaaat ttacggcatt tacatggacc gtcctttgag ccaagaagaa aatgagcgtt     60

ttatgtcgtt catcagcccg gaaaaacgcg agaagtgccg tcgtttctat cataaggagg    120

atgcccatcg cacgctgctg ggtgatgttc tggttcgttc cgtgatctcc cgccaatacc    180

agctggacaa aagcgatatc cgcttttcca cccaggagta cggcaaacca tgtatcccgg    240

acctgccgga cgctcacttc aacattagcc acagcggtcg ttgggtgatt tgtgcgttcg    300

atagccagcc gattggtatt gacattgaaa agacgaagcc tattagcctg gagatcgcca    360

agcgcttctt cagcaaaacc gagtatagcg atctgctggc gaaagacaaa gacgagcaaa    420

ccgactactt ttaccacctg tggagcatga aagaaagctt tatcaagcaa gaaggtaagg    480

gtttgagctt gccgctggac agctttagcg tgcgtctgca tcaggatggt caggtcagca    540

tcgagctgcc ggactctcac tctccgtgct atattaaaac ctacgaggtc gatccgggct    600

ataaaatggc ggtttgcgca gcacacccgg actttccgga ggatatcact atggtgagct    660

atgaagagtt gctgtaagaa ttc                                            683
```

<210> SEQ ID NO 26
<211> LENGTH: 8277
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
atggcaagct ggtcccaccc gcaattcgag aaagaagtac atcaccatca ccatcatggc     60
```

-continued

```
gcagtgggcc agtttgcgaa ctttgtagac ctgttgcaat accgtgccaa gctgcaagca    120
cgtaagaccg tctttagctt cctggcggac ggcgaagcgg agagcgccgc tctgacctat    180
ggtgagctgg atcaaaaggc gcaggcaatc gcggcgttcc tgcaagcaaa tcaggcacaa    240
ggccaacgtg cattgctgct gtatccgcca ggtctggagt tcatcggtgc cttcctgggt    300
tgtctgtatg cgggtgtcgt cgcggttccg gcatatcctc cgcgtccgaa caagtccttc    360
gaccgtttgc actccatcat tcaggacgcc caagcgaagt ttgcactgac gacgaccgag    420
ttgaaggata agattgcaga ccgtctggaa gcgctggagg gtacggactt ccattgcctg    480
gcgaccgacc aagtcgagct gatcagcggc aaaaactggc aaaagccgaa tatctccggt    540
acggatctgg cgtttctgca atacaccagc ggcagcacgg gtgatccaaa aggcgtgatg    600
gtcagccacc ataacctgat tcacaatagc ggtctgttgg cggaagcgtg cgaactgacc    660
gctgcgaccc cgatgggcgg ttggctgccg atgtaccatg atatgggctt gctgggtact    720
ctgacgccag cgttgtacct gggtactacc tgtgtcctga tgtctagcac cgccttcatc    780
aaacgcccgc atctgtggct gcgcaccatt gatcgctttg gtctggtttg gtctagcgct    840
ccggatttcg cgtacgatat gtgcctgaaa cgtgttaccg atgagcagat tgcgggtctg    900
gatctgtctc gctggcgctg ggcgggtaac ggtgcagagc cgattcgcgc tgtcacgctg    960
gaaaactttg cgaaaacgtt cgcaaccgcg ggtttccaga aatcggcctt ctacccttgt   1020
tacggtatgg cggaaaccac cctgatcgtg agcggtggca atggccgtgc ccaactgcca   1080
caggagatca tcgttagcaa gcagggcatt gaggcgaacc aagtgcgtcc ggctcaaggc   1140
acggaaacga ccgtgaccct ggtgggtagc ggtgaggtca ttggtgacca gatcgttaag   1200
atcgttgacc ctcaagcgct gaccgagtgc accgtcggtg aaattggcga ggtgtgggtt   1260
aaaggtgaaa gcgttgctca gggctactgg cagaagccgg acttgacgca gcagcagttc   1320
cagggtaacg tgggtgccga aacgggtttc ctgcgcaccg gcgatctggg tttcctgcaa   1380
ggcggcgagc tgtatatcac cggccgtctg aaggatctgc tgatcattcg tggccgtaat   1440
cactatcctc aggacattga gctgaccgtg gaagttgctc acccagccct gcgtcagggc   1500
gcaggtgccg cggtgagcgt ggacgttaat ggtgaagaac aactggtgat cgttcaagag   1560
gttgagcgta agtacgcacg caagctgaat gtggcagcag tcgctcaggc catccgtggt   1620
gcgattgcgg cagagcacca gttgcagccg caggcgatct gctttatcaa accgggcagc   1680
atcccgaaaa ctagcagcgg caaaatccgt cgtcacgcat gtaaggccgg ttttctggac   1740
ggaagcttgg cggttgttgg tgagtggcaa ccgagccatc agaaagaggg caaaggtatt   1800
ggtacccagg cagtgacccc gagcaccacg acgtccacca actttccgct gccggatcaa   1860
caccagcaac agatcgaggc gtggctgaag gacaacatcg cgcaccgcct gggtattacg   1920
ccgcagcagt tggatgaaac ggaaccgttc gcttcttacg gtctggacag cgttcaagca   1980
gtccaggtca ccgcagacct ggaggactgg ctgggccgca agctggaccc gactctggcc   2040
tatgattacc cgaccattcg cacgctggcg caattcctgg ttcagggcaa ccaggccttg   2100
gagaaaatcc cgcaagttcc aaagattcag ggtaaagaga ttgcggtggt gggcctgagc   2160
tgccgctttc cgcaggcgga caatccggag gcgttctggg aactgttgcg caatggcaag   2220
gatggcgtgc gtccgctgaa aacccgttgg gccactggtg agtggggtgg tttcctggag   2280
gatatcgacc agtttgagcc gcagttcttt ggtattagcc cgcgtgaggc ggagcaaatg   2340
gacccgcaac agcgtctgct gctggaggtc acctgggagg cactggagcg tgcgaatatc   2400
cctgccgaat ccctgcgtca cagccagacc ggcgtctttg tgggcattag caacagcgat   2460
```

-continued

```
tacgcacaac tgcaagtgcg tgagaacaac ccgatcaatc cgtacatggg tactggtaac   2520
gcacatagca tcgcggcgaa tcgtctgagc tactttctgg atctgcgcgg tgtctccctg   2580
agcattgata ccgcgtgttc tagcagcctg gtcgcagttc atctggcgtg ccaaagcctg   2640
attaacggcg agagcgagct ggcgattgct gcgggtgtta atctgattct gaccccggat   2700
gtcacgcaaa cctttaccca agcgggtatg atgagcaaga cgggccgttg ccagacgttt   2760
gatgcggagg cggacggcta cgtgcgcggt gaaggctgcg gcgttgttct gctgaaaccg   2820
ctggctcagg cggagcgtga tggcgacaat atcctggcgg tcatccacgg tagcgcggtt   2880
aaccaggacg gtcgcagcaa tggtctgact gcgccgaacg gccgctctca gcaagcggtt   2940
atccgtcagg ccctggcgca ggcgggcatc accgcggcag acctggcgta tttggaagcg   3000
catggtacgg gcaccccgct gggcgacccg attgaaatca acagcttgaa agcagtgctg   3060
caaaccgccc agcgcgagca accgtgcgtt gtgggcagcg tcaagacgaa cattggccac   3120
ctggaggcag cagcgggtat tgcaggtctg atcaaggtga ttctgtccct ggagcacggc   3180
atgattccgc aacacctgca ctttaagcaa ctgaatccgc gcatcgacct ggacggcctg   3240
gttaccatcg cgagcaaaga ccagccgtgg tcgggtggta gccagaagcg tttcgccggt   3300
gtcagcagct ttggttttgg cggtacgaat gctcacgtga ttgttggtga ttatgcccag   3360
caaaagtccc cgctggctcc gcctgcgacc caagaccgtc cttggcatct gctgactctg   3420
agcgcgaaga acgcacaagc gttgaacgcg ttgcaaaaga gctatggtga ctacctggcg   3480
caacatccga gcgttgaccc tcgcgatctg tgcctgagcg ctaacactgg tcgctctccg   3540
ctgaaagaac gccgcttctt cgtgttcaag caggttgccg acttgcaaca aaccctgaat   3600
caggactttc tggcgcagcc gaggctgagc agcccagcca agattgcgtt cctgttcacg   3660
ggtcagggca gccagtacta cggtatgggc cagcaactgt atcagacgtc cccggttttc   3720
cgtcaagtcc tggatgaatg cgaccgtctg tggcagacgt acagcccgga ggcaccggcg   3780
ctgaccgatc tgctgtacgg caatcataat cctgacctgg ttcatgaaac ggtttacacg   3840
caaccgctgc tgttcgcggt ggagtatgct atcgcgcagt tgtggttgag ctggggcgtt   3900
actccggatt tctgcatggg tcatagcgtc ggtgagtatg tggcggcctg cctggcgggt   3960
gtgtttagcc tggcggatgg catgaaactg attaccgcgc gtggtaaact gatgcatgca   4020
ctgccgagca atggcagcat ggcggctgtg tttgcggaca aaaccgttat caagccgtat   4080
ctgagcgaac acctgaccgt cggcgcagaa aatggcagcc acctggttct gagcggtaag   4140
accccttgtc tggaagcatc catccacaaa ctgcaaagcc agggcatcaa aaccaagcct   4200
ctgaaagtct cccatgcgtt ccactcgccg ctgatggcgc cgatgctggc ggaatttcgt   4260
gagatcgccg aacagattac gttccatccg ccacgtatcc cgctgattag caacgtgacg   4320
ggtggtcaaa tcgaggccga gatcgcgcaa gcagactatt gggttaaaca tgttagccag   4380
ccggtgaagt tcgttcagag cattcagacc ctggcccaag cgggtgtgaa tgtgtacctg   4440
gaaatcggtg ttaaaccagt cctgctgtct atgggtcgcc actgtctggc agagcaggaa   4500
gcggtttggc tgccgagcct gcgtccacat agcgagcctt ggccggaaat cttgactagt   4560
ctgggcaaac tgtacgagca aggtctgaat atcgactggc aaacggttga agccggtgat   4620
cgccgtcgta agctgatttt gccgacctac ccgttccagc gtcagcgtta ttggttcaac   4680
caaggtagct ggcaaaccgt cgaaactgag agcgtgaatc caggcccgga cgacctgaat   4740
gactggctgt accaagtggc atggactccg ctggatacgc tgccgcctgc accggaaccg   4800
tcggcgaaac tgtggctgat tctgggtgat cgtcacgatc accaaccgat tgaggcccag   4860
```

-continued

```
ttcaaaaacg cccaacgtgt gtacctgggc caaagcaacc actttccgac gaacgccccg   4920
tgggaggtga gcgcggacgc actggataac ttgtttaccc atgtgggtag ccaaaacctg   4980
gcaggcattc tgtatctgtg cccgcctggt gaagatccgg aggatctgga tgagattcag   5040
aaacaaactt ccggctttgc gttgcaactg attcagaccc tgtatcagca gaaaatcgca   5100
gtgccgtgtt ggtttgttac ccatcaaagc cagcgtgtgc tggaaacgga cgcggtgacg   5160
ggttttgccc aaggtggtct gtggggtttg gcgcaagcga ttgcactgga acatccggaa   5220
ctgtggggtg gtatcattga cgtggatgat agcctgccga acttcgcgca gatttgtcag   5280
caacgtcagg ttcagcaact ggctgtccgt caccagaaac tgtatggtgc gcaactgaag   5340
aagcagccga gcctgccgca gaagaatctg cagatccaac ctcaacagac ctacctggtc   5400
acgggcggtt tgggtgcaat cggtcgtaag attgcgcagt ggctggcggc tgcgggtgct   5460
gagaaagtta tcctggttag ccgtcgtgca ccggcagcgg atcaacaaac cttgccgacc   5520
aacgccgtgg tgtacccgtg cgatctggcg gatgcggcgc aggttgcgaa actgttccaa   5580
acctatccgc acattaaggg tatctttcat gcagccggta cgctggctga cggtttgctg   5640
caacagcaaa cctggcagaa attccagact gtcgctgcgg cgaagatgaa gggcacctgg   5700
cacctgcatc gccactctca gaagttggac ttggatttct ttgttttgtt ttcgtctgtt   5760
gcgggtgtgc tgggtagccc tggtcaaggc aattacgcgg cagccaaccg tggcatggcc   5820
gccatcgctc agtaccgcca ggctcaaggt ctgccggcac tggcgattca ctggggccct   5880
tgggcggaag gtggtatggc aaacagcttg agcaaccaaa atctggcatg gttgcctccg   5940
ccgcagggct tgaccattct ggaaaaagtt ttgggtgccc aaggcgaaat gggcgtgttc   6000
aaaccggact ggcagaactt ggccaaacaa ttcccggagt tcgcgaaaac ccattacttt   6060
gcggcggtca ttccgagcgc tgaagcggtt ccaccgaccg catctatctt cgacaagctg   6120
atcaatctgg aagcgagcca gcgcgcagat tacctgctgg actatctgcg tagatctgtg   6180
gcacaaattc tgaaactgga aattgagcag attcagagcc acgactccct gctggatctg   6240
ggtatggata gcctgatgat catggaggcg attgcgtccc tgaaacaaga cctgcaactg   6300
atgctgtatc cgcgtgagat ttacgagcgt ccgcgtctgg atgttctgac tgcttacttg   6360
gccgctgagt ttaccaaagc gcatgattct gaagcagcta ccgccgcagc tgcgatccct   6420
agccagagcc tgagcgtcaa aaccaaaaag caatggcaga aaccggatca taagaacccg   6480
aatccgattg cgttcatcct gagcagcccg cgtagcggta gcaccctgct gcgcgtgatg   6540
ctggccggtc acccgggtct gtattcccca ccggaactgc acctgctgcc gtttgaaacg   6600
atgggtgacc gccaccagga actgggtctg tctcatctgg gcgagggtct gcaacgtgcc   6660
ctgatggact tggaaaatct gacgccggaa gcatcccagg caaaggtgaa ccaatgggtg   6720
aaggcgaata cgccgattgc agacatctac gcatacctgc aacgtcaagc cgagcaacgt   6780
ctgctgattg acaaaagccc gagctatggc agcgaccgcc acattctgga tcacagcgag   6840
atcctgttcg atcaggcgaa atacatccac ctggttcgcc atccttatgc ggtcattgag   6900
agctttaccc gcctgcgtat ggacaagctg ctgggtgcag agcaacagaa tccgtatgcg   6960
ctggcggaaa gcatttggcg tacctcgaat cgcaacattc tggacttggg tcgtaccgtc   7020
ggcgctgacc gctacctgca agtcatctac gaggatctgg tgcgtgaccc gcgtaaagtt   7080
ctgaccaaca tttgtgattt tctgggtgtc gatttcgacg aggcactgct gaatccgtac   7140
tccggcgacc gcctgaccga cggcctgcac cagcaaagca tgggtgtggg tgacccgaac   7200
ttcttgcagc acaagaccat tgatccggcg ctagcggaca aatggcgtag cattaccctg   7260
```

ccggctgctc tgcaactgga tacgattcaa ctggccgaaa ccttcgcata cgacctgccg 7320
caggagccgc agttgacgcc gcagacccaa tctttgccat cgatggtcga acgtttcgtc 7380
acggttcgcg gcctggaaac ctgtctgtgc gagtggggtg atcgccatca acctctggtc 7440
ttgctgttgc acggtatcct ggagcaaggc gcgtcttggc agttgatcgc gcctcaactg 7500
gcagcgcagg gctattgggt cgtcgctccg gatctgcgcg gtcacggtaa atctgcgcac 7560
gcgcagtctt atagcatgct ggattttctg gccgatgtgg acgcgctggc caaacagttg 7620
ggcgaccgtc cgttcacctt ggttggtcac agcatgggtt ccatcattgg cgcaatgtat 7680
gctggcattc gtcaaaccca ggttgaaaaa ctgattctgg tcgaaaccat cgtcccgaat 7740
gatattgatg atgccgaaac cggcaatcac ctgaccaccc atctggatta cctggcagcc 7800
cctccgcagc acccgatctt tccgagcctg gaagttgcgg ctcgtcgtct gcgccaagcc 7860
accccgcagt tgccgaaaga cctgtctgca tttctgacgc aacgttccac gaagagcgtc 7920
gagaagggtg tgcagtggcg ctgggatgcc ttcttgcgca cccgtgcagg tatcgagttt 7980
aacggtatca gccgtcgccg ttatctggcg ctgctgaaag atatccaggc cccaattact 8040
ttgatttacg gtgatcagtc tgagttcaat cgcccagcag acctgcaagc gatccaggcg 8100
gcactgccgc aagcgcaacg cctgacggtt gctggcggtc acaacttgca ctttgagaat 8160
ccgcaggcca tcgcccagat tgtctatcag cagttgcaga caccggttcc gaaaacccaa 8220
ggtttgcacc atcaccacca tcatagcgcc tggagccacc cgcagtttga aaagtaa 8277

<210> SEQ ID NO 27
<211> LENGTH: 8277
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
atggcaagct ggtcccaccc gcaattcgag aaaagaagtac atcaccatca ccatcatggc 60
gcagtgggcc agtttgcgaa ctttgtagac ctgttgcaat accgtgccaa gctgcaagca 120
cgtaagaccg tctttagctt cctggcggac ggcgaagcgg agagcgccgc tctgacctat 180
ggtgagctgg atcaaaaggc gcaggcaatc gcggcgttcc tgcaagcaaa tcaggcacaa 240
ggccaacgtg cattgctgct gtatccgcca ggtctggagt tcatcggtgc cttcctgggt 300
tgtctgtatg cgggtgtcgt cgcggttccg gcatatcctc cgcgtccgaa caagtccttc 360
gaccgtttgc actccatcat tcaggacgcc caagcgaagt ttgcactgac gacgaccgag 420
ttgaaggata agattgcaga ccgtctggaa gcgctggagg gtacggactt ccattgcctg 480
gcgaccgacc aagtcgagct gatcagcggc aaaaactggc aaaagccgaa tatctccggt 540
acggatctgg cgtttctgca atacaccagc ggcagcacgg gtgatccaaa aggcgtgatg 600
gtcagccacc ataacctgat tcacaatagc ggtctgattt tcacctcttt tcacatgaac 660
gatgaaacta tcattttctc gtggctgccg ccacatcacg atatgggttt gattggctgc 720
attctgaccc cgatttacgg tggtattcag gctatcatga tgagcccgtt tagcttttg 780 cagaacccgc tgtcctggct gaaacatatc actaagtaca aagcgaccat ttctggtagc 840
ccgaactttg cgtacgacta ttgcgttaaa cgcattcgcg aagaaaagaa agagggtctg 900
gatctgtcta gctgggttac cgcgttcaat ggtgcagagc cgattcgcgc tgtcacgctg 960
gaaaactttg cgaaaacgtt cgcaaccgcg ggtttccaga aatcggcctt ctacccttgt 1020

-continued

```
tacggtatgg cggaaaccac cctgatcgtg agcggtggca atggccgtgc ccaactgcca   1080
caggagatca tcgttagcaa gcagggcatt gaggcgaacc aagtgcgtcc ggctcaaggc   1140
acggaaacga ccgtgaccct ggtgggtagc ggtgaggtca ttggtgacca gatcgttaag   1200
atcgttgacc ctcaagcgct gaccgagtgc accgtcggtg aaattggcga ggtgtgggtt   1260
aaaggtgaaa gcgttgctca gggctactgg cagaagccgg acttgacgca gcagcagttc   1320
cagggtaacg tgggtgccga aacgggtttc ctgcgcaccg gcgatctggg tttcctgcaa   1380
ggcggcgagc tgtatatcac cggccgtctg aaggatctgc tgatcattcg tggccgtaat   1440
cactatcctc aggacattga gctgaccgtg gaagttgctc acccagccct gcgtcagggc   1500
gcaggtgccg cggtgagcgt ggacgttaat ggtgaagaac aactggtgat cgttcaagag   1560
gttgagcgta agtacgcacg caagctgaat gtggcagcag tcgctcaggc catccgtggt   1620
gcgattgcgg cagagcacca gttgcagccg caggcgatct gctttatcaa accgggcagc   1680
atcccgaaaa ctagcagcgg caaaatccgt cgtcacgcat gtaaggccgg ttttctggac   1740
ggaagcttgg cggttgttgg tgagtggcaa ccgagccatc agaaagaggg caaaggtatt   1800
ggtacccagg cagtgacccc gagcaccacg acgtccacca actttccgct gccggatcaa   1860
caccagcaac agatcgaggc gtggctgaag gacaacatcg cgcaccgcct gggtattacg   1920
ccgcagcagt tggatgaaac ggaaccgttc gcttcttacg gtctggacag cgttcaagca   1980
gtccaggtca ccgcagacct ggaggactgg ctgggccgca agctggaccc gactctggcc   2040
tatgattacc cgaccattcg cacgctggcg caattcctgg ttcagggcaa ccaggccttg   2100
gagaaaatcc cgcaagttcc aaagattcag ggtaaagaga ttgcggtggt gggcctgagc   2160
tgccgctttc cgcaggcgga caatccggag gcgttctggg aactgttgcg caatggcaag   2220
gatggcgtgc gtccgctgaa aacccgttgg gccactggtg agtggggtgg tttcctggag   2280
gatatcgacc agtttgagcc gcagttcttt ggtattagcc cgcgtgaggc ggagcaaatg   2340
gacccgcaac agcgtctgct gctggaggtc acctgggagg cactggagcg tgcgaatatc   2400
cctgccgaat ccctgcgtca cagccagacc ggcgtctttg tgggcattag caacagcgat   2460
tacgcacaac tgcaagtgcg tgagaacaac ccgatcaatc cgtacatggg tactggtaac   2520
gcacatagca tcgcggcgaa tcgtctgagc tactttctgg atctgcgcgg tgtctccctg   2580
agcattgata ccgcgtgttc tagcagcctg gtcgcagttc atctggcgtg ccaaagcctg   2640
attaacggcg agagcgagct ggcgattgct gcgggtgtta atctgattct gaccccggat   2700
gtcacgcaaa cctttaccca agcgggtatg atgagcaaga cgggccgttg ccagacgttt   2760
gatgcggagg cggacggcta cgtgcgcggt gaaggctgcg gcgttgttct gctgaaaccg   2820
ctggctcagg cggagcgtga tggcgacaat atcctggcgg tcatccacgg tagcgcggtt   2880
aaccaggacg gtcgcagcaa tggtctgact gcgccgaacg gccgctctca gcaagcggtt   2940
atccgtcagg ccctggcgca ggcgggcatc accgcggcag acctggcgta tttggaagcg   3000
catggtacgg gcaccccgct gggcgacccg attgaaatca acagcttgaa agcagtgctg   3060
caaaccgccc agcgcgagca accgtgcgtt gtgggcagcg tcaagacgaa cattggccac   3120
ctggaggcag cagcgggtat tgcaggtctg atcaaggtga ttctgtccct ggagcacggc   3180
atgattccgc aacacctgca ctttaagcaa ctgaatccgc gcatcgacct ggacggcctg   3240
gttaccatcg cgagcaaaga ccagccgtgg tcgggtggta gccagaagcg tttcgccggt   3300
gtcagcagct ttggttttgg cggtacgaat gctcacgtga ttgttggtga ttatgcccag   3360
caaaagtccc cgctggctcc gcctgcgacc caagaccgtc cttggcatct gctgactctg   3420
```

-continued

```
agcgcgaaga acgcacaagc gttgaacgcg ttgcaaaaga gctatggtga ctacctggcg   3480
caacatccga gcgttgaccc tcgcgatctg tgcctgagcg ctaacactgg tcgctctccg   3540
ctgaaagaac gccgcttctt cgtgttcaag caggttgccg acttgcaaca aaccctgaat   3600
caggactttc tggcgcagcc gaggctgagc agcccagcca agattgcgtt cctgttcacg   3660
ggtcagggca gccagtacta cggtatgggc cagcaactgt atcagacgtc cccggttttc   3720
cgtcaagtcc tggatgaatg cgaccgtctg tggcagacgt acagcccgga ggcaccggcg   3780
ctgaccgatc tgctgtacgg caatcataat cctgacctgg ttcatgaaac ggtttacacg   3840
caaccgctgc tgttcgcggt ggagtatgct atcgcgcagt tgtggttgag ctggggcgtt   3900
actccggatt tctgcatggg tcatagcgtc ggtgagtatg tggcggcctg cctggcgggt   3960
gtgtttagcc tggcggatgg catgaaactg attaccgcgc gtggtaaact gatgcatgca   4020
ctgccgagca atggcagcat ggcggctgtg tttgcggaca aaaccgttat caagccgtat   4080
ctgagcgaac acctgaccgt cggcgcagaa aatggcagcc acctggttct gagcggtaag   4140
accccttgtc tggaagcatc catccacaaa ctgcaaagcc agggcatcaa aaccaagcct   4200
ctgaaagtct cccatgcgtt ccactcgccg ctgatggcgc cgatgctggc ggaatttcgt   4260
gagatcgccg aacagattac gttccatccg ccacgtatcc cgctgattag caacgtgacg   4320
ggtggtcaaa tcgaggccga gatcgcgcaa gcagactatt gggttaaaca tgttagccag   4380
ccggtgaagt tcgttcagag cattcagacc ctggcccaag cgggtgtgaa tgtgtacctg   4440
gaaatcggtg ttaaaccagt cctgctgtct atgggtcgcc actgtctggc agagcaggaa   4500
gcggtttggc tgccgagcct gcgtccacat agcgagcctt ggccggaaat cttgactagt   4560
ctgggcaaac tgtacgagca aggtctgaat atcgactggc aaacggttga agccggtgat   4620
cgccgtcgta agctgatttt gccgacctac ccgttccagc gtcagcgtta ttggttcaac   4680
caaggtagct ggcaaaccgt cgaaactgag agcgtgaatc caggcccgga cgacctgaat   4740
gactggctgt accaagtggc atggactccg ctggatacgc tgccgcctgc accggaaccg   4800
tcggcgaaac tgtggctgat tctgggtgat cgtcacgatc accaaccgat tgaggcccag   4860
ttcaaaaacg cccaacgtgt gtacctgggc caaagcaacc actttccgac gaacgccccg   4920
tgggaggtga gcgcggacgc actggataac ttgtttaccc atgtgggtag ccaaaacctg   4980
gcaggcattc tgtatctgtg cccgcctggt gaagatccgg aggatctgga tgagattcag   5040
aaacaaactt ccggctttgc gttgcaactg attcagaccc tgtatcagca gaaaatcgca   5100
gtgccgtgtt ggtttgttac ccatcaaagc cagcgtgtgc tggaaacgga cgcggtgacg   5160
ggttttgccc aaggtggtct gtggggtttg gcgcaagcga ttgcactgga acatccggaa   5220
ctgtggggtg gtatcattga cgtggatgat agcctgccga acttcgcgca gatttgtcag   5280
caacgtcagg ttcagcaact ggctgtccgt caccagaaac tgtatggtgc gcaactgaag   5340
aagcagccga gcctgccgca gaagaatctg cagatccaac ctcaacagac ctacctggtc   5400
acgggcggtt tgggtgcaat cggtcgtaag attgcgcagt ggctggcggc tgcgggtgct   5460
gagaaagtta tcctggttag ccgtcgtgca ccggcagcgg atcaacaaac cttgccgacc   5520
aacgccgtgg tgtacccgtg cgatctggcg gatgcggcgc aggttgcgaa actgttccaa   5580
acctatccgc acattaaggg tatctttcat gcagccggta cgctggctga cggtttgctg   5640
caacagcaaa cctggcagaa attccagact gtcgctgcgg cgaagatgaa gggcacctgg   5700
cacctgcatc gccactctca gaagttggac ttggatttct ttgttttgtt ttcgtctgtt   5760
gcgggtgtgc tgggtagccc tggtcaaggc aattacgcgg cagccaaccg tggcatggcc   5820
```

-continued

```
gccatcgctc agtaccgcca ggctcaaggt ctgccggcac tggcgattca ctggggccct   5880
tgggcggaag gtggtatggc aaacagcttg agcaaccaaa atctggcatg gttgcctccg   5940
ccgcagggct tgaccattct ggaaaaagtt ttgggtgccc aaggcgaaat gggcgtgttc   6000
aaaccggact ggcagaactt ggccaaacaa ttcccggagt tcgcgaaaac ccattacttt   6060
gcggcggtca ttccgagcgc tgaagcggtt ccaccgaccg catctatctt cgacaagctg   6120
atcaatctgg aagcgagcca gcgcgcagat tacctgctgg actatctgcg tagatctgtg   6180
gcacaaattc tgaaactgga aattgagcag attcagagcc acgactccct gctggatctg   6240
ggtatggata gcctgatgat catggaggcg attgcgtccc tgaaacaaga cctgcaactg   6300
atgctgtatc cgcgtgagat ttacgagcgt ccgcgtctgg atgttctgac tgcttacttg   6360
gccgctgagt ttaccaaagc gcatgattct gaagcagcta ccgccgcagc tgcgatccct   6420
agccagagcc tgagcgtcaa aaccaaaaag caatggcaga aaccggatca taagaacccg   6480
aatccgattg cgttcatcct gagcagcccg cgtagcggta gcaccctgct gcgcgtgatg   6540
ctggccggtc acccgggtct gtattcccca ccggaactgc acctgctgcc gtttgaaacg   6600
atgggtgacc gccaccagga actgggtctg tctcatctgg gcgagggtct gcaacgtgcc   6660
ctgatggact tggaaaatct gacgccggaa gcatcccagg caaaggtgaa ccaatgggtg   6720
aaggcgaata cgccgattgc agacatctac gcatacctgc aacgtcaagc cgagcaacgt   6780
ctgctgattg acaaaagccc gagctatggc agcgaccgcc acattctgga tcacagcgag   6840
atcctgttcg atcaggcgaa atacatccac ctggttcgcc atccttatgc ggtcattgag   6900
agctttaccc gcctgcgtat ggacaagctg ctgggtgcag agcaacagaa tccgtatgcg   6960
ctggcggaaa gcatttggcg tacctcgaat cgcaacattc tggacttggg tcgtaccgtc   7020
ggcgctgacc gctacctgca agtcatctac gaggatctgg tgcgtgaccc gcgtaaagtt   7080
ctgaccaaca tttgtgattt tctgggtgtc gatttcgacg aggcactgct gaatccgtac   7140
tccggcgacc gcctgaccga cggcctgcac cagcaaagca tgggtgtggg tgacccgaac   7200
ttcttgcagc acaagaccat tgatccggcg ctagcggaca aatggcgtag cattaccctg   7260
ccggctgctc tgcaactgga tacgattcaa ctggccgaaa ccttcgcata cgacctgccg   7320
caggagccgc agttgacgcc gcagacccaa tctttgccat cgatggtcga acgtttcgtc   7380
acggttcgcg gcctggaaac ctgtctgtgc gagtggggtg atcgccatca acctctggtc   7440
ttgctgttgc acggtatcct ggagcaaggc gcgtcttggc agttgatcgc gcctcaactg   7500
gcagcgcagg gctattgggt cgtcgctccg gatctgcgcg gtcacggtaa atctgcgcac   7560
gcgcagtctt atagcatgct ggattttctg gccgatgtgg acgcgctggc caaacagttg   7620
ggcgaccgtc cgttcacctt ggttggtcac agcatgggtt ccatcattgg cgcaatgtat   7680
gctggcattc gtcaaaccca ggttgaaaaa ctgattctgg tcgaaaccat cgtcccgaat   7740
gatattgatg atgccgaaac cggcaatcac ctgaccaccc atctggatta cctggcagcc   7800
cctccgcagc acccgatctt tccgagcctg gaagttgcgg ctcgtcgtct gcgccaagcc   7860
accccgcagt tgccgaaaga cctgtctgca tttctgacgc aacgttccac gaagagcgtc   7920
gagaagggtg tgcagtggcg ctgggatgcc ttcttgcgca cccgtgcagg tatcgagttt   7980
aacggtatca gccgtcgccg ttatctggcg ctgctgaaag atatccaggc cccaattact   8040
ttgatttacg gtgatcagtc tgagttcaat cgcccagcag acctgcaagc gatccaggcg   8100
gcactgccgc aagcgcaacg cctgacggtt gctggcggtc acaacttgca ctttgagaat   8160
ccgcaggcca tcgcccagat tgtctatcag cagttgcaga caccggttcc gaaaacccaa   8220
```

ggtttgcacc atcaccacca tcatagcgcc tggagccacc cgcagtttga aaagtaa 8277

<210> SEQ ID NO 28
<211> LENGTH: 8277
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 28
atggcaagct ggtcccaccc gcaattcgag aaagaagtac atcaccatca ccatcatggc 60
gcagtgggcc agtttgcgaa ctttgtagac ctgttgcaat accgtgccaa gctgcaagca 120
cgtaagaccg tctttagctt cctggcggac ggcgaagcgg agagcgccgc tctgacctat 180
ggtgagctgg atcaaaaggc gcaggcaatc gcggcgttcc tgcaagcaaa tcaggcacaa 240
ggccaacgtg cattgctgct gtatccgcca ggtctggagt tcatcggtgc cttcctgggt 300
tgtctgtatg cgggtgtcgt cgcggttccg gcatatcctc cgcgtccgaa caagtccttc 360
gaccgtttgc actccatcat tcaggacgcc caagcgaagt ttgcactgac gacgaccgag 420
ttgaaggata agattgcaga ccgtctggaa gcgctggagg gtacggactt ccattgcctg 480
gcgaccgacc aagtcgagct gatcagcggc aaaaactggc aaaagccgaa tatctccggt 540
acggatctgg cgtttctgca atacaccagc ggcagcacgg gtgatccaaa aggcgtgatg 600
gtcagccacc ataacctgat tcacaatagc ggtctgattc gcaacgcgct ggcgattgat 660
ctgaaagata ccctgctgtc ttggatgccg ttgactcacg atatgggttt gattgcgtgc 720
catctggttc cggcgctggc gggcattaac cagaatttga tgccgactga actgttcatt 780
cgtcgcccga ttctgtggat gaagaaagct cacgaacata aagcgtctat tctgtctagc 840
ccgaatttcg gttacaacta ctttctgaaa ttcctgaaag acaacaaaag ctacgattgg 900
gatctgtccc atattcgcgt tatcgcgaac ggtgcagagc cgattcgcgc tgtcacgctg 960
gaaaactttg cgaaaacgtt cgcaaccgcg ggtttccaga aatcggcctt ctacccttgt 1020
tacggtatgg cggaaaccac cctgatcgtg agcggtggca atggccgtgc ccaactgcca 1080
caggagatca tcgttagcaa gcagggcatt gaggcgaacc aagtgcgtcc ggctcaaggc 1140
acggaaacga ccgtgaccct ggtgggtagc ggtgaggtca ttggtgacca gatcgttaag 1200
atcgttgacc ctcaagcgct gaccgagtgc accgtcggtg aaattggcga ggtgtgggtt 1260
aaaggtgaaa gcgttgctca gggctactgg cagaagccgg acttgacgca gcagcagttc 1320
cagggtaacg tgggtgccga aacgggtttc ctgcgcaccg gcgatctggg tttcctgcaa 1380
ggcggcgagc tgtatatcac cggccgtctg aaggatctgc tgatcattcg tggccgtaat 1440
cactatcctc aggacattga gctgaccgtg gaagttgctc acccagccct gcgtcagggc 1500
gcaggtgccg cggtgagcgt ggacgttaat ggtgaagaac aactggtgat cgttcaagag 1560
gttgagcgta agtacgcacg caagctgaat gtggcagcag tcgctcaggc catccgtggt 1620
gcgattgcgg cagagcacca gttgcagccg caggcgatct gctttatcaa accgggcagc 1680
atcccgaaaa ctagcagcgg caaaatccgt cgtcacgcat gtaaggccgg ttttctggac 1740
ggaagcttgg cggttgttgg tgagtggcaa ccgagccatc agaaagaggg caaaggtatt 1800
ggtacccagg cagtgacccc gagcaccacg acgtccacca actttccgct gccggatcaa 1860
caccagcaac agatcgaggc gtggctgaag gacaacatcg cgcaccgcct gggtattacg 1920
ccgcagcagt tggatgaaac ggaaccgttc gcttcttacg gtctggacag cgttcaagca 1980
gtccaggtca ccgcagacct ggaggactgg ctgggccgca agctggaccc gactctggcc 2040

-continued

```
tatgattacc cgaccattcg cacgctggcg caattcctgg ttcagggcaa ccaggccttg   2100
gagaaaatcc cgcaagttcc aaagattcag ggtaaagaga ttgcggtggt gggcctgagc   2160
tgccgctttc cgcaggcgga caatccggag gcgttctggg aactgttgcg caatggcaag   2220
gatggcgtgc gtccgctgaa aacccgttgg gccactggtg agtggggtgg tttcctggag   2280
gatatcgacc agtttgagcc gcagttcttt ggtattagcc cgcgtgaggc ggagcaaatg   2340
gacccgcaac agcgtctgct gctggaggtc acctgggagg cactggagcg tgcgaatatc   2400
cctgccgaat ccctgcgtca cagccagacc ggcgtctttg tgggcattag caacagcgat   2460
tacgcacaac tgcaagtgcg tgagaacaac ccgatcaatc cgtacatggg tactggtaac   2520
gcacatagca tcgcggcgaa tcgtctgagc tactttctgg atctgcgcgg tgtctccctg   2580
agcattgata ccgcgtgttc tagcagcctg gtcgcagttc atctggcgtg ccaaagcctg   2640
attaacggcg agagcgagct ggcgattgct gcgggtgtta atctgattct gaccccggat   2700
gtcacgcaaa cctttaccca agcgggtatg atgagcaaga cgggccgttg ccagacgttt   2760
gatgcggagg cggacggcta cgtgcgcggt gaaggctgcg gcgttgttct gctgaaaccg   2820
ctggctcagg cggagcgtga tggcgacaat atcctggcgg tcatccacgg tagcgcggtt   2880
aaccaggacg gtcgcagcaa tggtctgact gcgccgaacg gccgctctca gcaagcggtt   2940
atccgtcagg ccctggcgca ggcgggcatc accgcggcag acctggcgta tttggaagcg   3000
catggtacgg gcaccccgct gggcgacccg attgaaatca acagcttgaa agcagtgctg   3060
caaaccgccc agcgcgagca accgtgcgtt gtgggcagcg tcaagacgaa cattggccac   3120
ctggaggcag cagcgggtat tgcaggtctg atcaaggtga ttctgtccct ggagcacggc   3180
atgattccgc aacacctgca ctttaagcaa ctgaatccgc gcatcgacct ggacggcctg   3240
gttaccatcg cgagcaaaga ccagccgtgg tcgggtggta gccagaagcg tttcgccggt   3300
gtcagcagct ttggttttgg cggtacgaat gctcacgtga ttgttggtga ttatgcccag   3360
caaaagtccc cgctggctcc gcctgcgacc caagaccgtc cttggcatct gctgactctg   3420
agcgcgaaga acgcacaagc gttgaacgcg ttgcaaaaga gctatggtga ctacctggcg   3480
caacatccga gcgttgaccc tcgcgatctg tgcctgagcg ctaacactgg tcgctctccg   3540
ctgaaagaac gccgcttctt cgtgttcaag caggttgccg acttgcaaca aaccctgaat   3600
caggactttc tggcgcagcc gaggctgagc agcccagcca agattgcgtt cctgttcacg   3660
ggtcagggca gccagtacta cggtatgggc cagcaactgt atcagacgtc cccggttttc   3720
cgtcaagtcc tggatgaatg cgaccgtctg tggcagacgt acagcccgga ggcaccggcg   3780
ctgaccgatc tgctgtacgg caatcataat cctgacctgg ttcatgaaac ggtttacacg   3840
caaccgctgc tgttcgcggt ggagtatgct atcgcgcagt tgtggttgag ctggggcgtt   3900
actccggatt tctgcatggg tcatagcgtc ggtgagtatg tggcggcctg cctggcgggt   3960
gtgtttagcc tggcggatgg catgaaactg attaccgcgc gtggtaaact gatgcatgca   4020
ctgccgagca atggcagcat ggcggctgtg tttgcggaca aaaccgttat caagccgtat   4080
ctgagcgaac acctgaccgt cggcgcagaa aatggcagcc acctggttct gagcggtaag   4140
accccttgtc tggaagcatc catccacaaa ctgcaaagcc agggcatcaa aaccaagcct   4200
ctgaaagtct cccatgcgtt ccactcgccg ctgatggcgc cgatgctggc ggaatttcgt   4260
gagatcgccg aacagattac gttccatccg ccacgtatcc cgctgattag caacgtgacg   4320
ggtggtcaaa tcgaggccga gatcgcgcaa gcagactatt gggttaaaca tgttagccag   4380
ccggtgaagt tcgttcagag cattcagacc ctggcccaag cgggtgtgaa tgtgtacctg   4440
```

gaaatcggtg ttaaaccagt cctgctgtct atgggtcgcc actgtctggc agagcaggaa 4500
gcggtttggc tgccgagcct gcgtccacat agcgagcctt ggccggaaat cttgactagt 4560
ctgggcaaac tgtacgagca aggtctgaat atcgactggc aaacggttga agccggtgat 4620
cgccgtcgta agctgatttt gccgacctac ccgttccagc gtcagcgtta ttggttcaac 4680
caaggtagct ggcaaaccgt cgaaactgag agcgtgaatc caggcccgga cgacctgaat 4740
gactggctgt accaagtggc atggactccg ctggatacgc tgccgcctgc accggaaccg 4800
tcggcgaaac tgtggctgat tctgggtgat cgtcacgatc accaaccgat tgaggcccag 4860
ttcaaaaacg cccaacgtgt gtacctgggc caaagcaacc actttccgac gaacgccccg 4920
tgggaggtga gcgcggacgc actggataac ttgtttaccc atgtgggtag ccaaaacctg 4980
gcaggcattc tgtatctgtg cccgcctggt gaagatccgg aggatctgga tgagattcag 5040
aaacaaactt ccggctttgc gttgcaactg attcagaccc tgtatcagca gaaaatcgca 5100
gtgccgtgtt ggtttgttac ccatcaaagc cagcgtgtgc tggaaacgga cgcggtgacg 5160
ggttttgccc aaggtggtct gtggggtttg gcgcaagcga ttgcactgga acatccggaa 5220
ctgtggggtg gtatcattga cgtggatgat agcctgccga acttcgcgca gatttgtcag 5280
caacgtcagg ttcagcaact ggctgtccgt caccagaaac tgtatggtgc gcaactgaag 5340
aagcagccga gcctgccgca gaagaatctg cagatccaac ctcaacagac ctacctggtc 5400
acgggcggtt tgggtgcaat cggtcgtaag attgcgcagt ggctggcggc tgcgggtgct 5460
gagaaagtta tcctggttag ccgtcgtgca ccggcagcgg atcaacaaac cttgccgacc 5520
aacgccgtgg tgtacccgtg cgatctggcg gatgcggcgc aggttgcgaa actgttccaa 5580
acctatccgc acattaaggg tatctttcat gcagccggta cgctggctga cggtttgctg 5640
caacagcaaa cctggcagaa attccagact gtcgctgcgg cgaagatgaa gggcacctgg 5700
cacctgcatc gccactctca gaagttggac ttggatttct ttgttttgtt ttcgtctgtt 5760
gcgggtgtgc tgggtagccc tggtcaaggc aattacgcgg cagccaaccg tggcatggcc 5820
gccatcgctc agtaccgcca ggctcaaggt ctgccggcac tggcgattca ctggggccct 5880
tgggcggaag gtggtatggc aaacagcttg agcaaccaaa atctggcatg gttgcctccg 5940
ccgcagggct tgaccattct ggaaaaagtt ttgggtgccc aaggcgaaat gggcgtgttc 6000
aaaccggact ggcagaactt ggccaaacaa ttcccggagt tcgcgaaaac ccattacttt 6060
gcggcggtca ttccgagcgc tgaagcggtt ccaccgaccg catctatctt cgacaagctg 6120
atcaatctgg aagcgagcca gcgcgcagat tacctgctgg actatctgcg tagatctgtg 6180
gcacaaattc tgaaactgga aattgagcag attcagagcc acgactccct gctggatctg 6240
ggtatggata gcctgatgat catggaggcg attgcgtccc tgaaacaaga cctgcaactg 6300
atgctgtatc cgcgtgagat ttacgagcgt ccgcgtctgg atgttctgac tgcttacttg 6360
gccgctgagt ttaccaaagc gcatgattct gaagcagcta ccgccgcagc tgcgatccct 6420
agccagagcc tgagcgtcaa aaccaaaaag caatggcaga aaccggatca taagaacccg 6480
aatccgattg cgttcatcct gagcagcccg cgtagcggta gcaccctgct gcgcgtgatg 6540
ctggccggtc acccgggtct gtattcccca ccggaactgc acctgctgcc gtttgaaacg 6600
atgggtgacc gccaccagga actgggtctg tctcatctgg gcgagggtct gcaacgtgcc 6660
ctgatggact tggaaaatct gacgccggaa gcatcccagg caaaggtgaa ccaatgggtg 6720
aaggcgaata cgccgattgc agacatctac gcatacctgc aacgtcaagc cgagcaacgt 6780
ctgctgattg acaaaagccc gagctatggc agcgaccgcc acattctgga tcacagcgag 6840
atcctgttcg atcaggcgaa atacatccac ctggttcgcc atccttatgc ggtcattgag 6900
agctttaccc gcctgcgtat ggacaagctg ctgggtgcag agcaacagaa tccgtatgcg 6960
ctggcggaaa gcatttggcg tacctcgaat cgcaacattc tggacttggg tcgtaccgtc 7020
ggcgctgacc gctacctgca agtcatctac gaggatctgg tgcgtgaccc gcgtaaagtt 7080
ctgaccaaca tttgtgattt tctgggtgtc gatttcgacg aggcactgct gaatccgtac 7140
tccggcgacc gcctgaccga cggcctgcac cagcaaagca tgggtgtggg tgacccgaac 7200
ttcttgcagc acaagaccat tgatccggcg ctagcggaca aatggcgtag cattaccctg 7260
ccggctgctc tgcaactgga tacgattcaa ctggccgaaa ccttcgcata cgacctgccg 7320
caggagccgc agttgacgcc gcagacccaa tctttgccat cgatggtcga acgtttcgtc 7380
acggttcgcg gcctggaaac ctgtctgtgc gagtggggtg atcgccatca acctctggtc 7440
ttgctgttgc acggtatcct ggagcaaggc gcgtcttggc agttgatcgc gcctcaactg 7500
gcagcgcagg gctattgggt cgtcgctccg gatctgcgcg gtcacggtaa atctgcgcac 7560
gcgcagtctt atagcatgct ggattttctg gccgatgtgg acgcgctggc caaacagttg 7620
ggcgaccgtc cgttcacctt ggttggtcac agcatgggtt ccatcattgg cgcaatgtat 7680
gctggcattc gtcaaaccca ggttgaaaaa ctgattctgg tcgaaaccat cgtcccgaat 7740
gatattgatg atgccgaaac cggcaatcac ctgaccaccc atctggatta cctggcagcc 7800
cctccgcagc acccgatctt tccgagcctg gaagttgcgg ctcgtcgtct gcgccaagcc 7860
accccgcagt tgccgaaaga cctgtctgca tttctgacgc aacgttccac gaagagcgtc 7920
gagaagggtg tgcagtggcg ctgggatgcc ttcttgcgca cccgtgcagg tatcgagttt 7980
aacggtatca gccgtcgccg ttatctggcg ctgctgaaag atatccaggc cccaattact 8040
ttgatttacg gtgatcagtc tgagttcaat cgcccagcag acctgcaagc gatccaggcg 8100
gcactgccgc aagcgcaacg cctgacggtt gctggcggtc acaacttgca ctttgagaat 8160
ccgcaggcca tcgcccagat tgtctatcag cagttgcaga caccggttcc gaaaacccaa 8220
ggtttgcacc atcaccacca tcatagcgcc tggagccacc cgcagtttga aaagtaa 8277

<210> SEQ ID NO 29
<211> LENGTH: 2758
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Met Ala Ser Trp Ser His Pro Gln Phe Glu Lys Glu Val His His His
1 5 10 15

His His His Gly Ala Val Gly Gln Phe Ala Asn Phe Val Asp Leu Leu
20 25 30

Gln Tyr Arg Ala Lys Leu Gln Ala Arg Lys Thr Val Phe Ser Phe Leu
35 40 45

Ala Asp Gly Glu Ala Glu Ser Ala Ala Leu Thr Tyr Gly Glu Leu Asp
50 55 60

Gln Lys Ala Gln Ala Ile Ala Ala Phe Leu Gln Ala Asn Gln Ala Gln
65 70 75 80

Gly Gln Arg Ala Leu Leu Leu Tyr Pro Pro Gly Leu Glu Phe Ile Gly
85 90 95

Ala Phe Leu Gly Cys Leu Tyr Ala Gly Val Val Ala Val Pro Ala Tyr
100 105 110

-continued

```
Pro Pro Arg Pro Asn Lys Ser Phe Asp Arg Leu His Ser Ile Ile Gln
        115                 120                 125

Asp Ala Gln Ala Lys Phe Ala Leu Thr Thr Thr Glu Leu Lys Asp Lys
    130                 135                 140

Ile Ala Asp Arg Leu Glu Ala Leu Glu Gly Thr Asp Phe His Cys Leu
145                 150                 155                 160

Ala Thr Asp Gln Val Glu Leu Ile Ser Gly Lys Asn Trp Gln Lys Pro
                165                 170                 175

Asn Ile Ser Gly Thr Asp Leu Ala Phe Leu Gln Tyr Thr Ser Gly Ser
            180                 185                 190

Thr Gly Asp Pro Lys Gly Val Met Val Ser His His Asn Leu Ile His
        195                 200                 205

Asn Ser Gly Leu Leu Ala Glu Ala Cys Glu Leu Thr Ala Ala Thr Pro
    210                 215                 220

Met Gly Gly Trp Leu Pro Met Tyr His Asp Met Gly Leu Leu Gly Thr
225                 230                 235                 240

Leu Thr Pro Ala Leu Tyr Leu Gly Thr Thr Cys Val Leu Met Ser Ser
                245                 250                 255

Thr Ala Phe Ile Lys Arg Pro His Leu Trp Leu Arg Thr Ile Asp Arg
            260                 265                 270

Phe Gly Leu Val Trp Ser Ser Ala Pro Asp Phe Ala Tyr Asp Met Cys
        275                 280                 285

Leu Lys Arg Val Thr Asp Glu Gln Ile Ala Gly Leu Asp Leu Ser Arg
    290                 295                 300

Trp Arg Trp Ala Gly Asn Gly Ala Glu Pro Ile Arg Ala Val Thr Leu
305                 310                 315                 320

Glu Asn Phe Ala Lys Thr Phe Ala Thr Ala Gly Phe Gln Lys Ser Ala
                325                 330                 335

Phe Tyr Pro Cys Tyr Gly Met Ala Glu Thr Thr Leu Ile Val Ser Gly
            340                 345                 350

Gly Asn Gly Arg Ala Gln Leu Pro Gln Glu Ile Ile Val Ser Lys Gln
        355                 360                 365

Gly Ile Glu Ala Asn Gln Val Arg Pro Ala Gln Gly Thr Glu Thr Thr
    370                 375                 380

Val Thr Leu Val Gly Ser Gly Glu Val Ile Gly Asp Gln Ile Val Lys
385                 390                 395                 400

Ile Val Asp Pro Gln Ala Leu Thr Glu Cys Thr Val Gly Glu Ile Gly
                405                 410                 415

Glu Val Trp Val Lys Gly Glu Ser Val Ala Gln Gly Tyr Trp Gln Lys
            420                 425                 430

Pro Asp Leu Thr Gln Gln Gln Phe Gln Gly Asn Val Gly Ala Glu Thr
        435                 440                 445

Gly Phe Leu Arg Thr Gly Asp Leu Gly Phe Leu Gln Gly Gly Glu Leu
    450                 455                 460

Tyr Ile Thr Gly Arg Leu Lys Asp Leu Leu Ile Ile Arg Gly Arg Asn
465                 470                 475                 480

His Tyr Pro Gln Asp Ile Glu Leu Thr Val Glu Val Ala His Pro Ala
                485                 490                 495

Leu Arg Gln Gly Ala Gly Ala Ala Val Ser Val Asp Val Asn Gly Glu
            500                 505                 510

Glu Gln Leu Val Ile Val Gln Glu Val Glu Arg Lys Tyr Ala Arg Lys
        515                 520                 525

Leu Asn Val Ala Ala Val Ala Gln Ala Ile Arg Gly Ala Ile Ala Ala
```

```
    530                 535                 540

Glu His Gln Leu Gln Pro Gln Ala Ile Cys Phe Ile Lys Pro Gly Ser
545                 550                 555                 560

Ile Pro Lys Thr Ser Ser Gly Lys Ile Arg Arg His Ala Cys Lys Ala
                565                 570                 575

Gly Phe Leu Asp Gly Ser Leu Ala Val Val Gly Glu Trp Gln Pro Ser
            580                 585                 590

His Gln Lys Glu Gly Lys Gly Ile Gly Thr Gln Ala Val Thr Pro Ser
        595                 600                 605

Thr Thr Thr Ser Thr Asn Phe Pro Leu Pro Asp Gln His Gln Gln Gln
    610                 615                 620

Ile Glu Ala Trp Leu Lys Asp Asn Ile Ala His Arg Leu Gly Ile Thr
625                 630                 635                 640

Pro Gln Gln Leu Asp Glu Thr Glu Pro Phe Ala Ser Tyr Gly Leu Asp
                645                 650                 655

Ser Val Gln Ala Val Gln Val Thr Ala Asp Leu Glu Asp Trp Leu Gly
            660                 665                 670

Arg Lys Leu Asp Pro Thr Leu Ala Tyr Asp Tyr Pro Thr Ile Arg Thr
        675                 680                 685

Leu Ala Gln Phe Leu Val Gln Gly Asn Gln Ala Leu Glu Lys Ile Pro
    690                 695                 700

Gln Val Pro Lys Ile Gln Gly Lys Glu Ile Ala Val Val Gly Leu Ser
705                 710                 715                 720

Cys Arg Phe Pro Gln Ala Asp Asn Pro Glu Ala Phe Trp Glu Leu Leu
                725                 730                 735

Arg Asn Gly Lys Asp Gly Val Arg Pro Leu Lys Thr Arg Trp Ala Thr
            740                 745                 750

Gly Glu Trp Gly Gly Phe Leu Glu Asp Ile Asp Gln Phe Glu Pro Gln
        755                 760                 765

Phe Phe Gly Ile Ser Pro Arg Glu Ala Glu Gln Met Asp Pro Gln Gln
    770                 775                 780

Arg Leu Leu Leu Glu Val Thr Trp Glu Ala Leu Glu Arg Ala Asn Ile
785                 790                 795                 800

Pro Ala Glu Ser Leu Arg His Ser Gln Thr Gly Val Phe Val Gly Ile
                805                 810                 815

Ser Asn Ser Asp Tyr Ala Gln Leu Gln Val Arg Glu Asn Asn Pro Ile
            820                 825                 830

Asn Pro Tyr Met Gly Thr Gly Asn Ala His Ser Ile Ala Ala Asn Arg
        835                 840                 845

Leu Ser Tyr Phe Leu Asp Leu Arg Gly Val Ser Leu Ser Ile Asp Thr
    850                 855                 860

Ala Cys Ser Ser Ser Leu Val Ala Val His Leu Ala Cys Gln Ser Leu
865                 870                 875                 880

Ile Asn Gly Glu Ser Glu Leu Ala Ile Ala Ala Gly Val Asn Leu Ile
                885                 890                 895

Leu Thr Pro Asp Val Thr Gln Thr Phe Thr Gln Ala Gly Met Met Ser
            900                 905                 910

Lys Thr Gly Arg Cys Gln Thr Phe Asp Ala Glu Ala Asp Gly Tyr Val
        915                 920                 925

Arg Gly Glu Gly Cys Gly Val Val Leu Leu Lys Pro Leu Ala Gln Ala
    930                 935                 940

Glu Arg Asp Gly Asp Asn Ile Leu Ala Val Ile His Gly Ser Ala Val
945                 950                 955                 960
```

-continued

```
Asn Gln Asp Gly Arg Ser Asn Gly Leu Thr Ala Pro Asn Gly Arg Ser
                965                 970                 975

Gln Gln Ala Val Ile Arg Gln Ala Leu Ala Gln Ala Gly Ile Thr Ala
            980                 985                 990

Ala Asp Leu Ala Tyr Leu Glu Ala  His Gly Thr Gly Thr  Pro Leu Gly
        995                 1000                 1005

Asp Pro  Ile Glu Ile Asn Ser  Leu Lys Ala Val Leu  Gln Thr Ala
    1010                 1015                 1020

Gln Arg  Glu Gln Pro Cys Val  Val Gly Ser Val Lys  Thr Asn Ile
    1025                 1030                 1035

Gly His  Leu Glu Ala Ala Ala  Gly Ile Ala Gly Leu  Ile Lys Val
    1040                 1045                 1050

Ile Leu  Ser Leu Glu His Gly  Met Ile Pro Gln His  Leu His Phe
    1055                 1060                 1065

Lys Gln  Leu Asn Pro Arg Ile  Asp Leu Asp Gly Leu  Val Thr Ile
    1070                 1075                 1080

Ala Ser  Lys Asp Gln Pro Trp  Ser Gly Gly Ser Gln  Lys Arg Phe
    1085                 1090                 1095

Ala Gly  Val Ser Ser Phe Gly  Phe Gly Gly Thr Asn  Ala His Val
    1100                 1105                 1110

Ile Val  Gly Asp Tyr Ala Gln  Gln Lys Ser Pro Leu  Ala Pro Pro
    1115                 1120                 1125

Ala Thr  Gln Asp Arg Pro Trp  His Leu Leu Thr Leu  Ser Ala Lys
    1130                 1135                 1140

Asn Ala  Gln Ala Leu Asn Ala  Leu Gln Lys Ser Tyr  Gly Asp Tyr
    1145                 1150                 1155

Leu Ala  Gln His Pro Ser Val  Asp Pro Arg Asp Leu  Cys Leu Ser
    1160                 1165                 1170

Ala Asn  Thr Gly Arg Ser Pro  Leu Lys Glu Arg Arg  Phe Phe Val
    1175                 1180                 1185

Phe Lys  Gln Val Ala Asp Leu  Gln Gln Thr Leu Asn  Gln Asp Phe
    1190                 1195                 1200

Leu Ala  Gln Pro Arg Leu Ser  Ser Pro Ala Lys Ile  Ala Phe Leu
    1205                 1210                 1215

Phe Thr  Gly Gln Gly Ser Gln  Tyr Tyr Gly Met Gly  Gln Gln Leu
    1220                 1225                 1230

Tyr Gln  Thr Ser Pro Val Phe  Arg Gln Val Leu Asp  Glu Cys Asp
    1235                 1240                 1245

Arg Leu  Trp Gln Thr Tyr Ser  Pro Glu Ala Pro Ala  Leu Thr Asp
    1250                 1255                 1260

Leu Leu  Tyr Gly Asn His Asn  Pro Asp Leu Val His  Glu Thr Val
    1265                 1270                 1275

Tyr Thr  Gln Pro Leu Leu Phe  Ala Val Glu Tyr Ala  Ile Ala Gln
    1280                 1285                 1290

Leu Trp  Leu Ser Trp Gly Val  Thr Pro Asp Phe Cys  Met Gly His
    1295                 1300                 1305

Ser Val  Gly Glu Tyr Val Ala  Ala Cys Leu Ala Gly  Val Phe Ser
    1310                 1315                 1320

Leu Ala  Asp Gly Met Lys Leu  Ile Thr Ala Arg Gly  Lys Leu Met
    1325                 1330                 1335

His Ala  Leu Pro Ser Asn Gly  Ser Met Ala Ala Val  Phe Ala Asp
    1340                 1345                 1350

Lys Thr  Val Ile Lys Pro Tyr  Leu Ser Glu His Leu  Thr Val Gly
    1355                 1360                 1365
```

```
Ala Glu  Asn Gly Ser His Leu  Val Leu Ser Gly Lys  Thr Pro Cys
    1370                 1375                 1380

Leu Glu  Ala Ser Ile His Lys  Leu Gln Ser Gln Gly  Ile Lys Thr
    1385                 1390                 1395

Lys Pro  Leu Lys Val Ser His  Ala Phe His Ser Pro  Leu Met Ala
    1400                 1405                 1410

Pro Met  Leu Ala Glu Phe Arg  Glu Ile Ala Glu Gln  Ile Thr Phe
    1415                 1420                 1425

His Pro  Pro Arg Ile Pro Leu  Ile Ser Asn Val Thr  Gly Gly Gln
    1430                 1435                 1440

Ile Glu  Ala Glu Ile Ala Gln  Ala Asp Tyr Trp Val  Lys His Val
    1445                 1450                 1455

Ser Gln  Pro Val Lys Phe Val  Gln Ser Ile Gln Thr  Leu Ala Gln
    1460                 1465                 1470

Ala Gly  Val Asn Val Tyr Leu  Glu Ile Gly Val Lys  Pro Val Leu
    1475                 1480                 1485

Leu Ser  Met Gly Arg His Cys  Leu Ala Glu Gln Glu  Ala Val Trp
    1490                 1495                 1500

Leu Pro  Ser Leu Arg Pro His  Ser Glu Pro Trp Pro  Glu Ile Leu
    1505                 1510                 1515

Thr Ser  Leu Gly Lys Leu Tyr  Glu Gln Gly Leu Asn  Ile Asp Trp
    1520                 1525                 1530

Gln Thr  Val Glu Ala Gly Asp  Arg Arg Arg Lys Leu  Ile Leu Pro
    1535                 1540                 1545

Thr Tyr  Pro Phe Gln Arg Gln  Arg Tyr Trp Phe Asn  Gln Gly Ser
    1550                 1555                 1560

Trp Gln  Thr Val Glu Thr Glu  Ser Val Asn Pro Gly  Pro Asp Asp
    1565                 1570                 1575

Leu Asn  Asp Trp Leu Tyr Gln  Val Ala Trp Thr Pro  Leu Asp Thr
    1580                 1585                 1590

Leu Pro  Pro Ala Pro Glu Pro  Ser Ala Lys Leu Trp  Leu Ile Leu
    1595                 1600                 1605

Gly Asp  Arg His Asp His Gln  Pro Ile Glu Ala Gln  Phe Lys Asn
    1610                 1615                 1620

Ala Gln  Arg Val Tyr Leu Gly  Gln Ser Asn His Phe  Pro Thr Asn
    1625                 1630                 1635

Ala Pro  Trp Glu Val Ser Ala  Asp Ala Leu Asp Asn  Leu Phe Thr
    1640                 1645                 1650

His Val  Gly Ser Gln Asn Leu  Ala Gly Ile Leu Tyr  Leu Cys Pro
    1655                 1660                 1665

Pro Gly  Glu Asp Pro Glu Asp  Leu Asp Glu Ile Gln  Lys Gln Thr
    1670                 1675                 1680

Ser Gly  Phe Ala Leu Gln Leu  Ile Gln Thr Leu Tyr  Gln Gln Lys
    1685                 1690                 1695

Ile Ala  Val Pro Cys Trp Phe  Val Thr His Gln Ser  Gln Arg Val
    1700                 1705                 1710

Leu Glu  Thr Asp Ala Val Thr  Gly Phe Ala Gln Gly  Gly Leu Trp
    1715                 1720                 1725

Gly Leu  Ala Gln Ala Ile Ala  Leu Glu His Pro Glu  Leu Trp Gly
    1730                 1735                 1740

Gly Ile  Ile Asp Val Asp Asp  Ser Leu Pro Asn Phe  Ala Gln Ile
    1745                 1750                 1755

Cys Gln  Gln Arg Gln Val Gln  Gln Leu Ala Val Arg  His Gln Lys
```

-continued

```
    1760                1765                1770

Leu Tyr  Gly Ala Gln Leu Lys  Lys Gln Pro Ser Leu  Pro Gln Lys
    1775                1780                1785

Asn Leu  Gln Ile Gln Pro Gln  Gln Thr Tyr Leu Val  Thr Gly Gly
    1790                1795                1800

Leu Gly  Ala Ile Gly Arg Lys  Ile Ala Gln Trp Leu  Ala Ala Ala
    1805                1810                1815

Gly Ala  Glu Lys Val Ile Leu  Val Ser Arg Arg Ala  Pro Ala Ala
    1820                1825                1830

Asp Gln  Gln Thr Leu Pro Thr  Asn Ala Val Val Tyr  Pro Cys Asp
    1835                1840                1845

Leu Ala  Asp Ala Ala Gln Val  Ala Lys Leu Phe Gln  Thr Tyr Pro
    1850                1855                1860

His Ile  Lys Gly Ile Phe His  Ala Ala Gly Thr Leu  Ala Asp Gly
    1865                1870                1875

Leu Leu  Gln Gln Gln Thr Trp  Gln Lys Phe Gln Thr  Val Ala Ala
    1880                1885                1890

Ala Lys  Met Lys Gly Thr Trp  His Leu His Arg His  Ser Gln Lys
    1895                1900                1905

Leu Asp  Leu Asp Phe Phe Val  Leu Phe Ser Ser Val  Ala Gly Val
    1910                1915                1920

Leu Gly  Ser Pro Gly Gln Gly  Asn Tyr Ala Ala Ala  Asn Arg Gly
    1925                1930                1935

Met Ala  Ala Ile Ala Gln Tyr  Arg Gln Ala Gln Gly  Leu Pro Ala
    1940                1945                1950

Leu Ala  Ile His Trp Gly Pro  Trp Ala Glu Gly Gly  Met Ala Asn
    1955                1960                1965

Ser Leu  Ser Asn Gln Asn Leu  Ala Trp Leu Pro Pro  Pro Gln Gly
    1970                1975                1980

Leu Thr  Ile Leu Glu Lys Val  Leu Gly Ala Gln Gly  Glu Met Gly
    1985                1990                1995

Val Phe  Lys Pro Asp Trp Gln  Asn Leu Ala Lys Gln  Phe Pro Glu
    2000                2005                2010

Phe Ala  Lys Thr His Tyr Phe  Ala Ala Val Ile Pro  Ser Ala Glu
    2015                2020                2025

Ala Val  Pro Pro Thr Ala Ser  Ile Phe Asp Lys Leu  Ile Asn Leu
    2030                2035                2040

Glu Ala  Ser Gln Arg Ala Asp  Tyr Leu Leu Asp Tyr  Leu Arg Arg
    2045                2050                2055

Ser Val  Ala Gln Ile Leu Lys  Leu Glu Ile Glu Gln  Ile Gln Ser
    2060                2065                2070

His Asp  Ser Leu Leu Asp Leu  Gly Met Asp Ser Leu  Met Ile Met
    2075                2080                2085

Glu Ala  Ile Ala Ser Leu Lys  Gln Asp Leu Gln Leu  Met Leu Tyr
    2090                2095                2100

Pro Arg  Glu Ile Tyr Glu Arg  Pro Arg Leu Asp Val  Leu Thr Ala
    2105                2110                2115

Tyr Leu  Ala Ala Glu Phe Thr  Lys Ala His Asp Ser  Glu Ala Ala
    2120                2125                2130

Thr Ala  Ala Ala Ala Ile Pro  Ser Gln Ser Leu Ser  Val Lys Thr
    2135                2140                2145

Lys Lys  Gln Trp Gln Lys Pro  Asp His Lys Asn Pro  Asn Pro Ile
    2150                2155                2160
```

```
Ala Phe Ile Leu Ser Ser Pro Arg Ser Gly Ser Thr Leu Leu Arg
    2165                2170                2175

Val Met Leu Ala Gly His Pro Gly Leu Tyr Ser Pro Pro Glu Leu
    2180                2185                2190

His Leu Leu Pro Phe Glu Thr Met Gly Asp Arg His Gln Glu Leu
    2195                2200                2205

Gly Leu Ser His Leu Gly Glu Gly Leu Gln Arg Ala Leu Met Asp
    2210                2215                2220

Leu Glu Asn Leu Thr Pro Glu Ala Ser Gln Ala Lys Val Asn Gln
    2225                2230                2235

Trp Val Lys Ala Asn Thr Pro Ile Ala Asp Ile Tyr Ala Tyr Leu
    2240                2245                2250

Gln Arg Gln Ala Glu Gln Arg Leu Leu Ile Asp Lys Ser Pro Ser
    2255                2260                2265

Tyr Gly Ser Asp Arg His Ile Leu Asp His Ser Glu Ile Leu Phe
    2270                2275                2280

Asp Gln Ala Lys Tyr Ile His Leu Val Arg His Pro Tyr Ala Val
    2285                2290                2295

Ile Glu Ser Phe Thr Arg Leu Arg Met Asp Lys Leu Leu Gly Ala
    2300                2305                2310

Glu Gln Gln Asn Pro Tyr Ala Leu Ala Glu Ser Ile Trp Arg Thr
    2315                2320                2325

Ser Asn Arg Asn Ile Leu Asp Leu Gly Arg Thr Val Gly Ala Asp
    2330                2335                2340

Arg Tyr Leu Gln Val Ile Tyr Glu Asp Leu Val Arg Asp Pro Arg
    2345                2350                2355

Lys Val Leu Thr Asn Ile Cys Asp Phe Leu Gly Val Asp Phe Asp
    2360                2365                2370

Glu Ala Leu Leu Asn Pro Tyr Ser Gly Asp Arg Leu Thr Asp Gly
    2375                2380                2385

Leu His Gln Gln Ser Met Gly Val Gly Asp Pro Asn Phe Leu Gln
    2390                2395                2400

His Lys Thr Ile Asp Pro Ala Leu Ala Asp Lys Trp Arg Ser Ile
    2405                2410                2415

Thr Leu Pro Ala Ala Leu Gln Leu Asp Thr Ile Gln Leu Ala Glu
    2420                2425                2430

Thr Phe Ala Tyr Asp Leu Pro Gln Glu Pro Gln Leu Thr Pro Gln
    2435                2440                2445

Thr Gln Ser Leu Pro Ser Met Val Glu Arg Phe Val Thr Val Arg
    2450                2455                2460

Gly Leu Glu Thr Cys Leu Cys Glu Trp Gly Asp Arg His Gln Pro
    2465                2470                2475

Leu Val Leu Leu Leu His Gly Ile Leu Glu Gln Gly Ala Ser Trp
    2480                2485                2490

Gln Leu Ile Ala Pro Gln Leu Ala Ala Gln Gly Tyr Trp Val Val
    2495                2500                2505

Ala Pro Asp Leu Arg Gly His Gly Lys Ser Ala His Ala Gln Ser
    2510                2515                2520

Tyr Ser Met Leu Asp Phe Leu Ala Asp Val Asp Ala Leu Ala Lys
    2525                2530                2535

Gln Leu Gly Asp Arg Pro Phe Thr Leu Val Gly His Ser Met Gly
    2540                2545                2550

Ser Ile Ile Gly Ala Met Tyr Ala Gly Ile Arg Gln Thr Gln Val
    2555                2560                2565
```

Glu Lys Leu Ile Leu Val Glu Thr Ile Val Pro Asn Asp Ile Asp
2570 2575 2580

Asp Ala Glu Thr Gly Asn His Leu Thr Thr His Leu Asp Tyr Leu
2585 2590 2595

Ala Ala Pro Pro Gln His Pro Ile Phe Pro Ser Leu Glu Val Ala
2600 2605 2610

Ala Arg Arg Leu Arg Gln Ala Thr Pro Gln Leu Pro Lys Asp Leu
2615 2620 2625

Ser Ala Phe Leu Thr Gln Arg Ser Thr Lys Ser Val Glu Lys Gly
2630 2635 2640

Val Gln Trp Arg Trp Asp Ala Phe Leu Arg Thr Arg Ala Gly Ile
2645 2650 2655

Glu Phe Asn Gly Ile Ser Arg Arg Arg Tyr Leu Ala Leu Leu Lys
2660 2665 2670

Asp Ile Gln Ala Pro Ile Thr Leu Ile Tyr Gly Asp Gln Ser Glu
2675 2680 2685

Phe Asn Arg Pro Ala Asp Leu Gln Ala Ile Gln Ala Ala Leu Pro
2690 2695 2700

Gln Ala Gln Arg Leu Thr Val Ala Gly Gly His Asn Leu His Phe
2705 2710 2715

Glu Asn Pro Gln Ala Ile Ala Gln Ile Val Tyr Gln Gln Leu Gln
2720 2725 2730

Thr Pro Val Pro Lys Thr Gln Gly Leu His His His His His His
2735 2740 2745

Ser Ala Trp Ser His Pro Gln Phe Glu Lys
2750 2755

<210> SEQ ID NO 30
<211> LENGTH: 2758
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Met Ala Ser Trp Ser His Pro Gln Phe Glu Lys Glu Val His His His
1 5 10 15

His His His Gly Ala Val Gly Gln Phe Ala Asn Phe Val Asp Leu Leu
20 25 30

Gln Tyr Arg Ala Lys Leu Gln Ala Arg Lys Thr Val Phe Ser Phe Leu
35 40 45

Ala Asp Gly Glu Ala Glu Ser Ala Ala Leu Thr Tyr Gly Glu Leu Asp
50 55 60

Gln Lys Ala Gln Ala Ile Ala Ala Phe Leu Gln Ala Asn Gln Ala Gln
65 70 75 80

Gly Gln Arg Ala Leu Leu Leu Tyr Pro Pro Gly Leu Glu Phe Ile Gly
85 90 95

Ala Phe Leu Gly Cys Leu Tyr Ala Gly Val Val Ala Val Pro Ala Tyr
100 105 110

Pro Pro Arg Pro Asn Lys Ser Phe Asp Arg Leu His Ser Ile Ile Gln
115 120 125

Asp Ala Gln Ala Lys Phe Ala Leu Thr Thr Thr Glu Leu Lys Asp Lys
130 135 140

Ile Ala Asp Arg Leu Glu Ala Leu Glu Gly Thr Asp Phe His Cys Leu
145 150 155 160

```
Ala Thr Asp Gln Val Glu Leu Ile Ser Gly Lys Asn Trp Gln Lys Pro
                165                 170                 175

Asn Ile Ser Gly Thr Asp Leu Ala Phe Leu Gln Tyr Thr Ser Gly Ser
            180                 185                 190

Thr Gly Asp Pro Lys Gly Val Met Val Ser His His Asn Leu Ile His
        195                 200                 205

Asn Ser Gly Leu Ile Phe Thr Ser Phe His Met Asn Asp Glu Thr Ile
    210                 215                 220

Ile Phe Ser Trp Leu Pro Pro His His Asp Met Gly Leu Ile Gly Cys
225                 230                 235                 240

Ile Leu Thr Pro Ile Tyr Gly Gly Ile Gln Ala Ile Met Met Ser Pro
                245                 250                 255

Phe Ser Phe Leu Gln Asn Pro Leu Ser Trp Leu Lys His Ile Thr Lys
            260                 265                 270

Tyr Lys Ala Thr Ile Ser Gly Ser Pro Asn Phe Ala Tyr Asp Tyr Cys
        275                 280                 285

Val Lys Arg Ile Arg Glu Glu Lys Lys Glu Gly Leu Asp Leu Ser Ser
    290                 295                 300

Trp Val Thr Ala Phe Asn Gly Ala Glu Pro Ile Arg Ala Val Thr Leu
305                 310                 315                 320

Glu Asn Phe Ala Lys Thr Phe Ala Thr Ala Gly Phe Gln Lys Ser Ala
                325                 330                 335

Phe Tyr Pro Cys Tyr Gly Met Ala Glu Thr Thr Leu Ile Val Ser Gly
            340                 345                 350

Gly Asn Gly Arg Ala Gln Leu Pro Gln Glu Ile Ile Val Ser Lys Gln
        355                 360                 365

Gly Ile Glu Ala Asn Gln Val Arg Pro Ala Gln Gly Thr Glu Thr Thr
    370                 375                 380

Val Thr Leu Val Gly Ser Gly Glu Val Ile Gly Asp Gln Ile Val Lys
385                 390                 395                 400

Ile Val Asp Pro Gln Ala Leu Thr Glu Cys Thr Val Gly Glu Ile Gly
                405                 410                 415

Glu Val Trp Val Lys Gly Glu Ser Val Ala Gln Gly Tyr Trp Gln Lys
            420                 425                 430

Pro Asp Leu Thr Gln Gln Gln Phe Gln Gly Asn Val Gly Ala Glu Thr
        435                 440                 445

Gly Phe Leu Arg Thr Gly Asp Leu Gly Phe Leu Gln Gly Gly Glu Leu
    450                 455                 460

Tyr Ile Thr Gly Arg Leu Lys Asp Leu Leu Ile Ile Arg Gly Arg Asn
465                 470                 475                 480

His Tyr Pro Gln Asp Ile Glu Leu Thr Val Glu Val Ala His Pro Ala
                485                 490                 495

Leu Arg Gln Gly Ala Gly Ala Ala Val Ser Val Asp Val Asn Gly Glu
            500                 505                 510

Glu Gln Leu Val Ile Val Gln Glu Val Glu Arg Lys Tyr Ala Arg Lys
        515                 520                 525

Leu Asn Val Ala Ala Val Ala Gln Ala Ile Arg Gly Ala Ile Ala Ala
    530                 535                 540

Glu His Gln Leu Gln Pro Gln Ala Ile Cys Phe Ile Lys Pro Gly Ser
545                 550                 555                 560

Ile Pro Lys Thr Ser Ser Gly Lys Ile Arg Arg His Ala Cys Lys Ala
                565                 570                 575

Gly Phe Leu Asp Gly Ser Leu Ala Val Val Gly Glu Trp Gln Pro Ser
```

-continued

```
            580                 585                 590

His Gln Lys Glu Gly Lys Gly Ile Gly Thr Gln Ala Val Thr Pro Ser
        595                 600                 605

Thr Thr Thr Ser Thr Asn Phe Pro Leu Pro Asp Gln His Gln Gln Gln
    610                 615                 620

Ile Glu Ala Trp Leu Lys Asp Asn Ile Ala His Arg Leu Gly Ile Thr
625                 630                 635                 640

Pro Gln Gln Leu Asp Glu Thr Glu Pro Phe Ala Ser Tyr Gly Leu Asp
                645                 650                 655

Ser Val Gln Ala Val Gln Val Thr Ala Asp Leu Glu Asp Trp Leu Gly
            660                 665                 670

Arg Lys Leu Asp Pro Thr Leu Ala Tyr Asp Tyr Pro Thr Ile Arg Thr
        675                 680                 685

Leu Ala Gln Phe Leu Val Gln Gly Asn Gln Ala Leu Glu Lys Ile Pro
    690                 695                 700

Gln Val Pro Lys Ile Gln Gly Lys Glu Ile Ala Val Val Gly Leu Ser
705                 710                 715                 720

Cys Arg Phe Pro Gln Ala Asp Asn Pro Glu Ala Phe Trp Glu Leu Leu
                725                 730                 735

Arg Asn Gly Lys Asp Gly Val Arg Pro Leu Lys Thr Arg Trp Ala Thr
            740                 745                 750

Gly Glu Trp Gly Gly Phe Leu Glu Asp Ile Asp Gln Phe Glu Pro Gln
        755                 760                 765

Phe Phe Gly Ile Ser Pro Arg Glu Ala Glu Gln Met Asp Pro Gln Gln
    770                 775                 780

Arg Leu Leu Leu Glu Val Thr Trp Glu Ala Leu Glu Arg Ala Asn Ile
785                 790                 795                 800

Pro Ala Glu Ser Leu Arg His Ser Gln Thr Gly Val Phe Val Gly Ile
                805                 810                 815

Ser Asn Ser Asp Tyr Ala Gln Leu Gln Val Arg Glu Asn Asn Pro Ile
            820                 825                 830

Asn Pro Tyr Met Gly Thr Gly Asn Ala His Ser Ile Ala Ala Asn Arg
        835                 840                 845

Leu Ser Tyr Phe Leu Asp Leu Arg Gly Val Ser Leu Ser Ile Asp Thr
    850                 855                 860

Ala Cys Ser Ser Ser Leu Val Ala Val His Leu Ala Cys Gln Ser Leu
865                 870                 875                 880

Ile Asn Gly Glu Ser Glu Leu Ala Ile Ala Ala Gly Val Asn Leu Ile
                885                 890                 895

Leu Thr Pro Asp Val Thr Gln Thr Phe Thr Gln Ala Gly Met Met Ser
            900                 905                 910

Lys Thr Gly Arg Cys Gln Thr Phe Asp Ala Glu Ala Asp Gly Tyr Val
        915                 920                 925

Arg Gly Glu Gly Cys Gly Val Val Leu Leu Lys Pro Leu Ala Gln Ala
    930                 935                 940

Glu Arg Asp Gly Asp Asn Ile Leu Ala Val Ile His Gly Ser Ala Val
945                 950                 955                 960

Asn Gln Asp Gly Arg Ser Asn Gly Leu Thr Ala Pro Asn Gly Arg Ser
                965                 970                 975

Gln Gln Ala Val Ile Arg Gln Ala Leu Ala Gln Ala Gly Ile Thr Ala
            980                 985                 990

Ala Asp Leu Ala Tyr Leu Glu Ala  His Gly Thr Gly Thr  Pro Leu Gly
        995                 1000                1005
```

```
Asp Pro  Ile Glu Ile Asn Ser  Leu Lys Ala Val Leu  Gln Thr Ala
    1010                 1015                 1020

Gln Arg  Glu Gln Pro Cys Val  Val Gly Ser Val Lys  Thr Asn Ile
    1025                 1030                 1035

Gly His  Leu Glu Ala Ala Ala  Gly Ile Ala Gly Leu  Ile Lys Val
    1040                 1045                 1050

Ile Leu  Ser Leu Glu His Gly  Met Ile Pro Gln His  Leu His Phe
    1055                 1060                 1065

Lys Gln  Leu Asn Pro Arg Ile  Asp Leu Asp Gly Leu  Val Thr Ile
    1070                 1075                 1080

Ala Ser  Lys Asp Gln Pro Trp  Ser Gly Gly Ser Gln  Lys Arg Phe
    1085                 1090                 1095

Ala Gly  Val Ser Ser Phe Gly  Phe Gly Gly Thr Asn  Ala His Val
    1100                 1105                 1110

Ile Val  Gly Asp Tyr Ala Gln  Gln Lys Ser Pro Leu  Ala Pro Pro
    1115                 1120                 1125

Ala Thr  Gln Asp Arg Pro Trp  His Leu Leu Thr Leu  Ser Ala Lys
    1130                 1135                 1140

Asn Ala  Gln Ala Leu Asn Ala  Leu Gln Lys Ser Tyr  Gly Asp Tyr
    1145                 1150                 1155

Leu Ala  Gln His Pro Ser Val  Asp Pro Arg Asp Leu  Cys Leu Ser
    1160                 1165                 1170

Ala Asn  Thr Gly Arg Ser Pro  Leu Lys Glu Arg Arg  Phe Phe Val
    1175                 1180                 1185

Phe Lys  Gln Val Ala Asp Leu  Gln Gln Thr Leu Asn  Gln Asp Phe
    1190                 1195                 1200

Leu Ala  Gln Pro Arg Leu Ser  Ser Pro Ala Lys Ile  Ala Phe Leu
    1205                 1210                 1215

Phe Thr  Gly Gln Gly Ser Gln  Tyr Tyr Gly Met Gly  Gln Gln Leu
    1220                 1225                 1230

Tyr Gln  Thr Ser Pro Val Phe  Arg Gln Val Leu Asp  Glu Cys Asp
    1235                 1240                 1245

Arg Leu  Trp Gln Thr Tyr Ser  Pro Glu Ala Pro Ala  Leu Thr Asp
    1250                 1255                 1260

Leu Leu  Tyr Gly Asn His Asn  Pro Asp Leu Val His  Glu Thr Val
    1265                 1270                 1275

Tyr Thr  Gln Pro Leu Leu Phe  Ala Val Glu Tyr Ala  Ile Ala Gln
    1280                 1285                 1290

Leu Trp  Leu Ser Trp Gly Val  Thr Pro Asp Phe Cys  Met Gly His
    1295                 1300                 1305

Ser Val  Gly Glu Tyr Val Ala  Ala Cys Leu Ala Gly  Val Phe Ser
    1310                 1315                 1320

Leu Ala  Asp Gly Met Lys Leu  Ile Thr Ala Arg Gly  Lys Leu Met
    1325                 1330                 1335

His Ala  Leu Pro Ser Asn Gly  Ser Met Ala Ala Val  Phe Ala Asp
    1340                 1345                 1350

Lys Thr  Val Ile Lys Pro Tyr  Leu Ser Glu His Leu  Thr Val Gly
    1355                 1360                 1365

Ala Glu  Asn Gly Ser His Leu  Val Leu Ser Gly Lys  Thr Pro Cys
    1370                 1375                 1380

Leu Glu  Ala Ser Ile His Lys  Leu Gln Ser Gln Gly  Ile Lys Thr
    1385                 1390                 1395

Lys Pro  Leu Lys Val Ser His  Ala Phe His Ser Pro  Leu Met Ala
    1400                 1405                 1410
```

```
Pro Met  Leu Ala Glu Phe Arg  Glu Ile Ala Glu Gln  Ile Thr Phe
    1415                 1420                 1425

His Pro  Pro Arg Ile Pro Leu  Ile Ser Asn Val Thr  Gly Gly Gln
    1430                 1435                 1440

Ile Glu  Ala Glu Ile Ala Gln  Ala Asp Tyr Trp Val  Lys His Val
    1445                 1450                 1455

Ser Gln  Pro Val Lys Phe Val  Gln Ser Ile Gln Thr  Leu Ala Gln
    1460                 1465                 1470

Ala Gly  Val Asn Val Tyr Leu  Glu Ile Gly Val Lys  Pro Val Leu
    1475                 1480                 1485

Leu Ser  Met Gly Arg His Cys  Leu Ala Glu Gln Glu  Ala Val Trp
    1490                 1495                 1500

Leu Pro  Ser Leu Arg Pro His  Ser Glu Pro Trp Pro  Glu Ile Leu
    1505                 1510                 1515

Thr Ser  Leu Gly Lys Leu Tyr  Glu Gln Gly Leu Asn  Ile Asp Trp
    1520                 1525                 1530

Gln Thr  Val Glu Ala Gly Asp  Arg Arg Arg Lys Leu  Ile Leu Pro
    1535                 1540                 1545

Thr Tyr  Pro Phe Gln Arg Gln  Arg Tyr Trp Phe Asn  Gln Gly Ser
    1550                 1555                 1560

Trp Gln  Thr Val Glu Thr Glu  Ser Val Asn Pro Gly  Pro Asp Asp
    1565                 1570                 1575

Leu Asn  Asp Trp Leu Tyr Gln  Val Ala Trp Thr Pro  Leu Asp Thr
    1580                 1585                 1590

Leu Pro  Pro Ala Pro Glu Pro  Ser Ala Lys Leu Trp  Leu Ile Leu
    1595                 1600                 1605

Gly Asp  Arg His Asp His Gln  Pro Ile Glu Ala Gln  Phe Lys Asn
    1610                 1615                 1620

Ala Gln  Arg Val Tyr Leu Gly  Gln Ser Asn His Phe  Pro Thr Asn
    1625                 1630                 1635

Ala Pro  Trp Glu Val Ser Ala  Asp Ala Leu Asp Asn  Leu Phe Thr
    1640                 1645                 1650

His Val  Gly Ser Gln Asn Leu  Ala Gly Ile Leu Tyr  Leu Cys Pro
    1655                 1660                 1665

Pro Gly  Glu Asp Pro Glu Asp  Leu Asp Glu Ile Gln  Lys Gln Thr
    1670                 1675                 1680

Ser Gly  Phe Ala Leu Gln Leu  Ile Gln Thr Leu Tyr  Gln Gln Lys
    1685                 1690                 1695

Ile Ala  Val Pro Cys Trp Phe  Val Thr His Gln Ser  Gln Arg Val
    1700                 1705                 1710

Leu Glu  Thr Asp Ala Val Thr  Gly Phe Ala Gln Gly  Gly Leu Trp
    1715                 1720                 1725

Gly Leu  Ala Gln Ala Ile Ala  Leu Glu His Pro Glu  Leu Trp Gly
    1730                 1735                 1740

Gly Ile  Ile Asp Val Asp Asp  Ser Leu Pro Asn Phe  Ala Gln Ile
    1745                 1750                 1755

Cys Gln  Gln Arg Gln Val Gln  Gln Leu Ala Val Arg  His Gln Lys
    1760                 1765                 1770

Leu Tyr  Gly Ala Gln Leu Lys  Lys Gln Pro Ser Leu  Pro Gln Lys
    1775                 1780                 1785

Asn Leu  Gln Ile Gln Pro Gln  Gln Thr Tyr Leu Val  Thr Gly Gly
    1790                 1795                 1800

Leu Gly  Ala Ile Gly Arg Lys  Ile Ala Gln Trp Leu  Ala Ala Ala
```

-continued

```
    1805                 1810                 1815

Gly Ala  Glu Lys Val Ile Leu  Val Ser Arg Arg Ala  Pro Ala Ala
    1820                 1825                 1830

Asp Gln  Gln Thr Leu Pro Thr  Asn Ala Val Val Tyr  Pro Cys Asp
    1835                 1840                 1845

Leu Ala  Asp Ala Ala Gln Val  Ala Lys Leu Phe Gln  Thr Tyr Pro
    1850                 1855                 1860

His Ile  Lys Gly Ile Phe His  Ala Ala Gly Thr Leu  Ala Asp Gly
    1865                 1870                 1875

Leu Leu  Gln Gln Gln Thr Trp  Gln Lys Phe Gln Thr  Val Ala Ala
    1880                 1885                 1890

Ala Lys  Met Lys Gly Thr Trp  His Leu His Arg His  Ser Gln Lys
    1895                 1900                 1905

Leu Asp  Leu Asp Phe Phe Val  Leu Phe Ser Ser Val  Ala Gly Val
    1910                 1915                 1920

Leu Gly  Ser Pro Gly Gln Gly  Asn Tyr Ala Ala Ala  Asn Arg Gly
    1925                 1930                 1935

Met Ala  Ala Ile Ala Gln Tyr  Arg Gln Ala Gln Gly  Leu Pro Ala
    1940                 1945                 1950

Leu Ala  Ile His Trp Gly Pro  Trp Ala Glu Gly Gly  Met Ala Asn
    1955                 1960                 1965

Ser Leu  Ser Asn Gln Asn Leu  Ala Trp Leu Pro Pro  Pro Gln Gly
    1970                 1975                 1980

Leu Thr  Ile Leu Glu Lys Val  Leu Gly Ala Gln Gly  Glu Met Gly
    1985                 1990                 1995

Val Phe  Lys Pro Asp Trp Gln  Asn Leu Ala Lys Gln  Phe Pro Glu
    2000                 2005                 2010

Phe Ala  Lys Thr His Tyr Phe  Ala Ala Val Ile Pro  Ser Ala Glu
    2015                 2020                 2025

Ala Val  Pro Pro Thr Ala Ser  Ile Phe Asp Lys Leu  Ile Asn Leu
    2030                 2035                 2040

Glu Ala  Ser Gln Arg Ala Asp  Tyr Leu Leu Asp Tyr  Leu Arg Arg
    2045                 2050                 2055

Ser Val  Ala Gln Ile Leu Lys  Leu Glu Ile Glu Gln  Ile Gln Ser
    2060                 2065                 2070

His Asp  Ser Leu Leu Asp Leu  Gly Met Asp Ser Leu  Met Ile Met
    2075                 2080                 2085

Glu Ala  Ile Ala Ser Leu Lys  Gln Asp Leu Gln Leu  Met Leu Tyr
    2090                 2095                 2100

Pro Arg  Glu Ile Tyr Glu Arg  Pro Arg Leu Asp Val  Leu Thr Ala
    2105                 2110                 2115

Tyr Leu  Ala Ala Glu Phe Thr  Lys Ala His Asp Ser  Glu Ala Ala
    2120                 2125                 2130

Thr Ala  Ala Ala Ala Ile Pro  Ser Gln Ser Leu Ser  Val Lys Thr
    2135                 2140                 2145

Lys Lys  Gln Trp Gln Lys Pro  Asp His Lys Asn Pro  Asn Pro Ile
    2150                 2155                 2160

Ala Phe  Ile Leu Ser Ser Pro  Arg Ser Gly Ser Thr  Leu Leu Arg
    2165                 2170                 2175

Val Met  Leu Ala Gly His Pro  Gly Leu Tyr Ser Pro  Pro Glu Leu
    2180                 2185                 2190

His Leu  Leu Pro Phe Glu Thr  Met Gly Asp Arg His  Gln Glu Leu
    2195                 2200                 2205
```

-continued

```
Gly Leu  Ser His Leu Gly Glu  Gly Leu Gln Arg Ala  Leu Met Asp
    2210                 2215                 2220

Leu Glu  Asn Leu Thr Pro Glu  Ala Ser Gln Ala Lys  Val Asn Gln
    2225                 2230                 2235

Trp Val  Lys Ala Asn Thr Pro  Ile Ala Asp Ile Tyr  Ala Tyr Leu
    2240                 2245                 2250

Gln Arg  Gln Ala Glu Gln Arg  Leu Leu Ile Asp Lys  Ser Pro Ser
    2255                 2260                 2265

Tyr Gly  Ser Asp Arg His Ile  Leu Asp His Ser Glu  Ile Leu Phe
    2270                 2275                 2280

Asp Gln  Ala Lys Tyr Ile His  Leu Val Arg His Pro  Tyr Ala Val
    2285                 2290                 2295

Ile Glu  Ser Phe Thr Arg Leu  Arg Met Asp Lys Leu  Leu Gly Ala
    2300                 2305                 2310

Glu Gln  Gln Asn Pro Tyr Ala  Leu Ala Glu Ser Ile  Trp Arg Thr
    2315                 2320                 2325

Ser Asn  Arg Asn Ile Leu Asp  Leu Gly Arg Thr Val  Gly Ala Asp
    2330                 2335                 2340

Arg Tyr  Leu Gln Val Ile Tyr  Glu Asp Leu Val Arg  Asp Pro Arg
    2345                 2350                 2355

Lys Val  Leu Thr Asn Ile Cys  Asp Phe Leu Gly Val  Asp Phe Asp
    2360                 2365                 2370

Glu Ala  Leu Leu Asn Pro Tyr  Ser Gly Asp Arg Leu  Thr Asp Gly
    2375                 2380                 2385

Leu His  Gln Gln Ser Met Gly  Val Gly Asp Pro Asn  Phe Leu Gln
    2390                 2395                 2400

His Lys  Thr Ile Asp Pro Ala  Leu Ala Asp Lys Trp  Arg Ser Ile
    2405                 2410                 2415

Thr Leu  Pro Ala Ala Leu Gln  Leu Asp Thr Ile Gln  Leu Ala Glu
    2420                 2425                 2430

Thr Phe  Ala Tyr Asp Leu Pro  Gln Glu Pro Gln Leu  Thr Pro Gln
    2435                 2440                 2445

Thr Gln  Ser Leu Pro Ser Met  Val Glu Arg Phe Val  Thr Val Arg
    2450                 2455                 2460

Gly Leu  Glu Thr Cys Leu Cys  Glu Trp Gly Asp Arg  His Gln Pro
    2465                 2470                 2475

Leu Val  Leu Leu Leu His Gly  Ile Leu Glu Gln Gly  Ala Ser Trp
    2480                 2485                 2490

Gln Leu  Ile Ala Pro Gln Leu  Ala Ala Gln Gly Tyr  Trp Val Val
    2495                 2500                 2505

Ala Pro  Asp Leu Arg Gly His  Gly Lys Ser Ala His  Ala Gln Ser
    2510                 2515                 2520

Tyr Ser  Met Leu Asp Phe Leu  Ala Asp Val Asp Ala  Leu Ala Lys
    2525                 2530                 2535

Gln Leu  Gly Asp Arg Pro Phe  Thr Leu Val Gly His  Ser Met Gly
    2540                 2545                 2550

Ser Ile  Ile Gly Ala Met Tyr  Ala Gly Ile Arg Gln  Thr Gln Val
    2555                 2560                 2565

Glu Lys  Leu Ile Leu Val Glu  Thr Ile Val Pro Asn  Asp Ile Asp
    2570                 2575                 2580

Asp Ala  Glu Thr Gly Asn His  Leu Thr Thr His Leu  Asp Tyr Leu
    2585                 2590                 2595

Ala Ala  Pro Pro Gln His Pro  Ile Phe Pro Ser Leu  Glu Val Ala
    2600                 2605                 2610
```

```
Ala Arg  Arg Leu Arg Gln Ala  Thr Pro Gln Leu Pro  Lys Asp Leu
    2615                 2620                 2625

Ser Ala  Phe Leu Thr Gln Arg  Ser Thr Lys Ser Val  Glu Lys Gly
    2630                 2635                 2640

Val Gln  Trp Arg Trp Asp Ala  Phe Leu Arg Thr Arg  Ala Gly Ile
    2645                 2650                 2655

Glu Phe  Asn Gly Ile Ser Arg  Arg Arg Tyr Leu Ala  Leu Leu Lys
    2660                 2665                 2670

Asp Ile  Gln Ala Pro Ile Thr  Leu Ile Tyr Gly Asp  Gln Ser Glu
    2675                 2680                 2685

Phe Asn  Arg Pro Ala Asp Leu  Gln Ala Ile Gln Ala  Ala Leu Pro
    2690                 2695                 2700

Gln Ala  Gln Arg Leu Thr Val  Ala Gly Gly His Asn  Leu His Phe
    2705                 2710                 2715

Glu Asn  Pro Gln Ala Ile Ala  Gln Ile Val Tyr Gln  Gln Leu Gln
    2720                 2725                 2730

Thr Pro  Val Pro Lys Thr Gln  Gly Leu His His His  His His His
    2735                 2740                 2745

Ser Ala  Trp Ser His Pro Gln  Phe Glu Lys
    2750                 2755


<210> SEQ ID NO 31
<211> LENGTH: 2758
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Ala Ser Trp Ser His Pro Gln Phe Glu Lys Glu Val His His His
1               5                   10                  15

His His His Gly Ala Val Gly Gln Phe Ala Asn Phe Val Asp Leu Leu
            20                  25                  30

Gln Tyr Arg Ala Lys Leu Gln Ala Arg Lys Thr Val Phe Ser Phe Leu
        35                  40                  45

Ala Asp Gly Glu Ala Glu Ser Ala Ala Leu Thr Tyr Gly Glu Leu Asp
    50                  55                  60

Gln Lys Ala Gln Ala Ile Ala Ala Phe Leu Gln Ala Asn Gln Ala Gln
65                  70                  75                  80

Gly Gln Arg Ala Leu Leu Leu Tyr Pro Pro Gly Leu Glu Phe Ile Gly
                85                  90                  95

Ala Phe Leu Gly Cys Leu Tyr Ala Gly Val Val Ala Val Pro Ala Tyr
            100                 105                 110

Pro Pro Arg Pro Asn Lys Ser Phe Asp Arg Leu His Ser Ile Ile Gln
        115                 120                 125

Asp Ala Gln Ala Lys Phe Ala Leu Thr Thr Thr Glu Leu Lys Asp Lys
    130                 135                 140

Ile Ala Asp Arg Leu Glu Ala Leu Glu Gly Thr Asp Phe His Cys Leu
145                 150                 155                 160

Ala Thr Asp Gln Val Glu Leu Ile Ser Gly Lys Asn Trp Gln Lys Pro
                165                 170                 175

Asn Ile Ser Gly Thr Asp Leu Ala Phe Leu Gln Tyr Thr Ser Gly Ser
            180                 185                 190

Thr Gly Asp Pro Lys Gly Val Met Val Ser His His Asn Leu Ile His
        195                 200                 205
```

```
Asn Ser Gly Leu Ile Arg Asn Ala Leu Ala Ile Asp Leu Lys Asp Thr
    210                 215                 220

Leu Leu Ser Trp Met Pro Leu Thr His Asp Met Gly Leu Ile Ala Cys
225                 230                 235                 240

His Leu Val Pro Ala Leu Ala Gly Ile Asn Gln Asn Leu Met Pro Thr
                245                 250                 255

Glu Leu Phe Ile Arg Arg Pro Ile Leu Trp Met Lys Lys Ala His Glu
            260                 265                 270

His Lys Ala Ser Ile Leu Ser Ser Pro Asn Phe Gly Tyr Asn Tyr Phe
        275                 280                 285

Leu Lys Phe Leu Lys Asp Asn Lys Ser Tyr Asp Trp Asp Leu Ser His
    290                 295                 300

Ile Arg Val Ile Ala Asn Gly Ala Glu Pro Ile Arg Ala Val Thr Leu
305                 310                 315                 320

Glu Asn Phe Ala Lys Thr Phe Ala Thr Ala Gly Phe Gln Lys Ser Ala
                325                 330                 335

Phe Tyr Pro Cys Tyr Gly Met Ala Glu Thr Thr Leu Ile Val Ser Gly
            340                 345                 350

Gly Asn Gly Arg Ala Gln Leu Pro Gln Glu Ile Ile Val Ser Lys Gln
        355                 360                 365

Gly Ile Glu Ala Asn Gln Val Arg Pro Ala Gln Gly Thr Glu Thr Thr
    370                 375                 380

Val Thr Leu Val Gly Ser Gly Glu Val Ile Gly Asp Gln Ile Val Lys
385                 390                 395                 400

Ile Val Asp Pro Gln Ala Leu Thr Glu Cys Thr Val Gly Glu Ile Gly
                405                 410                 415

Glu Val Trp Val Lys Gly Glu Ser Val Ala Gln Gly Tyr Trp Gln Lys
            420                 425                 430

Pro Asp Leu Thr Gln Gln Gln Phe Gln Gly Asn Val Gly Ala Glu Thr
        435                 440                 445

Gly Phe Leu Arg Thr Gly Asp Leu Gly Phe Leu Gln Gly Gly Glu Leu
    450                 455                 460

Tyr Ile Thr Gly Arg Leu Lys Asp Leu Leu Ile Ile Arg Gly Arg Asn
465                 470                 475                 480

His Tyr Pro Gln Asp Ile Glu Leu Thr Val Glu Val Ala His Pro Ala
                485                 490                 495

Leu Arg Gln Gly Ala Gly Ala Ala Val Ser Val Asp Val Asn Gly Glu
            500                 505                 510

Glu Gln Leu Val Ile Val Gln Glu Val Glu Arg Lys Tyr Ala Arg Lys
        515                 520                 525

Leu Asn Val Ala Ala Val Ala Gln Ala Ile Arg Gly Ala Ile Ala Ala
    530                 535                 540

Glu His Gln Leu Gln Pro Gln Ala Ile Cys Phe Ile Lys Pro Gly Ser
545                 550                 555                 560

Ile Pro Lys Thr Ser Ser Gly Lys Ile Arg Arg His Ala Cys Lys Ala
                565                 570                 575

Gly Phe Leu Asp Gly Ser Leu Ala Val Val Gly Glu Trp Gln Pro Ser
            580                 585                 590

His Gln Lys Glu Gly Lys Gly Ile Gly Thr Gln Ala Val Thr Pro Ser
        595                 600                 605

Thr Thr Thr Ser Thr Asn Phe Pro Leu Pro Asp Gln His Gln Gln Gln
    610                 615                 620

Ile Glu Ala Trp Leu Lys Asp Asn Ile Ala His Arg Leu Gly Ile Thr
```

```
625                 630                 635                 640

Pro Gln Gln Leu Asp Glu Thr Glu Pro Phe Ala Ser Tyr Gly Leu Asp
                645                 650                 655

Ser Val Gln Ala Val Gln Val Thr Ala Asp Leu Glu Asp Trp Leu Gly
            660                 665                 670

Arg Lys Leu Asp Pro Thr Leu Ala Tyr Asp Tyr Pro Thr Ile Arg Thr
        675                 680                 685

Leu Ala Gln Phe Leu Val Gln Gly Asn Gln Ala Leu Glu Lys Ile Pro
    690                 695                 700

Gln Val Pro Lys Ile Gln Gly Lys Glu Ile Ala Val Val Gly Leu Ser
705                 710                 715                 720

Cys Arg Phe Pro Gln Ala Asp Asn Pro Glu Ala Phe Trp Glu Leu Leu
                725                 730                 735

Arg Asn Gly Lys Asp Gly Val Arg Pro Leu Lys Thr Arg Trp Ala Thr
            740                 745                 750

Gly Glu Trp Gly Gly Phe Leu Glu Asp Ile Asp Gln Phe Glu Pro Gln
        755                 760                 765

Phe Phe Gly Ile Ser Pro Arg Glu Ala Glu Gln Met Asp Pro Gln Gln
    770                 775                 780

Arg Leu Leu Leu Glu Val Thr Trp Glu Ala Leu Glu Arg Ala Asn Ile
785                 790                 795                 800

Pro Ala Glu Ser Leu Arg His Ser Gln Thr Gly Val Phe Val Gly Ile
                805                 810                 815

Ser Asn Ser Asp Tyr Ala Gln Leu Gln Val Arg Glu Asn Asn Pro Ile
            820                 825                 830

Asn Pro Tyr Met Gly Thr Gly Asn Ala His Ser Ile Ala Ala Asn Arg
        835                 840                 845

Leu Ser Tyr Phe Leu Asp Leu Arg Gly Val Ser Leu Ser Ile Asp Thr
    850                 855                 860

Ala Cys Ser Ser Ser Leu Val Ala Val His Leu Ala Cys Gln Ser Leu
865                 870                 875                 880

Ile Asn Gly Glu Ser Glu Leu Ala Ile Ala Ala Gly Val Asn Leu Ile
                885                 890                 895

Leu Thr Pro Asp Val Thr Gln Thr Phe Thr Gln Ala Gly Met Met Ser
            900                 905                 910

Lys Thr Gly Arg Cys Gln Thr Phe Asp Ala Glu Ala Asp Gly Tyr Val
        915                 920                 925

Arg Gly Glu Gly Cys Gly Val Val Leu Leu Lys Pro Leu Ala Gln Ala
    930                 935                 940

Glu Arg Asp Gly Asp Asn Ile Leu Ala Val Ile His Gly Ser Ala Val
945                 950                 955                 960

Asn Gln Asp Gly Arg Ser Asn Gly Leu Thr Ala Pro Asn Gly Arg Ser
                965                 970                 975

Gln Gln Ala Val Ile Arg Gln Ala Leu Ala Gln Ala Gly Ile Thr Ala
            980                 985                 990

Ala Asp Leu Ala Tyr Leu Glu Ala  His Gly Thr Gly Thr  Pro Leu Gly
        995                 1000                1005

Asp Pro  Ile Glu Ile Asn Ser  Leu Lys Ala Val Leu  Gln Thr Ala
    1010                1015                1020

Gln Arg  Glu Gln Pro Cys Val  Val Gly Ser Val Lys  Thr Asn Ile
    1025                1030                1035

Gly His  Leu Glu Ala Ala Ala  Gly Ile Ala Gly Leu  Ile Lys Val
    1040                1045                1050
```

-continued

```
Ile Leu  Ser Leu Glu His Gly  Met Ile Pro Gln His  Leu His Phe
    1055                 1060                 1065

Lys Gln  Leu Asn Pro Arg Ile  Asp Leu Asp Gly Leu  Val Thr Ile
    1070                 1075                 1080

Ala Ser  Lys Asp Gln Pro Trp  Ser Gly Gly Ser Gln  Lys Arg Phe
    1085                 1090                 1095

Ala Gly  Val Ser Ser Phe Gly  Phe Gly Gly Thr Asn  Ala His Val
    1100                 1105                 1110

Ile Val  Gly Asp Tyr Ala Gln  Gln Lys Ser Pro Leu  Ala Pro Pro
    1115                 1120                 1125

Ala Thr  Gln Asp Arg Pro Trp  His Leu Leu Thr Leu  Ser Ala Lys
    1130                 1135                 1140

Asn Ala  Gln Ala Leu Asn Ala  Leu Gln Lys Ser Tyr  Gly Asp Tyr
    1145                 1150                 1155

Leu Ala  Gln His Pro Ser Val  Asp Pro Arg Asp Leu  Cys Leu Ser
    1160                 1165                 1170

Ala Asn  Thr Gly Arg Ser Pro  Leu Lys Glu Arg Arg  Phe Phe Val
    1175                 1180                 1185

Phe Lys  Gln Val Ala Asp Leu  Gln Gln Thr Leu Asn  Gln Asp Phe
    1190                 1195                 1200

Leu Ala  Gln Pro Arg Leu Ser  Ser Pro Ala Lys Ile  Ala Phe Leu
    1205                 1210                 1215

Phe Thr  Gly Gln Gly Ser Gln  Tyr Tyr Gly Met Gly  Gln Gln Leu
    1220                 1225                 1230

Tyr Gln  Thr Ser Pro Val Phe  Arg Gln Val Leu Asp  Glu Cys Asp
    1235                 1240                 1245

Arg Leu  Trp Gln Thr Tyr Ser  Pro Glu Ala Pro Ala  Leu Thr Asp
    1250                 1255                 1260

Leu Leu  Tyr Gly Asn His Asn  Pro Asp Leu Val His  Glu Thr Val
    1265                 1270                 1275

Tyr Thr  Gln Pro Leu Leu Phe  Ala Val Glu Tyr Ala  Ile Ala Gln
    1280                 1285                 1290

Leu Trp  Leu Ser Trp Gly Val  Thr Pro Asp Phe Cys  Met Gly His
    1295                 1300                 1305

Ser Val  Gly Glu Tyr Val Ala  Ala Cys Leu Ala Gly  Val Phe Ser
    1310                 1315                 1320

Leu Ala  Asp Gly Met Lys Leu  Ile Thr Ala Arg Gly  Lys Leu Met
    1325                 1330                 1335

His Ala  Leu Pro Ser Asn Gly  Ser Met Ala Ala Val  Phe Ala Asp
    1340                 1345                 1350

Lys Thr  Val Ile Lys Pro Tyr  Leu Ser Glu His Leu  Thr Val Gly
    1355                 1360                 1365

Ala Glu  Asn Gly Ser His Leu  Val Leu Ser Gly Lys  Thr Pro Cys
    1370                 1375                 1380

Leu Glu  Ala Ser Ile His Lys  Leu Gln Ser Gln Gly  Ile Lys Thr
    1385                 1390                 1395

Lys Pro  Leu Lys Val Ser His  Ala Phe His Ser Pro  Leu Met Ala
    1400                 1405                 1410

Pro Met  Leu Ala Glu Phe Arg  Glu Ile Ala Glu Gln  Ile Thr Phe
    1415                 1420                 1425

His Pro  Pro Arg Ile Pro Leu  Ile Ser Asn Val Thr  Gly Gly Gln
    1430                 1435                 1440

Ile Glu  Ala Glu Ile Ala Gln  Ala Asp Tyr Trp Val  Lys His Val
    1445                 1450                 1455
```

```
Ser Gln  Pro Val Lys Phe Val  Gln Ser Ile Gln Thr  Leu Ala Gln
    1460                 1465                 1470

Ala Gly  Val Asn Val Tyr Leu  Glu Ile Gly Val Lys  Pro Val Leu
    1475                 1480                 1485

Leu Ser  Met Gly Arg His Cys  Leu Ala Glu Gln Glu  Ala Val Trp
    1490                 1495                 1500

Leu Pro  Ser Leu Arg Pro His  Ser Glu Pro Trp Pro  Glu Ile Leu
    1505                 1510                 1515

Thr Ser  Leu Gly Lys Leu Tyr  Glu Gln Gly Leu Asn  Ile Asp Trp
    1520                 1525                 1530

Gln Thr  Val Glu Ala Gly Asp  Arg Arg Arg Lys Leu  Ile Leu Pro
    1535                 1540                 1545

Thr Tyr  Pro Phe Gln Arg Gln  Arg Tyr Trp Phe Asn  Gln Gly Ser
    1550                 1555                 1560

Trp Gln  Thr Val Glu Thr Glu  Ser Val Asn Pro Gly  Pro Asp Asp
    1565                 1570                 1575

Leu Asn  Asp Trp Leu Tyr Gln  Val Ala Trp Thr Pro  Leu Asp Thr
    1580                 1585                 1590

Leu Pro  Pro Ala Pro Glu Pro  Ser Ala Lys Leu Trp  Leu Ile Leu
    1595                 1600                 1605

Gly Asp  Arg His Asp His Gln  Pro Ile Glu Ala Gln  Phe Lys Asn
    1610                 1615                 1620

Ala Gln  Arg Val Tyr Leu Gly  Gln Ser Asn His Phe  Pro Thr Asn
    1625                 1630                 1635

Ala Pro  Trp Glu Val Ser Ala  Asp Ala Leu Asp Asn  Leu Phe Thr
    1640                 1645                 1650

His Val  Gly Ser Gln Asn Leu  Ala Gly Ile Leu Tyr  Leu Cys Pro
    1655                 1660                 1665

Pro Gly  Glu Asp Pro Glu Asp  Leu Asp Glu Ile Gln  Lys Gln Thr
    1670                 1675                 1680

Ser Gly  Phe Ala Leu Gln Leu  Ile Gln Thr Leu Tyr  Gln Gln Lys
    1685                 1690                 1695

Ile Ala  Val Pro Cys Trp Phe  Val Thr His Gln Ser  Gln Arg Val
    1700                 1705                 1710

Leu Glu  Thr Asp Ala Val Thr  Gly Phe Ala Gln Gly  Gly Leu Trp
    1715                 1720                 1725

Gly Leu  Ala Gln Ala Ile Ala  Leu Glu His Pro Glu  Leu Trp Gly
    1730                 1735                 1740

Gly Ile  Ile Asp Val Asp Asp  Ser Leu Pro Asn Phe  Ala Gln Ile
    1745                 1750                 1755

Cys Gln  Gln Arg Gln Val Gln  Gln Leu Ala Val Arg  His Gln Lys
    1760                 1765                 1770

Leu Tyr  Gly Ala Gln Leu Lys  Lys Gln Pro Ser Leu  Pro Gln Lys
    1775                 1780                 1785

Asn Leu  Gln Ile Gln Pro Gln  Gln Thr Tyr Leu Val  Thr Gly Gly
    1790                 1795                 1800

Leu Gly  Ala Ile Gly Arg Lys  Ile Ala Gln Trp Leu  Ala Ala Ala
    1805                 1810                 1815

Gly Ala  Glu Lys Val Ile Leu  Val Ser Arg Arg Ala  Pro Ala Ala
    1820                 1825                 1830

Asp Gln  Gln Thr Leu Pro Thr  Asn Ala Val Val Tyr  Pro Cys Asp
    1835                 1840                 1845

Leu Ala  Asp Ala Ala Gln Val  Ala Lys Leu Phe Gln  Thr Tyr Pro
```

```
    1850                1855                1860

His Ile Lys Gly Ile Phe His Ala Ala Gly Thr Leu Ala Asp Gly
    1865                1870                1875

Leu Leu Gln Gln Gln Thr Trp Gln Lys Phe Gln Thr Val Ala Ala
    1880                1885                1890

Ala Lys Met Lys Gly Thr Trp His Leu His Arg His Ser Gln Lys
    1895                1900                1905

Leu Asp Leu Asp Phe Phe Val Leu Phe Ser Ser Val Ala Gly Val
    1910                1915                1920

Leu Gly Ser Pro Gly Gln Gly Asn Tyr Ala Ala Ala Asn Arg Gly
    1925                1930                1935

Met Ala Ala Ile Ala Gln Tyr Arg Gln Ala Gln Gly Leu Pro Ala
    1940                1945                1950

Leu Ala Ile His Trp Gly Pro Trp Ala Glu Gly Gly Met Ala Asn
    1955                1960                1965

Ser Leu Ser Asn Gln Asn Leu Ala Trp Leu Pro Pro Pro Gln Gly
    1970                1975                1980

Leu Thr Ile Leu Glu Lys Val Leu Gly Ala Gln Gly Glu Met Gly
    1985                1990                1995

Val Phe Lys Pro Asp Trp Gln Asn Leu Ala Lys Gln Phe Pro Glu
    2000                2005                2010

Phe Ala Lys Thr His Tyr Phe Ala Ala Val Ile Pro Ser Ala Glu
    2015                2020                2025

Ala Val Pro Pro Thr Ala Ser Ile Phe Asp Lys Leu Ile Asn Leu
    2030                2035                2040

Glu Ala Ser Gln Arg Ala Asp Tyr Leu Leu Asp Tyr Leu Arg Arg
    2045                2050                2055

Ser Val Ala Gln Ile Leu Lys Leu Glu Ile Glu Gln Ile Gln Ser
    2060                2065                2070

His Asp Ser Leu Leu Asp Leu Gly Met Asp Ser Leu Met Ile Met
    2075                2080                2085

Glu Ala Ile Ala Ser Leu Lys Gln Asp Leu Gln Leu Met Leu Tyr
    2090                2095                2100

Pro Arg Glu Ile Tyr Glu Arg Pro Arg Leu Asp Val Leu Thr Ala
    2105                2110                2115

Tyr Leu Ala Ala Glu Phe Thr Lys Ala His Asp Ser Glu Ala Ala
    2120                2125                2130

Thr Ala Ala Ala Ala Ile Pro Ser Gln Ser Leu Ser Val Lys Thr
    2135                2140                2145

Lys Lys Gln Trp Gln Lys Pro Asp His Lys Asn Pro Asn Pro Ile
    2150                2155                2160

Ala Phe Ile Leu Ser Ser Pro Arg Ser Gly Ser Thr Leu Leu Arg
    2165                2170                2175

Val Met Leu Ala Gly His Pro Gly Leu Tyr Ser Pro Pro Glu Leu
    2180                2185                2190

His Leu Leu Pro Phe Glu Thr Met Gly Asp Arg His Gln Glu Leu
    2195                2200                2205

Gly Leu Ser His Leu Gly Glu Gly Leu Gln Arg Ala Leu Met Asp
    2210                2215                2220

Leu Glu Asn Leu Thr Pro Glu Ala Ser Gln Ala Lys Val Asn Gln
    2225                2230                2235

Trp Val Lys Ala Asn Thr Pro Ile Ala Asp Ile Tyr Ala Tyr Leu
    2240                2245                2250
```

-continued

```
Gln Arg  Gln Ala Glu Gln Arg  Leu Leu Ile Asp Lys  Ser Pro Ser
    2255                 2260                 2265

Tyr Gly  Ser Asp Arg His Ile  Leu Asp His Ser Glu  Ile Leu Phe
    2270                 2275                 2280

Asp Gln  Ala Lys Tyr Ile His  Leu Val Arg His Pro  Tyr Ala Val
    2285                 2290                 2295

Ile Glu  Ser Phe Thr Arg Leu  Arg Met Asp Lys Leu  Leu Gly Ala
    2300                 2305                 2310

Glu Gln  Gln Asn Pro Tyr Ala  Leu Ala Glu Ser Ile  Trp Arg Thr
    2315                 2320                 2325

Ser Asn  Arg Asn Ile Leu Asp  Leu Gly Arg Thr Val  Gly Ala Asp
    2330                 2335                 2340

Arg Tyr  Leu Gln Val Ile Tyr  Glu Asp Leu Val Arg  Asp Pro Arg
    2345                 2350                 2355

Lys Val  Leu Thr Asn Ile Cys  Asp Phe Leu Gly Val  Asp Phe Asp
    2360                 2365                 2370

Glu Ala  Leu Leu Asn Pro Tyr  Ser Gly Asp Arg Leu  Thr Asp Gly
    2375                 2380                 2385

Leu His  Gln Gln Ser Met Gly  Val Gly Asp Pro Asn  Phe Leu Gln
    2390                 2395                 2400

His Lys  Thr Ile Asp Pro Ala  Leu Ala Asp Lys Trp  Arg Ser Ile
    2405                 2410                 2415

Thr Leu  Pro Ala Ala Leu Gln  Leu Asp Thr Ile Gln  Leu Ala Glu
    2420                 2425                 2430

Thr Phe  Ala Tyr Asp Leu Pro  Gln Glu Pro Gln Leu  Thr Pro Gln
    2435                 2440                 2445

Thr Gln  Ser Leu Pro Ser Met  Val Glu Arg Phe Val  Thr Val Arg
    2450                 2455                 2460

Gly Leu  Glu Thr Cys Leu Cys  Glu Trp Gly Asp Arg  His Gln Pro
    2465                 2470                 2475

Leu Val  Leu Leu Leu His Gly  Ile Leu Glu Gln Gly  Ala Ser Trp
    2480                 2485                 2490

Gln Leu  Ile Ala Pro Gln Leu  Ala Ala Gln Gly Tyr  Trp Val Val
    2495                 2500                 2505

Ala Pro  Asp Leu Arg Gly His  Gly Lys Ser Ala His  Ala Gln Ser
    2510                 2515                 2520

Tyr Ser  Met Leu Asp Phe Leu  Ala Asp Val Asp Ala  Leu Ala Lys
    2525                 2530                 2535

Gln Leu  Gly Asp Arg Pro Phe  Thr Leu Val Gly His  Ser Met Gly
    2540                 2545                 2550

Ser Ile  Ile Gly Ala Met Tyr  Ala Gly Ile Arg Gln  Thr Gln Val
    2555                 2560                 2565

Glu Lys  Leu Ile Leu Val Glu  Thr Ile Val Pro Asn  Asp Ile Asp
    2570                 2575                 2580

Asp Ala  Glu Thr Gly Asn His  Leu Thr Thr His Leu  Asp Tyr Leu
    2585                 2590                 2595

Ala Ala  Pro Pro Gln His Pro  Ile Phe Pro Ser Leu  Glu Val Ala
    2600                 2605                 2610

Ala Arg  Arg Leu Arg Gln Ala  Thr Pro Gln Leu Pro  Lys Asp Leu
    2615                 2620                 2625

Ser Ala  Phe Leu Thr Gln Arg  Ser Thr Lys Ser Val  Glu Lys Gly
    2630                 2635                 2640

Val Gln  Trp Arg Trp Asp Ala  Phe Leu Arg Thr Arg  Ala Gly Ile
    2645                 2650                 2655
```

```
Glu Phe  Asn Gly Ile Ser Arg  Arg Arg Tyr Leu Ala  Leu Leu Lys
    2660                 2665                 2670

Asp Ile  Gln Ala Pro Ile Thr  Leu Ile Tyr Gly Asp  Gln Ser Glu
    2675                 2680                 2685

Phe Asn  Arg Pro Ala Asp Leu  Gln Ala Ile Gln Ala  Ala Leu Pro
    2690                 2695                 2700

Gln Ala  Gln Arg Leu Thr Val  Ala Gly Gly His Asn  Leu His Phe
    2705                 2710                 2715

Glu Asn  Pro Gln Ala Ile Ala  Gln Ile Val Tyr Gln  Gln Leu Gln
    2720                 2725                 2730

Thr Pro  Val Pro Lys Thr Gln  Gly Leu His His His  His His His
    2735                 2740                 2745

Ser Ala  Trp Ser His Pro Gln  Phe Glu Lys
    2750                 2755


<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

gggagctcaa ggaattatag ttatgcgcaa accctggtta ga                          42


<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

ggcctgcagg ttatagggac tggatcgcca gttttttctg ct                          42


<210> SEQ ID NO 34
<211> LENGTH: 294
<212> TYPE: DNA
<213> ORGANISM: Streptomyces roseosporus

<400> SEQUENCE: 34

ctcgccgagg cctgcgagct gaccgccgcc actcccatgg gcggctggct gcccatgtac     60

cacgacatgg ggctcctggg cacgctgaca ccggccctgt acctcggcac cacgtgcgtg    120

ctgatgagct ccacggcatt catcaaacgg ccgcacctgt ggctacggac catcgaccgg    180

ttcggcctgg tctggtcgtc ggctcccgac ttcgcgtacg acatgtgtct gaagcgcgtc    240

accgacgagc agatcgccgg gctggacctg tcccgctggc ggtgggccgg caac          294


<210> SEQ ID NO 35
<211> LENGTH: 294
<212> TYPE: DNA
<213> ORGANISM: Legionella pneumophila

<400> SEQUENCE: 35

atttttacct cttttcatat gaatgatgaa accattattt tcagctggct gcccccacat     60

catgatatgg gtttgattgg ctgcattctg acccccatct atggtggaat tcaggcaatc    120

atgatgtccc ctttctcatt tttacaaaac ccgctttcct ggttaaaaca tattaccaaa    180
```

tacaaagcaa ctatcagtgg aagccctaac ttcgcttacg attattgtgt caaacgaatc 240
agggaagaaa aaaaagaagg gctggattta agttcatggg tgactgcttt caac 294

<210> SEQ ID NO 36
<211> LENGTH: 294
<212> TYPE: DNA
<213> ORGANISM: Bacillus subtilis

<400> SEQUENCE: 36
atccggaatg cgctggctat cgacttaaaa gatactcttt tatcttggat gcccttaacc 60
catgacatgg ggctcatagc ttgccacctt gttcctgcct tagccggaat caatcaaaat 120
ttaatgccga cagaattatt tattcgaaga cctattctct ggatgaaaaa agctcatgaa 180
cataaagcca gcattctatc ctcacctaat tttggataca attactttct taaatttctg 240
aaagacaata aaagttacga ctgggattta tcccatatca gggtcattgc aaac 294

<210> SEQ ID NO 37
<211> LENGTH: 951
<212> TYPE: DNA
<213> ORGANISM: Synechococcus sp.

<400> SEQUENCE: 37
gtgcgcaaac cctggttaga acttcccttg gcgatttttt cctttggctt ttataaagtc 60
aacaaatttc tgattgggaa tctctacact ttgtatttag cgctgaataa aaaaaatgct 120
aaggaatggc gcattattgg agaaaaatcc ctccagaaat tcctgagttt acccgtttta 180
atgaccaaag cgccccggtg gaatacccac gccattatcg gcaccctggg accactctct 240
gtagaaaaag aactcaccat taacctcgaa acgattcgtc aatccacgga agcttgggtc 300
ggttgcatct atgactttcc gggctatcgc acggtgttaa atttcacgca actcaccgat 360
gaccccaacc aaacagaact caaaattttc ttacctaaag ggaaatatac cgtcgggtta 420
cgttactacc atcccaaggt aaatcctcgc tttccggtcg ttaaaacaga tctaaatcta 480
accgtgccga ctttggttgt ttcgccccaa aacaacgact tttatcaagc cctggcccag 540
aaaacaaacc tttattttcg tctgcttcac tactacattt ttacgctatt taaatttcgc 600
gatgtcttac ccgctgcttt tgtgaaagga gaattcctcc ctgtcggcgc caccgatact 660
caattttttt acggcgcttt agaagcagca gaaaacttag agattaccat cccagccccc 720
tggcttcaga cctttgattt ttatctcacc ttctataacc gcgccagttt tcccctacgt 780
tggcaaaaaa tcaccgaagc gatgatctgt gatcccctgg gagaaaaagg ctattaccta 840
attcggatgc ggccccgtac tcaggacgcc gaggcacaat taccaacggt tagaggagaa 900
gaaacccagg tcacgcccca gcagaaaaaa ctggcgatcc agtccctata a 951

<210> SEQ ID NO 38
<211> LENGTH: 316
<212> TYPE: PRT
<213> ORGANISM: Synechococcus sp.

<400> SEQUENCE: 38

Met Arg Lys Pro Trp Leu Glu Leu Pro Leu Ala Ile Phe Ser Phe Gly
1 5 10 15

Phe Tyr Lys Val Asn Lys Phe Leu Ile Gly Asn Leu Tyr Thr Leu Tyr
20 25 30

Leu Ala Leu Asn Lys Lys Asn Ala Lys Glu Trp Arg Ile Ile Gly Glu
35 40 45

Lys Ser Leu Gln Lys Phe Leu Ser Leu Pro Val Leu Met Thr Lys Ala

```
    50                  55                  60

Pro Arg Trp Asn Thr His Ala Ile Ile Gly Thr Leu Gly Pro Leu Ser
65                  70                  75                  80

Val Glu Lys Glu Leu Thr Ile Asn Leu Glu Thr Ile Arg Gln Ser Thr
                85                  90                  95

Glu Ala Trp Val Gly Cys Ile Tyr Asp Phe Pro Gly Tyr Arg Thr Val
            100                 105                 110

Leu Asn Phe Thr Gln Leu Thr Asp Asp Pro Asn Gln Thr Glu Leu Lys
        115                 120                 125

Ile Phe Leu Pro Lys Gly Lys Tyr Thr Val Gly Leu Arg Tyr Tyr His
    130                 135                 140

Pro Lys Val Asn Pro Arg Phe Pro Val Val Lys Thr Asp Leu Asn Leu
145                 150                 155                 160

Thr Val Pro Thr Leu Val Val Ser Pro Gln Asn Asn Asp Phe Tyr Gln
                165                 170                 175

Ala Leu Ala Gln Lys Thr Asn Leu Tyr Phe Arg Leu Leu His Tyr Tyr
            180                 185                 190

Ile Phe Thr Leu Phe Lys Phe Arg Asp Val Leu Pro Ala Ala Phe Val
        195                 200                 205

Lys Gly Glu Phe Leu Pro Val Gly Ala Thr Asp Thr Gln Phe Phe Tyr
    210                 215                 220

Gly Ala Leu Glu Ala Ala Glu Asn Leu Glu Ile Thr Ile Pro Ala Pro
225                 230                 235                 240

Trp Leu Gln Thr Phe Asp Phe Tyr Leu Thr Phe Tyr Asn Arg Ala Ser
                245                 250                 255

Phe Pro Leu Arg Trp Gln Lys Ile Thr Glu Ala Met Ile Cys Asp Pro
            260                 265                 270

Leu Gly Glu Lys Gly Tyr Tyr Leu Ile Arg Met Arg Pro Arg Thr Gln
        275                 280                 285

Asp Ala Glu Ala Gln Leu Pro Thr Val Arg Gly Glu Glu Thr Gln Val
    290                 295                 300

Thr Pro Gln Gln Lys Lys Leu Ala Ile Gln Ser Leu
305                 310                 315


<210> SEQ ID NO 39
<211> LENGTH: 522
<212> TYPE: PRT
<213> ORGANISM: Bacillus subtilis

<400> SEQUENCE: 39

Ser Tyr Arg Gln Leu Phe Asp Glu Ala Gln Gly Phe Leu Gly Tyr Leu
1               5                   10                  15

Gln His Ile Gly Ile Gln Pro Lys Gln Glu Ile Val Phe Gln Ile Gln
            20                  25                  30

Glu Asn Lys Ser Phe Val Val Ala Phe Trp Ala Cys Leu Leu Gly Gly
        35                  40                  45

Met Ile Pro Val Pro Val Ser Ile Gly Glu Asp Asn Asp His Lys Leu
    50                  55                  60

Lys Val Trp Arg Ile Trp Asn Ile Leu Asn Asn Pro Phe Leu Leu Ala
65                  70                  75                  80

Ser Glu Thr Val Leu Asp Lys Met Lys Lys Phe Ala Ala Asp His Asp
                85                  90                  95

Leu Gln Asp Phe His His Gln Leu Ile Glu Lys Ser Asp Ile Ile Gln
            100                 105                 110

Asp Arg Ile Tyr Asp His Pro Ala Ser Gln Tyr Glu Pro Glu Ala Asp
```

```
        115                 120                 125

Glu Leu Ala Phe Ile Gln Phe Ser Ser Gly Ser Thr Gly Asp Pro Lys
    130                 135                 140

Gly Val Met Leu Thr His His Asn Leu Ile His Asn Thr Cys Ala Ile
145                 150                 155                 160

Arg Asn Ala Leu Ala Ile Asp Leu Lys Asp Thr Leu Leu Ser Trp Met
                165                 170                 175

Pro Leu Thr His Asp Met Gly Leu Ile Ala Cys His Leu Val Pro Ala
            180                 185                 190

Leu Ala Gly Ile Asn Gln Asn Leu Met Pro Thr Glu Leu Phe Ile Arg
        195                 200                 205

Arg Pro Ile Leu Trp Met Lys Lys Ala His Glu His Lys Ala Ser Ile
    210                 215                 220

Leu Ser Ser Pro Asn Phe Gly Tyr Asn Tyr Phe Leu Lys Phe Leu Lys
225                 230                 235                 240

Asp Asn Lys Ser Tyr Asp Trp Asp Leu Ser His Ile Arg Val Ile Ala
                245                 250                 255

Asn Gly Ala Glu Pro Ile Leu Pro Glu Leu Cys Asp Glu Phe Leu Thr
            260                 265                 270

Arg Cys Ala Ala Phe Asn Met Lys Arg Ser Ala Ile Leu Asn Val Tyr
        275                 280                 285

Gly Leu Ala Glu Ala Ser Val Gly Ala Thr Phe Ser Asn Ile Gly Glu
    290                 295                 300

Arg Phe Val Pro Val Tyr Leu His Arg Asp His Leu Asn Leu Gly Glu
305                 310                 315                 320

Arg Ala Val Glu Val Ser Lys Glu Asp Gln Asn Cys Ala Ser Phe Val
                325                 330                 335

Glu Val Gly Lys Pro Ile Asp Tyr Cys Gln Ile Arg Ile Cys Asn Glu
            340                 345                 350

Ala Asn Glu Gly Leu Glu Asp Gly Phe Ile Gly His Ile Gln Ile Lys
        355                 360                 365

Gly Glu Asn Val Thr Gln Gly Tyr Tyr Asn Asn Pro Glu Ser Thr Asn
    370                 375                 380

Arg Ala Leu Thr Pro Asp Gly Trp Val Lys Thr Gly Asp Leu Gly Phe
385                 390                 395                 400

Ile Arg Lys Gly Asn Leu Val Val Thr Gly Arg Glu Lys Asp Ile Ile
                405                 410                 415

Phe Val Asn Gly Lys Asn Val Tyr Pro His Asp Ile Glu Arg Val Ala
            420                 425                 430

Ile Glu Leu Glu Asp Ile Asp Leu Gly Arg Val Ala Ala Cys Gly Val
        435                 440                 445

Tyr Asp Gln Glu Thr Arg Ser Arg Glu Ile Val Leu Phe Ala Val Tyr
    450                 455                 460

Lys Lys Ser Ala Glu Gln Phe Ala Pro Leu Val Lys Asp Ile Lys Lys
465                 470                 475                 480

His Leu Tyr Gln Arg Gly Gly Trp Ser Ile Lys Glu Ile Leu Pro Ile
                485                 490                 495

Arg Lys Leu Pro Lys Thr Thr Ser Gly Lys Val Lys Arg Tyr Glu Leu
            500                 505                 510

Ala Glu Gln Tyr Glu Ser Gly Lys Phe Ala
        515                 520
```

<210> SEQ ID NO 40
<211> LENGTH: 548

<212> TYPE: PRT
<213> ORGANISM: Synechococcus sp.

<400> SEQUENCE: 40

Asp Leu Leu Gln Tyr Arg Ala Lys Leu Gln Ala Arg Lys Thr Val Phe
1 5 10 15

Ser Phe Leu Ala Asp Gly Glu Ala Glu Ser Ala Ala Leu Thr Tyr Gly
20 25 30

Glu Leu Asp Gln Lys Ala Gln Ala Ile Ala Ala Phe Leu Gln Ala Asn
35 40 45

Gln Ala Gln Gly Gln Arg Ala Leu Leu Leu Tyr Pro Pro Gly Leu Glu
50 55 60

Phe Ile Gly Ala Phe Leu Gly Cys Leu Tyr Ala Gly Val Val Ala Val
65 70 75 80

Pro Ala Tyr Pro Pro Arg Pro Asn Lys Ser Phe Asp Arg Leu His Ser
85 90 95

Ile Ile Gln Asp Ala Gln Ala Lys Phe Ala Leu Thr Thr Thr Glu Leu
100 105 110

Lys Asp Lys Ile Ala Asp Arg Leu Glu Ala Leu Glu Gly Thr Asp Phe
115 120 125

His Cys Leu Ala Thr Asp Gln Val Glu Leu Ile Ser Gly Lys Asn Trp
130 135 140

Gln Lys Pro Asn Ile Ser Gly Thr Asp Leu Ala Phe Leu Gln Tyr Thr
145 150 155 160

Ser Gly Ser Thr Gly Asp Pro Lys Gly Val Met Val Ser His His Asn
165 170 175

Leu Ile His Asn Ser Gly Leu Ile Asn Gln Gly Phe Gln Asp Thr Glu
180 185 190

Ala Ser Met Gly Val Ser Trp Leu Pro Pro Tyr His Asp Met Gly Leu
195 200 205

Ile Gly Gly Ile Leu Gln Pro Ile Tyr Val Gly Ala Thr Gln Ile Leu
210 215 220

Met Pro Pro Val Ala Phe Leu Gln Arg Pro Phe Arg Trp Leu Lys Ala
225 230 235 240

Ile Asn Asp Tyr Arg Val Ser Thr Ser Gly Ala Pro Asn Phe Ala Tyr
245 250 255

Asp Leu Cys Ala Ser Gln Ile Thr Pro Glu Gln Ile Arg Glu Leu Asp
260 265 270

Leu Ser Cys Trp Arg Leu Ala Phe Ser Gly Ala Glu Pro Ile Arg Ala
275 280 285

Val Thr Leu Glu Asn Phe Ala Lys Thr Phe Ala Thr Ala Gly Phe Gln
290 295 300

Lys Ser Ala Phe Tyr Pro Cys Tyr Gly Met Ala Glu Thr Thr Leu Ile
305 310 315 320

Val Ser Gly Gly Asn Gly Arg Ala Gln Leu Pro Gln Glu Ile Ile Val
325 330 335

Ser Lys Gln Gly Ile Glu Ala Asn Gln Val Arg Pro Ala Gln Gly Thr
340 345 350

Glu Thr Thr Val Thr Leu Val Gly Ser Gly Glu Val Ile Gly Asp Gln
355 360 365

Ile Val Lys Ile Val Asp Pro Gln Ala Leu Thr Glu Cys Thr Val Gly
370 375 380

Glu Ile Gly Glu Val Trp Val Lys Gly Glu Ser Val Ala Gln Gly Tyr
385 390 395 400

-continued

```
Trp Gln Lys Pro Asp Leu Thr Gln Gln Gln Phe Gln Gly Asn Val Gly
                405                 410                 415

Ala Glu Thr Gly Phe Leu Arg Thr Gly Asp Leu Gly Phe Leu Gln Gly
            420                 425                 430

Gly Glu Leu Tyr Ile Thr Gly Arg Leu Lys Asp Leu Leu Ile Ile Arg
        435                 440                 445

Gly Arg Asn His Tyr Pro Gln Asp Ile Glu Leu Thr Val Glu Val Ala
    450                 455                 460

His Pro Ala Leu Arg Gln Gly Ala Gly Ala Ala Val Ser Val Asp Val
465                 470                 475                 480

Asn Gly Glu Glu Gln Leu Val Ile Val Gln Glu Val Glu Arg Lys Tyr
                485                 490                 495

Ala Arg Lys Leu Asn Val Ala Ala Val Ala Gln Ala Ile Arg Gly Ala
            500                 505                 510

Ile Ala Ala Glu His Gln Leu Gln Pro Gln Ala Ile Cys Phe Ile Lys
        515                 520                 525

Pro Gly Ser Ile Pro Lys Thr Ser Ser Gly Lys Ile Arg Arg His Ala
    530                 535                 540

Cys Lys Ala Gly
545
```

METHODS AND COMPOSITIONS FOR PRODUCING ALKENES OF VARIOUS CHAIN LENGTH

CROSS-REFERENCE TO RELATED APPLICATIONS

This application claims priority to earlier filed U.S. Provisional Patent Application No. 61/441,619, filed Feb. 10, 2011.

SEQUENCE LISTING

The instant application contains a Sequence Listing which has been submitted in ASCII format via EFS-Web and is hereby incorporated by reference in its entirety. Said ASCII copy, created on Feb. 10, 2012, is named 20073US.txt and is 368,275 bytes in size.

BACKGROUND OF THE INVENTION

Unsaturated linear hydrocarbons such as α-olefins or 1-alkenes are an industrially important group of molecules which can serve as feedstocks for producing various materials such as detergents, fuels, pharmaceutical products, plastics, synthetic rubbers and viscosity additives. Olefins or alkenes are unsaturated hydrocarbons whose molecules contain one or more pairs of carbon atoms linked together by a double bond.

Shorter alkene products are desirable in industry because of their usefulness as surfactants and lubricants. Because 1-alkenes are hydrocarbons, they can also serve as fuels. In this context, 1-alkenes with shorter carbon chain lengths are also preferred because they have lower melting points (FIG. 1). Thus, a need exists for improved methods and compositions for synthesizing 1-alkenes of desired chain lengths.

SUMMARY OF THE INVENTION

The invention described herein relates to compositions and methods for synthesizing 1-alkenes with defined chain lengths. In one embodiment, the disclosure provides alkene synthases that are modified such that the resulting chain length of the primary alkene product is different than the primary product produced by the unmodified or native alkene synthase. For example, an alkene synthase that produces primarily nonadecene can be modified to produce primarily shorter alkenes, e.g., heptadecene, tridecene, pentadecene, etc.

The present disclosure provides an isolated or recombinant NonA alkene synthase comprising a heterologous acyl binding pocket. In one embodiment, the heterologous acyl binding pocket comprises a polypeptide sequence of SEQ ID NO: 8. In another embodiment, the heterologous acyl binding pocket comprises a polypeptide sequence of SEQ ID NO: 12. In still another embodiment, the heterologous acyl binding pocket comprises a polypeptide sequence of SEQ ID NO: 16. In further embodiments, the heterologous acyl binding pocket comprises a polypeptide sequence at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 8, SEQ ID NO: 12, or SEQ ID NO: 16.

The present disclosure also provides an isolated or recombinant polynucleotide encoding a heterologous acyl binding pocket. In one aspect, the nucleotide sequence encoding the heterologous acyl binding pocket comprises SEQ ID NO: 35. In another aspect, the nucleotide sequence encoding the heterologous acyl binding pocket comprises SEQ ID NO: 36. In yet another aspect, the nucleotide sequence encoding the heterologous acyl binding pocket comprises SEQ ID NO: 34. In one embodiment, the nucleotide sequence encoding the heterologous acyl binding pocket comprises a nucleotide sequence that is a degenerate variant of SEQ ID NO: 35, SEQ ID NO: 36, or SEQ ID NO: 34. In another embodiment, the nucleotide sequence encoding the heterologous acyl binding pocket comprises a nucleotide sequence that is at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 90%, at least 95%, at least 98%, at least 99% or at least 99.9% identical to SEQ ID NO: 35, SEQ ID NO: 36, or SEQ ID NO: 34. In yet another embodiment, the nucleotide sequence encoding the heterologous acyl binding pocket comprises a nucleotide sequence that encodes a polypeptide at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 8, SEQ ID NO: 12, or SEQ ID NO: 16. In still another embodiment, the nucleotide sequence encoding the heterologous acyl binding pocket comprises a nucleotide sequence that hybridizes under stringent conditions to SEQ ID NO: 35, SEQ ID NO: 36, or SEQ ID NO: 34.

The invention relates to an isolated or recombinant polypeptide encoding a chimeric alkene synthase comprising or consisting of an amino acid sequence SEQ ID NO: 30, SEQ ID NO: 31, or SEQ ID NO: 29. In one embodiment, the polypeptide sequence is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 30, SEQ ID NO: 31, or SEQ ID NO: 29.

The present disclosure provides an isolated or recombinant polynucleotide encoding a chimeric alkene synthase comprising or consisting of a nucleotide sequence selected from the group consisting of SEQ ID NO: 27, SEQ ID NO: 28, and SEQ ID NO: 26. In one embodiment, the nucleotide sequence is a degenerate variant of SEQ ID NO: 27, SEQ ID NO: 28, or SEQ ID NO: 26. In another embodiment, the nucleotide sequence is at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 90%, at least 95%, at least 98%, at least 99% or at least 99.9% identical to SEQ ID NO: 27, SEQ ID NO: 28, or SEQ ID NO: 26. In still another embodiment, the nucleotide sequence encodes a polypeptide having the amino acid sequence of SEQ ID NO: 30, SEQ ID NO: 31, or SEQ ID NO: 29. In yet another embodiment, the nucleotide sequence encodes a polypeptide at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NO: 30, SEQ ID NO: 31, or SEQ ID NO: 29. In one aspect, the nucleotide sequence hybridizes under stringent conditions to a nucleic acid sequence that encodes a polypeptide having the amino acid sequence of SEQ ID NO: 27, SEQ ID NO: 28, or SEQ ID NO: 26.

In one aspect, the isolated polynucleotide of the invention is operably linked to one or more expression control sequences. In another aspect, a vector is provided, wherein said vector comprises an isolated polynucleotide described herein. In yet another aspect, a fusion protein comprising the isolated polypeptide is fused to a heterologous amino acid sequence is provided.

In one embodiment, the invention provides a host cell comprising one or more isolated polynucleotides described herein. In a further embodiment, the host cell is a photoautotroph. In another further embodiment, the host cell is *E. coli*. In another embodiment, the host cell is a prokaryote, a eukaryote, a yeast, a filamentous fungus, a protozoa, an algae, or a synthetic cell. In yet another embodiment, the host cell produces a carbon-based product of interest. Also provided is an isolated antibody or antigen-binding fragment or derivative thereof which binds selectively to an isolated polypeptide described herein.

The present disclosure also provides methods for producing carbon-based products of interest, comprising: culturing a host cell to produce the carbon-based product of interest, wherein the host cell comprises a recombinant nucleotide sequence encoding a chimeric alkene synthase comprising a heterologous acyl binding pocket; and isolating the carbon-based product of interest. In another embodiment, the chimeric alkene synthase is an engineered NonA protein. In a further embodiment, the NonA comprises SEQ ID NO: 2. In another further embodiment, the NonA comprises SEQ ID NO: 24. In still another embodiment, the heterologous acyl binding pocket comprises the amino acid sequence SEQ ID NO: 8, SEQ ID NO: 12, or SEQ ID NO: 14. In still another embodiment, the chimeric alkene synthase selectively synthesizes an alkene with a specific chain length. In a further embodiment, the synthesized alkene is a propene, a butene, a pentene, a heptene, an octene, a nonene, a decene, an undecene, a dodecane, a tridecene, a tetradecene, a pentadecene, a hexadecene, a heptadecene, an octadecene, a nonadecene, an eicosene, an uneicosene, or a doeicosene, or isomers and mixtures thereof. In yet another embodiment, the synthesized alkene is 1-tridecene, 1-pentadecene, 1, heptadecene, or 1-nonadecene.

In yet another embodiment, a method is provided for identifying a modified alkene synthase gene that selectively catalyzes the formation of a desired alkene, comprising: modifying an alkene synthase by replacing the acyl carrier binding domain with a heterologous acyl carrier binding domain; expressing the modified alkene synthase in a host cell; and screening the host cell for production of the selected alkene. Also provided is an improved alkene synthase enzyme identified by the above method.

In one aspect, a method for producing a carbon-based product of interest is provided, comprising the steps of: culturing a host cell to produce the carbon-based product of interest, wherein the host cell comprises an engineered chimeric NonA comprising a heterologous binding pocket; and isolating the carbon-based product of interest. In a further aspect, the chimeric alkene synthase selectively synthesizes one or more alkenes with specific chain lengths. In yet another further aspect, the one or more alkenes are selected from the group consisting of: propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene, and isomers and mixtures thereof. In yet another embodiment, the synthesized alkene is 1-tridecene, 1-pentadecene, 1, heptadecene, or 1-nonadecene.

In one embodiment, a method for producing a tridecene or pentadecene is provided, comprising the steps of: culturing a host cell to produce the tridecene or pentadecene, wherein the host cell comprises an engineered chimeric NonA comprising a heterologous SafB binding pocket (SEQ ID NO: 8); and isolating the tridecene or pentadecene. In another embodiment, a method for producing a heptadecene is provided, comprising the steps of: culturing a host cell to produce the heptadecene, wherein the host cell comprises an engineered chimeric NonA comprising a heterologous MycA binding pocket (SEQ ID NO: 12); and isolating the heptadecene. In still another embodiment, a method for producing a heptadecene is provided, comprising the steps of: culturing a host cell to produce the heptadecene, wherein the host cell comprises an engineered chimeric NonA comprising a heterologous DptE binding pocket (SEQ ID NO: 16); and isolating the heptadecene.

In still another embodiment, a method for producing a nonadecene or heptadecene is provided, comprising the steps of: culturing a host cell to produce the nonadecene or heptadecene, wherein the host cell comprises an engineered NonA (SEQ ID NO: 24); and isolating the nonadecene or heptadecene.

Additional information related to the invention may be found in the following Drawings and Detailed Description.

DRAWINGS

FIG. 1 provides melting and boiling points of alkenes with various chain lengths.

FIG. 2 is a representation of the domains found in the 1-alkene synthase YP_001734428 (NonA), as identified by the conserved domain (CD) searching program available on the NCBI website. Abbreviations for domains: acyl-carrier protein (ACP); phosphopantetheinyl (PP); ketosynthase (KS); acyltransferase (AT); ketoreductase (KR); sulfotransferase (ST); and thioesterase (TE). By reference to the YP_001734428 gene sequence, the domains are located at the following residues: LuxE domain: 10-557; ACP domain: 598-675; KS domain: 693-1095; AT domain: 1216-1490; KR domain: 1777-1943; ST domain: 2145-2360; TE domain: 2449-2708.

FIG. 3 illustrates the putative mechanism of 1-nonadecene biosynthesis from stearic acid, stearyl-ACP or stearyl-CoA. AT, acyltransferase; ACP, acyl-carrier protein; KS, ketosynthase; KR, ketoreductase; ST, sulfotransferase; TE, thioesterase.

FIG. 4 is a representation of the residues of the acyl binding domain of saframycin Mx1 synthetase B complexed with an acyl-adenylate ligand. (A) The residues of the acyl binding pocket of the saframycin Mx1 synthetase B acyl-transferase are shown surrounding the dodecanoyl-ligand (white). The end of the acyl chain of the ligand is indicated. (B) The residues of the binding pocket which are not strictly conserved between the four acyl binding pockets are show in black while the others are shown in grey. "*" indicates Cys324.

FIG. 5 is an amino acid alignment of acyl ligase domains of NonA (SEQ ID NO: 40), DptE (SEQ ID NO: 14), MycA (SEQ ID NO: 39), and SafB (SEQ ID NO: 6). The interior acyl binding domain (IABD) of NonA, DptE, MycA, and SafB is underlined in black.

FIG. 6 provides representations of the interior acyl binding pocket of the SafB acyl ligase domain. (A) The amino acids of the interior acyl binding pocket in the SafB acyl ligase domain are black while the rest are grey. (B) View of the binding pocket with all residues 5 angstroms or closer to the acyl-adenylate (white) indicated. The end of the acyl chain of the ligand is indicated.

FIG. 7 depicts a stack of GC/MS chromatograms comparing cell pellet extracts of JCC2157 and JCC308. The interval between the tick marks on the MS detector axis is 1000.

FIG. 8 provides mass spectra of identified 1-alkenes in cell extracts. (A) The MS fragmentation spectrum of the JCC2157 1-heptadecene peak plotted above the spectrum in the NIST database. (B) The MS fragmentation spectrum of the JCC2157 1-octadecene peak plotted above the spectrum in the NIST database. (C) The MS fragmentation spectrum of the JCC2157 1-nonadecene peak plotted above the spectrum in the NIST database. (D) The mass spectrum of the JCC2157 peak identified as 1,x-nonadecadiene (C19:2).

DETAILED DESCRIPTION OF THE INVENTION

Figure 2:
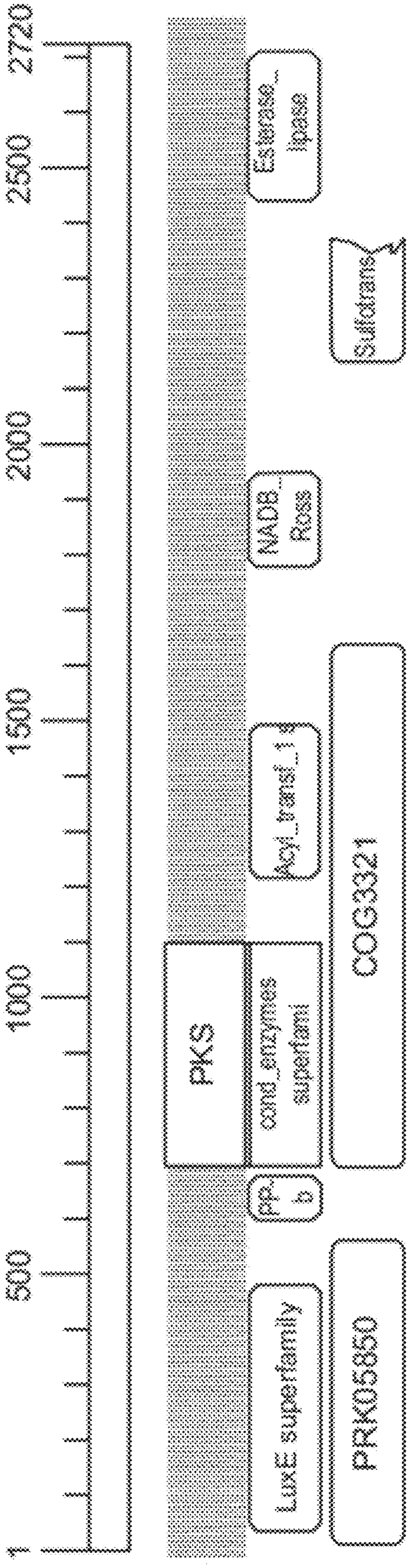

Unless otherwise defined herein, scientific and technical terms used in connection with the invention shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well known and commonly used in the art.

The methods and techniques are generally performed according to conventional methods well known in the art and as described in various general and more specific references that are cited and discussed throughout the present specification unless otherwise indicated. See, e.g., Sambrook et al. *Molecular Cloning: A Laboratory Manual,* 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol. I, CRC Press (1976); *Handbook of Biochemistry: Section A Proteins*, Vol. II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" RNA, DNA or a mixed polymer is one which is substantially separated from other cellular components that naturally accompany the native polynucleotide in its natural host cell, e.g., ribosomes, polymerases and genomic sequences with which it is naturally associated.

As used herein, an "isolated" organic molecule (e.g., an alkane, alkene, or alkanal) is one which is substantially separated from the cellular components (membrane lipids, chromosomes, proteins) of the host cell from which it originated, or from the medium in which the host cell was cultured. The term does not require that the biomolecule has been separated from all other chemicals, although certain isolated biomolecules may be purified to near homogeneity.

The term "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, or (4) does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "recombinant" because it is separated from at least some of the sequences that naturally flank it.

A nucleic acid is also considered "recombinant" if it contains any modifications that do not naturally occur to the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

A particular, non-limiting example of a mathematical algorithm utilized for the comparison of sequences is that of Karlin and Altschul (*Proc. Natl. Acad. Sci.* (1990) USA 87:2264-68; *Proc. Natl. Acad. Sci.* USA (1993) 90: 5873-77) as used in the NBLAST and XBLAST programs (version 2.0) of Altschul et al. (*J. Mol. Biol.* (1990) 215:403-10). BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (*Nucleic Acids Research* (1997) 25(17):3389-3402). When utilizing BLAST and Gapped BLAST programs, the default parameters of the respective programs (e.g., XBLAST and NBLAST) can be used (http://www.ncbi.nlm.nih.gov). One skilled in the art may also use the ALIGN program incorporating the non-linear algorithm of Myers and Miller (*Comput. Appl. Biosci.* (1988) 4:11-17). For amino acid sequence comparison using the ALIGN program one skilled in the art may use a PAM120 weight residue table, a gap length penalty of 12, and a gap penalty of 4.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 71%, 72%, 73%, 74%, 75%, 76%, 77%, 78%, 79%, 80%, 81%, 82%, 83%, 84%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual,* 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Intermediate ranges e.g., at 65-70° C. or at 42-50° C. are also within the scope of the invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$(° C.)=81.5+16.6($\log_{10}$ [$Na^+$])+0.41 (% G+C)−(600/N), where N is the number of bases in the hybrid, and [$Na^+$] is the concentration of sodium ions in the hybridization buffer ([$Na^+$] for 1×SSC=0.165 M).

The skilled practitioner recognizes that reagents can be added to hybridization and/or wash buffers. For example, to decrease non-specific hybridization of nucleic acid molecules to, for example, nitrocellulose or nylon membranes, blocking agents, including but not limited to, BSA or salmon or herring sperm carrier DNA and/or detergents, including but not limited to, SDS, chelating agents EDTA, Ficoll, PVP and the like can be used. When using nylon membranes, in particular, an additional, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (Church and Gilbert (1984) *Proc. Natl. Acad. Sci*. USA 81:1991-1995,) or, alternatively, 0.2×SSC, 1% SDS.

The nucleic acids (also referred to as polynucleotides) may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., Technique, 1:11-15 (1989) and Caldwell and Joyce, PCR *Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "attenuate" as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

A "deletion" is the removal of one or more nucleotides from a nucleic acid molecule or one or more amino acids from a protein, the regions on either side being joined together.

A "knock-out" is a gene whose level of expression or activity has been reduced to zero. In some examples, a gene is knocked-out via deletion of some or all of its coding sequence. In other examples, a gene is knocked-out via introduction of one or more nucleotides into its open-reading frame, which results in translation of a non-sense or otherwise non-functional protein product.

The term "vector" as used herein is intended to refer to a nucleic acid molecule capable of transporting another nucleic acid to which it has been linked. One type of vector is a "plasmid," which refers to a circular double stranded DNA loop into which additional DNA segments may be ligated. Other vectors include cosmids, bacterial artificial chromosomes (BAC) and yeast artificial chromosomes (YAC), fosmids, phage and phagemids. Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply "expression vectors").

"Operatively linked" or "operably linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

An isolated or purified polypeptide is substantially free of cellular material or other contaminating polypeptides from the expression host cell from which the polypeptide is derived, or substantially free from chemical precursors or other chemicals when chemically synthesized. In one embodiment, an isolated or purified polypeptide has less than about 30% (by dry weight) of contaminating polypeptide or chemicals, more advantageously less than about 20% of contaminating polypeptide or chemicals, still more advantageously less than about 10% of contaminating polypeptide or chemicals, and most advantageously less than about 5% contaminating polypeptide or chemicals.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The terms "thermal stability" and "thermostability" are used interchangeably and refer to the ability of an enzyme (e.g., whether expressed in a cell, present in an cellular extract, cell lysate, or in purified or partially purified form) to exhibit the ability to catalyze a reaction at least at about 20° C., preferably at about 25° C. to 35° C., more preferably at about 37° C. or higher, in more preferably at about 50° C. or higher, and even more preferably at least about 60° C. or higher.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins have particular utility. The heterologous polypeptide included within the fusion protein is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives.

Fragments within the scope of the term "antibody" include those produced by digestion with various proteases, those produced by chemical cleavage and/or chemical dissociation and those produced recombinantly, so long as the fragment remains capable of specific binding to a target molecule. Among such fragments are Fab, Fab', Fv, F(ab')$_2$, and single chain Fv (scFv) fragments.

Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., *Intracellular Antibodies: Research and Disease Applications* (1998) Marasco, ed., Springer-Verlag New York, Inc.), the disclosure of which is incorporated herein by reference in its entirety).

As used herein, antibodies can be produced by any known technique, including harvest from cell culture of native B lymphocytes, harvest from culture of hybridomas, recombinant expression systems and phage display.

The term "non-peptide analog" refers to a compound with properties that are analogous to those of a reference polypeptide. A non-peptide compound may also be termed a "peptide mimetic" or a "peptidomimetic." See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 85% overall sequence homology to its wild-type counterpart. Even more preferred are muteins having at least 90% overall sequence homology to the wild-type protein.

In an even more preferred embodiment, a mutein exhibits at least 95% sequence identity, even more preferably 98%, even more preferably 99% and even more preferably 99.9% overall sequence identity.

Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., 2$^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-331 and 25:365-389 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., Nucleic Acids Res. 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. (Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

"Specific binding" refers to the ability of two molecules to bind to each other in preference to binding to other molecules in the environment. Typically, "specific binding" discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

"Percent dry cell weight" refers to a measurement of hydrocarbon production obtained as follows: a defined volume of culture is centrifuged to pellet the cells. Cells are washed then dewetted by at least one cycle of microcentrifugation and aspiration. Cell pellets are lyophilized overnight, and the tube containing the dry cell mass is weighed again such that the mass of the cell pellet can be calculated within ±0.1 mg. At the same time cells are processed for dry cell weight determination, a second sample of the culture in question is harvested, washed, and dewetted. The resulting cell pellet, corresponding to 1-3 mg of dry cell weight, is then extracted by vortexing in approximately 1 ml acetone plus butylated hydroxytolune (BHT) as antioxidant and an internal standard, e.g., n-heptacosane. Cell debris is then pelleted by centrifugation and the supernatant (extractant) is taken for analysis by GC. For accurate quantitation of 1-alkene, flame ionization detection (FID) was used as opposed to MS total ion count. 1-alkene concentrations in the biological extracts were calculated using calibration relationships between GC-FID peak area and known concentrations of authentic 1-alkene standards. Knowing the volume of the extractant, the resulting concentrations of the 1-alkenespecies in the extracant, and the dry cell weight of the cell pellet extracted, the percentage of dry cell weight that comprised 1-alkene can be determined.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

The term "substrate affinity" as used herein refers to the binding kinetics, $K_m$, the Michaelis-Menten constant as understood by one having skill in the art, for a substrate. Various chimeric alkene synthases can have a higher substrate affinity for alkenes of a certain chain length, making them selective for these alkenes.

The term "carbon source" as used herein refers to inorganic carbon, exogenous sugar or biomass.

Inorganic carbon is carbon provided in a molecule that cannot itself be metabolized for energy by an organism, such as $CO_2$, carbonic acid, and carbonate. Sources of inorganic carbon include $CO_2$, air, carbonic acid, carbonate salts, and emissions such as flue gas.

Carbon dioxide (which, along with carbonic acid, bicarbonate and/or carbonate define the term "inorganic carbon") is converted in the photosynthetic process to organic compounds. The inorganic carbon source includes any way of delivering inorganic carbon, optionally in admixture with any other combination of compounds which do not serve as the primary carbon feedstock, but only as a mixture or carrier (for example, emissions from biofuel (e.g., ethanol) plants, power plants, petroleum-based refineries, as well as atmospheric and subterranean sources).

A reduced or organic carbon source is a carbon based molecule that can be metabolized by an organism for energy such as, for example, a carbohydrate (including a sugar or polysaccharide), amino acid, protein, organic acid, fatty acid, lipid, acetyl CoA, or any biosynthetic precursor of any of these biomolecules.

"Carbon-based products of interest" include alkenes such as propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene, and isomers and mixtures thereof.

A "biofuel" as used herein is any fuel that derives from a biological source. Biofuel refers to one or more hydrocarbons (e.g., 1-nonadecene), one or more alcohols, one or more fatty esters or a mixture thereof. Preferably, liquid hydrocarbons are used.

As used herein, the term "hydrocarbon" generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Nucleic Acid Sequences

Cyanobacteria are known to be producers of hydrocarbons (Lin et al. (1996) *Bioch. Biophy. Res. Comm.,* 228: 764-773; Chang et al., (2004) *J. Nat. Prod.* 67: 1356-1367). WO/2011/005548, herein incorporated by reference, describes genes responsible for the production of 1-alkenes in *Synechococcus* sp. PCC 7002. Other long chain hydrocarbons are known to be produced in related, but distinct, microorganisms, e.g., *Synechococcus* sp. PCC 7942 (produces heptadecane), *Synechocystis* sp. PCC 6803 (reported to produce heptadecane), *Nostoc* sp. PCC 7120 (produces heptadecane), *Thermosynechococcus* sp. BP-1 (produces heptadecane) and *Cyanothece* sp. ATCC 51142 (produces pentadecane).

The 1-alkene synthase YP_001734428 contains 7 domains which implicate it in the biosynthesis of 1-nonadecene (FIG. 2). A LuxE domain is present which indicates that the protein can attach a fatty acid by acting as an acyltransferase (AT). LuxE is the protein which serves as an acyl-protein synthetase in the Lux operon (Lin et al. (1996)). A phosphopantetheinyl (PP) attachment site is next which is characteristic of acyl-carrier protein (ACP) domains present in polyketide synthases (i.e. alkene synthases). Several other domains characteristic of polyketide synthases are also present including: a ketosynthase (KS) domain; an acyltransferase (AT) domain; an NADP site which indicates a ketoreductase (KR) domain; a sulfotransferase (ST) domain; and a thioesterase (TE) domain.

Figure 3:
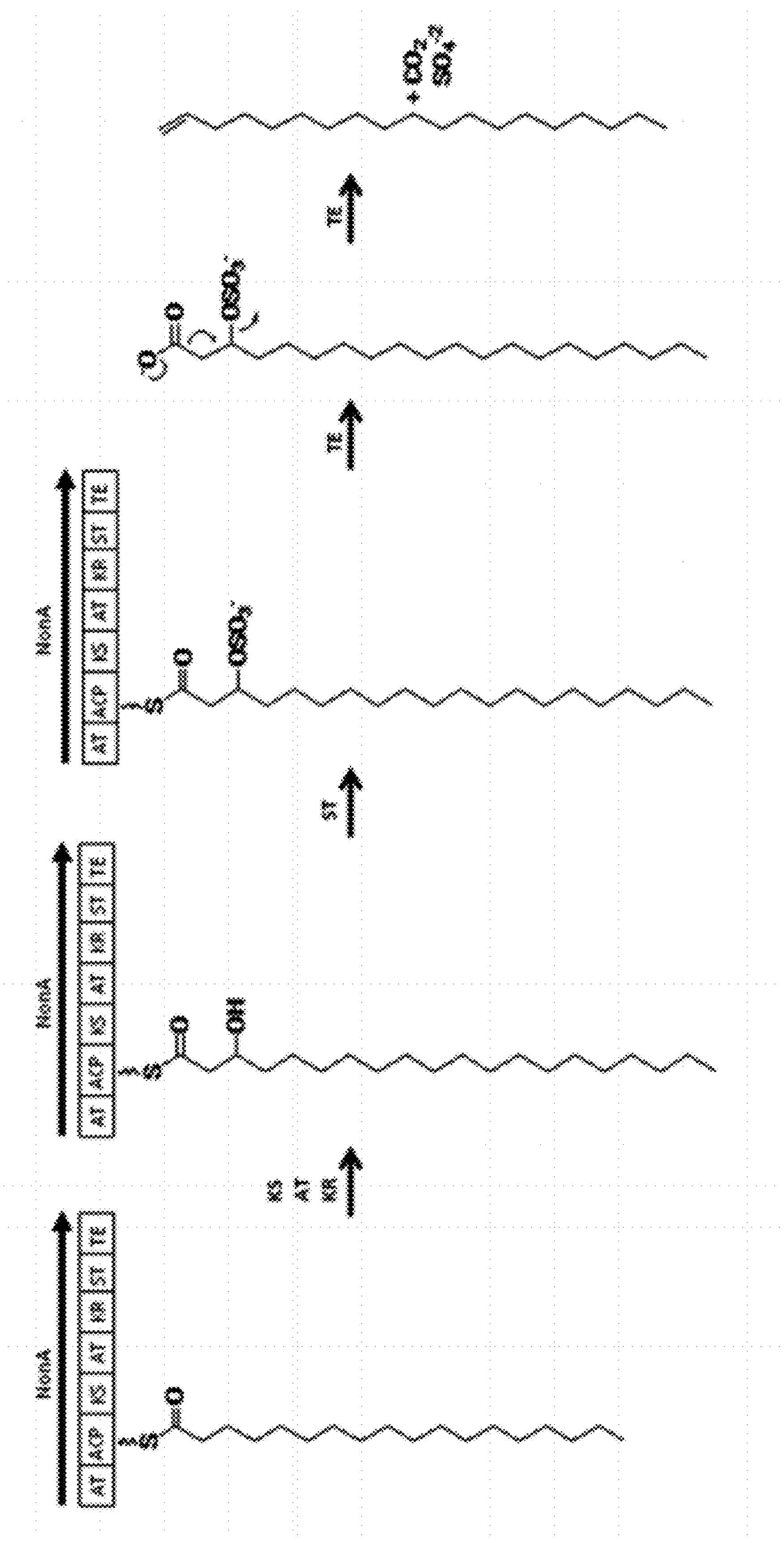

The biosynthesis of alkenes is similar to polyketide biosynthesis, where a thioester bond is formed between the acyl starter unit and the ACP domain of the enzyme. A Claisen condensation catalyzed by a β-ketosynthase (KS) occurs between the acyl-thioester substrate and malonyl-CoA to extend the chain by two carbons. The β-carbonyl is reduced by the ketoreductase domain, and the sulfotransferase domain serves to attach a sulfonate to the β-hydroxy group to form a sulfate intermediate. The last step in the pathway is a decarboxylative elimination of sulfate catalyzed by the thioesterase domain to yield the terminal alkene (FIG. 3). This mechanism of terminal alkene formation via action of a sulfotransferase and thioesterase domain has been demonstrated for the unrelated metabolite curacin A (Gu et al. 2009).

An object of the invention described herein is to express in a host cell a gene encoding a chimeric alkene synthase which selectively binds to an alkene precursor of a pre-defined carbon chain length in an alkene synthesis pathway to produce 1-alkenes of chain length-specific alkenes and other carbon-based products of interest. The pathway and/or chimeric alkene synthase can be over-expressed in a *Synechococcus* strain such as *Synechococcus* sp. PCC 7002 or expressed in any other photosynthetic organism to produce a hydrocarbon from light and inorganic carbon. It can also be expressed in non-photosynthetic organisms to produce hydrocarbons from sugar sources.

Accordingly, one embodiment provides isolated nucleic acid molecules encoding proteins having alkene synthase activity and/or hydrolase activity, and variants thereof, including expression optimized forms of acyl binding pockets, and methods of improvement thereon. The full-length nucleic acid sequence (SEQ ID NO: 1) for the alkene synthase gene from *Synechococcus* sp. PCC 7002, YP_001734428, is provided herein, as is the protein sequence (SEQ ID NO: 2) (see FIG. 2). Also provided herein are optimized coding sequences for the alkene synthase gene, nonA_optV6, encoded by the nucleotide sequence of SEQ ID NO: 23, and expressing the recombinant NonA_optV6 protein encoded by SEQ ID NO: 24. Also provided herein is a coding (SEQ ID NO: 5) and amino acid sequence (SEQ ID NO: 6) for a saframycin Mx1 synthetase from *Legionella pneumophila*, a coding (SEQ ID NO: 9) and amino acid sequence (SEQ ID NO: 10) for a mycosubtilin synthase from *Bacillus subtilis*, and a coding (SEQ ID NO: 13) and amino acid sequence (SEQ ID NO: 14) for an acyl-CoA ligase from *Streptomyces filamentosus*. Also provided herein are sequences of acyl binding pocket alignments of the above genes, and chimeric forms of the full-length nucleic acid sequence.

In addition, one embodiment provides a chimeric alkene synthase consisting of the *Synechococcus* sp. PCC 7002 NonA alkene synthase with a heterologous acyl binding pocket replacing the native binding pocket. In one embodiment, the heterologous binding pocket may be selected from the group consisting of SEQ ID NO: 18, SEQ ID NO: 20, and SEQ ID NO: 22. In another embodiment, the heterologous binding pocket may be selected from the group consisting of SEQ ID NO: 30, SEQ ID NO: 31, and SEQ ID NO: 29. Locations for insertion of the heterologous binding pocket into the NonA alkene synthase gene for one embodiment are provided. In other embodiments, the heterologous binding pocket is inserted into the NonA alkene synthase gene in a region comparable to the native heterologous binding pocket region location i.e., less than 5 peptides, less than 10 peptides, less than 20 peptides, less than 50 peptides, less than 75 peptides, less than 100 peptides, less than 150 peptides, or less than 200 peptides upstream or downstream from the location of the native binding pocket region. The invention also includes nucleic acids encoding the above-mentioned chimeric alkene synthases.

One embodiment provides an isolated nucleic acid molecule having a nucleic acid sequence comprising or consisting of a chimeric alkene synthase gene homologs, variants and derivatives of the chimeric alkene synthase selected from the gene coding sequences SEQ ID NO:17, SEQ ID NO:19, SEQ ID NO:21, SEQ ID NO: 26, SEQ ID NO: 27, and SEQ ID NO: 28. Another embodiment provides nucleic acid molecules comprising or consisting of sequences which are structurally and functionally optimized versions of the chimeric alkene synthase gene. In a preferred embodiment, nucleic acid molecules and homologs, variants and derivatives comprising or consisting of sequences optimized for substrate affinity and/or substrate catalytic conversion rate are provided.

A further embodiment provides nucleic acid molecules and homologs, variants and derivatives thereof comprising or consisting of sequences which are variants of the chimeric NonA gene having at least 90% identity to SEQ ID NO:17, SEQ ID NO:19, SEQ ID NO:21, SEQ ID NO: 26, SEQ ID NO: 27, and SEQ ID NO: 28. Another embodiment provides nucleic acid molecules and homologs, variants and derivatives comprising or consisting of sequences which are variants of the chimeric alkene synthase gene having at least 90% identity to SEQ ID NO:17, SEQ ID NO:19, SEQ ID NO:21, SEQ ID NO: 26, SEQ ID NO: 27, and SEQ ID NO: 28 and optimized for substrate affinity, substrate catalytic conversion rate, improved thermostability, activity at a different pH and/or optimized codon usage for improved expression in a host cell. The nucleic acid sequences can be preferably 71%, 72%, 73%, 74%, 75%, 76%, 77%, 78%, 79%, 80%, 81%, 82%, 83%, 84%, 85%, 90%, 95%, 98%, 99%, 99.9% or even higher identity to the chimeric alkene synthase gene.

In one embodiment, the nucleic acid molecule encodes a polypeptide having the amino acid sequence of SEQ ID NO: 2, SEQ ID NO: 18, SEQ ID NO: 20, or SEQ ID NO: 22. In another embodiment, the nucleic acid molecule encodes a polypeptide having the amino acid sequence of SEQ ID NO: 24, SEQ ID NO: 29, SEQ ID NO: 30, or SEQ ID NO: 31. Also provided is a nucleic acid molecule encoding a polypeptide sequence that is at least 50% identical to either SEQ ID NO: 2, SEQ ID NO: 18, SEQ ID NO: 20, SEQ ID NO: 22, SEQ ID NO: 24, SEQ ID NO: 29, SEQ ID NO: 30, or SEQ ID NO: 31. Preferably, the nucleic acid molecule encodes a polypeptide sequence of at least 55%, 60%, 70%, 80%, 90% or 95% identical to SEQ ID NO: 2, SEQ ID NO: 18, SEQ ID NO: 20, SEQ ID NO: 22, SEQ ID NO: 24, SEQ ID NO: 29, SEQ ID NO: 30, or SEQ ID NO: 31, and the identity can even more preferably be 98%, 99%, 99.9% or even higher.

Provided also are nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing can be performed at temperatures about 5° C. lower than the $T_m$ for the specific DNA hybrid under a particular set of conditions.

The nucleic acid molecule includes DNA molecules (e.g., linear, circular, cDNA, chromosomal DNA, double stranded or single stranded) and RNA molecules (e.g., tRNA, rRNA, mRNA) and analogs of the DNA or RNA molecules of the described herein using nucleotide analogs. The isolated nucleic acid molecule of the invention includes a nucleic acid molecule free of naturally flanking sequences (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of naturally flanking nucleotide chromosomal DNA sequences of the microorganism from which the nucleic acid molecule is derived.

The chimeric alkene synthase genes, as described herein, include nucleic acid molecules, for example, a polypeptide or RNA-encoding nucleic acid molecule, separated from another gene or other genes by intergenic DNA (for example, an intervening or spacer DNA which naturally flanks the gene and/or separates genes in the chromosomal DNA of the organism).

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

In another embodiment, an isolated alkene synthase-encoding nucleic acid molecule hybridizes to all or a portion of a nucleic acid molecule having the nucleotide sequence set forth in SEQ ID NO: 17, SEQ ID NO: 19, SEQ ID NO: 21, SEQ ID NO: 26, SEQ ID NO: 27, SEQ ID NO: 28; or hybridizes to all or a portion of a nucleic acid molecule having a nucleotide sequence that encodes a polypeptide having the amino acid sequence of SEQ ID NO: 18, SEQ ID NO: 20, SEQ ID NO: 22, SEQ ID NO: 29, SEQ ID NO: 30, SEQ ID NO: 31. The nucleic acid sequence fragments display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hybridization to target sequences can be detected and optionally quantified. One of skill in the art will appreciate that the nucleic acid fragments may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in *DNA Microarrays: A Practical Approach* (Practical Approach Series), Schena (ed.), Oxford University Press (1999) (ISBN: 0199637768); *Nature Genet.* 21(1)(suppl):1-60 (1999); Microarray Biochip: Tools and Technology, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., *Trends Biochem. Sci.* 24:168-173 (1999) and Zweiger, *Trends Biotechnol.* 17:429-436 (1999); DNA Microarrays: A Practical Approach (Practical Approach Series), Schena (ed.), Oxford University Press (1999) (ISBN: 0199637768); *Nature Genet.* 21(1)(suppl):1-60 (1999); Microarray Biochip: Tools and Technology, Schena (ed.), Eaton Publishing Company/BioTechniques Books Division (2000) (ISBN: 1881299376), the disclosures of each of which is incorporated herein by reference in its entirety.

In another embodiment, the present disclosure provides isolated nucleic acid molecules encoding a chimeric alkene synthase which exhibits increased activity relative to the unmodified, native protein. For example, a particular chimeric alkene synthase may synthesize more 1-pentadecene over a given time period, under identical conditions, when compared to the unmodified native protein from which it is derived. As is well known in the art, enzyme activities are measured in various ways, e.g. spectroscopically. (Grubmeyer et al., *J. Biol. Chem.* 268:20299-20304 (1993)), or chromatographically, including the use of high performance liquid chromatography (Chung and Sloan, *J. Chromatogr.* 371:

71-81 (1986)). As another alternative the activity is indirectly measured by determining the levels of product made from the enzyme activity. More modern techniques include using gas chromatography linked to mass spectrometry (Niessen, W. M. A. (2001). *Current practice of gas chromatography-mass spectrometry*. New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G., R. O. Dunn, and M. O. Bagby. 1997. Biodiesel: The use of vegetable oils and their derivatives as alternative diesel fuels. *Am. Chem. Soc. Symp*. Series 666: 172-208), physical property-based methods, wet chemical methods, etc. are used to analyze the levels and the identity of the product produced by the organisms. Other methods and techniques may also be suitable for the measurement of enzyme activity, as would be known by one of skill in the art.

Vectors

The recombinant vector can be altered, modified or engineered to have different or a different quantity of nucleic acid sequences than in the derived or natural recombinant vector nucleic acid molecule. Preferably, the recombinant vector includes a gene or recombinant nucleic acid molecule operably linked to regulatory sequences including, but not limited to, promoter sequences, terminator sequences and/or artificial ribosome binding sites (RBSs), as defined herein.

Typically, a gene encoding a chimeric alkene synthase is operably linked to regulatory sequence(s) in a manner which allows for the desired expression characteristics of the nucleotide sequence. Preferably, the gene encoding a chimeric alkene synthase in a 1-nonadecene biosynthetic pathway is transcribed and translated into a gene product encoded by the nucleotide sequence when the recombinant nucleic acid molecule is included in a recombinant vector, as defined herein, and is introduced into a microorganism.

The regulatory sequence may be comprised of nucleic acid sequences which modulate, regulate or otherwise affect expression of other nucleic acid sequences. In one embodiment, a regulatory sequence can be in a similar or identical position and/or orientation relative to a nucleic acid sequence as observed in its natural state, e.g., in a native position and/or orientation. For example, a gene of interest can be included in a recombinant nucleic acid molecule or recombinant vector operably linked to a regulatory sequence which accompanies or is adjacent to the gene of interest in the natural host cell, or can be adjacent to a different gene in the natural host cell, or can be operably linked to a regulatory sequence from another organism. Regulatory sequences operably linked to a gene can be from other bacterial regulatory sequences, bacteriophage regulatory sequences and the like.

In one embodiment, a regulatory sequence is a sequence which has been modified, mutated, substituted, derivated, deleted, including sequences which are chemically synthesized. Preferably, regulatory sequences include promoters, enhancers, termination signals, anti-termination signals and other expression control elements that, for example, serve as sequences to which repressors or inducers bind or serve as or encode binding sites for transcriptional and/or translational regulatory polypeptides, for example, in the transcribed mRNA (see Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989). Regulatory sequences include promoters directing constitutive expression of a nucleotide sequence in a host cell, promoters directing inducible expression of a nucleotide sequence in a host cell and promoters which attenuate or repress expression of a nucleotide sequence in a host cell. Regulating expression of a gene of interest also can be done by removing or deleting regulatory sequences. For example, sequences involved in the negative regulation of transcription can be removed such that expression of a gene of interest is enhanced. In one embodiment, a recombinant nucleic acid molecule or recombinant vector includes a nucleic acid sequence or gene that encodes at least one chimeric alkene synthase in an alkene biosynthetic pathway, wherein the gene encoding the enzyme(s) is operably linked to a promoter or promoter sequence. Preferably, promoters include native promoters, surrogate promoters and/or bacteriophage promoters.

In one embodiment, a promoter is associated with a biochemical housekeeping gene or a promoter associated with an ethanologenic pathway. In another embodiment, a promoter is a bacteriophage promoter. Other promoters include tef (the translational elongation factor (TEF) promoter) which promotes high level expression in *Bacillus* (e.g. *Bacillus subtilis*). Additional advantageous promoters, for example, for use in Gram positive microorganisms include, but are not limited to, the amyE promoter or phage SP02 promoters. Additional advantageous promoters, for example, for use in Gram negative microorganisms include, but are not limited to tac, trp, tet, trp-tet, lpp, lac, lpp-lac, lacIq, T7, T5, T3, gal, trc, ara, SP6, $\lambda$-$p_R$ or $\lambda$-$p_L$.

In another embodiment, a recombinant nucleic acid molecule or recombinant vector includes a transcription terminator sequence or sequences. Typically, terminator sequences refer to the regulatory sequences which serve to terminate transcription of a gene. Terminator sequences (or tandem transcription terminators) can further serve to stabilize mRNA (e.g., by adding structure to mRNA), for example, against nucleases.

In another embodiment, a recombinant nucleic acid molecule or recombinant vector has sequences allowing for detection of the vector containing sequences (i.e., detectable and/or selectable markers), for example, sequences that overcome auxotrophic mutations, for example, ura3 or ilvE, fluorescent markers, and/or calorimetric markers (e.g., lacZ/β-galactosidase), and/or antibiotic resistance genes (e.g., bla or tet).

It is understood that any one of the chimeric alkene synthase gene of the invention can be introduced into a vector also comprising one or more genes involved in the biosynthesis of alkenes from light, water and inorganic carbon.

Also provided are vectors, including expression vectors, which comprise the above nucleic acid molecules, as described further herein. In a first embodiment, the vectors include the isolated nucleic acid molecules described above. In an alternative embodiment, the vectors include the above-described nucleic acid molecules operably linked to one or more expression control sequences. The vectors of the instant invention may thus be used to express a polypeptide having chimeric alkene synthase activity in an alkene biosynthetic pathway.

Vectors useful for expression of nucleic acids in prokaryotes are well known in the art. A useful vector herein is plasmid pCDF Duet-1 that is available from Novagen. Another useful vector is the endogenous *Synechococcus* sp. PCC 7002 plasmid pAQ1 (Genbank accession number NC_010476).

Isolated Polypeptides

In one embodiment, polypeptides encoded by nucleic acid sequences are produced by recombinant DNA techniques and can be isolated from expression host cells by an appropriate purification scheme using standard polypeptide purification techniques. In another embodiment, polypeptides encoded by nucleic acid sequences are synthesized chemically using standard peptide synthesis techniques.

Included within the scope of the invention are chimeric alkene synthase polypeptides or gene products that are derived polypeptides or gene products encoded by naturally-occurring bacterial genes. Further, included within the inventive scope, are bacteria-derived polypeptides or gene products which differ from wild-type genes, including genes that have altered, inserted or deleted nucleic acids but which encode polypeptides substantially similar in structure and/or function to the wild-type and/or chimeric alkene synthase gene.

For example, it is well understood that one of skill in the art can mutate (e.g., substitute) nucleic acids which, due to the degeneracy of the genetic code, encode for an identical amino acid as that encoded by the naturally-occurring gene. This may be desirable in order to improve the codon usage of a nucleic acid to be expressed in a particular organism. Moreover, it is well understood that one of skill in the art can mutate (e.g., substitute) nucleic acids which encode for conservative amino acid substitutions. It is further well understood that one of skill in the art can substitute, add or delete amino acids to a certain degree to improve upon or at least insubstantially affect the function and/or structure of a gene product (e.g., alcohol dehydrogenase activity) as compared with a naturally-occurring gene product, each instance of which is intended to be included within the scope of the invention.

In various aspects, isolated polypeptides (including muteins, allelic variants, fragments, derivatives, and analogs) encoded by the nucleic acid molecules are provided. In one embodiment, the isolated polypeptide comprises the polypeptide sequence corresponding to SEQ ID NO: 18, SEQ ID NO: 20, SEQ ID NO: 22, SEQ ID NO: 29, SEQ ID NO: 30, or SEQ ID NO: 31. In an alternative embodiment, the isolated polypeptide comprises a polypeptide sequence at least 50% identical to SEQ ID NO: 18, SEQ ID NO: 20, SEQ ID NO: 22, SEQ ID NO: 29, SEQ ID NO: 30, or SEQ ID NO: 31. Preferably the isolated polypeptide has preferably 50%, 60%-70%, 70%-80%, 80%-90%, 90%-95%, 95%-98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to the sequences optimized for substrate affinity and/or substrate catalytic conversion rate.

According to other embodiments, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides also include fusions between the above-described polypeptide sequences and heterologous polypeptides. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Host Cell Transformants

In other aspects, host cells transformed with the nucleic acid molecules or vectors, and descendants thereof, are provided. In some embodiments, these cells carry the nucleic acid sequences on vectors, which may but need not be freely replicating vectors. In other embodiments, the nucleic acids have been integrated into the genome of the host cells.

In a preferred embodiment, the host cell comprises one or more nucleic acids of SEQ ID NO: 17, SEQ ID NO: 19, SEQ ID NO: 21, SEQ ID NO: 26, SEQ ID NO: 27, or SEQ ID NO: 28 operably linked to promoters for the expression of chimeric alkene synthase in an alkene biosynthesis pathway.

In another embodiment, the host cell containing a chimeric alkene synthase in the alkene pathway is suitable for producing 1-alkenes. In a particular embodiment, the host cell is a recombinant host cell that produces 1-alkenes comprising a chimeric nucleic acid encoding a nucleic acid of SEQ ID NO: 17, SEQ ID NO: 19, SEQ ID NO: 21, SEQ ID NO: 26, SEQ ID NO: 27, or SEQ ID NO: 28.

In certain aspects, methods for expressing a polypeptide under suitable culture conditions and choice of host cell line for optimal enzyme expression, activity and stability (codon usage, salinity, pH, temperature, etc.) are provided.

In another aspect, methods for producing 1-alkene by culturing a host cell under conditions in which the chimeric alkene synthase is expressed at sufficient levels to produce a measureable quantity of 1-alkene are described. In a related embodiment, methods for producing 1-alkene are performed by contacting a cell lysate obtained from the above host cell under conditions in which 1-alkene is produced from light, water and inorganic carbon. Accordingly, the present disclosure provides enzyme extracts having chain-length specific alkene synthase activity, and having, for example, thermal stability, activity at various pH, and/or superior substrate affinity or specificity.

Selected or Engineered Microorganisms for the Production of Carbon-Based Products of Interest Microorganism: Includes prokaryotic and eukaryotic microbial species from the Domains *Archaea, Bacteria* and *Eucarya*, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Host cells can be a Gram-negative bacterial cell or a Gram-positive bacterial cell. A Gram-negative host cell of the invention can be, e.g., *Gluconobacter, Rhizobium, Bradyrhizobium, Alcaligenes, Rhodobacter, Rhodococcus. Azospirillum, Rhodospirillum, Sphingomonas, Burkholderia, Desuifomonas, Geospirillum, Succinomonas, Aeromonas, Shewanella, Halochromatium, Citrobacter, Escherichia, Klebsiella, Zymomonas Zymobacter*, or *Acetobacter*. A Gram-positive host cell of the invention can be, e.g., *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, or *Sarcina*.

Extremophiles are also contemplated as suitable organisms. Such organisms withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure tolerant organisms include piezophiles or barophiles which tolerate pressure of 130 MPa. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt tolerant organisms include halophiles (e.g., 2-5 M NaCl) *Halobacteriacea* and *Dunaliella salina*. pH tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Wertheimer, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycla-*

*della, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium.*

Green non-sulfur bacteria include but are not limited to the following genera: *Chloroflexus, Chloronema, Oscillochloris, Heliothrix, Herpetosiphon, Roseiflexus*, and *Thermomicrobium.*

Green sulfur bacteria include but are not limited to the following genera: *Chlorobium, Clathrochloris*, and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic sulfur-metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

HyperPhotosynthetic conversion requires extensive genetic modification; thus, in preferred embodiments the parental photoautotrophic organism can be transformed with exogenous DNA.

Preferred organisms for HyperPhotosynthetic conversion include: *Arabidopsis thaliana, Panicum virgatum, Miscanthus giganteus*, and *Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix inorganic carbon, such as *Escherichia coli, Acetobacter aceti, Bacillus subtilis*, yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis.*

A common theme in selecting or engineering a suitable organism is autotrophic fixation of $CO_2$ to products. This would cover photosynthesis and methanogenesis. Acetogenesis, encompassing the three types of $CO_2$ fixation; Calvin cycle, acetyl CoA pathway and reductive TCA pathway is also covered. The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. Fuchs, G. 1989. Alternative pathways of autotrophic $CO_2$ fixation, p. 365-382. In H. G. Schlegel, and B. Bowien (ed.), *Autotrophic*

*bacteria*. Springer-Verlag, Berlin, Germany. The reductive pentose phosphate cycle (Calvin-Bassham-Benson cycle) represents the $CO_2$ fixation pathway in many aerobic autotrophic bacteria, for example, cyanobacteria.

Gene Integration and Propagation

The 1-alkene producing genes can be propagated by insertion into the host cell genome. Integration into the genome of the host cell is optionally done at particular loci to impair or disable unwanted gene products or metabolic pathways.

In another embodiment is described the integration of a chimeric alkene synthase gene into a plasmid. The plasmid can express one or more genes, optionally an operon including one or more genes, preferably one or more chimeric genes involved in the synthesis of 1-alkene, or more preferably one or more chimeric genes of a related metabolic pathway that feeds into the biosynthetic pathway for 1-alkenes.

Antibodies

In another aspect, provided herein are isolated antibodies, including fragments and derivatives thereof that bind specifically to the isolated polypeptides and polypeptide fragments or to one or more of the polypeptides encoded by the isolated nucleic acids. The antibodies may be specific for linear epitopes, discontinuous epitopes or conformational epitopes of such polypeptides or polypeptide fragments, either as present on the polypeptide in its native conformation or, in some cases, as present on the polypeptides as denatured, as, e.g., by solubilization in SDS. Among the useful antibody fragments are Fab, Fab', Fv, $F(ab')_2$, and single chain Fv fragments.

By "bind specifically" and "specific binding" is here intended the ability of the antibody to bind to a first molecular species in preference to binding to other molecular species with which the antibody and first molecular species are admixed. An antibody is said specifically to "recognize" a first molecular species when it can bind specifically to that first molecular species.

As is well known in the art, the degree to which an antibody can discriminate as among molecular species in a mixture will depend, in part, upon the conformational relatedness of the species in the mixture; typically, the antibodies will discriminate over adventitious binding to unrelated polypeptides by at least two-fold, more typically by at least 5-fold, typically by more than 10-fold, 25-fold, 50-fold, 75-fold, and often by more than 100-fold, and on occasion by more than 500-fold or 1000-fold.

Typically, the affinity or avidity of an antibody (or antibody multimer, as in the case of an IgM pentamer) for a polypeptide or polypeptide fragment will be at least about $1\times10^{-6}$ M, typically at least about $5\times10^{-7}$M, usefully at least about $1\times10^{-7}$ M, with affinities and avidities of $1\times10^{-8}$ M, $5\times10^{-9}$ M, $1\times10^{-10}$ M and even stronger proving especially useful.

The isolated antibodies may be naturally-occurring forms, such as IgG, IgM, IgD, IgE, and IgA, from any mammalian species. For example, antibodies are usefully obtained from species including rodents-typically mouse, but also rat, guinea pig, and hamster-lagomorphs, typically rabbits, and also larger mammals, such as sheep, goats, cows, and horses. The animal is typically affirmatively immunized, according to standard immunization protocols, with the polypeptide or polypeptide fragment.

Virtually all fragments of 8 or more contiguous amino acids of the polypeptides may be used effectively as immunogens when conjugated to a carrier, typically a protein such as bovine thyroglobulin, keyhole limpet hemocyanin, or bovine serum albumin, conveniently using a bifunctional linker. Immunogenicity may also be conferred by fusion of the polypeptide and polypeptide fragments to other moieties. For example, peptides can be produced by solid phase synthesis on a branched polylysine core matrix; these multiple antigenic peptides (MAPs) provide high purity, increased avidity, accurate chemical definition and improved safety in vaccine development. See, e.g., Tam et al., *Proc. Natl. Acad. Sci*. USA 85:5409-5413 (1988); Posnett et al., *J. Biol. Chem.* 263, 1719-1725 (1988).

Protocols for immunization are well-established in the art. Such protocols often include multiple immunizations, either with or without adjuvants such as Freund's complete adjuvant and Freund's incomplete adjuvant. Antibodies may be polyclonal or monoclonal, with polyclonal antibodies having certain advantages in immunohistochemical detection of the proteins and monoclonal antibodies having advantages in identifying and distinguishing particular epitopes of the proteins. Following immunization, the antibodies may be produced using any art-accepted technique. Host cells for recombinant antibody production—either whole antibodies, antibody fragments, or antibody derivatives—can be prokaryotic or eukaryotic. Prokaryotic hosts are particularly useful for producing phage displayed antibodies, as is well known in the art. Eukaryotic cells, including mammalian, insect, plant and fungal cells are also useful for expression of the antibodies, antibody fragments, and antibody derivatives. Antibodies can also be prepared by cell free translation.

The isolated antibodies, including fragments and derivatives thereof, can usefully be labeled. It is, therefore, another aspect to provide labeled antibodies that bind specifically to one or more of the polypeptides and polypeptide fragments. The choice of label depends, in part, upon the desired use. In some cases, the antibodies may usefully be labeled with an enzyme. Alternatively, the antibodies may be labeled with colloidal gold or with a fluorophore. For secondary detection using labeled avidin, streptavidin, captavidin or neutravidin, the antibodies may usefully be labeled with biotin. When the antibodies are used, e.g., for Western blotting applications, they may usefully be labeled with radioisotopes, such as $^{33}P$, $^{32}P$, $^{35}S$, $^{3}H$ and $^{125}I$. As would be understood, use of the labels described above is not restricted to any particular application.

Methods for Designing Chimeric Protein Variants

Chain length-specific alkene production can be achieved through the expression and optimization of chimeric alkene synthase in organisms well suited for modern genetic engineering techniques, i.e., those that rapidly grow, are capable of thriving on inexpensive food resources and from which isolation of a desired product is easily and inexpensively achieved. To control the chain length of alkene production it would be advantageous to design and select variants of the chimeric enzymes, including but not limited to, variants optimized for substrate affinity, substrate specificity, substrate catalytic conversion rate, improved thermostability, activity at a different pH and/or optimized codon usage for improved expression in a host cell. See, for example, amino acid changes correlated to alterations in the catalytic rate while maintaining similar affinities (R L Zheng and R G Kemp, *J. Biol. Chem.* (1994) Vol. 269:18475-18479) or amino acid changes correlated with changes in the stability of the transition state that affect catalytic turnover (M A Phillips, et al., *J. Biol. Chem*., (1990) Vol. 265:20692-20698). It would be another advantage to design and select for chimeric enzymes altered to have substantially decreased reverse reaction activity in which enzyme-substrate products would be the result of energetically unfavorable bond formation or molecular reconfiguration of the substrate, and have improved forward reaction activity in which enzyme-substrate products would be the result of energetically favorable molecular bond reduction or molecular re-configuration.

Accordingly, one method for the design of improved chimeric alkene synthase proteins for synthesing 1-alkenes utilizes computational and bioinformatic analysis to design and select for advantageous changes in chimeric amino acid sequences encoding alkene synthase enzyme activity. Computational methods and bioinformatics provide tractable alternatives for rational design of protein structure and function. Recently, algorithms analyzing protein structure for biophysical character (for example, motional dynamics and total energy or Gibb's Free Energy evaluations) have become a commercially feasible methodology supplementing protein sequence analysis data that assess homology, identity and/or degree of sequence and domain conservation to improve upon or design the desirable qualities of a protein (Rosetta++, University of Washington). For example, an in silico redesign of the endonuclease I-MsoI was based on computational evaluation of biophysical parameters of rationally selected changes to the primary amino acid sequence. Researchers were able to maintain wild-type binding selectivity and affinity yet improve the catalytic turnover by four orders of magnitude (Ashworth, et al., *Nature* (2006) vol. 441:656-659).

In one embodiment, chimeric polypeptide sequences or related homologues in a complex with a substrate are obtained for computational analysis on steady state and/or changes in Gibb's free energy relative to the wild type protein. Substitutions of one amino acid residue for another are accomplished in silico interactively as a means for identifying specific residue substitutions that optimize structural or catalytic contacts between the protein and substrate using standard software programs for viewing molecules as is well known to those skilled in the art. To the extent that in silico structures for the chimeric polypeptides (and homologues) described herein are available, those structures can be used to rationally design modified proteins with desired (typically, improved) activities. Specific amino acid substitutions are rationally chosen based on substituted residue characteristics that optimize, for example, Van der Waal's interactions, hydrophobicity, hydrophilicity, steric non-interferences, pH-dependent electrostatics and related chemical interactions. The overall energetic change of the substitution protein model when unbound and bound to its substrate is calculated and assessed by one having skill in the art to be evaluated for the change in free energy for correlations to overall structural stability (e.g., Meiler, J. and D. Baker, *Proteins* (2006) 65:538-548). In addition, such computational methods provide a means for accurately predicting quaternary protein structure interactions such that in silico modifications are predictive or determinative of overall multimeric structural stability (Wollacott, A M, et al., *Protein Science* (2007) 16:165-175; Joachimiak, L A, et al., *J. Mol. Biol.* (2006) 361:195-208).

Preferably, a rational design change to the primary structure of chimeric alkene synthase protein sequences minimally alter the Gibb's free energy state of the unbound polypeptide and maintain a folded, functional and similar wild-type enzyme structure. More preferably a lower computational total free energy change of the protein sequence is achieved to indicate the potential for optimized enzyme structural stability.

Although lower free energy of a protein structure relative to the original chimeric structure is an indicator of thermodynamic stability, the positive correlation of increased thermal stability to optimized function does not always exist. Therefore, preferably, optimal catalytic contacts between the modified chimeric alkene synthase and the substrate are achieved with a concomitant predicted favorable change in total free energy of the catabolic reaction, for example by rationally designing chimeric alkene synthase protein/substrate interactions that stabilize the transition state of the enzymatic reaction while maintaining a similar or favorable change in free energy of the unbound chimeric alkene synthase protein for a desired environment in which a host cell expresses the mutant chimeric alkene synthase protein. Even more preferably, rationally selected amino acid changes result in a substantially decreased chimeric alkene synthase enzyme's anabolic protein/substrate reaction or increase the chimeric alkene synthases protein/substrate reaction, for example wherein specific chain-length 1-alkenes are synthesized for a desired environment in which a host cell expresses the mutant chimeric alkene synthase. In a further embodiment any and/or all chimeric alkene synthase sequences are expression optimized for the specific expression host cell.

Methods for Generating Protein Variants

Several methods well known to those with skill in the art are available to generate random nucleotide sequence variants for a corresponding chimeric polypeptide sequence using the Polymerase Chain Reaction ("PCR") (U.S. Pat. No. 4,683,202). One embodiment is the generation of chimeric alkene synthase gene variants using the method of error prone PCR. (R. Cadwell and G. Joyce, *PCR Meth. Appl.* (1991) Vol. 2:28-33; Leung, et al., *Technique* (1989) Vol. 1:11-15). Error prone PCR is achieved by the establishment of a chemical environment during the PCR experiment that causes an increase in unfaithful replication of a parent copy of DNA sought to be replicated. For example, increasing the manganese or magnesium ion content of the chemical admixture used in the PCR experiment, very low annealing temperatures, varying the balance among di-deoxy nucleotides added, starting with a low population of parent DNA templates or using polymerases designed to have increased inefficiencies in accurate DNA replication all result in nucleotide changes in progeny DNA sequences during the PCR replication process. The resultant mutant DNA sequences are genetically engineered into an appropriate vector to be expressed in a host cell and analyzed to screen and select for the desired effect on whole cell production of a product or process of interest. In one embodiment, random mutagenesis of the chimeric alkene synthase-encoding nucleotide sequences is generated through error prone PCR using techniques well known to one skilled in the art. Resultant nucleotide sequences are analyzed for structural and functional attributes through clonal screening assays and other methods as described herein.

Another embodiment is generating a specifically desired protein mutant using site-directed mutagenesis. For example, with overlap extension (An, et al., *Appl. Microbiol. Biotech.* (2005) vol. 68(6):774-778) or mega-primer PCR (E. Burke and S. Barik, *Methods Mol. Bio.* (2003) vol 226:525-532) one can use nucleotide primers that have been altered at corresponding codon positions in the parent nucleotide to yield DNA progeny sequences containing the desired mutation. Alternatively, one can use cassette mutagenesis (Kegler-Ebo, et al., *Nucleic Acids Res.* (1994) vol. 22(9):1593-1599) as is commonly known by one skilled in the art.

Several authors (Korkhin, et al., *J. Mol. Bio.* (1998) vol. 278:967-981; E. Goiberg, et al., *Proteins* (2008) vol. 72:711-719) have demonstrated protein amino acid substitutions at single positions in the alcohol dehydrogenase protein sequence enhance protein fold thermostability. In one aspect, using site-directed mutagenesis and cassette mutagenesis, all possible positions in SEQ ID NO: 18, SEQ ID NO: 20, SEQ ID NO: 22, SEQ ID NO: 29, SEQ ID NO: 30, or SEQ ID NO:

31 are changed to a proline, transformed into a suitable high expression vector and expressed at high levels in a suitable expression host cell. Purified aliquots at concentrations necessary for the appropriate biophysical analytical technique are obtained by methods as known to those with skill in the art (P. Rellos and R. K. Scopes, *Prot. Exp. Purific*. (1994) Vol. 5:270-277) and evaluated for increased thermostability.

Another embodiment is to select for a polypeptide variant for expression in a recipient host cell by comparing a first nucleic acid sequence encoding the polypeptide with the nucleic acid sequence of a second, related nucleic acid sequence encoding a polypeptide having more desirable qualities, and altering at least one codon of the first nucleic acid sequence to have identity with the corresponding codon of the second nucleic acid sequence, such that improved polypeptide activity, substrate specificity, substrate affinity (for example, NADPH and acetaldehyde), substrate catalytic conversion rate, improved thermostability, activity at a different pH and/or optimized codon usage for expression and/or structure of the altered polypeptide is achieved in the host cell.

In yet another embodiment, all amino acid residue variations are encoded at any desired, specified nucleotide codon position using such methods as site saturation mutagenesis (Meyers, et al., *Science* (1985) Vol. 229:242-247; Derbyshire, et al., *Gene* (1986) Vol. 46:145-152; U.S. Pat. No. 6,171,820). Whole gene site saturation mutagenesis (K. Kretz, et al., *Meth. Enzym*. (2004) Vol. 388:3-11) is preferred wherein all amino acid residue variations are encoded at every nucleotide codon position. Both methods yield a population of protein variants differing from the parent polypeptide by one amino acid, with each amino acid substitution being correlated to structural/functional attributes at any position in the polypeptide. Saturation mutagenesis uses PCR and primers homologous to the parent sequence wherein one or more codon encoding nucleotide triplets is randomized. Randomization results in the incorporation of codons corresponding to all amino acid replacements in the final, translated polypeptide. Each PCR product is genetically engineered into an expression vector to be introduced into an expression host and screened for structural and functional attributes through clonal screening assays and other methods as described herein.

In one aspect of saturation mutagenesis, correlated saturation mutagenesis ("CSM") is used wherein two or more amino acids at rationally designated positions are changed concomitantly to different amino acid residues to engineer improved enzyme function and structure. Correlated saturation mutagenesis allows for the identification of complimentary amino acid changes having positive, synergistic effects on chimeric alkene synthase enzyme structure and function. Such synergistic effects include, but are not limited to, significantly altered enzyme stability, substrate affinity, substrate specificity or catalytic turnover rate, independently or concomitantly increasing advantageously the production of 1-alkenes.

In yet another embodiment, amino acid substitution combinations of CSM derived protein variants being optimized for a particular function are combined with one or more CSM derived protein variants being optimized for another particular function to derive a chimeric alkene synthase protein variant exhibiting multiple optimized structural and functional characteristics. For example, amino acid changes in combinatorial mutants showing optimized protomer interactions are combined with amino acid changes in combinatorial mutants showing optimized catalytic turnover.

In one embodiment, mutational variants derived from the methods described herein are cloned. DNA sequences produced by saturation mutagenesis are designed to have restriction sites at the ends of the gene sequences to allow for excision and transformation into a host cell plasmid. Generated plasmid stocks are transformed into a host cell and incubated at optimal growth conditions to identify successfully transformed colonies.

In a further embodiment any and/or all sequences additionally are expression optimized for the specific expression host cell.

Methods for Measuring Protein Variant Efficacy

Variations in expressed polypeptide sequences may result in measurable differences in the whole-cell rate of substrate conversion. It is desirable to determine differences in the rate of substrate conversion by assessing productivity in a host cell having a particular protein variant relative to other whole cells having a different protein variant. Additionally, it would be desirable to determine the efficacies of whole-cell substrate conversion as a function of environmental factors including, but not limited to, pH, temperature nutrient concentration and salinity.

Therefore, in one embodiment, the biophysical analyses described herein on protein variants are performed to measure structural/functional attributes. Standard analyses of polypeptide activity are well known to one of ordinary skill in the art. Such analysis can require the expression and high purification of large quantities of polypeptide, followed by various physical methods (including, but not limited to, calorimetry, fluorescence, spectrophotometric, spectrometric, liquid chromatography (LC), mass spectrometry (MS), LC-MS, affinity chromatography, light scattering, nuclear magnetic resonance and the like) to assay function in a specific environment or functional differences among homologues.

In another embodiment, the polypeptides are expressed, purified and subject to the aforementioned analytical techniques to assess the functional difference among polypeptide sequence homologues, for example, the rate of substrate conversion specific for a particular enzyme function.

Batch culture (or closed system culture) analysis is well known in the art and can provide information on host cell population effects for host cells expressing genetically engineered genes. In batch cultures a host cell population will grow until available nutrients are depleted from the culture media.

In one embodiment, the polypeptides are expressed in a batch culture and analyzed for approximate doubling times, expression efficacy of the engineered polypeptide and end-point net product formation and net biomass production.

Turbidostats are well known in the art as one form of a continuous culture within which media and nutrients are provided on an uninterrupted basis and allow for non-stop propagation of host cell populations. Turbidostats allow the user to determine information on whole cell propagation and steady-state productivity for a particular biologically produced end product such as host cell doubling time, temporally delimited biomass production rates for a particular host cell population density, temporally delimited host cell population density effects on substrate conversion and net productivity of a host cell substrate conversion of, for example, octadecanoic acid to 1-nonadecene. Turbidostats can be designed to monitor the partitioning of substrate conversion products to the liquid or gaseous state. Additionally, quantitative evaluation of net productivity of a carbon-based product of interest can be accurately performed due to the exacting level of control that one skilled in the art has over the operation of the turbidostat. These types of information are useful to assess the parsed and net efficacies of a host cell genetically engineered to produce a specific carbon-based product of interest.

In one embodiment, identical host cell lines differing only in the nucleic acid and expressed polypeptide sequence of a homologous enzyme are cultured in a uniform-environment turbidostat to determine highest whole cell efficacy for the desired carbon-based product of interest.

In another embodiment, identical host cell lines differing only in the nucleic acid and expressed polypeptide sequence of a homologous enzyme are cultured in a batch culture or a turbidostat in varying environments (e.g. temperature, pH, salinity, nutrient exposure) to determine highest whole cell efficacy for the desired carbon-based product of interest.

In one embodiment, mutational variants derived from the methods described herein are cloned. DNA sequences produced by saturation mutagenesis are designed to have restriction sites at the ends of the gene sequences to allow for cleavage and transformation into a host cell plasmid. Generated plasmid stocks are transformed into a host cell and incubated at optimal growth conditions to identify successfully transformed colonies.

In one embodiment, to select protein variants, a colorimetric assay is used to screen for acetaldehyde to qualitatively determine the activity of variants of chimeric alkene synthase in a 1-alkene biosynthetic pathway.

Methods for Producing 1-Alkenes

It is desirable to engineer into an organism suited for industrial use a genetic system from which a chain length-specific 1-alkene can be produced efficiently and cleanly.

Accordingly, the invention includes the conversion of water, inorganic carbon, and light into a selected 1-alkene using the chimeric alkene synthase described herein. In one embodiment, the genetically engineered host cells expresses a chimeric alkene synthase and one or more genes in an alkene biosynthetic pathway enabling the host cell to convert water, light and inorganic carbon and/or a selected 1-alkene precursor into a specific pre-selected 1-alkene.

In another embodiment of the invention, the genetically engineered host cell is processed into an enzymatic lysate for performing the above conversion reaction. In yet another embodiment, the chimeric alkene synthase is purified, as described herein, for carrying out the conversion reaction.

The host cells and/or enzymes, for example in the lysate, partially purified, or purified, used in the conversion reactions are in a form allowing them to perform their intended function, producing a desired 1-alkene, for example, 1-pentadecene. The microorganisms used can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeabilized (e.g., have permeabilized membranes and/or walls such that compounds, for example, substrates, intermediates or products can more easily pass through said membrane or wall).

In yet another embodiment, purified or unpurified chimeric alkene synthase enzymes (e.g., SEQ ID NO: 18, SEQ ID NO: 20, SEQ ID NO: 22, SEQ ID NO: 29, SEQ ID NO: 30, or SEQ ID NO: 31) are used in the conversion reactions. The enzyme is in a form that allows it to perform its intended function. For example, the enzyme can be immobilized, conjugated or floating freely.

The following examples are for illustrative purposes and are not intended to limit the scope of the invention.

Example 1

Identification and Characterization of the Acyl Binding Pocket of Alkene Synthase NonA has several catalytic domains (FIG. 2) with a LuxE-superfamily acyltransferase domain at the N-terminus. This domain serves to load a C18, C17 or C16 acyl chain to the acyl-carrier protein (ACP) domain (i.e. the acyl binding pocket or the interior acyl binding pocket) triggering the biosynthetic pathway of 1-alkenes (FIG. 3, showing 1-nonadecene biosynthesis from a C18:0 acyl chain substrate). In order to identify the acyl binding pocket of NonA, the primary amino acid sequence was aligned with the acyl binding pocket of saframycin Mx1 synthetase B (i.e. SafB) (Li et al. 2008) for which two crystal structures exist with the protein in a complex with 5'-O—[(S)(dodecanoyloxy)(hydroxy)phosphoryl]adenosine (PDB #3KXW, 3LNV). The amino acids comprising the acyl binding pocket were annotated using PyMOL 0.99rc6 by identifying the amino acids located five angstroms or less from the acyl-adenylate ligand (FIG. 4A).

Figure 4:
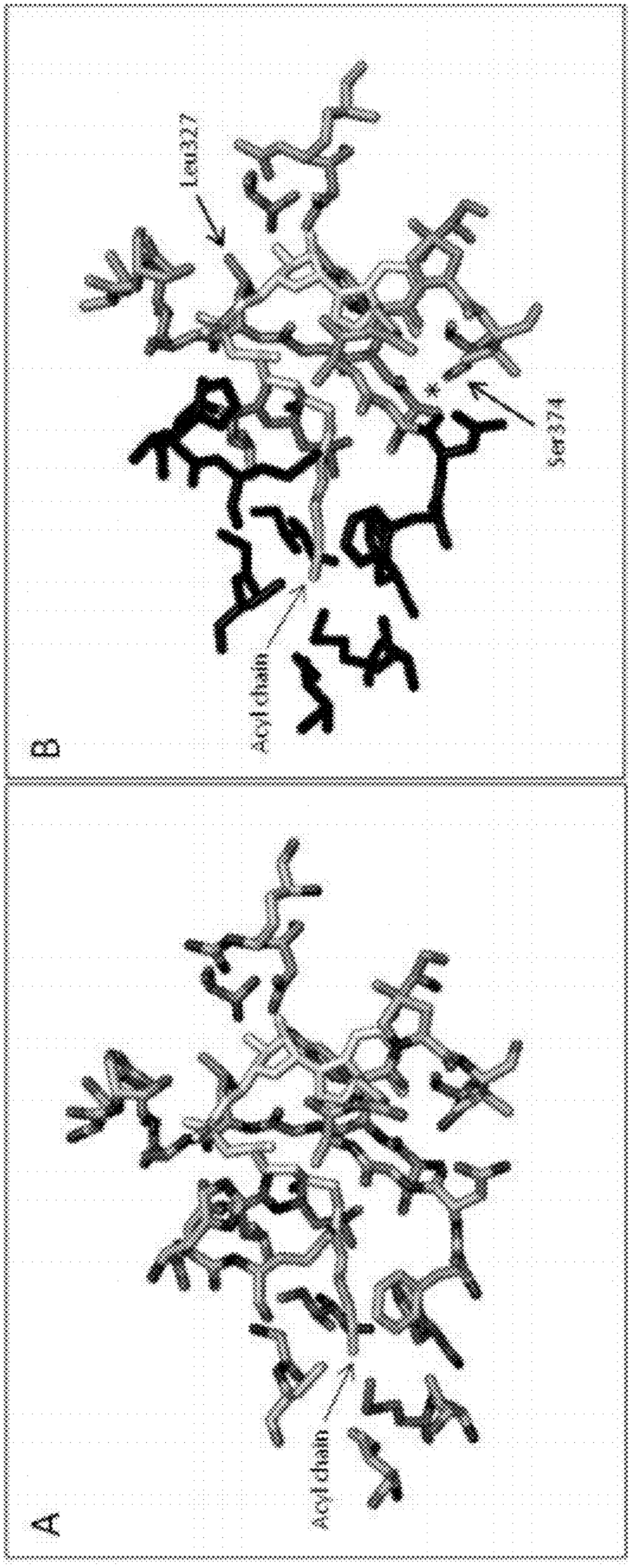
Figure 5:
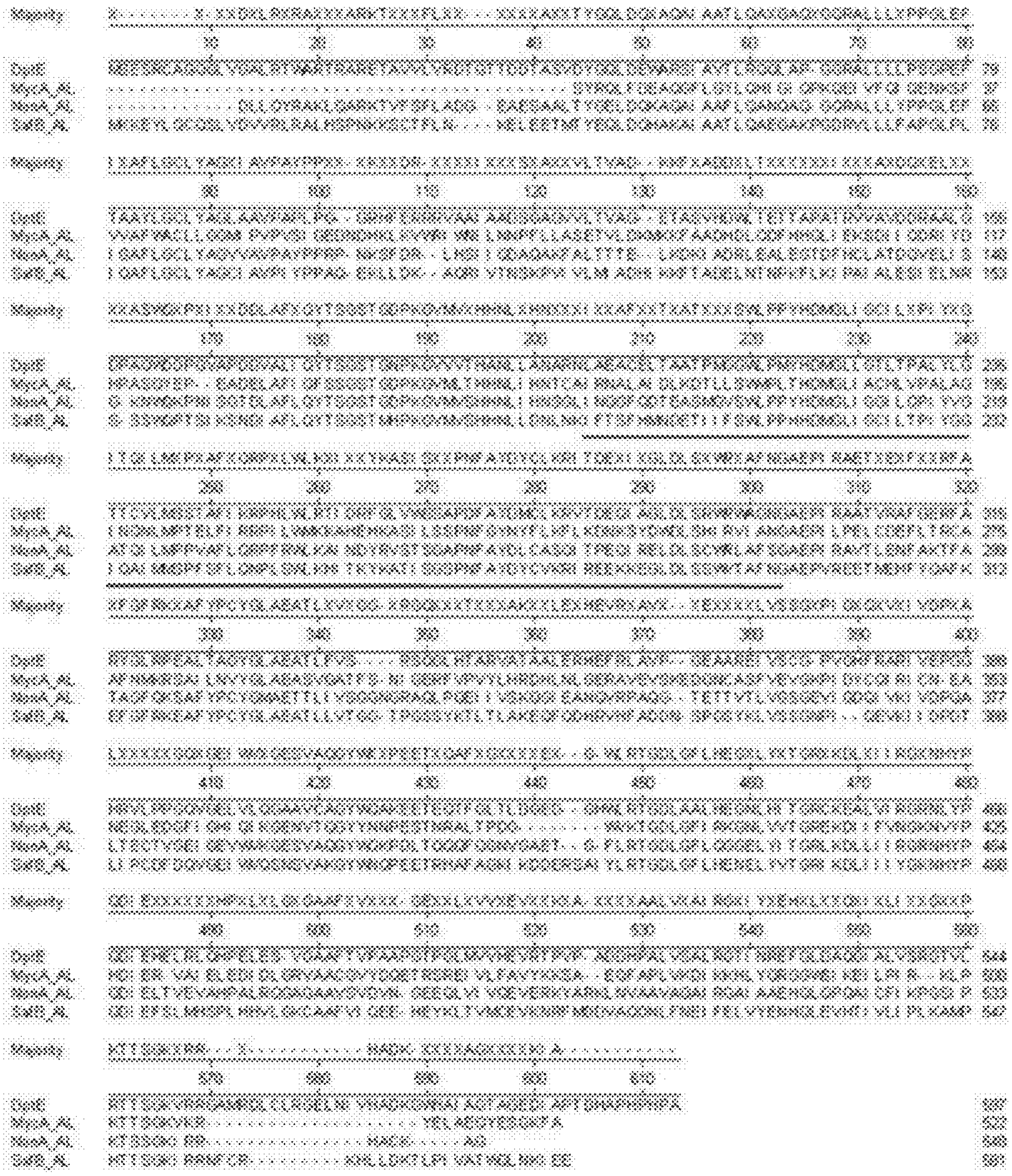

Alignment of the amino acids comprising the SafB acyl binding pocket domain with the corresponding amino acids in NonA and two other acyl binding pocket domains of known substrate specificity for saturated acyl chains of different lengths (Table 1) showed that each acyl binding pocket domain is strongly conserved towards the front of the acyl binding pocket (FIG. 4B, FIG. 5). One residue (327) of SafB at the front of the acyl binding pocket was changed from leucine in SafB to methionine in NonA (FIG. 4B, FIG. 5). This residue may play a role with substrate selectivity, as the other enzymes specifically bind acyl-CoA or acyl-adenylate substrates. The amino acid Ser374, which was close to the adenylate core, is not conserved in all four enzymes and is separated from Cys324 by 4.2 angstroms. Cys324 is at the front of the acyl binding pocket and is also not conserved (FIG. 4B). Ser374-Cys324 (also found in NonA) therefore may be important in stabilizing the pocket. The amino acid residues toward the back of the pocket varied considerably between the four enzymes (FIG. 4B, FIG. 5) as would be expected given their anticipated role in chain length selectivity.

Example 2

Figure 6:
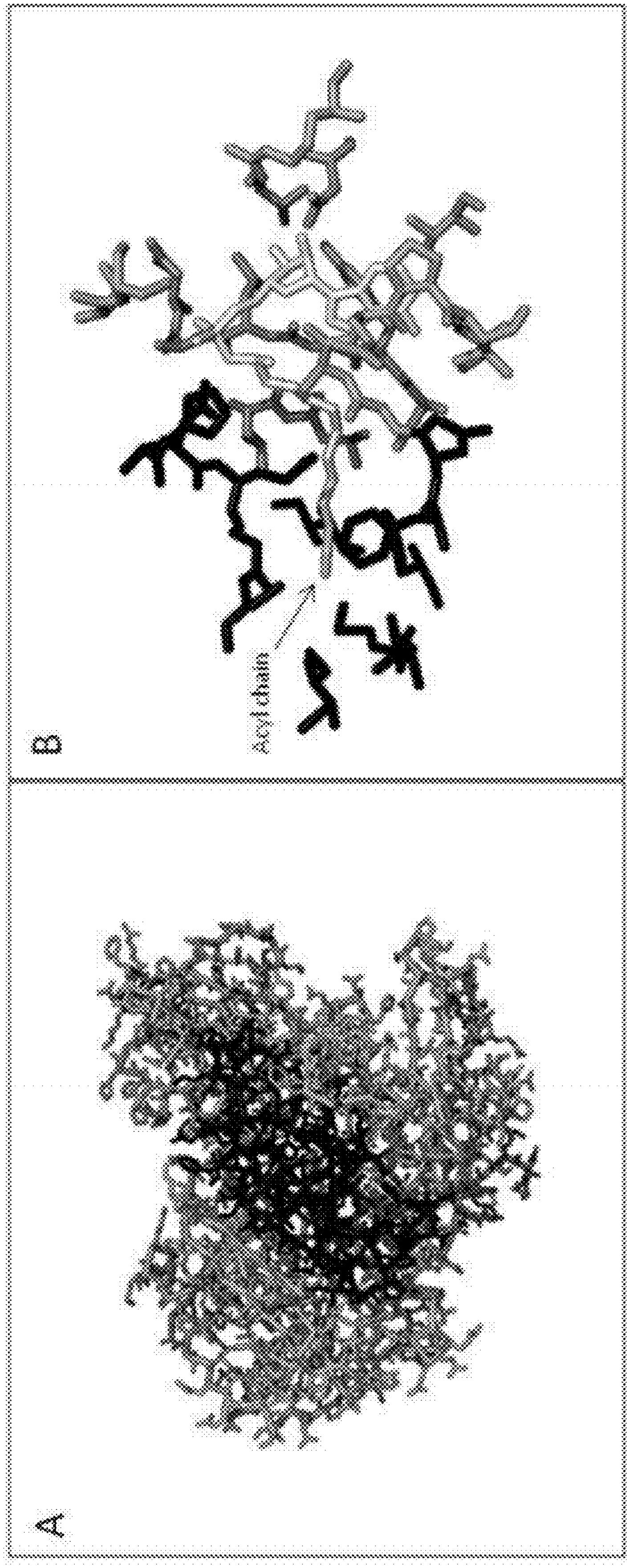

Identification of NonA Synthase Enzymes with Varied Alkene Substrate Specificity Two conserved regions in the primary amino acid sequence of the four acyl binding pocket domains were identified that flanked the interior acyl binding pocket (IABP) of the SafB acyl binding pocket domain. These conserved regions were aligned with NonA as described above and used as the points to designate where to replace the IABP sequence of NonA with IABP sequences of the three other heterologous enzymes, each having a unique chain length specificity (FIG. 5). The IABP residues in SafB are 197-294 (SEQ ID NO:8), and spatially these amino acids form a compact subunit in SafB (FIG. 6A). The IABP residues surround the middle to end of the acyl chain of the ligand (FIG. 6B) and comprise the surrounding pocket.

Example 3

Engineering and Expression of Chimeric NonA Synthase

The corresponding nucleotides of the acyl binding pocket of NonA (SEQ ID NO: 3) are replaced with the coding nucleotides for the acyl binding pocket of SafB (SEQ ID NO:7), MycA (SEQ ID NO:11), or DptE (SEQ ID NO:15), resulting in a NonA chimeric alkene synthase encoded by SEQ ID NO:17, SEQ ID NO:19, or SEQ ID NO:21. The chimeric NonA alkene synthase enzyme comprises a heterologous acyl binding pocket with its native NonA IABP amino acid residues (SEQ ID NO:4) replaced with the IABP amino acids from SafB (SEQ ID NO: 8), MycA (SEQ ID NO:12), and DptE (SEQ ID NO:16). The resulting chimeric alkene synthase has a polypeptide sequence of SEQ ID NO:18, SEQ ID NO:20, or SEQ ID NO:22.

The resulting chimeric alkene synthases are assayed and characterized by their differing acyl-binding pocket specificities. The pre-determined specific chain length 1-alkenes produced by a chimeric NonA alkene synthase having a heterologous acyl binding pocket are consistent with the chain length specificities of the protein source of the acyl binding pocket as shown in Table 1, where the last column indicates the expected 1-alkenes produced by a chimeric NonA alkene synthase containing a heterologous interior acyl binding pocket from the indicated proteins.

TABLE 1

Proteins that contain acyl binding pockets and their anticipated substrate preference for fatty acids.

| Proteins | Accession # | Chain length preference | Reference | Expected 1-alkene(s) |
|---|---|---|---|---|
| NonA | YP_001734428.1 | C16:0, C18:0 | Our results | C17:1, C19:1 (WT) |
| SafB | AAU28294.1 | C14:0, C16:0 | Koketsu et al. 2010 | C15:1, C17:1 |
| MycA | YP_003866245.1 | C16:0 | Hansen et al. 2007 | C17:1 |
| DptE | AAX31555.1 | C12:0 | Wittmann et al. 2008 | C13:1 |

Example 4

Construction of *Escherichia coli* Comprising Recombinant NonA

The *Synechococcus* sp. PCC 7002 nonA (Genbank NC_010475, locus A1173) was purchased from DNA 2.0. The sequence of nonA was codon optimized and optimized for mRNA secondary structure. Unwanted restriction sites were removed from nonA and unique restriction sites flanking domains and N- and C-terminal Strep-tag II and His tags were added to the nonA sequence. The resulting gene and encoded protein sequence for this optimized gene (nonA_optV6) is given in SEQ ID NO: 23 and 24, respectively. The broad spectrum phosphopantetheinyl transferase sfp (Quadri et al. 1998, Genbank protein P39135.2) was purchased from DNA 2.0 following codon optimization, checking for mRNA secondary structure effects and removal of unwanted restriction sites (SEQ ID NO: 25). The *Synechococcus* sp. PCC 7002 gene A2265 (SEQ ID NO: 37) (Genbank NC_010475, locus A2265) was amplified from *Synechococcus* sp. PCC 7002 genomic DNA using the Phusion high-fidelity PCR kit (New England Biolabs) following the manufacturer's instructions and the PCR primers A2265 FP SacI (ggGAGCTCaaggaattatagttatgcgcaaaccctggttaga) (SEQ ID NO: 32) and A2265 RP SbfI (ggCCTGCAGGttatagggactg-gatcgccagttttttctgct) (SEQ ID NO: 33). NonA_optV6 was cloned into the NdeI-MfeI and sfp was cloned into the NcoI-EcoRI restriction sites of pCDFDuet-1 (Novagen) to yield pJB1412. A2265 was cloned into the SacI-SbfI restriction sites of pJB1412 to yield pJB1522. The NonA interior acyl-binding pocket (IABP) variants were generated by cloning in the respective expression-optimized sequences from DptE, SafB and MycA (prepared by DNA 2.0) into the AccI-HindIII restriction sites present in nonA_optV6 to yield nonA_dptE, nonA_safB and nonA_mycA, respectively. The gene and encoded protein sequence for these chimeric alkene synthases are given in SEQ ID NOs: 26 through 31. The IABPs from nonA_dptE, nonA_safB and nonA_mycA were cloned into the NdeI-StuI restriction sites of nonA_optV6 in pJB1522 to yield pJB1629, pJB1630 and pJB1639, respectively. The plasmids containing the four nonA variants (pJB1522, pJB1629, pJB1630 and pJB1639) and pCDF-Duet-1 were transformed into chemically competent *E. coli* BL21 DE(3) (Invitrogen) following the manufacturer's directions to generate strains JCC2157, JCC2358, JCC2375, and JCC2372 (Table 2).

TABLE 2

Engineered *E. coli* BL21 DE(3) strains investigated for the production of 1-alkenes.

| Strain | Plasmid | Genes |
|---|---|---|
| JCC308 | pCDFDuet-1 | — |
| JCC2157 | pJB1522 | sfp, nonA_optV6, A2265 |
| JCC2358 | pJB1629 | sfp, nonA_dptE, A2265 |
| JCC2375 | pJB1630 | sfp, nonA_safB, A2265 |
| JCC2372 | pJB1639 | sfp, nonA_mycA, A2265 |

Example 5

Olefin Chain-Lengths Produced Via Expression of NonA-optV6 in *Escherichia coli*

Culture Conditions and Sampling:

Single colonies of JCC308 and JCC2157 from LB plates containing 1% glucose and 50 mg/L spectinomycin were grown for 6 h at 37° C. in 4 ml of LB medium containing the same glucose and antibiotic concentration. These starter cultures were used to inoculate 15 ml cultures at a starting $OD_{600}$ of 0.05 in a 2% casamino acid M9-derived medium that was amended to contain three times the M9 concentration of phosphate (33.9 g/L $Na_2HPO_4$ and 9 g/L $KH_2PO_4$) and was supplemented with 3 mg/L $FeSO_4.7H_2O$, 0.01 mM IPTG and 50 mg/L spectinomycin. The cultures were incubated for 68 h at 30° C./225 rpm in a New Brunswick shaking incubator. At this point, 50 μl of the cultures were removed to determine the $OD_{600}$ and the remaining volume of the cultures (13 ml) was pelleted by centrifugation. The supernatant was discarded, the cells resuspended in 1 ml of milli-Q water, transferred to a microcentrifuge tube and pelleted by centrifugation. After removing any residual aqueous medium, the cell pellets were vortexed for 20 seconds in 1 ml of acetone (Acros Organics 326570010) containing 25 mg/L butylated hydroxytoluene (antioxidant) and 25 mg/L eicosane (internal standard). The debris was pelleted by centrifugation and the acetone supernatants were analyzed for the presence of 1-alkenes.

Identification and Quantification of 1-Alkenes

An Agilent 7890A GC/5975C EI-MS equipped with a 7683B autosampler was used to identify the 1-alkenes. One μL of each sample was injected into the GC inlet using pulsed splitless injection (pressure: 20 psi, pulse time: 0.3 min, purge time: 0.2 min, purge flow: 15 mL/min) and an inlet temperature of 290° C. The column was a HP-5MS-UI (Agilent, 20 m×0.18 mm×0.18 μm) and the carrier gas was helium at a flow of 0.72 mL/min. The GC oven temperature program was 80° C., hold 0.3 minute; 17.6°/min increase to 290° C.; hold six minutes. The GC/MS interface was 290° C., the MS mass range monitored was 25 to 400 amu and the temperatures of the source and quadrupole were 230° and 150° C., respectively. 1-nonadecene (rt 8.4 min), 1-octadecene (rt 7.8) and 1-heptadecene (rt 7.2 min) were identified based on comparison of their mass spectra (NIST MS database; 2008) and retention times with authentic standards. Shorter chain-length 1-alkenes were not detected in this experiment. The C19:2 1,x-nonadecadiene (rt 8.3) was identified based on interpretation of the mass spectrum and a chemically consistent retention time. In some embodiments, 1,12-(cis)-nonadecadiene as cis-vaccenic acid is the precursor for NonA to generate the nonadecadiene.

An Agilent 7890A GC/FID equipped with a 7683 series autosampler was used to quantify the 1-alkenes. One μL of each sample was injected into the GC inlet (split 8:1, pressure: 20 psi, pulse time: 0.3 min, purge time: 0.2 min, purge flow: 15 mL/min) which had an inlet temperature of 290° C. The column was a HP-5MS (Agilent, 20 m×0.18 mm×0.18 μm) and the carrier gas was helium at a flow of 1.0 mL/min. The GC oven temperature program was 80° C., hold 0.3 minute; 17.6°/min increase to 290° C.; hold 6 minutes. Calibration curves were constructed for the detected 1-alkenes using commercially available standards (Sigma-Aldrich), and the concentrations of the 1-alkenes present in the extracts were determined based on the linear regressions of the peak areas and concentrations. The concentration of 1-nonadecadiene in the samples was determined using the calibration curve for 1-nonadecene. The concentrations of the compounds were normalized to the internal standard (eicosane) and reported as mg/L of culture.

Figure 7:
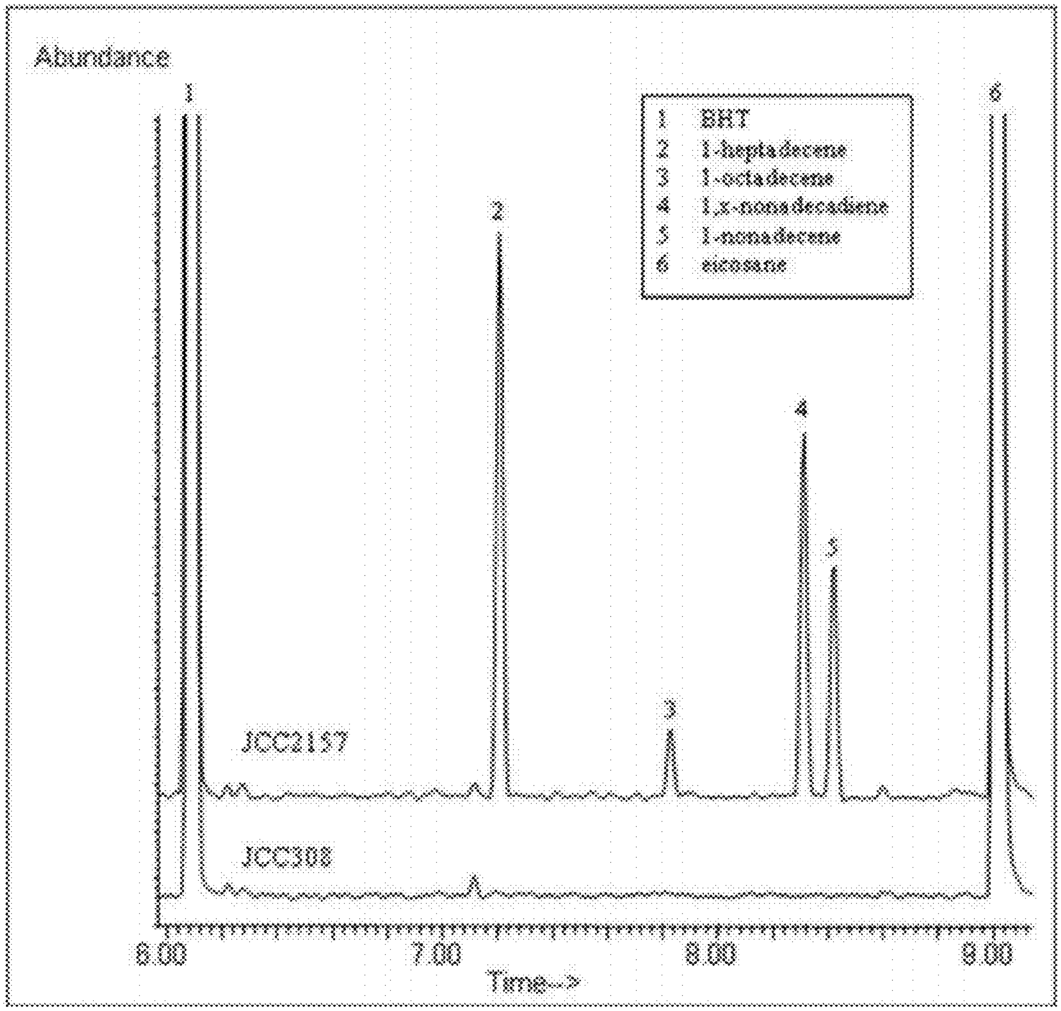
Figure 8:
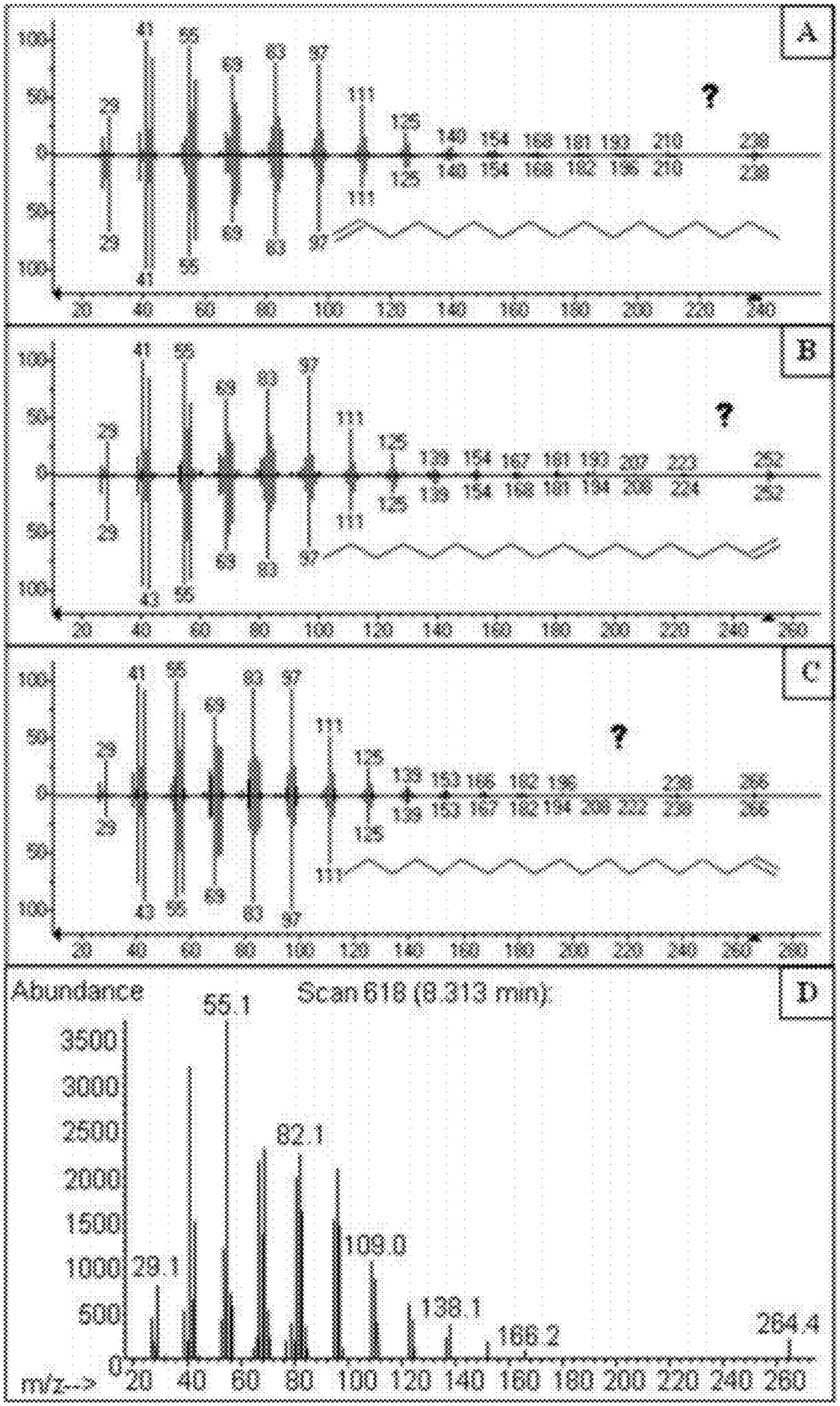

The total ion count (TIC) chromatograms for JCC2157 and JCC308 are shown in FIG. 7. Four 1-alkenes are present in JCC2157 that are not found in JCC308. The mass spectra for the 1-alkenes and comparison with authentic standards where possible are shown in FIG. 8. The quantification data from the experiment are summarized in Table 3.

TABLE 3

The optical densities of the cultures and the total mg/L of 1-alkenes produced by the BL21 DE(3) strains. The % DCW was estimated based on the OD measurement using an average of 400 mg $L^{-1}$ $OD_{600}^{-1}$

| Strain | $OD_{600}$ | 1-alkenes (mg/L) | 1-alkenes (% of DCW) |
|---|---|---|---|
| JCC308 | 2.7 | — | — |
| JCC2157 | 3.2 | 0.28 | 0.022 |

Example 6

Production of Shorter Chain-Length 1-Alkenes with Engineered Alkene Synthases

Culture Conditions and Sampling:

Single colonies of JCC2157, JCC2358, JCC2375 and JCC2372 from LB plates containing 50 mg/L spectinomycin were incubated for 18 h at 37° C. in 4 ml of LB medium containing 50 mg/L spectinomycin. These starter cultures were used to inoculate 15 ml cultures at a starting $OD_{600}$ of 0.05 in a 2% glucose M9-derived medium that was amended to contain three times the M9 concentration of phosphate (33.9 g/L $Na_2HPO_4$ and 9 g/L $KH_2PO_4$) and was supplemented with 3 mg/L $FeSO_4.7H_2O$, 0.01 mM IPTG and 50 mg/L spectinomycin. The cultures were incubated for 54 h at 30° C./225 rpm in a New Brunswick shaking incubator. At this point, 50 μl of the cultures were removed to determine the $OD_{600}$ and the remaining volume of the cultures (14 ml) was pelleted by centrifugation. The supernatant was discarded, the cells resuspended in 1 ml of milli-Q water, transferred to a microcentrifuge tube and pelleted by centrifugation. After removing any residual aqueous medium, the cell pellets were vortexed for 20 seconds in 1 ml of acetone (Acros Organics 326570010) containing 25 mg/L butylated hydroxytoluene (antioxidant) and 25 mg/L eicosane (internal standard). The debris was pelleted by centrifugation and the acetone supernatants were analyzed for the presence of 1-alkenes. The cell pellet extractions and GC analysis was performed as described in Example 5.

Figure 9:
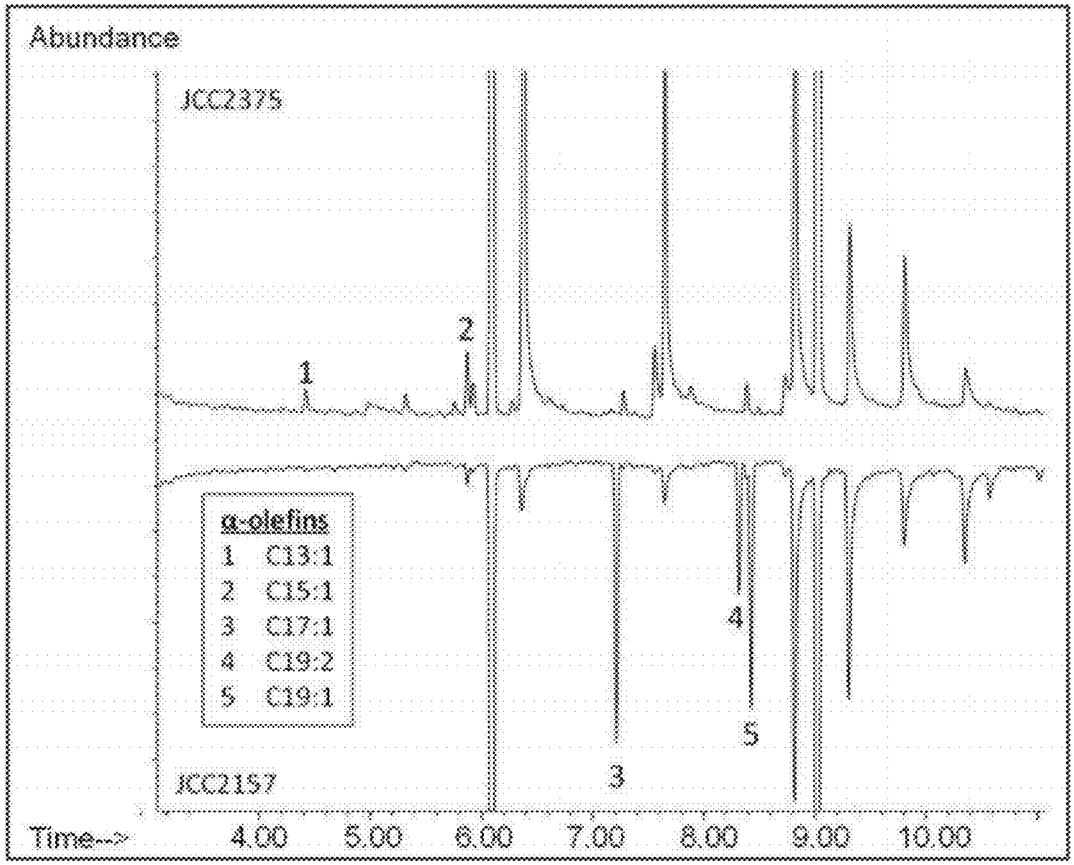
FIG. 9 shows the GC/MS chromatogram of the cell pellet extract of JCC2375 plotted above the chromatogram of the cell pellet extract of JCC2157. The interval between the tick marks on the MS detector axis is 2000.
Figure 10:
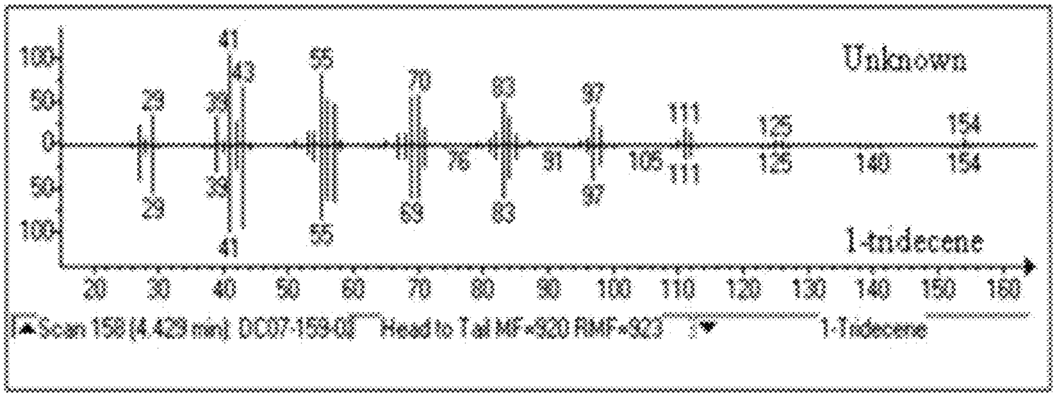
FIG. 10 represents the MS fragmentation spectrum of the JCC23751-tridecene peak plotted above the spectrum in the NIST database.

Analysis of the GC chromatograms and quantification of peaks with the same retention times as authentic standards revealed the presence of shorter chain-length alkenes produced by some of the engineered alkene synthases (Table 4). JCC2375 (nonA_safB) was particularly noteworthy as the 1-alkenes produced were primarily 1-tridecene and 1-pentadecene as opposed to the longer chain length 1-alkenes detected from JCC2157 bearing nonA_optV6 (FIG. 9). The mass spectra for the 1-tridecene peak in comparison with the authentic standard is shown in FIG. 10. This olefin (1-tridecene) is 4-6 methylene units shorter than the 1-alkenes produced by the wild-type enzyme. This demonstrates that the chain length specificity of these enzymes can be changed via tailoring of their acyl-binding pockets.

TABLE 4

The optical densities of the cultures and the mg/L of the 1-alkenes produced by the BL21 DE(3) strains.

| BL21 | | | Total 1-alkenes | Distribution of 1-alkenes in cells as mg/L of culture | | | | |
|---|---|---|---|---|---|---|---|---|
| strain | IABP | $OD_{600}$ | (mg/L of culture) | C19:1 | C19:2 | C17:1 | C15:1 | C13:1 |
| JCC2358 | dptE | 6.2 | 0.03 | 0.007 | — | 0.027 | — | 0.008 |
| JCC2375 | safB | 6.2 | 0.05 | 0.006 | — | 0.004 | 0.036 | 0.015 |
| JCC2372 | mycA | 5.9 | 0.04 | 0.009 | 0.009 | 0.026 | — | 0.009 |
| JCC2157 | nonA | 6.1 | 0.39 | 0.153 | 0.088 | 0.149 | 0.004 | — |

Complete cites to various articles referred to herein are provided below:

Arora, P., Goyal, A., Natarajan, V. T., Rajakumara, E., Verma, P., Gupta, R., Yousuf, M., Triveda, O. A., Mohanty, D., Tyagi, A., Sankaranarayanan, R. and Gokhale, R. S. 2009. Mechanistic and functional insights into fatty acid activation in *Mycobacterium tuberculosis*. Nature Chemical Biology 5: 166-173.

Gu, L., Wang, B., Kulkarni, A., Gehret, J. J., Lloyd, K. R., Gerwick, L., Gerwick, W. H., Wipf, P., Håkannson, K., Smith, J. L. and Sherman, D. H. 2009. Polyketide decarboxylative chain termination preceded by O-sulfonation in curacin A biosynthesis. Journal of the American Chemical Society 131: 16033-16035.

Hansen, D. B., Bumpus, S. B., Aron, Z. D., Kelleher, N. L. and Walsh, C. T. 2007. The loading module of mycosubtilin: An adenylation domain with fatty acid selectivity. Journal of the American Chemical Society 129: 6366-6367.

Koketsu, K., Watanabe, K., Suda, H., Oguri, H. and Oikawa, H. 2010. Reconstruction of the saframycin core scaffold defines dual Pictet-Spengler mechanisms. Nature Chemical Biology 6: 408-410.

Kopp, F., Linne, U., Oberthür, M. and Marahiel, M. A. 2008. Harnessing the chemical activation inherent to carrier protein-bound thioesters for the characterization of lipopeptide fatty acid tailoring enzymes. Journal of the American Chemical Society 130: 2656-2666.

Li, L., Deng, W., Song, J., Ding, W., Zhao, Q.-F., Peng, C., Song, W.-W., Tang, G.-L. and Liu, W. 2008. Characterization of the Saframycin A gene cluster from *Streptomyces lavendulae* NRRL 11002 revealing a nonribosomal peptide synthetase system for assembling the unusual tetrapeptidyl skeleton in an iterative manner. Journal of Bacteriology 190: 251-263.

Lin, J.-W., Chao, Y.-F. and Weng, S.-F. 1996. Nucleotide sequence and functional analysis of the luxE gene encoding acyl-protein synthetase of the lux operon from *Photobacterium leiognathi*. Biochemical and Biophysical Research Communications 228: 764-773.

Murata, N., Wada, H. and Gombos, Z. 1992. Modes of fatty-acid desaturation in cyanobacteria. Plant Cell Physiology 33: 933-941.

Wittmann, M., Linne, U., Pohlmann, V. and Marahiel, M. A. 2008. Role of DptE and DptF in the lipidation reaction of daptomycin. FEBS Journal 275: 5343-5354.

Wyckoff, T. J. O., Lin, S., Cotter, R. J., Dotson, G. D. and Raetz, C. R. H. 1998. Hydrocarbon rulers in UDP-N-acetylglucosamine acyltransferases. The Journal of Biological Chemistry 273: 32369-32372.

Yuan, L., Voelker, T. A. and Hawkins, D. J. 1995. Modification in the substrate specificity of an acyl-acyl carrier protein thioesterase by protein engineering. Proceedings of the National Academy of Sciences of the United States of America 92: 10639-10643.

All publications, patents and other references mentioned herein are hereby incorporated by reference in their entireties and for all purposes.

What is claimed is:

1. An isolated or recombinant chimeric NonA alkene synthase comprising a heterologous acyl binding pocket, wherein said alkene synthase comprises the polypeptide sequence of SEQ ID NO: 30.

2. The alkene synthase of claim 1, wherein said heterologous acyl binding pocket comprises the polypeptide sequence of SEQ ID NO: 8.

3. The alkene synthase of claim 1, wherein said alkene synthase is fused to a heterologous amino acid sequence.

4. The alkene synthase of claim 1, wherein said alkene synthase is encoded by an isolated or recombinant polynucleotide comprising SEQ ID NO: 27.

5. The alkene synthase of claim 1, wherein said alkene synthase catalyzes the production of an alkene selected from the group consisting of: 1-tridecene, 1-pentadecene, 1-heptadecene, and 1-nonadecene.

6. A method for producing an comprising:

a. culturing a host cell to produce an alkene, wherein said host cell comprises an engineered chimeric NonA comprising a heterologous binding pocket, wherein said alkene synthase comprises the polypeptide sequence of SEQ ID NO: 30; and b. isolating the alkene.

* * * * *

UNITED STATES PATENT AND TRADEMARK OFFICE

CERTIFICATE OF CORRECTION

PATENT NO. : 8,580,542 B2
APPLICATION NO. : 13/370654
DATED : November 12, 2013
INVENTOR(S) : Christian Perry Ridley It is certified that error appears in the above-identified patent and that said Letters Patent is hereby corrected as shown below:

In the Claims

Claim 6, Column 264, line 32, after "producing an," insert --alkene--.

Signed and Sealed this
Eighteenth Day of February, 2014

Michelle K. Lee
*Deputy Director of the United States Patent and Trademark Office*